(12) United States Patent
Vlasuk et al.

(10) Patent No.: US 6,872,808 B1
(45) Date of Patent: Mar. 29, 2005

(54) NEMATODE-EXTRACTED SERINE PROTEASE INHIBITORS AND ANTICOAGULANT PROTEINS

(75) Inventors: George Phillip Vlasuk, Carlsbad, CA (US); Patrick Eric Hugo Stanssens, St-Martens-Latem (BE); Joris Hilda Lieven Messens, Dilbeek (BE); Marc Josef Lauwereys, Haabert (BE); Yves Rene LaRoche, Brussels (BE); Laurent Stephane Jespers, Tervuren (BE); Yannick Georges Jozef Gansemans, Ichtegem (BE); Matthew Moyle, Boulder, CO (US); Peter W. Bergum, San Diego, CA (US)

(73) Assignee: Corvas International, Inc., San Diego, CA (US)

( * ) Notice: Subject to any disclaimer, the term of this patent is extended or adjusted under 35 U.S.C. 154(b) by 0 days.

(21) Appl. No.: 09/498,556

(22) Filed: Feb. 4, 2000

Related U.S. Application Data

(63) Continuation of application No. 08/809,455, filed as application No. PCT/US95/13231 on Oct. 17, 1995, now Pat. No. 6,090,916, and a continuation-in-part of application No. 08/461,965, filed on Jun. 5, 1995, now Pat. No. 5,872,098, and a continuation-in-part of application No. 08/465,380, filed on Jun. 5, 1995, now Pat. No. 5,863,894, and a continuation-in-part of application No. 08/486,397, filed on Jun. 5, 1995, now Pat. No. 5,866,542, and a continuation-in-part of application No. 08/486,399, filed on Jun. 5, 1995, now Pat. No. 5,866,543, and a continuation-in-part of application No. 08/326,110, filed on Oct. 18, 1994, now Pat. No. 5,945,275.

(51) Int. Cl.$^7$ .................. A61K 35/14; C07K 14/00; C07K 38/00
(52) U.S. Cl. .............. 530/384; 530/381; 530/350; 530/324; 530/300; 530/829; 514/12
(58) Field of Search ................ 530/300, 324, 530/350, 381, 384, 829; 514/12

(56) References Cited

U.S. PATENT DOCUMENTS

| | | | |
|---|---|---|---|
| 4,458,066 A | 7/1984 | Caruthers et al. | 536/27 |
| 4,683,293 A | 7/1987 | Craig | 530/359 |
| 4,745,051 A | 5/1988 | Smith et al. | 435/68 |
| 4,777,242 A | 10/1988 | Nelles | 530/351 |
| 4,808,537 A | 2/1989 | Stroman et al. | 435/6 |
| 4,812,405 A | 3/1989 | Lair et al. | 435/255 |
| 4,818,700 A | 4/1989 | Cregg et al. | 435/252.33 |
| 4,837,148 A | 6/1989 | Cregg | 435/172.3 |

(List continued on next page.)

FOREIGN PATENT DOCUMENTS

| | | |
|---|---|---|
| EP | 0255771 | 2/1988 |
| EP | 0419099 | 3/1991 |

(List continued on next page.)

OTHER PUBLICATIONS

Aoki, Y., et al., "Effects of Recombinant Human Soluble Thrombomodulin (rhs–Tm) on a Rat Model of Disseminated Intravascular Coagulation with Decreased Levels of Plasma Antithrombin" *Thrombosis and Hemostasis* 71(4):452–455 (1994).

(List continued on next page.)

*Primary Examiner*—Jon Weber
*Assistant Examiner*—Rita Mitra
(74) *Attorney, Agent, or Firm*—Fish & Richardson P.C.

(57) ABSTRACT

Proteins which have activity as anticoagulants and/or serine protease inhibitors and have at least one NAP domain and are described. Certain of these proteins have factor Xa inhibitory activity and others have activity as inhibitors of factor VIIa/TF. These proteins can be isolated from natural sources as nematodes, chemically synthesized or made by recombinant methods using various DNA expression systems.

13 Claims, 51 Drawing Sheets

U.S. PATENT DOCUMENTS

| | | | |
|---|---|---|---|
| 4,855,231 A | 8/1989 | Stroman et al. | 435/68 |
| 4,857,467 A | 8/1989 | Sreekrishna et al. | 435/255 |
| 4,879,231 A | 11/1989 | Stroman et al. | 435/172.3 |
| 4,882,279 A | 11/1989 | Cregg | 435/172.3 |
| 4,885,242 A | 12/1989 | Cregg et al. | 435/68 |
| 4,895,800 A | 1/1990 | Tschopp et al. | 435/69.3 |
| 5,002,876 A | 3/1991 | Sreekrishma et al. | 435/69.5 |
| 5,004,688 A | 4/1991 | Craig et al. | 435/69.3 |
| 5,023,236 A | 6/1991 | Edgington et al. | 514/18 |
| 5,032,516 A | 7/1991 | Cregg | 435/172.3 |
| 5,106,833 A | 4/1992 | Broze et al. | 514/12 |
| 5,122,465 A | 6/1992 | Cregg et al. | 435/172.3 |
| 5,135,868 A | 8/1992 | Cregg | 435/255 |
| 5,166,329 A | 11/1992 | Cregg | 536/27 |
| 5,189,019 A | 2/1993 | Palladino et al. | 514/12 |
| 5,204,261 A | 4/1993 | Prevatt et al. | 435/255 |
| 5,239,058 A | 8/1993 | Vlasuk et al. | 530/524 |
| 5,239,059 A | 8/1993 | Zasloff et al. | 530/325 |
| 5,268,273 A | 12/1993 | Buckholz | 435/69.1 |
| 5,330,901 A | 7/1994 | Prevatt et al. | 435/69.6 |
| 5,427,937 A | 6/1995 | Cappello et al. | 435/212 |
| 5,525,477 A | 6/1996 | Hassouna | 435/13 |
| 5,605,671 A | 2/1997 | Lyle et al. | 424/1.41 |
| 5,864,009 A * | 1/1999 | Vlasuk et al. | 530/324 |
| 5,866,542 A * | 2/1999 | Vlasuk et al. | 514/12 |
| 5,872,098 A * | 2/1999 | Vlasuk et al. | 514/12 |
| 6,090,916 A * | 7/2000 | Vlasuk et al. | 530/350 |

FOREIGN PATENT DOCUMENTS

| | | |
|---|---|---|
| EP | 0439442 | 7/1991 |
| EP | 0454372 | 10/1991 |
| WO | 88/09811 | 12/1988 |
| WO | 91/02753 | 3/1991 |
| WO | 94/25000 | 4/1994 |
| WO | 95/12615 | 5/1995 |
| WO | 96/04378 | 2/1996 |
| WO | 96/12021 | 4/1996 |
| WO | 96/04377 | 2/1997 |

OTHER PUBLICATIONS

Babin et al., "The Isoinhibitors of Chymotrypsin/Elastase from *Ascaris lumbricoides*: The Primary Structure" *Arch. of Biochem. and Biophy.* 232(1):143–161 (1984).

Beaucage et al., "Deoxynucleoside Phosphoramidites–A New Class of Key Intermediates for Deoxypolynucleotide Synthesis" *Tetrahedron Letters*, 22(20):1859–1862 (1981).

Bernard, et al., "The Serine Protease Inhibitor Family from Ascaris Suum: Chemical Determination of the Five Disulfide Bridges" *Arch. Biochem. Biophys.*, 303(2):367–376 (1993).

Bock, P.E. et al. "Isolation of Human Coagulation a–Factor $X_a$ by Soybean Trypsin Inhibitor–Sepharose Chromatography and Its Active–Site Titration with Fluorescein Mono–p–guanidinobenzoate" *Archives of Biochem. Biophys.* 273(2):375–388 (1989).

Bolivar et al., "Construction and Characterization of New Cloning Vehicles" *Gene*, 2:95–113 (1977).

Broach, J. et al., "Transformation In Yeast: Development of a Hybrid Cloning Vector and Isolation of the CAN1 Gene" *Gene*, 8:121–133 (1978).

Brown, E. et al., "Chemical Synthesis and Cloning of a Tyrosine tRNA Gene" *Methods in Enzymology, 68*, 109–151 (1979).

Bullock et al., "XL1–Blue: A High Efficiency Plasmid Transforming recA *Escherichia coli* Strain with Beta–Galactosidase Selection" *Biotechniques* 5(4):376–379 (1987).

Cairns et al., "Antithrombotic Agents in Coronary Artery Disease" *Chest* 102:456S–481S (1992).

Crameri et al., "Display of Biologically Active Proteins on the Surface of Filamentous Phages: a cDNA Cloning System for Selection of Functional Gene Products Linked to the Genetic Information Responsible for their Production" *Gene*, 137:69–75 (1993).

Cappello et al., "Ancylostoma Factor Xa Inhibitor: Partial Purification and Its Identification as a Major Hookworm–Derived Anticoagulant In Vitro" *J. Infect. Diseases*, 167:1474–1477 (1993).

Cappello et al., "Ancylostoma caninum anticoagulant peptide: A hookworm–derived Inhibitor of Human Coagulation Factor Xa," *Proc. Natl. Acad. Sci. U.S.A.* 92:6152–6156 (1995).

Carroll et al., " The Anticoagulant Effects of the Hookworm, Ancylostoma Ceylanicum: Observations on Human and Dog Blood In Vitro and Infected Dogs In Vivo" *Thromb. Haemostas.* (Stuttgart), 51(2):222–227 (1984).

Carson, "Computerized Analysis of Enzyme Cascade Reactions Using Continuous Rate Data Obtained with an ELISA Reader" *Comput. Prog. Biomed* 19:151–157 (1985).

Clements et al., "Secretion of Human Epidermal Growth Factor from *Saccharomyces cerevisiae* Using Synthetic Leader Sequences" *Gene* 106:267–272 (1991).

Cohen, Nonchromosomal Antibiotic Resistance in Bacteria: Genetic Transformation of *Escherichia coli* by R–Factor DNA *Proc. Natl. Acad. Sci. USA*, 69(8):2110–2114 (1972).

Crawford, et al., "Inhibition of Human Blood Clotting By Extracts of Ascaris Suum" *J. Parasitol.*, 68(6):1044–1047 (1982).

Curtis, *Biology Fourth ed.* N.Y. Worth Publishers, Inc. pp. 500–501 (1983).

Depicker et al., "Nopaline Synthase: Transcript Mapping and DNA Sequence" *J. Mol. Appl. Gen.*, 1(6):561–573 (1978).

Despreaux et al., "The dac A Gene of Bacillus Stearothermophilus Coding for D–Alanine Carboxypeptidase: Cloning, Structure and Expression in *Escherichia coli* and Pichia Pastoris" *Gene* 131:35–41 (1993).

Fiers, et al., "Complete Nucleotide Sequence of SV40 DNA" *Nature*, 273:113–120 (1978).

Fuster, V. The Pathogenesis of Coronary Artery Disease and the Acute Coronary Syndromes *New Engl. J. Med.* 326(5):310–318 (1992).

Glaser–Wuttke, G., "Pore–Forming Properties of the Adsorption protein of Filamentous Phage fd" *Biochem. Biophys. Acta*, 985:239–247 (1989).

Glover, "Gene Cloning: The Mechanics of DNA Manipulation" 1–20 (1984).

Goeddel et al., "Synthesis of Human Fibroblast Interferon by *E.coli*" *Nucleic Acids Res.*, 8(18):4057–4074 (1980).

Gold et al., "Evidence for a Rebound Coagulation Phenomenon After Cessation of a 4–hour Infusion of a Specific Thrombin Inhibitor in Patients with Unstable Angina Pectoris" *JACC* 21(5):1039–1047 (1993).

Grasberger et al., "High–Resolution Structure of Ascaris Trypsin Inhibitor in Solution: Direct Evidence for a pH–induced Conformational Transition in the Reactive Site" *Structure*, 2:669–678 (1994).

Hemker et al., "Feedback Mechanisms in Coagulation" *Hemostasis* 21:189–196 (1991).

Hirsh, J., "Heparin" *N. Engl. J.Med* 324(22):1565–1574 (1992).

Hitzeman et al., "Isolation and Characterization of the Yeast 3–Phosphoglycerokinase Gene (PKG) by an Immunological Screening Technique" *J. Biol. Chem.*, 255(24):12073–12080 (1980).

Holland et al., "The Primary Structures of Two Yeast Enolase Genes" *J. Biol. Chem.*, 256(3):1385–1395 (1981).

Houghten, "General Method for the Rapid Solid–Phase Synthesis of Large Numbers of Peptides: Specificity of Antigen–Antibody Interaction at the level of Individual Amino Acids" *Proc. Natl. Acad. Sci.*, 82:5131–5135 (1985).

Hsiao, C.L. et al.,. "High–Frequency Transformation of Yeast by Plasmids Containing the Cloned Yeast ARG4 Gene" *Proc.Natl. Acad. Sci.* USA 76(8):3829–3822 (1979).

Huang et al., "The Molecular Structure of the Complex of the Complex of Ascaris Chymotrypsin/Elastase Inhibitor with Porcine Elastase" *Structure* 2:679–689 (1994).

Itakura et al., "Expression in *Escherichia coli* of a Chmically Synthesized Gene for the Hormone Somatostatin" Science 198:1056–1063 (1977).

Kasten, B.L., "Specimen Collection", *Laboratory Test Handbook*, 2nd Edition, Lexi–Comp Inc., Cleveland pp. 16–17 (Edits. Jacobs, D.S. et al. 1990).

Kessler, C. "The Pharmacology of Aspirin, Heparin, Coumarin and Thrombolytic Agents" *Chest* 99:97S–112S (1991).

Kurz, K.D., et al., " Rat Model of Arterial Thrombosis Induced by Ferric Chloride" *Thromb. Res.* 60:269–280 (1990).

Lawson et al., "A Model for the Tissue Factor Pathway to Thrombin" *J. Biol. Chem.* 269(37):23357–23366 (1994).

Levine et al., "Hemorrhagic Complications of Anticoagulant Treatment" *Chest* 102:352S–363S (1992).

Lidon et al., "Initial Experience with Direct Antithrombin Hirulog, in Unstable Angina" *Circulation* 88(4):1495–1501 (1993).

Loeb et al., "The Presence of a Substance Inhibiting the Coagulation of the Blood in Ancylostoma" *Proc. Pathol. Soc.of Philadelphia*, 7(6):173–178 (1904).

Lucchesi et al., "Prevention of Thrombosis and Rethrombosis and Enhancement of the Thrombolytic Actions of Recombinant Tissue–Type Plasminogen Activator in the Canine Heart of DMP728, A Glycoprotein Iib/IIIa Antagonist" *Brit. J. Pharmacol.* 113:1333–1343 (1994).

Maniatis et al., "Molecular Cloning: A Laboratory Manual" *Cold Spring Harbor Press* p. 254–255 (1982).

Mann et al., "Surface–Dependent Hemostasis" *Sem. Hematology* 29(3):213–226 (1992).

Mann et al., "Blood" *Journal of The American Society of Hematology* 76(1):1–16 (1990).

Merrifield, "Solid Phase Peptide Synthesis. I. The Synthesis of a Tetrapeptide" *J. Amer. Chem. Soc.* 85:2149–2154 (1963).

Messing et al., "A System for Shotgun DNA Sequencing" *Nucleic Acids Res.* 9(2): 309–321 (1981).

*Methods of Enzymology*, 65:499–560 (1980).

Mizushima et al., "pEF–BOS, A Powerful Mammalian Expression Vector" *Nucl. Acids Res.*, 18(17):5322 (1990).

Morrison et al., "The Behavior and Significance of Slow–Binding Enzyme Inhibitors" *C.T. Adv. Enzymol.* 61:201–301 (1988).

Maruyama et al., "Lambda foo: a phage vector for the expression of foreign proteins" *Proc. Nat'l. Acad. Sci., USA* 91:8273–8277 (1994).

Soumillion et al., "Selection of –lactamase on Filamentous Bacteriophage by Catalytic Activity" *J. Mol. Biol.* 237:415–422 (1994).

Spellman et al., "Anticoagulant Activity of Dog Hookworm" *Am. J. Physiol.* 220(4):922–927 (1971).

Stanssens et al., "Anticoagulant Repertoire of the Hookworm Ancylostoma Caninum" *Proc. Natl. Acad. Sci. U.S.A.* 93:2149–2154 (1996).

Taylor, "Identification of Protein Sequence Homology by Consensus Template Alignment" *J. Mol. Biol.* 188:233–258 (1986).

Tuszynski et al., "Isolation and Characterization of Antistatin" *J. Biol. Chem.* 262(20):9718–9723 (1987).

Van Solingen et al., "Fusion of Yeast Spheroplasts" *J. Bacter.* 130:946–947 (1977).

Van Lenten et al., "Studies on the Chemical and Enzymatic Modification of Glycoproteins" *J. of Biol. Chem.* 246(6):1889–1894 (1971).

Vieira et al., "Production of Single–Stranded Plasmid DNA" *Methods in Enzymol. 153*, 3–11 (1987).

Vlasuk, et al., "Structural and Functional Characterization of Tick Anticoagulant Peptide (TAP): A Potent and Selective Inhibitor of Blood Coagulation Factor Xa" *Thromb. Haemostas.* 70(1):212–216 (1993).

Vrijsen et al., "Resolution of the Major Poliovirus Polypeptides into Doublets" *Virology*, 86:546–555 (1978).

Waxman et al., "Tick Anticoagulant Peptide (TAP) Is a Novel Inhibitor of Blood Coagulation Factor Xa" *Science*, 248:593–596 (1990).

Weitz et al., "New Anticoagulant Strategies" *J. Lab. Clin. Med.* 122(4):364–373 (1993).

Zell et al., "DNA Mismatch –Repair in *Escherichia coli* Counteracting the Hydrolytic Deamination of 5–Methyl–Cytosine Residues" *Embo J.*, 6(6):1809–1815 (1987).

Hotez and Pritchard, "Hookworm Infection", *Sci.Am.*, Jun. 1995, pp. 68–74.

Cappello et al., "Ancyclostoma caninum anticoagulant peptide: cloning by PCR and expression of soluble, active protein in *E. coli*", *Molec. Biochem. Parasitol.* 80:113–117 (1996).

Jespers et al., "Surface Expression and Ligand–Based Selection of cDNAs Fused to Fileamentous Phage Gene VI", *Bio/Technology* 13:378–382 (1995).

Jock Friedly, "New Anticoagulant Promps Bad Blood Between Partner", *Science* 271:1800–1801 (1996).

May 10, 1996 letter from David Kabakoff to *Science*; not published.

May 13, 1996 fax from Yale University to Corvas including letter (May 10, 1996) said to have been sent to *Science*; not published.

Jul. 16, 1996 e–mail from Science to Jean Ellis noting receipt of May 10, 1996 Kabakoff letter.

Sep. 17, 1996 e–mail from *Science* to Jean Ellis noting Science decision to not publish May 10, 1996 Kabakoff letter.

Sep. 26, 1996 letter from Randall Woods to *Science*; not published.

Apr. 21, 1995 letter from George Vlasuk to *Thrombosis and Haemostasis*; not published.

* cited by examiner

Figure 1

```
      1           10              20              30
      *            *               *               *
G AATTCCGCTA CTACTCAACA ATG AAG ATG CTT TAC GCT ATC GCT
                       Met Lys Met Leu Tyr Ala Ile Ala 40          50              60              70
      *           *               *               *
ATA ATG TTT CTC CTG GTA TCA TTA TGC AGC GCA AGA ACA GTG
Ile Met Phe Leu Leu Val Ser Leu Cys Ser Ala Arg Thr Val 80          90             100             110            120
      *           *               *               *              *
AGG AAG GCA TAC CCG GAG TGT GGT GAG AAT GAA TGG CTC GAC
Arg Lys Ala Tyr Pro Glu Cys Gly Glu Asn Glu Trp Leu Asp 130             140             150            160
            *               *               *              *
GAC TGT GGA ACT CAG AAG CCA TGC GAG GCC AAG TGC AAT GAG
Asp Cys Gly Thr Gln Lys Pro Cys Glu Ala Lys Cys Asn Glu 170             180             190            200
           *               *               *              *
GAA CCC CCT GAG GAG GAA GAT CCG ATA TGC CGC TCA CGT GGT
Glu Pro Pro Glu Glu Glu Asp Pro Ile Cys Arg Ser Arg Gly 210             220             230            240
           *               *               *              *
TGT TTA TTA CCT CCT GCT TGC GTA TGC AAA GAC GGA TTC TAC
Cys Leu Leu Pro Pro Ala Cys Val Cys Lys Asp Gly Phe Tyr 250             260             270            280
           *               *               *              *
AGA GAC ACG GTG ATC GGC GAC TGT GTT AGG GAA GAA GAA TGC
Arg Asp Thr Val Ile Gly Asp Cys Val Arg Glu Glu Glu Cys 290         300             310             320           330
      *           *               *               *             *
GAC CAA CAT GAG ATT ATA CAT GTC TGA ACGAGAAAGC AACAATAACC
Asp Gln His Glu Ile Ile His Val 340         350             360             370           380
      *           *               *               *             *
AAAGGTTCCA ACTCTCGCTC TGCAAAATCG CTAGTTGGAT GTCTCTTTTG 390         400             410             420           430
      *           *               *               *             *
CGTCCGAATA GTTTTAGTTG ATGTTAAGTA AGAACTCCTG CTGGAGAGAA 440         450
      *           *
TAAAGCTTTC CAACTCC poly(A)
```

Figure 2

| | | | | | | | | | | | |
|---|---|---|---|---|---|---|---|---|---|---|---|
|Lys|Ala|Tyr|Pro|Glu|Cys|Gly|Glu|Asn|Glu|Trp|Leu|Asp|Asp
1||||5||||10

Lys Ala Tyr Pro Glu Cys Gly Glu Asn Glu Trp Leu Asp Asp
1                5                       10

Cys Gly Thr Gln Lys Pro Cys Glu Ala Lys Cys Asn Glu Glu
15              20                      25

Pro Pro Glu Glu Glu Asp Pro Ile Cys Arg Ser Arg Gly Cys
    30              35                  40

Leu Leu Pro Pro Ala Cys Val Cys Lys Asp Gly Phe Tyr Arg
        45              50                      55

Asp Thr Val Ile Gly Asp Cys Val Arg Glu Glu Cys Asp
            60              65              70

Gln His Glu Ile Ile His Val
            75

Figure 3

```
          1          10              20              30
          *           *               *               *
G AATTCCGCTA CTACTCAACA ATG AAG ATG CTT TAC GCT ATC GCT
                       Met Lys Met Leu Tyr Ala Ile Ala 40          50              60              70
      *           *               *               *
ATA ATG TTT CTC CTG GTG TCA TTA TGC AGC ACA AGA ACA GTG
Ile Met Phe Leu Leu Val Ser Leu Cys Ser Thr Arg Thr Val 80          90             100             110         120
  *           *               *               *           *
AGG AAG GCA TAC CCG GAG TGT GGT GAG AAT GAA TGG CTC GAC
Arg Lys Ala Tyr Pro Glu Cys Gly Glu Asn Glu Trp Leu Asp 130             140             150         160
              *               *               *           *
GTC TGT GGA ACT AAG AAG CCA TGC GAG GCC AAG TGC AGT GAG
Val Cys Gly Thr Lys Lys Pro Cys Glu Ala Lys Cys Ser Glu 170             180             190         200
              *               *               *           *
GAA GAG GAG GAA GAT CCG ATA TGC CGA TCA TTT TCT TGT CCG
Glu Glu Glu Glu Asp Pro Ile Cys Arg Ser Phe Ser Cys Pro 210             220             230         240
          *               *               *           *
GGT CCC GCT GCT TGC GTA TGC GAA GAC GGA TTC TAC AGA GAC
Gly Pro Ala Ala Cys Val Cys Glu Asp Gly Phe Tyr Arg Asp 250             260             270         280
      *               *               *           *
ACG GTG ATC GGC GAC TGT GTT AAG GAA GAA GAA TGC GAC CAA
Thr Val Ile Gly Asp Cys Val Lys Glu Glu Glu Cys Asp Gln 290             300             310         320         330
  *               *               *           *           *
CAT GAG ATT ATT CAT GTC TGA ACGAGAGAGC AGTAATAACC
His Glu Ile Ile His Val 340        350        360        370        380
              *          *          *          *          *
           AAAGGTTCCA ACTTTGCTC TACAAAATCG CTAGTTGGAT TTCTCCTTTG 390        400        410        420        430
              *          *          *          *          *
           CGTGCGAATA GTTTTAGTTG ATATTAAGTA AAACCTCCTG TTGAAGAGAA

440
              *
           TAAAGCTTTC CAACTTC poly(A)
```

Figure 4

Lys Ala Tyr Pro Glu Cys Gly Glu Asn Glu Trp Leu Asp <u>Val</u>
1            5                    10

Cys Gly Thr <u>Lys</u> Lys Pro Cys Glu Ala Lys Cys <u>Ser</u> Glu Glu
15              20                      25

Glu Glu Glu Asp Pro Ile Cys Arg Ser <u>Phe</u> <u>Ser</u> Cys <u>Pro</u> <u>Gly</u>
    30              35                      40

Pro <u>Ala</u> Ala Cys Val Cys <u>Glu</u> Asp Gly Phe Tyr Arg Asp Thr
        45              50                      55

Val Ile Gly Asp Cys Val <u>Lys</u> Glu Glu Glu Cys Asp Gln His
            60              65                      70

Glu Ile Ile His Val
            75

Figure 5

```
Arg Thr Val Arg Lys Ala Tyr Pro Glu Cys Gly Glu Asn Glu
             1               5                      10

Trp Leu Asp Asp Cys Gly Thr Gln Lys Pro Cys Glu Ala Lys
                15              20

Cys Asn Glu Glu Pro Pro Glu Glu Glu Asp Pro Ile Cys Arg
25              30                      35

Ser Arg Gly Cys Leu Leu Pro Pro Ala Cys Val Cys Lys Asp
        40          45                  50

Gly Phe Tyr Arg Asp Thr Val Ile Gly Asp Cys Val Arg Glu
            55              60                  65

Glu Glu Cys Asp Gln His Glu Ile Ile His Val
            70              75
```

Figure 6

Arg Thr Val Arg Lys Ala Tyr Pro Glu Cys Gly Glu Asn Glu
            1               5                       10

Trp Leu Asp Val Cys Gly Thr Lys Lys Pro Cys Glu Ala Lys
                15              20

Cys Ser Glu Glu Glu Glu Asp Pro Ile Cys Arg Ser Phe
25              30                  35

Ser Cys Pro Gly Pro Ala Ala Cys Val Cys Glu Asp Gly Phe
    40              45                  50

Tyr Arg Asp Thr Val Ile Gly Asp Cys Val Lys Glu Glu Glu
        55              60              65

Cys Asp Gln His Glu Ile Ile His Val
            70              75

Figure 7A-1

```
  1            10            20                    30                    40
  *             *             *                     *                     *
GAATTCACTA  TTATCCAACA  ATG  GCG  GTG  CTT  TAT  TCA  GTA  GCA
EcoRI                   Met  Ala  Val  Leu  Tyr  Ser  Val  Ala 50            60            70            80
        *             *             *             *
ATA  GCG  TTA  CTA  CTG  GTA  TCA  CAA  TGC  AGT  GGG  AAA  CCG  AAC
Ile  Ala  Leu  Leu  Leu  Val  Ser  Gln  Cys  Ser  Gly  Lys  Pro  Asn 90           100           110           120
        *             *             *             *
AAT  GTG  ATG  ACT  AAC  GCT  TGT  GGT  CTT  AAT  GAA  TAT  TTC  GCT
Asn  Val  Met  Thr  Asn  Ala  Cys  Gly  Leu  Asn  Glu  Tyr  Phe  Ala 130           140           150           160           170
   *             *             *             *             *
GAG  TGT  GGC  AAT  ATG  AAG  GAA  TGC  GAG  CAC  AGA  TGC  AAT  GAG
Glu  Cys  Gly  Asn  Met  Lys  Glu  Cys  Glu  His  Arg  Cys  Asn  Glu 180           190           200           210
              *             *             *             *
GAG  GAA  AAT  GAG  GAA  AGG  GAC  GAG  GAA  AGA  ATA  ACG  GCA  TGC
Glu  Glu  Asn  Glu  Glu  Arg  Asp  Glu  Glu  Arg  Ile  Thr  Ala  Cys 220           230           240           250
              *             *             *             *
CTC  ATC  CGT  GTG  TGT  TTC  CGT  CCT  GGT  GCT  TGC  GTA  TGC  AAA
Leu  Ile  Arg  Val  Cys  Phe  Arg  Pro  Gly  Ala  Cys  Val  Cys  Lys 260           270           280           290
              *             *             *             *
GAC  GGA  TTC  TAT  AGA  AAC  AGA  ACA  GGC  AGC  TGT  GTG  GAA  GAA
Asp  Gly  Phe  Tyr  Arg  Asn  Arg  Thr  Gly  Ser  Cys  Val  Glu  Glu 300           310           320           330
              *             *             *             *
GAT  GAC  TGC  GAG  TAC  GAG  AAT  ATG  GAG  TTC  ATT  ACT  TTT  GCA
Asp  Asp  Cys  Glu  Tyr  Glu  Asn  Met  Glu  Phe  Ile  Thr  Phe  Ala 340           350           360           370           380
   *             *             *             *             *
CCA  GAA  GTA  CCG  ATA  TGT  GGT  TCC  AAC  GAA  AGG  TAC  TCC  GAC
Pro  Glu  Val  Pro  Ile  Cys  Gly  Ser  Asn  Glu  Arg  Tyr  Ser  Asp 390           400           410           420
              *             *             *             *
TGC  GGC  AAT  GAC  AAA  CAA  TGC  GAG  CGC  AAA  TGC  AAC  GAG  GAC
Cys  Gly  Asn  Asp  Lys  Gln  Cys  Glu  Arg  Lys  Cys  Asn  Glu  Asp 430           440           450           460
              *             *             *             *
GAT  TAT  GAG  AAG  GGA  GAT  GAG  GCA  TGC  CGC  TCA  CAT  GTT  TGT
Asp  Tyr  Glu  Lys  Gly  Asp  Glu  Ala  Cys  Arg  Ser  His  Val  Cys
```

Figure 7A-2

```
        470              480              490              500
         *                *                *                *
GAA CGT CCT GGT GCC TGT GTA TGC GAA GAC GGG TTC TAC AGA
Glu Arg Pro Gly Ala Cys Val Cys Glu Asp Gly Phe Tyr Arg 510              520              530              540
         *                *                *                *
AAC AAA AAA GGT AGC TGT GTG GAA AGC GAT GAC TGC GAA TAC
Asn Lys Lys Gly Ser Cys Val Glu Ser Asp Asp Cys Glu Tyr 550              560              570              580              590
         *                *                *                *                *
GAT AAT ATG GAT TTC ATC ACT TTT GCA CCA GAA ACC TCA CGA
Asp Asn Met Asp Phe Ile Thr Phe Ala Pro Glu Thr Ser Arg 600        610        620        630        640
              *          *          *          *          *
TAA CCAAAGATGC TACCTCTCGT ACGCAACTCC GCTGATTGAGGTTGATTC 650        660        670        680        690
         *          *          *          *          *
ACTCCCTTGCATCTCAACATTTTTTTTGTGATGCTGTGCATCTGAGCTTAACCTG 700        710
    *          *
ATAAAGCCTATGGTG poly(A)
```

Figure 7B

```
1            10            20            30            40
*            *             *             *             *
GAATTCCGC ATG CGG ACG CTC TAC CTC ATT TCT ATC TGG TTG
EcoRI     Met Arg Thr Leu Tyr Leu Ile Ser Ile Trp Leu 50            60            70            80
          *             *             *             *
TTC CTC ATC TCG CAA TGT AAT GGA AAA GCA TTC CCG AAA TGT
Phe Leu Ile Ser Gln Cys Asn Gly Lys Ala Phe Pro Lys Cys 90            100           110           120
          *             *             *             *
GAC GTC AAT GAA AGA TTC GAG GTG TGT GGC AAT CTG AAG GAG
Asp Val Asn Glu Arg Phe Glu Val Cys Gly Asn Leu Lys Glu 130           140           150           160
          *             *             *             *
TGC GAG CTC AAG TGC GAT GAG GAC CCT AAG ATA TGC TCT CGT
Cys Glu Leu Lys Cys Asp Glu Asp Pro Lys Ile Cys Ser Arg 170          180           190           200           210
*            *             *             *             *
GCA TGT ATT CGT CCC CCT GCT TGC GTA TGC GAT GAC GGA TTC
Ala Cys Ile Arg Pro Pro Ala Cys Val Cys Asp Asp Gly Phe 220           230           240           250
          *             *             *             *
TAC AGA GAC AAA TAT GGC TTC TGT GTT GAA GAA GAC GAA TGT
Tyr Arg Asp Lys Tyr Gly Phe Cys Val Glu Glu Asp Glu Cys 260           270           280           290
          *             *             *             *
AAC GAT ATG GAG ATT ATT ACT TTT CCA CCA GAA ACC AAA TGA
Asn Asp Met Glu Ile Ile Thr Phe Pro Pro Glu Thr Lys 300           310           320           330           340
          *             *             *             *             *
TGACCGAAGC TTCCACCTTT CTATACATAT CTTCACTGCTTGACAGGCTTCT 350           360           370           380           390           400
    *             *             *             *             *             *
CGACAATTTAGAAGTTCTGCTTGACTTTGTCTATTTGAAATTGTTCACACTAATG 410           420
          *             *
GGGGAAGTAAAGCATTTTCACGAC poly(A)
```

Figure 7C

```
  1            10              20                 30              40
  *             *               *                  *               *
GAATTCCGCT ACATTTTCAA CA ATG TCG ACG CTT TAT GTT ATC
EcoRI                    Met Ser Thr Leu Tyr Val Ile 50              60              70              80
         *               *               *               *
GCA ATA TGT TTG CTG CTT GTT TCG CAA TGC AAT GGA AGA ACG
Ala Ile Cys Leu Leu Leu Val Ser Gln Cys Asn Gly Arg Thr 90             100             110             120
         *               *               *               *
GTG AAG AAG TGT GGC AAG AAT GAA AGA TAC GAC GAC TGT GGC
Val Lys Lys Cys Gly Lys Asn Glu Arg Tyr Asp Asp Cys Gly 130             140             150             160
 *               *               *               *
AAT GCA AAG GAC TGC GAG ACC AAG TGC GGT GAA GAG GAA AAG
Asn Ala Lys Asp Cys Glu Thr Lys Cys Gly Glu Glu Glu Lys 170             180             190             200             210
 *               *               *               *               *
GTG TGC CGT TCG CGT GAG TGT ACT AGT CCT GGT GCC TGC GTA
Val Cys Arg Ser Arg Glu Cys Thr Ser Pro Gly Ala Cys Val 220             230             240             250
         *               *               *               *
TGC GAA CAA GGA TTC TAC AGA GAT CCG GCT GGC GAC TGT GTC
Cys Glu Gln Gly Phe Tyr Arg Asp Pro Ala Gly Asp Cys Val 260             270             280             290
         *               *               *               *
ACT GAT GAA GAA TGT GAT GAA TGG AAC AAT ATG GAG ATC ATT
Thr Asp Glu Glu Cys Asp Glu Trp Asn Asn Met Glu Ile Ile 300             310             320             330             340
         *               *               *               *               *
ACT ATG CCA AAA CAG TAG TGCGAAGTTC CCTTCTTTCT CCAAATCTG
Thr Met Pro Lys Gln 350             360             370             380             390
         *               *               *               *               *
C TCCGTGCTCAATTATCACACACCTCCACTAGTTAAGATTGACTGACTCTCTTG 400             410             420             430             440             450
 *               *               *               *               *               *
CATTGTAGTATTTTCGCTTGACTCTGTGCATTTAAGCATGAGATACTACTAGGGA 460             470
         *               *
GAATAAAAATTACTAACTAC poly(A)
```

Figure 7D

```
  1            10            20            30            40
  *             *             *             *             *
GAATTCCGG   AAA  TGT  CCT  ACC  GAT  GAA  TGG  TTC  GAT  TGG  TGT
 EcoRI      Lys  Cys  Pro  Thr  Asp  Glu  Trp  Phe  Asp  Trp  Cys 50            60            70            80
           *             *             *             *
GGA  ACT  TAC  AAG  CAT  TGC  GAA  CTC  AAG  TGC  GAT  AGG  GAG  CTA
Gly  Thr  Tyr  Lys  His  Cys  Glu  Leu  Lys  Cys  Asp  Arg  Glu  Leu 90           100           110           120
      *             *             *             *
ACT  GAG  AAA  GAA  GAG  CAG  GCA  TGT  CTC  TCA  CGT  GTT  TGT  GAG
Thr  Glu  Lys  Glu  Glu  Gln  Ala  Cys  Leu  Ser  Arg  Val  Cys  Glu 130           140           150           160
     *             *             *             *
AAG  TCC  GCT  TGC  GTA  TGC  AAT  GAC  GGA  TTA  TAC  AGA  GAC  AAG
Lys  Ser  Ala  Cys  Val  Cys  Asn  Asp  Gly  Leu  Tyr  Arg  Asp  Lys 170           180           190           200           210
     *             *             *             *             *
TTT  GGC  AAC  TGT  GTT  GAA  AAA  GAC  GAA  TGC  AAC  GAT  ATG  GAG
Phe  Gly  Asn  Cys  Val  Glu  Lys  Asp  Glu  Cys  Asn  Asp  Met  Glu 220           230           240           250
           *             *             *             *
ATT  ATT  ACT  TTT  GCA  CCA  GAA  ACC  AAA  TAA  TGGCCTAAGG  TTCC
Ile  Ile  Thr  Phe  Ala  Pro  Glu  Thr  Lys 260          270          280          290         300
        *            *            *            *           *
AAACCT  TGCTACACAC  CGTCAGTGCTTTACTGTTTCCTCTACGTGTTAGTAGT 310          320          330          340          350         360
 *            *            *            *            *           *
TTTGCTTGACTCTGTGTATTTAAGCATTGTCTACTAATGGGCAAAGTAAAGCATT 370         380         390
       *           *           *
GTAAGGACATAATAATGAGTAAACCTTCTGATTT poly(A)
```

Figure 7E-1

```
    1              10              20                       30                40
    *               *               *                        *                 *
GAATTCCGGG  CGGCAGAAAG  ATG CGA ATG CTC TAC CTT GTT CCT
EcoRI                   Met Arg Met Leu Tyr Leu Val Pro 50                   60                   70                   80
          *                    *                    *                    *
ATC TGG TTG CTG CTC ATT TCG CTA TGC AGT GGA AAA GCT GCG
Ile Trp Leu Leu Leu Ile Ser Leu Cys Ser Gly Lys Ala Ala 90                  100                  110                  120
          *                    *                    *                    *
AAG AAA TGT GGT CTC AAT GAA AGG CTG GAC TGT GGC AAT CTG
Lys Lys Cys Gly Leu Asn Glu Arg Leu Asp Cys Gly Asn Leu 130                  140                  150                  160                  170
          *                    *                    *                    *                    *
AAG CAA TGC GAG CCC AAG TGC AGC GAC TTG GAA AGT GAG GAG
Lys Gln Cys Glu Pro Lys Cys Ser Asp Leu Glu Ser Glu Glu 180                  190                  200                  210
                    *                    *                    *                    *
TAT GAG GAG GAA GAT GAG TCG AAA TGT CGA TCA CGT GAA TGT
Tyr Glu Glu Glu Asp Glu Ser Lys Cys Arg Ser Arg Glu Cys 220                  230                  240                  250
          *                    *                    *                    *
TCT CGT CGT GTT TGT GTA TGC GAT GAA GGA TTC TAC AGA AAC
Ser Arg Arg Val Cys Val Cys Asp Glu Gly Phe Tyr Arg Asn 260                  270                  280                  290
          *                    *                    *                    *
AAG AAG GGC AAG TGT GTT GCA AAA GAT GTT TGC GAG GAC GAC
Lys Lys Gly Lys Cys Val Ala Lys Asp Val Cys Glu Asp Asp 300                  310                  320                  330
          *                    *                    *                    *
AAT ATG GAG ATT ATC ACT TTT CCA CCA GAA GAC GAA TGT GGT
Asn Met Glu Ile Ile Thr Phe Pro Pro Glu Asp Glu Cys Gly 340                  350                  360                  370                  380
          *                    *                    *                    *                    *
CCC GAT GAA TGG TTC GAC TAC TGT GGA AAT TAT AAG AAG TGC
Pro Asp Glu Trp Phe Asp Tyr Cys Gly Asn Tyr Lys Lys Cys 390                  400                  410                  420
                   *                    *                    *                    *
GAA CGC AAG TGC AGT GAG GAG ACA AGT GAG AAA AAT GAG GAG
Glu Arg Lys Cys Ser Glu Glu Thr Ser Glu Lys Asn Glu Glu 430                  440                  450                  460
          *                    *                    *                    *
GCA TGC CTC TCT CGT GCT TGT ACT GGT CGT GCT TGC GTA TGC
Ala Cys Leu Ser Arg Ala Cys Thr Gly Arg Ala Cys Val Cys
```

Figure 7E-2

```
          470            480            490            500
           *              *              *              *
AAA GAC GGA TTG TAC AGA GAC GAC TTT GGC AAC TGT GTT CCA
Lys Asp Gly Leu Tyr Arg Asp Asp Phe Gly Asn Cys Val Pro 510            520            530            540
       *              *              *              *
CAT GAC GAA TGC AAC GAT ATG GAG ATC ATC ACT TTT CCA CCG
His Asp Glu Cys Asn Asp Met Glu Ile Ile Thr Phe Pro Pro 550            560           570          580            590
    *              *             *            *              *
GAA ACC AAA CAT TGA CCAGAGGCTC CAACTCTCGC TACACAACGT CA
Glu Thr Lys His 600          610          620          630          640          650
         *            *            *            *            *            *
GGGCTAGAATGGCCCCTCTGCGAGTTAGTAGTTTTGCTTGACTCTGCTTATTTGA 660         670         680
           *           *           *
GCACTTTCTATTGATGGCGAAAATAAAGCATTTAAAAC poly(A)
```

Figure 7F

```
  1          10         20         30         40
  *          *          *          *          *
GAATTCCGCG CACCTGAGAG GTGAGCTACG CAAGTCTTCG CTGGTACA
EcoRI
```

```
 50          60         70         80         90
  *          *          *          *          *
ATG ATC CGA AAG CTC GTT CTG CTG ACT GCT ATC GTC ACG GTG
Met Ile Arg Lys Leu Val Leu Leu Thr Ala Ile Val Thr Val
```

```
            100        110        120        130
             *          *          *          *
GTG CTA AGT GCG AAG ACC TGT GGA CCA AAC GAG GAG TAC ACT
Val Leu Ser Ala Lys Thr Cys Gly Pro Asn Glu Glu Tyr Thr
```

```
          140        150        160        170
           *          *          *          *
GAA TGC GGG ACG CCA TGC GAG CCG AAG TGC AAT GAA CCG ATG
Glu Cys Gly Thr Pro Cys Glu Pro Lys Cys Asn Glu Pro Met
```

```
           180        190        200        210
            *          *          *          *
CCA GAC ATC TGT ACT CTG AAC TGC ATC GTG AAC GTG TGT CAG
Pro Asp Ile Cys Thr Leu Asn Cys Ile Val Asn Val Cys Gln
```

```
          220        230        240        250
           *          *          *          *
TGC AAA CCC GGC TTC AAG CGC GGA CCG AAA GGA TGC GTC GCC
Cys Lys Pro Gly Phe Lys Arg Gly Pro Lys Gly Cys Val Ala
```

```
          260        270        280        290        300
           *          *          *          *          *
CCC GGA CCA GGC TGT AAA TAG TTCTCCACCT GCCCTTTCGT TGGAA
Pro Gly Pro Gly Cys Lys
```

```
       310        320        330        340
        *          *          *          *
CAAAT GGCTGTCTTTTTACATTCTGAATCAATAAAGCCGAACGGT poly(A)
```

Figure 8A

```
 1          10          20          30          40
 *           *           *           *           *
AAGCTTTGCT AACATACTGC GTAATAAGGA GTCTTAATC ATG CCA GTT
HindIII                                      Met Pro Val 50          60          70          80          90
 *           *           *           *           *
CTT TTG GGT ATT CCG TTA TTA TTG CGT TTC CTC GGT TTC CTT
Leu Leu Gly Ile Pro Leu Leu Leu Arg Phe Leu Gly Phe Leu 100         110         120         130
            *           *           *           *
CTG GTA ACT TTG TTC GGC TAT CTG CTT ACT TTC CTT AAA AAG
Leu Val Thr Leu Phe Gly Tyr Leu Leu Thr Phe Leu Lys Lys 140         150         160         170
            *           *           *           *
GGC TTC GGT AAG ATA GCT ATT GCT ATT TCA TTG TTT CTT GCT
Gly Phe Gly Lys Ile Ala Ile Ala Ile Ser Leu Phe Leu Ala 180         190         200         210
            *           *           *           *
CTT ATT ATT GGG CTT AAC TCA ATT CTT GTG GGT TAT CTC TCT
Leu Ile Ile Gly Leu Asn Ser Ile Leu Val Gly Tyr Leu Ser 220         230         240         250
            *           *           *           *
GAT ATT AGC GCA CAA TTA CCC TCT GAT TTT GTT CAG GGC GTT
Asp Ile Ser Ala Gln Leu Pro Ser Asp Phe Val Gln Gly Val 260        270         280         290         300
    *          *           *           *           *
CAG TTA ATT CTC CCG TCT AAT GCG CTT CCC TGT TTT TAT GTT
Gln Leu Ile Leu Pro Ser Asn Ala Leu Pro Cys Phe Tyr Val 310         320         330         340
            *           *           *           *
ATT CTC TCT GTA AAG GCT GCT ATT TTC ATT TTT GAC GTT AAA
Ile Leu Ser Val Lys Ala Ala Ile Phe Ile Phe Asp Val Lys 350         360         370         380
            *           *           *           *
CAA AAA ATC GTT TCT TAT TTG GAT TGG GAT AAA GGT GGA GGC
Gln Lys Ile Val Ser Tyr Leu Asp Trp Asp Lys Gly Gly Gly 390         400         410         420         430
            *           *           *           *           *
TCA GGC GGA GGCCAAGTCGGCC ATCCCATATCAC GCGGCCGC GGATCC
Ser Gly Gly      SfiI                   NotI     BamHI
```

Figure 8B

```
1          10         20         30         40
*          *          *          *          *
AAGCTTTGCT AACATACTGC GTAATAAGGA GTCTTAATC ATG CCA GTT
HindIII                                    Met Pro Val 50            60            70            80            90
*             *             *             *             *
CTT TTG GGT ATT CCG TTA TTA TTG CGT TTC CTC GGT TTC CTT
Leu Leu Gly Ile Pro Leu Leu Leu Arg Phe Leu Gly Phe Leu 100           110           120           130
              *             *             *             *
CTG GTA ACT TTG TTC GGC TAT CTG CTT ACT TTC CTT AAA AAG
Leu Val Thr Leu Phe Gly Tyr Leu Leu Thr Phe Leu Lys Lys 140           150           160           170
          *             *             *             *
GGC TTC GGT AAG ATA GCT ATT GCT ATT TCA TTG TTT CTT GCT
Gly Phe Gly Lys Ile Ala Ile Ala Ile Ser Leu Phe Leu Ala 180           190           200           210
          *             *             *             *
CTT ATT ATT GGG CTT AAC TCA ATT CTT GTG GGT TAT CTC TCT
Leu Ile Ile Gly Leu Asn Ser Ile Leu Val Gly Tyr Leu Ser 220           230           240           250
      *             *             *             *
GAT ATT AGC GCA CAA TTA CCC TCT GAT TTT GTT CAG GGC GTT
Asp Ile Ser Ala Gln Leu Pro Ser Asp Phe Val Gln Gly Val 260           270           280           290           300
  *             *             *             *             *
CAG TTA ATT CTC CCG TCT AAT GCG CTT CCC TGT TTT TAT GTT
Gln Leu Ile Leu Pro Ser Asn Ala Leu Pro Cys Phe Tyr Val 310           320           330           340
          *             *             *             *
ATT CTC TCT GTA AAG GCT GCT ATT TTC ATT TTT GAC GTT AAA
Ile Leu Ser Val Lys Ala Ala Ile Phe Ile Phe Asp Val Lys 350           360           370           380
      *             *             *             *
CAA AAA ATC GTT TCT TAT TTG GAT TGG GAT AAA GGT GGA GGC
Gln Lys Ile Val Ser Tyr Leu Asp Trp Asp Lys Gly Gly Gly 390           400           410           420           430
      *             *             *             *             *
TCA GGC GGA G GGCCAAGTCGGCC ATCCCATATCAC GCGGCCGC GGATCC
Ser Gly Gly       SfiI                    NotI     BamHI
```

Figure 8C

```
1           10          20          30          40
*           *           *           *           *
AAGCTTTGCT  AACATACTGC  GTAATAAGGA  GTCTTAATC  ATG CCA GTT
HindIII                                         Met Pro Val 50          60          70          80          90
*           *           *           *           *
CTT TTG GGT ATT CCG TTA TTA TTG CGT TTC CTC GGT TTC CTT
Leu Leu Gly Ile Pro Leu Leu Leu Arg Phe Leu Gly Phe Leu 100         110         120         130
            *           *           *           *
CTG GTA ACT TTG TTC GGC TAT CTG CTT ACT TTC CTT AAA AAG
Leu Val Thr Leu Phe Gly Tyr Leu Leu Thr Phe Leu Lys Lys 140         150         160         170
        *           *           *           *
GGC TTC GGT AAG ATA GCT ATT GCT ATT TCA TTG TTT CTT GCT
Gly Phe Gly Lys Ile Ala Ile Ala Ile Ser Leu Phe Leu Ala 180         190         200         210
        *           *           *           *
CTT ATT ATT GGG CTT AAC TCA ATT CTT GTG GGT TAT CTC TCT
Leu Ile Ile Gly Leu Asn Ser Ile Leu Val Gly Tyr Leu Ser 220         230         240         250
    *           *           *           *
GAT ATT AGC GCA CAA TTA CCC TCT GAT TTT GTT CAG GGC GTT
Asp Ile Ser Ala Gln Leu Pro Ser Asp Phe Val Gln Gly Val 260         270         280         290         300
*           *           *           *           *
CAG TTA ATT CTC CCG TCT AAT GCG CTT CCC TGT TTT TAT GTT
Gln Leu Ile Leu Pro Ser Asn Ala Leu Pro Cys Phe Tyr Val 310         320         330         340
        *           *           *           *
ATT CTC TCT GTA AAG GCT GCT ATT TTC ATT TTT GAC GTT AAA
Ile Leu Ser Val Lys Ala Ala Ile Phe Ile Phe Asp Val Lys 350         360         370         380
        *           *           *           *
CAA AAA ATC GTT TCT TAT TTG GAT TGG GAT AAA GGT GGA GGC
Gln Lys Ile Val Ser Tyr Leu Asp Trp Asp Lys Gly Gly Gly 390         400         410         420         430
        *           *           *           *           *
TCA GGC GGA TC GGCCAAGTCGGCC ATCCCATATCAC GCGGCCGC GGATCC
Ser Gly Gly     SfiI                      NotI     BamHI
```

Figure 9

```
  1                    10                   20                   30                   40
  *                    *                    *                    *                    *
  GAATTCCGG  CTG  GTW  TCC  TAC  TGC  AGT  GGA  AAA  GCA  ACG  ATG
  EcoRI      Leu  Val  Ser  Tyr  Cys  Ser  Gly  Lys  Ala  Thr  Met 50                   60                   70                   80
             *                    *                    *                    *
  CAG  TGT  GGT  GAG  AAT  GAA  AAG  TAC  GAT  TCG  TGC  GGT  AGC  AAG
  Gln  Cys  Gly  Glu  Asn  Glu  Lys  Tyr  Asp  Ser  Cys  Gly  Ser  Lys 90                  100                  110                  120
             *                    *                    *                    *
  GAG  TGC  GAT  AAG  AAG  TGC  AAA  TAT  GAC  GGA  GTT  GAG  GAG  GAA
  Glu  Cys  Asp  Lys  Lys  Cys  Lys  Tyr  Asp  Gly  Val  Glu  Glu  Glu 130                  140                  150                  160
             *                    *                    *                    *
  GAC  GAC  GAG  GAA  CCT  AAT  GTG  CCA  TGC  CTA  GTA  CGT  GTG  TGT
  Asp  Asp  Glu  Glu  Pro  Asn  Val  Pro  Cys  Leu  Val  Arg  Val  Cys 170                  180                  190                  200                  210
  *                    *                    *                    *                    *
  CAT  CAA  GAT  TGC  GTA  TGC  GAA  GAA  GGA  TTC  TAT  AGA  AAC  AAA
  His  Gln  Asp  Cys  Val  Cys  Glu  Glu  Gly  Phe  Tyr  Arg  Asn  Lys 220                  230                  240                  250
             *                    *                    *                    *
  GAT  GAC  AAA  TGT  GTA  TCA  GCA  GAA  GAC  TGC  GAA  CTT  GAC  AAT
  Asp  Asp  Lys  Cys  Val  Ser  Ala  Glu  Asp  Cys  Glu  Leu  Asp  Asn 260                  270                  280                  290
             *                    *                    *                    *
  ATG  GAC  TTT  ATA  TAT  CCC  GGA  ACT  CGA  AAC  TGA  ACGAAGGCTC
  Met  Asp  Phe  Ile  Tyr  Pro  Gly  Thr  Arg  Asn 300         310         320         330         340
           *           *           *           *           *
  CATTCTTGCT  GCACAAGATC  GATTGTCTCTCCCCTGCATCTCAGTAGTTTTGC 350         360         370         380         390         400
   *           *           *           *           *           *
  TACATTGTATATGGTAGCAAAAAATTAGCTTAGGGAGAATAAAATCTTTACCTAT 410         420         430
         *           *           *
  ATTTAATCAATGAAGTATTCTCTTTCT  poly(A)
```

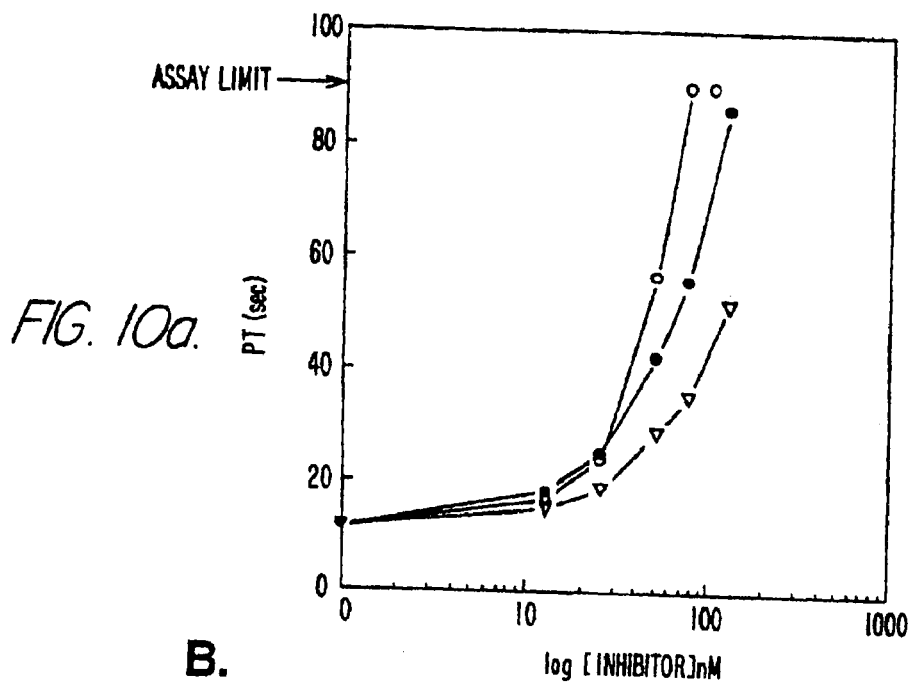
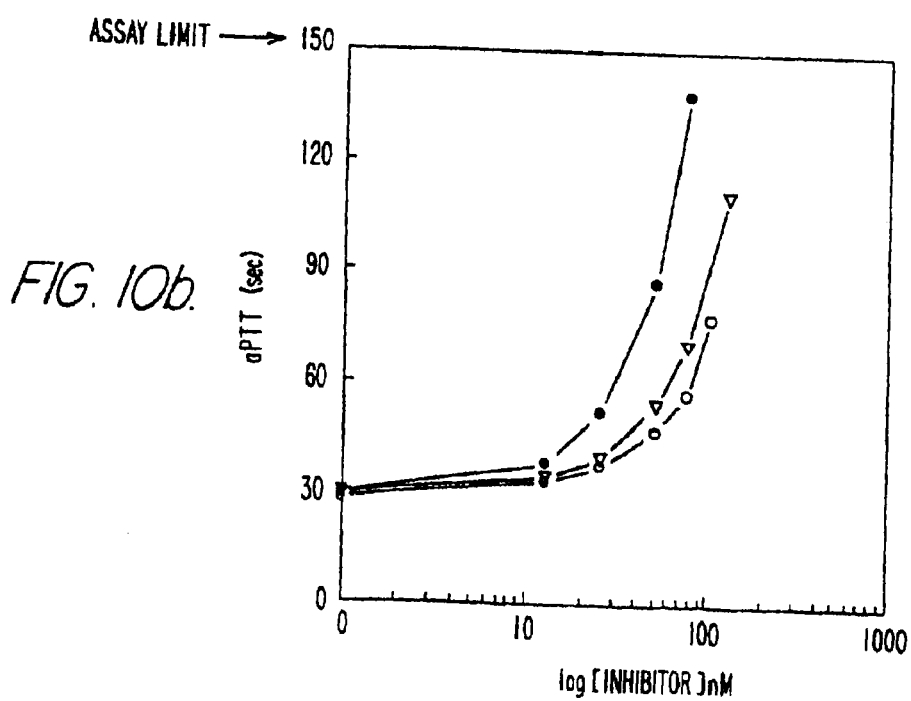
FIG. 10a.
FIG. 10b.

Figure 11-1

| | | | | | | | | | | | | |
|---|---|---|---|---|---|---|---|---|---|---|---|---|
| NAP5 | Met | Lys | Met | Leu | Tyr | Ala | Ile | Ala | Met | Phe | Leu | Leu | Val |
| NAP6 | Met | Lys | Met | Leu | Tyr | Ala | Ile | Ala | Met | Phe | Leu | Leu | Val |
| NAPc2 | | | | | | | | | | | Leu | Val |
| AceNAP5 | Met | Arg | Thr | Leu | Tyr | Leu | Ile | Ser | Ile | Trp | Leu | Phe | Leu | Ile |
| AceNAP7 | Met | Ser | Thr | Leu | Tyr | Val | Ile | Ala | Ile | Cys | Leu | Leu | Leu | Val |
| AceNAP4d1 | Met | Ala | Val | Leu | Tyr | Ser | Val | Ala | Ile | Ala | Leu | Leu | Leu | Val |
| AceNAP4d2 | | | | | | | | | | | | | |
| AduNAP4 | | | | | | | | | | | | | |
| AduNAP7d1 | Met | Arg | Met | Leu | Tyr | Leu | Val | Pro | Ile | Trp | Leu | Leu | Ile |
| AduNAP7d2 | | | | | | | | | | | | | |
| HpoNAP5 | Met | Ile | Arg | Lys | Leu | Val | Leu | Leu | Thr | Ala | Ile | Val | Thr |

Figure 11-2

| | | | | | | | | | | | | | | | | |
|---|---|---|---|---|---|---|---|---|---|---|---|---|---|---|---|---|
| NAP5 | Ser | Leu | Cys | Ser | Ala | Arg | Thr | Val | Arg | Lys | Ala | Tyr | Pro | Glu |
| NAP6 | Ser | Leu | Cys | Ser | Thr | Arg | Thr | Val | Arg | Lys | Ala | Tyr | Pro | Glu |
| NAPc2 | Ser | Tyr | Cys | Ser | Gly | - - - | - - - | - - - | - - - | Lys | Ala | Thr | Met | Gln |
| AceNAP5 | Ser | Gln | Cys | Asn | Gly | - - - | - - - | - - - | - - - | Lys | Ala | Phe | Pro | Lys |
| AceNAP7 | Ser | Gln | Cys | Asn | Gly | - - - | - - - | - - - | - - - | Arg | Thr | Val | Lys | Lys |
| AceNAP4d1 | Ser | Gln | Cys | Ser | Gly | Lys | Pro | Asn | Asn | Val | Met | Thr | Asn | Ala |
| AceNAP4d2 | | | | | | | | | | | | Val | Pro | Ile |
| AduNAP4 | | | | | | | | | | | | | | Lys |
| AduNAP7d1 | Ser | Leu | Cys | Ser | Gly | - - - | - - - | - - - | - - - | Lys | Ala | Ala | Lys | Lys |
| AduNAP7d2 | | | | | | | | | | | | | Asp | Glu |
| HpoNAP5 | Val | Val | Leu | Ser | Ala | - - - | - - - | - - - | - - - | - - - | - - - | - - - | Lys | Thr |

Figure 11-3

```
              1                                           2
NAP5       Cys Gly Glu Asn Glu Trp Leu Asp Asp Cys Gly Thr Gln
NAP6       Cys Gly Glu Asn Glu Trp Leu Asp Val Cys Gly Thr Lys
NAPc2      Cys Gly Glu Asn Glu Lys Tyr Asp Ser Cys Gly Ser Lys
AceNAP5    Cys Asp Val Asn Glu Arg Phe Glu Val Cys Gly Asn Leu
AceNAP7    Cys Gly Lys Asn Glu Arg Tyr Asp Asp Cys Gly Asn Ala
AceNAP4d1  Cys Gly Leu Asn Glu Tyr Phe Ala Glu Cys Gly Asn Met
AceNAP4d2  Cys Gly Ser Asn Glu Arg Tyr Ser Asp Cys Gly Asn Asp
AduNAP4    Cys Pro Thr Asp Glu Trp Phe Asp Trp Cys Gly Thr Tyr
AduNAP7d1  Cys Gly Leu Asn Glu Arg Leu Asp --- Cys Gly Asn Leu
AduNAP7d2  Cys Gly Pro Asp Glu Trp Phe Asp Tyr Cys Gly Asn Tyr
HpoNAP5    Cys Gly Pro Asn Glu Glu Tyr Thr Glu Cys Gly Thr ---
```

Figure 11-4

| | | | | | 3 | | | | 4 | | | | | | |
|---|---|---|---|---|---|---|---|---|---|---|---|---|---|---|---|
| NAP5 | Lys | Pro | Cys | Glu | Ala | Lys | Cys | — | — | — | — | — | Asn | Glu | Glu |
| NAP6 | Lys | Pro | Cys | Glu | Ala | Lys | Cys | — | — | — | — | — | Ser | Glu | Glu |
| NAPc2 | Glu | — | Cys | Asp | Lys | Lys | Cys | Lys | Tyr | Asp | Gly | Val | Glu | Glu | — |
| AceNAP5 | Lys | Glu | Cys | Glu | Leu | Lys | Cys | — | — | — | — | — | — | — | — |
| AceNAP7 | Lys | Asp | Cys | Glu | Thr | Lys | Cys | — | — | — | Gly | — | — | — | — |
| AceNAP4d1 | Lys | Glu | Cys | Glu | His | Arg | Cys | Asn | Glu | Glu | Asn | Glu | Asn | Glu | Glu |
| AceNAP4d2 | Lys | Gln | Cys | Glu | Arg | Lys | Cys | Asn | Glu | Asp | Asp | Tyr | Glu | Glu | Lys |
| AduNAP4 | Lys | His | Cys | Glu | Leu | Lys | Cys | Asp | Arg | Glu | Leu | Thr | Glu | Glu | Lys |
| AduNAP7d1 | Lys | Gln | Cys | Glu | Pro | Lys | Cys | Ser | Asp | Leu | Glu | Ser | Glu | Glu | Glu |
| AduNAP7d2 | Lys | Lys | Cys | Glu | Arg | Lys | Cys | Ser | Glu | Glu | Thr | Ser | Glu | Glu | Lys |
| HpoNAP5 | — | — | Pro | Cys | Glu | Pro | Lys | Cys | — | — | — | — | — | — | — |

Figure 11-5

| | | | | | | | | | | 5 | | | |
|---|---|---|---|---|---|---|---|---|---|---|---|---|---|
| NAP5 | Pro | Pro | Glu | Glu | Asp | Pro | Ile | --- | --- | Cys | Arg | Ser | Arg |
| NAP6 | --- | --- | Glu | Glu | Asp | Pro | Ile | --- | --- | Cys | Arg | Ser | Phe |
| NAPc2 | --- | Glu | Asp | Asp | Glu | Pro | Asn | Val | Pro | Cys | Leu | Val | Arg |
| AceNAP5 | --- | --- | Asp | Asp | Pro | Lys | Ile | --- | --- | Cys | --- | Ser | Arg |
| AceNAP7 | --- | --- | Glu | Glu | Glu | --- | Lys | --- | Val | Cys | Arg | Ser | Arg |
| AceNAP4d1 | Arg | --- | Asp | Glu | Glu | --- | Arg | Ile | Thr | Ala | Cys | Leu | Ile | Arg |
| AceNAP4d2 | Gly | --- | Asp | Glu | --- | --- | --- | --- | Ala | Cys | Arg | Ser | His |
| AduNAP4 | --- | --- | Glu | Glu | --- | --- | Gln | --- | Ala | Cys | Leu | Ser | Arg |
| AduNAP7d1 | Tyr | --- | Glu | Glu | Asp | Glu | Ser | Lys | --- | Cys | Arg | Ser | Arg |
| AduNAP7d2 | Asn | --- | Glu | Glu | --- | --- | --- | --- | Ala | Cys | Leu | Ser | Arg |
| HpoNAP5 | --- | --- | Asn | Glu | Pro | Met | Pro | Asp | Ile | --- | Cys | --- | Thr | Leu |

Figure 11-6

| | | 6 | | | | | 7 | | 8 | |
|---|---|---|---|---|---|---|---|---|---|---|
| NAP5 | Gly | Cys | Leu | Leu | Pro | Pro | Ala | Cys | Val | Cys | Lys Asp |
| NAP6 | Ser | Cys | Pro | Gly | Pro | Ala | Ala | Cys | Val | Cys | Glu Asp |
| NAPc2 | Val | Cys | His | Gln | Asp | --- | --- | Cys | Val | Cys | Glu Glu |
| AceNAP5 | Ala | Cys | Ile | Arg | Pro | Pro | Ala | Cys | Val | Cys | Asp Asp |
| AceNAP7 | Glu | Cys | Thr | Ser | Pro | Gly | Ala | Cys | Val | Cys | Glu Gln |
| AceNAP4d1 | Val | Cys | Phe | Arg | Pro | Gly | Ala | Cys | Val | Cys | Lys Asp |
| AceNAP4d2 | Val | Cys | Glu | Arg | Pro | Gly | Ala | Cys | Val | Cys | Glu Asp |
| AduNAP4 | Val | Cys | Glu | Lys | --- | Ser | Ala | Cys | Val | Cys | Asn Asp |
| AduNAP7d1 | Glu | Cys | Ser | Arg | Arg | --- | Val | Cys | Val | Cys | Asp Glu |
| AduNAP7d2 | Ala | Cys | Thr | Gly | Arg | --- | Ala | Cys | Val | Cys | Lys Asp |
| HpoNAP5 | Asn | Cys | Ile | Val | Asn | --- | Val | Cys | Gln | Cys | Lys Pro |

Figure 11-7

|  | | | | | | | | | | 9 | | | |
|---|---|---|---|---|---|---|---|---|---|---|---|---|---|
| NAP5 | Gly Phe Tyr Arg Asp Thr Val Ile Gly Asp | | | | | | | | | Cys | Val Arg Glu | | |
| NAP6 | Gly Phe Tyr Arg Asp Thr Val Ile Gly Asp | | | | | | | | | Cys | Val Lys Glu | | |
| NAPc2 | Gly Phe Tyr Arg Asn Lys --- Asp Asp Lys | | | | | | | | | Cys | Val Ser Ala | | |
| AceNAP5 | Gly Phe Tyr Arg Asp Lys Tyr --- Gly Phe | | | | | | | | | Cys | Val Glu Glu | | |
| AceNAP7 | Gly Phe Tyr Arg Asp Pro Ala --- Gly Asp | | | | | | | | | Cys | Val Thr Asp | | |
| AceNAP4d1 | Gly Phe Tyr Arg Asn Arg Thr --- Gly Ser | | | | | | | | | Cys | Val Glu Glu | | |
| AceNAP4d2 | Gly Phe Tyr Arg Asn Lys Lys --- Gly Ser | | | | | | | | | Cys | Val Glu Ser | | |
| AduNAP4 | Gly Leu Tyr Arg Asp Lys Phe --- Gly Asn | | | | | | | | | Cys | Val Glu Lys | | |
| AduNAP7d1 | Gly Phe Tyr Arg Asn Lys Lys --- Gly Lys | | | | | | | | | Cys | Val Ala Lys | | |
| AduNAP7d2 | Gly Leu Tyr Arg Asp Asp Phe --- Gly Asn | | | | | | | | | Cys | Val Pro His | | |
| HpoNAP5 | Gly Phe Lys Arg Gly Pro Lys --- Gly --- | | | | | | | | | Cys | Val Ala Pro | | |

Figure 11-8

```
                                  10
NAP5      Glu Glu  -   -   -  Cys Asp Gln His  -   -   -   -   -   -  Glu Ile Ile His
NAP6      Glu Glu  -   -   -  Cys Asp Gln His  -   -   -   -   -   -  Glu Ile Ile His
NAPc2     Glu Asp  -   -   -  Cys Glu  -   -  Leu Asp Asn Met Asp Phe Ile Tyr
AceNAP5   Asp Glu  -   -   -  Cys Asn Asp  -   -   -   -   -  Met Glu Ile Ile Thr
AceNAP7   Glu Glu  -   -   -  Cys Glu Trp Asn Asn  -  Met Glu Ile Ile Thr
AceNAP4d1 Asp Asp  -   -   -  Cys Asp  -  Tyr Glu Asn Asn Met Glu Phe Ile Thr
AceNAP4d2 Asp Asp  -   -   -  Cys Glu  -  Tyr Asn Asn Met Asp Phe Ile Thr
AduNAP4   Asp Glu  -   -   -  Cys Asn Asp  -   -   -   -   -  Met Glu Ile Ile Thr
AduNAP7d1 Asp Val  -   -   -  Cys Glu Asp  -   -   -  Asp Asn Met Glu Ile Ile Thr
AduNAP7d2 Asp Glu  -   -   -  Cys Asn Asp  -   -   -   -   -   -  Glu Ile Ile Thr
AdoNAP5   Asp Glu  -   -   -  Cys Asn Asp  -   -   -   -   -  Met Glu Ile Ile Thr

HpoNAP5   Gly Pro Gly Cys Lys end
```

Figure 11-9

| | | | | | | | | | |
|---|---|---|---|---|---|---|---|---|---|
| NAP5 | Val | end | | | | | | | |
| NAP6 | Val | end | | | | | | | |
| NAPc2 | Pro | Gly | Thr | Arg | Asn | end | | | |
| AceNAP5 | Phe | Pro | Pro | Glu | Thr | Lys | end | | |
| AceNAP7 | Met | Pro | Lys | Gln | end | | | | |
| AceNAP4d1 | Phe | Ala | Pro | Glu | | | | | |
| AceNAP4d2 | Phe | Ala | Pro | Glu | Thr | Ser | Arg | end | |
| AduNAP4 | Phe | Ala | Pro | Glu | | | | | |
| AduNAP7d1 | Phe | Pro | Pro | Glu | Thr | Lys | end | | |
| AduNAP7d2 | Phe | Pro | Pro | Glu | Thr | Lys | His | end | |
| HpoNAP5 | | | | | | | | | |

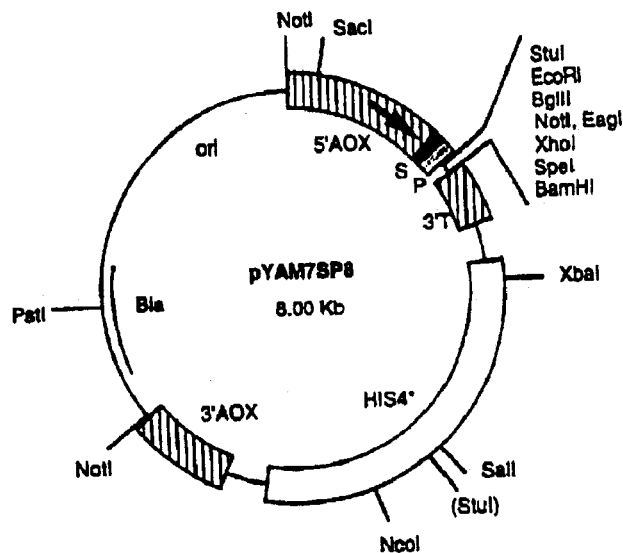

```
<----5'AOX1------><---------PHO1 secretion signal (S)--
......TTATTCGAAACGATGTTCTCTCCAATTTTGTCCTTGGAAATTATTTTA
```

```
-------------------------><----Pro Sequence (P)---------
GCTACTTTGCAATCTGTCTTCGCCCAGCCAGTTATCTCCACTACCGTTGGTTCC
```

```
-------------------------><-Multi-Cloning Site (MCS)
GCTGCCGAGGGTTCTTTGGACAAGAGGCCTATCCGCGGAATTCAGATCTGAAT
                              StuI    SacII EcoRI BglII
```

```
------------------------><---3'T---->
GCGGCCGCTCGAGACTAGTGGATCCTTAGACA...
NotI   XhoI  SpeI   BamHI
  EagI
```

Figure 13 A-1 (AcaNAP23)

```
              10              20              30              40
               *               *               *               *
     GAATTCCGCG GAATTCCGCT TGCTACTACT CAACG ATG AAG ACG CTC
     EcoRI                                  Met Lys Thr Leu 50              60              70              80
       *               *               *               *
     TAT ATT GTC GCT ATA TGC TCG CTC CTC ATT TCG CTG TGT ACT
     Tyr Ile Val Ala Ile Cys Ser Leu Leu Ile Ser Leu Cys Thr 90             100             110             120             130
      *               *               *               *               *
     GGA AAA CCT TCG GAG AAA GAA TGT GGT CCC CAT GAA AGA CTC
     Gly Lys Pro Ser Glu Lys Glu Cys Gly Pro His Glu Arg Leu
              140             150             160             170
               *               *               *               *
     GAC TGT GGC AAC AAG AAG CCA TGC GAG CGC AAG TGC AAA ATA
     Asp Cys Gly Asn Lys Lys Pro Cys Glu Arg Lys Cys Lys Ile
             180             190             200             210
              *               *               *               *
     GAG ACA AGT GAG GAG GAG GAT GAC TAC GAA GAG GGA ACC GAA
     Glu Thr Ser Glu Glu Glu Asp Asp Tyr Glu Glu Gly Thr Glu 220             230             240             250
            *               *               *               *
     CGT TTT CGA TGC CTC TTA CGT GTG TGT GAT CAG CCT TAT GAA
     Arg Phe Arg Cys Leu Leu Arg Val Cys Asp Gln Pro Tyr Glu 260             270             280             290
          *               *               *               *
     TGC ATA TGC GAT GAT GGA TAC TAC AGA AAC AAG AAA GGC GAA
     Cys Ile Cys Asp Asp Gly Tyr Tyr Arg Asn Lys Lys Gly Glu 300             310             320             330             340
      *               *               *               *               *
     TGT GTG ACT GAT GAT GTA TGC CAG GAA GAC TTT ATG GAG TTT
     Cys Val Thr Asp Asp Val Cys Gln Glu Asp Phe Met Glu Phe 350             360             370             380
               *               *               *               *
     ATT ACT TTC GCA CCA TAA ACCCAATAAT GACCAATGAC TCCCATTCTT
     Ile Thr Phe Ala Pro
```

Figure 13 A-2

```
     390        400        410        420        430
      *          *          *          *          *
   CGTGATCAGC GTCGGTGGTT GACAGTCTCC CCTACATCTT AGTAGTTTTG 440        450        460        470        480
      *          *          *          *          *
   CTTGATAATG TATACATAAA CTGTACTTTC TGAGATAGAA TAAAGCTCTC

490
      *
   AACTAC poly(A)
```

Figure 13 B-1 (AcaNAP24)

```
          10          20              30              40
           *           *               *               *
     GAATTCCGCG  GAATTCCGCA  ACG ATG AAG ACG CTC TAT ATT ATC
     EcoRI                       Met Lys Thr Leu Tyr Ile Ile 50          60              70              80
           *           *               *               *
     GCT ATA TGC TCG CTC CTC ATT TCG TTG TGT ACT GGA AGA CCG
     Ala Ile Cys Ser Leu Leu Ile Ser Leu Cys Thr Gly Arg Pro 90         100             110             120
           *           *               *               *
     GAA AAA AAG TGC GGT CCC GGT GAA AGA CTC GCC TGT GGC AAT
     Glu Lys Lys Cys Gly Pro Gly Glu Arg Leu Ala Cys Gly Asn 130         140             150             160            170
      *           *               *               *              *
     AAG AAG CCA TGC GAG CGC AAG TGC AAA ATA GAG ACA AGT GAG
     Lys Lys Pro Cys Glu Arg Lys Cys Lys Ile Glu Thr Ser Glu 180             190             200             210
                *               *               *               *
     GAG GAG GAT GAC TAC CCA GAG GGA ACC GAA CGT TTT CGA TGC
     Glu Glu Asp Asp Tyr Pro Glu Gly Thr Glu Arg Phe Arg Cys 220             230             240             250
                *               *               *               *
     CTC TTA CGT GTG TGT GAT CAG CCT TAT GAA TGC ATA TGC GAT
     Leu Leu Arg Val Cys Asp Gln Pro Tyr Glu Cys Ile Cys Asp 260             270             280             290
                *               *               *               *
     GAT GGA TAC TAC AGA AAC AAG AAA GGC GAA TGT GTG ACT GAT
     Asp Gly Tyr Tyr Arg Asn Lys Lys Gly Glu Cys Val Thr Asp 300             310             320             330
                *               *               *               *
     GAT GTA TGC CAG GAA GAC TTT ATG GAG TTT ATT ACT TTC GCA
     Asp Val Cys Gln Glu Asp Phe Met Glu Phe Ile Thr Phe Ala 340         350             360             370            380
      *           *               *               *              *
     CCA TAA ACCCAATAAT GACCACTGGC TCCCATTCTT CGTGACCAGC
     Pro
```

Figure 13 B-2

```
         390        400        410        420        430
          *          *          *          *          *
     GTCGGTGGTT GACAGTCTCC CCTGCATCTT AGTAGTTTTG CTTGATAATG 440        450        460        470
          *          *          *          *
     TATCCATAAA CAGTACTTTC TGAGATAGAA TAAAGCTCTC AACT poly(A)
```

Figure 13 C (AcaNAP25)

```
           10          20          30          40
            *           *           *           *
     GAATTCCGTA CTACTCAACG ATG AAG ACG CTC TAT ATT ATC GCT
     EcoRI                 Met Lys Thr Leu Tyr Ile Ile Ala 50          60          70          80
            *           *           *           *
     ATA TGC TCG CTG CTC TTT TCA CTG TGT ACT GGA AGA CCG GAA
     Ile Cys Ser Leu Leu Phe Ser Leu Cys Thr Gly Arg Pro Glu 90         100         110         120
            *           *           *           *
     AAA AAG TGC GGT CCC GGT GAA AGA CTC GAC TGT GCC AAC AAG
     Lys Lys Cys Gly Pro Gly Glu Arg Leu Asp Cys Ala Asn Lys 130         140         150         160         170
       *           *           *           *           *
     AAG CCA TGC GAG CCC AAG TGC AAA ATA GAG ACA AGT GAG GAG
     Lys Pro Cys Glu Pro Lys Cys Lys Ile Glu Thr Ser Glu Glu 180         190         200         210
               *           *           *           *
     GAG GAT GAC GAC GTA GAG GAT ACC GAT GTG AGA TGC CTC GTA
     Glu Asp Asp Asp Val Glu Asp Thr Asp Val Arg Cys Leu Val 220         230         240         250
               *           *           *           *
     CGT GTG TGT GAA CGT CCT CTT AAA TGC ATA TGC AAG GAT GGA
     Arg Val Cys Glu Arg Pro Leu Lys Cys Ile Cys Lys Asp Gly 260         270         280         290
               *           *           *           *
     TAC TAC AGA AAC AAG AAA GGC GAA TGT GTG ACT GAT GAT GTA
     Tyr Tyr Arg Asn Lys Lys Gly Glu Cys Val Thr Asp Asp Val 300         310         320         330
               *           *           *           *
     TGC CAG GAA GAC TTT ATG GAG TTT ATT ACT TTC GCA CCA TAA
     Cys Gln Glu Asp Phe Met Glu Phe Ile Thr Phe Ala Pro 340         350         360         370         380
       *           *           *           *           *
     ACCCAATAAT GACCACTGGC TCCCATTCTT CGTGATCAGC GTCGGTGGTT 390         400         410         420         430
       *           *           *           *           *
     GACAGTCTCC CCTGCATCTT AGTTGCTTTG CTTGATAATC TATACATAAA 440         450         460         470
       *           *           *           *
     CAGTACTTTC TGAGATAGAA TAAAGCTCTC AACT poly(A)
```

Figure 13 D-1 (AcaNAP31)

```
              10         20         30         40         50
              *          *          *          *          *
      GAATTCCGGA CTTACTAGTA CTCAGCGAAT CAAATACGAC TTACTACTAC
      EcoRI
              60         70         80         90
              *          *          *          *
      TCAACG ATG AAG ACG CTC TCT GCT ATC CCT ATA ATG CTG CTC
             Met Lys Thr Leu Ser Ala Ile Pro Ile Met Leu Leu 100        110        120        130
            *          *          *          *
      CTG GTA TCG CAA TGC AGT GGA AAA TCA CTG TGG GAT CAG AAG
      Leu Val Ser Gln Cys Ser Gly Lys Ser Leu Trp Asp Gln Lys 140        150        160        170
            *          *          *          *
      TGT GGT GAG AAT GAA AGG CTC GAC TGT GGC AAT CAG AAG GAC
      Cys Gly Glu Asn Glu Arg Leu Asp Cys Gly Asn Gln Lys Asp 180        190        200        210
            *          *          *          *
      TGT GAG CGC AAG TGC GAT GAT AAA AGA AGT GAA GAA GAA ATT
      Cys Glu Arg Lys Cys Asp Asp Lys Arg Ser Glu Glu Glu Ile 220        230        240        250        260
      *          *          *          *          *
      ATG CAG GCA TGT CTC ACA CGT CAA TGT CTT CCT CCT GTT TGC
      Met Gln Ala Cys Leu Thr Arg Gln Cys Leu Pro Pro Val Cys 270        280        290        300
            *          *          *          *
      GTA TGT GAA GAT GGA TTC TAC AGA AAT GAC AAC GAC CAA TGT
      Val Cys Glu Asp Gly Phe Tyr Arg Asn Asp Asn Asp Gln Cys 310        320        330        340
            *          *          *          *
      GTT GAT GAA GAA GAA TGC AAT ATG GAG TTT ATT ACT TTC GCA
      Val Asp Glu Glu Glu Cys Asn Met Glu Phe Ile Thr Phe Ala 350        360        370        380        390
            *          *          *          *          *
      CCA TGA AGCAAATGAC AGCCGATGGT TTGGACTCTC GCTACAGATC
      Pro 400        410        420        430        440
            *          *          *          *          *
      ACAGCTTTAC TGTTTCCCTT GCATCATAGT AGTTTTGCTA GATAGTGTAT
```

Figure 13 D-2

```
          450         460         470         480
           *           *           *           *
ATATTAGCAT GATTTTCTGA TAGGGAGAAT AAAGCTTTCC AATTTTC
poly(A)
```

Figure 13 E-1 (AcaNAP44)

```
           10              20                30              40
            *               *                 *               *
   GAATTCCGCG GAATTCCGCA ACG ATG AAG ACG CTC TAT ATT ATC
   EcoRI                     Met Lys Thr Leu Tyr Ile Ile 50              60              70              80
           *               *               *               *
   GCT ATA TGC TCG CTC CTC ATT TCG CTG TGT ACT GGA AGA CCG
   Ala Ile Cys Ser Leu Leu Ile Ser Leu Cys Thr Gly Arg Pro 90             100             110             120
           *               *               *               *
   GAA AAA AAG TGC GGT CCC GGT GAA AGA CTC GAC TGT GCC AAC
   Glu Lys Lys Cys Gly Pro Gly Glu Arg Leu Asp Cys Ala Asn 130             140             150             160             170
   *               *               *               *               *
   AAG AAG CCA TGC GAG CCC AAG TGC AAA ATA GAG ACA AGT GAG
   Lys Lys Pro Cys Glu Pro Lys Cys Lys Ile Glu Thr Ser Glu 180             190             200             210
                  *               *               *               *
   GAG GAG GAT GAC GAC GTA GAG GAA ACC GAT GTG AGA TGC CTC
   Glu Glu Asp Asp Asp Val Glu Glu Thr Asp Val Arg Cys Leu 220             230             240             250
           *               *               *               *
   GTA CGT GTG TGT GAA CGG CCT CTT AAA TGC ATA TGC AAG GAT
   Val Arg Val Cys Glu Arg Pro Leu Lys Cys Ile Cys Lys Asp 260             270             280             290
           *               *               *               *
   GGA TAC TAC AGA AAC AAG AAA GGC GAA TGT GTG ACT GAT GAT
   Gly Tyr Tyr Arg Asn Lys Lys Gly Glu Cys Val Thr Asp Asp 300             310             320             330
           *               *               *               *
   GTA TGC CAG GAA GAC TTT ATG GAG TTT ATT ACT TTC GCA CCA
   Val Cys Gln Glu Asp Phe Met Glu Phe Ile Thr Phe Ala Pro 340            350             360             370             380
   *              *               *               *               *
   TAA ACCCAATAAT GACCACTGGC TCCCATTCTT CGTGATCAGC 390             400             410             420             430
          *               *               *               *               *
   GTCGGTGGTT GACAGTCTCC CCTGCATCTT AGTTGCTTTG CTTGATAATC
```

Figure 13 E-2

```
         440        450        460        470
          *          *          *          *
    TATACATAAA CAGTACTTTC TGAGATAGAA TAAAGCTCTC AACTAC
    poly(A)
```

Figure 13 F-1 (AcaNAP45)

```
          10              20              30              40
           *               *               *               *
GAATTCCGGA AAA ATG CTG ATG CTC TAC CTT GTT CCT ATC TGG
EcoRI          Met Leu Met Leu Tyr Leu Val Pro Ile Trp 50              60              70              80
           *               *               *               *
TTG CTA CTC ATT TCG CAA TGC AGT GGA AAA TCC GCG AAG AAA
Leu Leu Leu Ile Ser Gln Cys Ser Gly Lys Ser Ala Lys Lys 90             100             110             120
           *               *               *               *
TGT GGT CTC AAT GAA AAA TTG GAC TGT GGC AAT CTG AAG GCA
Cys Gly Leu Asn Glu Lys Leu Asp Cys Gly Asn Leu Lys Ala 130             140             150             160
           *               *               *               *
TGC GAG AAA AAG TGC AGC GAC TTG GAC AAT GAG GAG GAT TAT
Cys Glu Lys Lys Cys Ser Asp Leu Asp Asn Glu Glu Asp Tyr 170             180             190             200             210
  *               *               *               *               *
AAG GAG GAA GAT GAG TCG AAA TGC CGA TCA CGT GAA TGT AGT
Lys Glu Glu Asp Glu Ser Lys Cys Arg Ser Arg Glu Cys Ser 220             230             240             250
           *               *               *               *
CGT CGT GTT TGT GTA TGC GAT GAA GGA TTC TAC AGA AAC AAG
Arg Arg Val Cys Val Cys Asp Glu Gly Phe Tyr Arg Asn Lys 260             270             280             290
           *               *               *               *
AAG GGC CAA TGT GTG ACA AGA GAT GAT TGC GAG TAT GAC AAT
Lys Gly Gln Cys Val Thr Arg Asp Asp Cys Glu Tyr Asp Asn 300             310             320             330
           *               *               *               *
ATG GAG ATT ATC ACT TTT CCA CCA GAA GAT AAA TGT GGT CCC
Met Glu Ile Ile Thr Phe Pro Pro Glu Asp Lys Cys Gly Pro 340             350             360             370
           *               *               *               *
GAT GAA TGG TTC GAC TGG TGT GGA ACT TAC AAG CAG TGT GAG
Asp Glu Trp Phe Asp Trp Cys Gly Thr Tyr Lys Gln Cys Glu 380             390             400             410             420
  *               *               *               *               *
CGC AAG TGC AAT AAG GAG CTA AGT GAG AAA GAT GAA GAG GCA
Arg Lys Cys Asn Lys Glu Leu Ser Glu Lys Asp Glu Glu Ala
```

Figure 13 F-2

```
            430                 440                 450                 460
             *                   *                   *                   *
TGC CTC TCA CGT GCT TGT ACT GGT CGT GCT TGT GTT TGC AAC
Cys Leu Ser Arg Ala Cys Thr Gly Arg Ala Cys Val Cys Asn 470                 480                 490                 500
             *                   *                   *                   *
GAC GGA CTG TAC AGA GAC GAT TTT GGC AAT TGT GTT GAG AAA
Asp Gly Leu Tyr Arg Asp Asp Phe Gly Asn Cys Val Glu Lys 510                 520                 530                 540
       *                   *                   *                   *
GAC GAA TGT AAC GAT ATG GAG ATT ATC ACT TTT CCA CCG GAA
Asp Glu Cys Asn Asp Met Glu Ile Ile Thr Phe Pro Pro Glu 550           560         570         580
     *             *           *           *
ACC AAA CAC TGA CCAAAGGCTC TAACTCTCGC TACATAACGT
Thr Lys His 590         600         610         620         630
 *           *           *           *           *
CAGTGCTTGA ATTGCCCCTT TACGAGTTAG TAATTTTGAC TAACTCTGTG 640         650         660         670         680
 *           *           *           *           *
TAATTGAGCA TTGTCTACTG ATGGTGAAAA TGAAGTGTTC AATGTCT poly(A)
```

Figure 13 G-1 (AcaNAP47)

```
              10            20            30              40
               *             *             *               *
         GAATTCCGCG GAATTCCGGT TGGCGGCAGA AAA ATG CTG ATG CTC
         EcoRI                                Met Leu Met Leu 50            60            70            80
         *             *             *             *
    TAC CTT GTT CCT ATC TGG TTC CTC ATT TCG CAA TGC AGT
    Tyr Leu Val Pro Ile Trp Phe Leu Leu Ile Ser Gln Cys Ser 90           100           110           120
         *             *             *             *
    GGA AAA TCC GCG AAG AAA TGT GGC CTC AAT GAA AAA TTG GAC
    Gly Lys Ser Ala Lys Lys Cys Gly Leu Asn Glu Lys Leu Asp 130           140           150           160           170
    *             *             *             *             *
    TGT GGC AAT CTG AAG GCA TGC GAG AAA AAG TGC AGC GAC TTG
    Cys Gly Asn Leu Lys Ala Cys Glu Lys Lys Cys Ser Asp Leu 180           190           200           210
            *             *             *             *
    GAC AAT GAG GAG GAT TAT GGG GAG GAA GAT GAG TCG AAA TGC
    Asp Asn Glu Glu Asp Tyr Gly Glu Glu Asp Glu Ser Lys Cys 220           230           240           250
            *             *             *             *
    CGA TCA CGT GAA TGT ATT GGT CGT GTT TGC GTA TGC GAT GAA
    Arg Ser Arg Glu Cys Ile Gly Arg Val Cys Val Cys Asp Glu 260           270           280           290
            *             *             *             *
    GGA TTC TAC AGA AAC AAG AAG GGC CAA TGT GTG ACA AGA GAC
    Gly Phe Tyr Arg Asn Lys Lys Gly Gln Cys Val Thr Arg Asp 300           310           320           330
    *             *             *             *
    GAT TGC GAG TAT GAC AAT ATG GAG ATT ATC ACT TTT CCA CCA
    Asp Cys Glu Tyr Asp Asn Met Glu Ile Ile Thr Phe Pro Pro 340           350           360           370           380
    *             *             *             *             *
    GAA GAT AAA TGT GGT CCC GAT GAA TGG TTC GAC TGG TGT GGA
    Glu Asp Lys Cys Gly Pro Asp Glu Trp Phe Asp Trp Cys Gly 390           400           410           420
            *             *             *             *
    ACT TAC AAG CAG TGT GAG CGC AAG TGC AGT GAG GAG CTA AGT
    Thr Tyr Lys Gln Cys Glu Arg Lys Cys Ser Glu Glu Leu Ser
```

Figure 13 G-2

```
              430             440             450             460
               *               *               *               *
        GAG AAA AAT GAG GAG GCA TGC CTC TCA CGT GCT TGT ACT GGT
        Glu Lys Asn Glu Glu Ala Cys Leu Ser Arg Ala Cys Thr Gly 470             480             490             500
               *               *               *               *
        CGT GCT TGC GTT TGC AAC GAC GGA TTG TAT AGA GAC GAT TTT
        Arg Ala Cys Val Cys Asn Asp Gly Leu Tyr Arg Asp Asp Phe 510             520             530             540
          *               *               *               *
        GGC AAT TGT GTT GAG AAA GAC GAA TGT AAC GAT ATG GAG ATT
        Gly Asn Cys Val Glu Lys Asp Glu Cys Asn Asp Met Glu Ile 550             560             570             580
     *               *               *               *
    ATC ACT TTT CCA CCG GAA ACC AAA CAC TGA CCAAAGGCTC
    Ile Thr Phe Pro Pro Glu Thr Lys His 590         600          610         620         630
     *           *            *           *           *
    TAGCTCTCGC TACATAACGT CAGTGCTTGA ATTGTCCCTT TACGTGTTAG 640         650          660         670         680
     *           *            *           *           *
    TAATTTTGAC TAACTCTGTG TATTTGAGCA TTGTCTACTA ATGGTGAAAA 690         700
     *           *
    TGAAGCTTTT CAATGACT poly(A)
```

Figure 13 H-1 (AcaNAP48)

```
              10          20          30              40
               *           *           *               *
       GAATTCCGTA CGACCTACTA CTACTCAACG ATG AAG GCG CTC TAT
       EcoRI                           Met Lys Ala Leu Tyr 50          60          70          80
            *           *           *           *
       GTT ATC TCT ATA ACG TTG CTC CTG GTA TGG CAA TGC AGT GCA
       Val Ile Ser Ile Thr Leu Leu Leu Val Trp Gln Cys Ser Ala 90         100         110         120
            *           *           *           *
       AGA ACA GCG AGG AAA CCC CCA ACG TGT GGT GAA AAT GAA AGG
       Arg Thr Ala Arg Lys Pro Pro Thr Cys Gly Glu Asn Glu Arg 130         140         150         160         170
        *           *           *           *           *
       GTC GAA TGG TGT GGC AAG CAG TGC GAG ATC ACA TGT GAC GAC
       Val Glu Trp Cys Gly Lys Gln Cys Glu Ile Thr Cys Asp Asp 180         190         200         210
               *           *           *           *
       CCA GAT AAG ATA TGC CGC TCA CTC GCT TGT CCT GGT CCT CCT
       Pro Asp Lys Ile Cys Arg Ser Leu Ala Cys Pro Gly Pro Pro 220         230         240         250
               *           *           *           *
       GCT TGC GTA TGC GAC GAC GGA TAC TAC AGA GAC ACG AAC GTT
       Ala Cys Val Cys Asp Asp Gly Tyr Tyr Arg Asp Thr Asn Val 260         270         280         290
               *           *           *           *
       GGC TTG TGT GTA CAA TAT GAC GAA TGC AAC GAT ATG GAT ATT
       Gly Leu Cys Val Gln Tyr Asp Glu Cys Asn Asp Met Asp Ile 300         310         320         330         340
        *           *           *           *           *
       ATT ATG GTT TCA TAG GGTTGACTGA AGAATCGAAC AACCGGTGCA
       Ile Met Val Ser 350         360         370         380         390
               *           *           *           *           *
       CAACTTCTAT GCTTGACTAT CTCTCTTGCA TCATGCAAGT TTAGCTAGAT 400         410         420         430         440
               *           *           *           *           *
       AGTGTATATA TTAGCAAGAC CCCTTGGGGA GAATGAAGCT TCCCAACTAT 450         460         470         480         490
               *           *           *           *           *
       ATTAAATCAA TAACGTTTTC GCTTCATGTA CACGTGCTCA GCACATTCAT
```

Figure 13 H-2

```
       500        510        520
         *          *          *
ATCCACTCCT CACACTCCAT GAAAGCAGTG AAATGTT poly(A)
```

Figure 14

```
               10              20              30              40
                *               *               *               *
GCC AAC TCT TCG AAC ATG ATT CGA GGC CTC GTT CTT CTT TCT CTC CTG
                    Met Ile Arg Gly Leu Val Leu Leu Ser Leu Leu>

50              60              70              80              90
      *               *               *               *               *
TTT TGC GTC ACT TTT GCA GCG AAG AGA GAT TGT CCA GCA AAT GAG GAA
Phe Cys Val Thr Phe Ala Ala Lys Arg Asp Cys Pro Ala Asn Glu Glu>

100             110             120             130             140
          *               *               *               *               *
TGG AGG GAA TGT GGC ACT CCA TGT GAA CCA AAA TGC AAT CAA CCG ATG
Trp Arg Glu Cys Gly Thr Pro Cys Glu Pro Lys Cys Asn Gln Pro Met>

150             160             170             180             190
              *               *               *               *               *
CCA GAT ATA TGT ACT ATG AAT TGT ATC GTC GAT GTG TGT CAA TGC AAG
Pro Asp Ile Cys Thr Met Asn Cys Ile Val Asp Val Cys Gln Cys Lys>

200             210             220             230             240
                  *               *               *               *               *
GAG GGA TAC AAG CGT CAT GAA ACG AAG GGA TGC TTA AAG GAA GGA TCA
Glu Gly Tyr Lys Arg His Glu Thr Lys Gly Cys Leu Lys Glu Gly Ser>

250             260             270             280
              *               *               *               *
GCT GAT TGT AAA TAA GTT ATC AGA ACG CTC GTT TTG TCT TAC ATT AGA
Ala Asp Cys Lys ***

290             300             310             320             330
  *               *               *               *               *
TGG GTG AGC TGA TGT ATC TGT CAG ATA AAC TCT TTC TTC TAA AAA AAA 340             350             360
      *               *               *
AAA AAA AAA AAA AAA AAA AAA AAA A
```

FIGURE 16

```
              A1              A2      A3           A4              A5    A6   A7       A8          A9          A10
AcaNAP5      KAYPECGE NEWLDDC GTYKP CEAKC     NEEPPE          EE DPIC RS RGCL LPP ACVCK D GFYRD TV IGDCVR E EECDQ H EIIHV
AcaNAP6      KAYPECGE NEWLDVC GTKKP CEAKC     SEEE            EE DPIC RS FSCP GPA ACVCE D GFYRD TV IGDCVK E EECDQ H EIIHV

AcaNAP48     RTARKPPTCGE NERVEMC G  KQ CEITC  DDP             DKIC RS LACP GPP ACVCD D GYYRD TN VGLCVQ Y DECND     MDIIMVS

AcaNAP23     KPSEKECGP HERLD C GNKKP CERKC   KIETSEEEDDYEEGTE RFRC LL RVCD QPY ECICD D GYYRN K KGECVT D DVCQE DFMEFITFAP
AcaNAP24     RPEKKCGP GERLA C GNKKP CERKC    KIETSEEEDDYPEGTE RFRC LL RVCD QPY ECICD D GYYRN K KGECVT D DVCQE DFMEFITFAP
AcaNAP25     RPEKKCGP GERLD C ANKKP CEPKC    KIETSEEEDDDVE DT DVRC LV RVCE RPL KCICK D GYYRN K KGECVT D DVCQE DFMEFITFAP
AcaNAP44     RPEKKCGP GERLD C ANKKP CEPKC    KIETSEEEDDDVE ET DVRC LV RVCE RPL KCICK D GYYRN K KGECVT D DVCQE DFMEFITFAP
AcaNAP31,42,46 KSLWDQKCGE NERLD C GNQKD CERKC DDKRSEE         EI MQAC LT RQCL PP  VCVCE D NDQCVD E EECN           MEFITFAP
AceNAP4-d1   KPNNVMTNACGL NEYFAEC GNMGE CEHRC NEE ENEERDE     ER ITAC LI RVCF RPG ACVCK D GFYRN R TGSCVE F DDCE YENMEFITFAPE->
AceNAP4-d2   VPICGS NERYSDC GNDKQ CERKC      NED DYEKG        DEAC RS HVCE RPG ACVCE D GFYRN K KGSCVE S DDCE YDNMDFITFAPETSR

AcaNAP45d1   KSAKKCGL NEKLD C GNLKA CERKC    SDL DNEEDYKE     ED ESKC RS RECSR R  VCVCD E GFYRN K KGQCVT R DDCEY DNMEIITFPPE->
AcaNAP47d1   KSARKCGL NEKLD C GNLKA CEKKC    SDL DNEEDYGE     ED ESKC RS REDCIG R VCVCD E GFYRN K KGQCVT R DDCEY DNMEIITFPPE->
AduNAP7-d1   KAAKKCGL NERLD C GNLKQ CEPKC    SDL ESEEYEE      ED ESKC RS RDCS R R VCVCD E GFYRN K KGKCVA K DVCED DNMEIITFPPE->
AcaNAP45d2   DKCGP DEWFDWC GTYKQ CERKC       NKE LSEKD        EEAC LS RACTG R     ACVCN D GLYRD D FGNCVE K DECND  MEIITFPPETKH
AcaNAP47d2   DKCGP DEWFDWC GTYKQ CERKC       SEE LSEKN        EEAC LS RACTG R     ACVCN D GLYRD D FGNCVE K DECND  MEIITFPPETKH
AduNAP4      KCPT DEWFDWC GTYKH CELKC        DRE LTEKE        EQAC LS RVCE K S    ACVCN D GLYRD K FGNCVE K DECND  MEIITFAPEETK
AduNAP7-d2   DECGP DEWFDYC GNYKK CERKC       SEE TSEKN        EEAC LS RACT G R    ACVCK D GLYRD D FGNCVP H DECND  MEIITFPPETKH
AceNAP5      KAFPKCDV NERFEVC GNLKE CELKC    D                ED PKIC S RACI RPP ACVCD D GFYRD K YGPCVE E DECND   MEIITFPPETK
AceNAP7      RTVKRCGK NERYDDC GNAKD CETKC    G                EE EKVC RS RECT SPG ACVGE Q GFYRD P AGDCVT D EECDE WNNMEIITMPKQ

AcaNAPc2     KATMOCGE NEKYDSC GSKE CDKKC KYDGVEEEDE           EP NVPC LV RVCH  Q DCVCE E GFYRN K DDKCVS A EDCEL DNMDFIYPGTRN

HpoNAP5      KTCGP NEEYTEC GTP CEPKC         NEPMPDI                          C TLN CI VNV  CQCK P GFKRGPKG   CVA PGPGC K
NamNAP       KRDCPA NEEWREC GTP CEPKC        NQPMPDI                          C TMN CI VDV  CQCK E GYKRHETKG  CLKDGSADC K
```

NAP = nematode anticoagulant protein

Aca = Ancyclostoma caninum
Ace = Ancyclostoma ceylanium
Adu = Ancyclostoma duodenale
Hpo = Heligmosmoides polygyrus
Asu = Ascaris suum
Nam = Necator americanus

Figure 17

```
Lys Pro Asn Asn Val Met Thr Asn Ala Cys Gly Leu Asn Glu
1               5                   10

Tyr Phe Ala Glu Cys Gly Asn Met Lys Glu Cys Glu His Arg
15              20                  25

Cys Asn Glu Glu Glu Asn Glu Glu Arg Asp Glu Glu Arg Ile
    30                  35              40

Thr Ala Cys Leu Ile Arg Val Cys Phe Arg Pro Gly Ala Cys
        45          50              55
Val Cys Lys Asp Gly Phe Tyr Arg Asn Arg Thr Gly Ser Cys
            60              65                      70

Val Glu Glu Asp Asp Cys Glu Tyr Glu Asn Met Glu Phe Ile
            75              80

Thr Phe Ala Pro Glu Val Pro Ile Cys Gly Ser Asn Glu Arg
85              90              95

Tyr Ser Asp Cys Gly Asn Asp Lys Gln Cys Glu Arg Lys Cys
        100             105         110

Asn Glu Asp Asp Tyr Glu Lys Gly Asp Glu Ala Cys Arg Ser
            115             120             125

His Val Cys Glu Arg Pro Gly Ala Cys Val Cys Glu Asp Gly
        130             135             140

Phe Tyr Arg Asn Lys Lys Gly Ser Cys Val Glu Ser Asp Asp
                145             150

Cys Glu Tyr Asp Asn Met Asp Phe Ile Thr Phe Ala Pro Glu
155             160             165

Thr Ser Arg
    170
```

Figure 18

Lys Ser Ala Lys Lys Cys Gly Leu Asn Glu Lys Leu Asp Cys
1                    5                    10

Gly Asn Leu Lys Ala Cys Glu Lys Lys Cys Ser Asp Leu Asp
15                   20                  25

Asn Glu Glu Asp Tyr Lys Glu Glu Asp Glu Ser Lys Cys Arg
    30                  35                  40

Ser Arg Glu Cys Ser Arg Arg Val Cys Val Cys Asp Glu Gly
        45          50              55

Phe Tyr Arg Asn Lys Lys Gly Gln Cys Val Thr Arg Asp Asp
            60              65                      70

Cys Glu Tyr Asp Asn Met Glu Ile Ile Thr Phe Pro Pro Glu
                75              80

Asp Lys Cys Gly Pro Asp Glu Trp Phe Asp Trp Cys Gly Thr
85              90                  95

Tyr Lys Gln Cys Glu Arg Lys Cys Asn Lys Glu Leu Ser Glu
    100             105                     110

Lys Asp Glu Glu Ala Cys Leu Ser Arg Ala Cys Thr Gly Arg
        115             120             125

Ala Cys Val Cys Asn Asp Gly Leu Tyr Arg Asp Asp Phe Gly
            130             135                 140

Asn Cys Val Glu Lys Asp Glu Cys Asn Asp Met Glu Ile Ile
                145             150

Thr Phe Pro Pro Glu Thr Lys His
155                 160

Figure 19

Lys Ser Ala Lys Lys Cys Gly Leu Asn Glu Lys Leu Asp Cys
1                5                    10

Gly Asn Leu Lys Ala Cys Glu Lys Lys Cys Ser Asp Leu Asp
15                  20                  25

Asn Glu Glu Asp Tyr Gly Glu Glu Asp Glu Ser Lys Cys Arg
    30              35                  40

Ser Arg Glu Cys Ile Gly Arg Val Cys Val Cys Asp Glu Gly
        45          50              55

Phe Tyr Arg Asn Lys Lys Gly Gln Cys Val Thr Arg Asp Asp
            60              65                      70

Cys Glu Tyr Asp Asn Met Glu Ile Ile Thr Phe Pro Pro Glu
                75              80

Asp Lys Cys Gly Pro Asp Glu Trp Phe Asp Trp Cys Gly Thr
85              90                  95

Tyr Lys Gln Cys Glu Arg Lys Cys Ser Glu Glu Leu Ser Glu
    100             105                 110

Lys Asn Glu Glu Ala Cys Leu Ser Arg Ala Cys Thr Gly Arg
        115             120             125

Ala Cys Val Cys Asn Asp Gly Leu Tyr Arg Asp Asp Phe Gly
        130             135                     140

Asn Cys Val Glu Lys Asp Glu Cys Asn Asp Met Glu Ile Ile
            145             150

Thr Phe Pro Pro Glu Thr Lys His
155                 160

Figure 20

Lys Ala Ala Lys Lys Cys Gly Leu Asn Glu Arg Leu Asp Cys
1            5                    10

Gly Asn Leu Lys Gln Cys Glu Pro Lys Cys Ser Asp Leu Glu
15               20                  25

Ser Glu Glu Tyr Glu Glu Glu Asp Glu Ser Lys Cys Arg Ser
    30              35                  40

Arg Glu Cys Ser Arg Arg Val Cys Val Cys Asp Glu Gly Phe
        45          50          55

Tyr Arg Asn Lys Lys Gly Lys Cys Val Ala Lys Asp Val Cys
            60              65                      70

Glu Asp Asp Asn Met Glu Ile Ile Thr Phe Pro Pro Glu Asp
                75                  80

Glu Cys Gly Pro Asp Glu Trp Phe Asp Tyr Cys Gly Asn Tyr
85              90                  95

Lys Lys Cys Glu Arg Lys Cys Ser Glu Glu Thr Ser Glu Lys
    100             105             110

Asn Glu Glu Ala Cys Leu Ser Arg Ala Cys Thr Gly Arg Ala
        115             120             125

Cys Val Cys Lys Asp Gly Leu Tyr Arg Asp Asp Phe Gly Asn
            130             135             140

Cys Val Pro His Asp Glu Cys Asn Asp Met Glu Ile Ile Thr
                145             150

Phe Pro Pro Glu Thr Lys His
155             160

NEMATODE-EXTRACTED SERINE PROTEASE INHIBITORS AND ANTICOAGULANT PROTEINS

CROSS REFERENCE TO RELATED APPLICATION

This application is a continuation of U.S. Ser. No. 08/809,455, filed Apr. 24, 1997, now U.S. Pat. No. 6,090,916, which was a 371 of PCT/US95/13231, filed Oct. 17, 1995 and a continuation-in-part of U.S. Ser. No. 08/461,965, now U.S. Pat. No. 5,872,098, Ser. No. 08/465,380, now U.S. Pat. No. 5,863,894, Ser. No. 08/486,397, now U.S. Pat. No. 5,866,542 and Ser. No. 08/486,399, now U.S. Pat. No. 5,866,543, all filed Jun. 5, 1995, each of which is a continuation-in-part of U.S. Ser. No. 08/326,110, now U.S. Pat. No. 5,945,275, filed Oct. 18, 1994, the disclosures of all of which are incorporated herein by reference.

FIELD OF THE INVENTION

The present invention relates to specific proteins as well as recombinant versions of these proteins which are serine protease inhibitors, including potent anticoagulants in human plasma. These proteins include certain proteins extracted from nematodes. In another aspect, the present invention relates to compositions comprising these proteins, which are useful as potent and specific inhibitors of blood coagulation enzymes in vitro and in vivo, and methods for their use as in vitro diagnostic agents, or as in vivo therapeutic agents, to prevent the clotting of blood. In a further aspect, the invention relates to nucleic acid sequences, including mRNA and DNA, encoding the proteins and their use in vectors to transfect or transform host cells and as probes to isolate certain related genes in other species and organisms.

BACKGROUND AND INTRODUCTION TO THE INVENTION

Normal hemostasis is the result of a delicate balance between the processes of clot formation (blood coagulation) and clot dissolution (fibrinolysis). The complex interactions between blood cells, specific plasma proteins and the vascular surface, maintain the fluidity of blood unless injury occurs. Damage to the endothelial barrier lining the vascular wall exposes underlying tissue to these blood components. This in turn triggers a series of biochemical reactions altering the hemostatic balance in favor of blood coagulation which can either result in the desired formation of a hemostatic plug stemming the loss of blood or the undesirable formation of an occlusive intravascular thrombus resulting in reduced or complete lack of blood flow to the affected organ.

The blood coagulation response is the culmination of a series of amplified reactions in which several specific zymogens of serine proteases in plasma are activated by limited proteolysis. This series of reactions results in the formation of an insoluble matrix composed of fibrin and cellular components which is required for the stabilization of the primary hemostatic plug or thrombus. The initiation and propagation of the proteolytic activation reactions occurs through a series of amplified pathways which are localized to membranous surfaces at the site of vascular injury (Mann, K. G., Nesheim, M. E., Church, W. R., Haley, P. and Krishnaswamy, S. (1990) Blood 76: 1–16. and Lawson, J. H., Kalafatis, M., Stram, S., and Mann, K. G. (1994) J. Biol. Chem. 269: 23357–23366).

Initiation of the blood coagulation response to vascular injury follows the formation of a catalytic complex composed of serine protease factor VIIa and the non-enzymatic co-factor, tissue factor (TF)(Rappaport, S.I. and Rao, L.V.M. (1992) *Arteriosclerosis and Thrombosis* 12: 1112–1121). This response appears to be exclusively regulated by the exposure of subendothelial TF to trace circulating levels of factor VIIa and its zymogen factor VII, following a focal breakdown in vascular integrity. Autoactivation results in an increase in the number of factor VIIa/TF complexes which are responsible for the formation of the serine protease factor Xa. It is believed that in addition to the factor VIIa/TF complex, the small amount of factor Xa which is formed primes the coagulation response through the proteolytic modification of factor IX to factor $IX_{alpha}$ which in turn is converted to the active serine protease factor $IXa_{beta}$ by the factor VIIa/TF complex (Mann, K. G., Krishnaswamy, S. and Lawson, J. H. (1992) *Sem. Hematology* 29: 213–226.). It is factor $IXa_{beta}$ in complex with activated factor VIIIa, which appears to be responsible for the production of significant quantities of factor Xa which subsequently catalyzes the penultimate step in the blood coagulation cascade; the formation of the serine protease thrombin.

Factor Xa catalyzes the formation of thrombin following the assembly of the prothrombinase complex which is composed of factor Xa, the non-enzymatic co-factor Va and the substrate prothrombin (factor II) assembled in most cases, on the surface of activated platelets which are adhered at the site of injury (Fuster, V., Badimon, L., Badimon, J. J. and Chesebro, J. H. (1992) *New Engl. J. Med.* 32: 310–318). In the arterial vasculature, the resulting amplified burst, of thrombin generation catalyzed by prothrombinase causes a high level of this protease locally which is responsible for the formation of fibrin and the further recruitment of additional platelets as well as the covalent stabilization of the clot through the activation of the transglutaminase zymogen factor XIII. In addition, the coagulation response is further propagated through the thrombin-mediated proteolytic feedback activation of the non-enzymatic co-factors V and VIII resulting in more prothrombinase formation and subsequent thrombin generation (Hemker, H. C. and Kessels, H. (1991) *Haemostasis* 21: 189–196).

Substances which interfere in the process of blood coagulation (anticoagulants) have been demonstrated to be important therapeutic agents in the treatment and prevention of thrombotic disorders (Kessler, C. M. (1991) Chest 99: 97S–112S and Cairns, J. A., Hirsh, J., Lewis, H. D., Resnekov, L., and Theroux, P. (1992) Chest 102: 456S–481S). The currently approved clinical anticoagulants have been associated with a number of adverse effects owing to the relatively non-specific nature of their effects on the blood coagulation cascade (Levine, M. N., Hirsh, J., Landefeld, S., and Raskob, G. (1992) Chest 10: 352S–363S). This has stimulated the search for more effective anticoagulant agents which can more effectively control the activity of the coagulation cascade by selectively interfering with specific reactions in this process which may have a positive effect in reducing the complications of anticoagulant therapy (Weitz, J., and Hirsh, J. (1993) J. Lab. Clin. Med. 122: 364–373). In another aspect, this search has focused on normal human proteins which serve as endogenous anticoagulants in controlling the activity of the blood coagulation cascade. In addition, various hematophageous organisms have been investigated because of their ability to effectively anticoagulate the blood meal during and following feeding on their hosts suggesting that they have evolved effective anticoagulant strategies which may be useful as therapeutic agents.

A plasma protein, Tissue Factor Pathway Inhibitor (TFPI), contains three consecutive Kunitz domains and has been reported to inhibit the enzyme activity of factor Xa directly and, in a factor Xa-dependent manner, inhibit the enzyme activity of the factor VIIa-tissue factor complex. Salvensen,G., and Pizzo, S. V., "Proteinase Inhibitors: α-Macroglobulins, Serpins, and Kunis", "Hemostasis and Thrombosis, Third Edition, pp. 251–253, J. B. Lippincott Company (Edit. R. W. Colman et al. 1994). A cDNA sequence encoding TFPI has been reported, and the cloned protein was reported to have a molecular weight of 31,950 daltons and contain 276 amino acids. Broze, G. J. and Girad, T. J., U.S. Pat. No. 5,106,833, col. 1, (1992). Various recombinant proteins derived from TFPI have been reported. Girad, T. J. and Broze, G. J., EP 439,442 (1991); Rasmussen, J. S. and Nordfand, O. J., WO 91/02753 (1991); and Broze, G. J. and Girad, T. J., U.S. Pat. No. 5,106,833, col. 1, (1992).

Antistasin, a protein comprised of 119 amino acids and found in the salivary gland of the Mexican leech, *Haementeria officinalis*, has been reported to inhibit the enzyme activity of factor Xa. Tuszynski et al., J. Biol. Chem, 262: 9718 (1987); Nutt, et al., J. Biol. Chem, 26:10162 (1988). A 6,000 daltons recombinant protein containing 58 amino acids with a high degree homology to antistasin's amino-terminus amino acids 1 through 58 has been reported to inhibit the enzyme activity of factor Xa. Tung, J. et al., EP 454,372 (Oct. 30, 1991); Tung, J. et al., U.S. Pat. No. 5,189,019 (Feb. 23, 1993).

Tick Anticoagulant Peptide (TAP), a protein comprised of 60 amino acids and isolated from the soft tick, *Ornithodoros moubata*, has been reported to inhibit the enzyme activity of factor Xa but not factor VIIa. Waxman, L. et al., Science, 248:593 (1990). TAP made by recombinant methods has been reported. Vlausk, G. P. et al., EP 419,099 (1991) and Vlausk, G. P. et al., U.S. Pat. No. 5,239,058 (1993).

The dog hookworm, *Ancylostoma caninum*, which can also infect humans, has been reported to contain a potent anticoagulant substance which inhibited coagulation of blood in vitro. Loeb, L. and Smith, A. J., Proc. Pathol. Soc. Philadelphia, 7:173–187 (1904). Extracts of *A. caninum* were reported to prolong prothrombin time and partial thromboplastin time in human plasma with the anticoagulant effect being reported attributable to inhibition of factor Xa but not thrombin. Spellman, Jr., J. J. and Nossel, H. L., Am. J. Physiol., 220: 922–927 (1971). More recently, soluble protein extracts of *A. caninum* were reported to prolong prothrombin time and partial thromboplastin time in human plasma in vitro. The anticoagulant effect was reported to be attributable to inhibition of human factor Xa but not thrombin, Cappello, M, et al., J. Infect. Diseases, 67:1474–1477 (1993), and to inhibition of factor Xa and factor VIIa (WO94/25000; U.S. Pat. No. 5,427,937).

The human hookworm, *Ancylostoma ceylanicum*, has also been reported to contain an anticoagulant. Extracts of *A. ceylanicum* have been reported to prolong prothrombin time and partial thromboplastin time in dog and human plasma in vitro. Carroll, S. M., et al., Thromb. Haemostas. (Stuttgart), 51:222–227 (1984).

Soluble extracts of the non-hematophagous parasite, *Ascaris suum*, have been reported to contain an anticoagulant. These extracts were reported to prolong the clotting of whole blood, as well as clotting time in the kaolin-activated partial thromboplastin time test but not in the prothrombin time test. Crawford, G.P.M. et al., J. Parasitol., 68: 1044–1047 (1982).

Chymotrypsin/elastase inhibitor-1 and its major isoforms, trypsin inhibitor-1 and chymotrypsin/elastase inhibitor-4, isolated from *Ascaris suum*, were reported to be serine protease inhibitors and share a common pattern of five-disulfide bridges. Bernard, V. D. and Peanasky, R. J., Arch. Biochem. Biophys., 3:367–376 (1993); Huang, K. et al., Structure, Z:679–689 (1994); and Grasberger, B. L. et al., Structure, 2:669–678 (1994). There was no indication that the reported serine protease inhibitors had anticoagulant activity.

Secretions of the hookworm *Necator americanus* are reported to prolong human plasma clotting times, inhibit the amidolytic activity of human FXa using a fluorogenic substrate, inhibit multiple agonist-induced platelet dense granule release, and degrade fibrinogen. Pritchard, D. I. and B. Furmidge, Thromb. Haemost. 73: 546 (1995) (WO95/12615)

SUMMARY OF THE INVENTION

The present invention is directed to isolated proteins having serine protease inhibiting activity and/or anticoagulant activity and including at least one NAP domain. We refer to these proteins as Nematode-extracted Anticoagulant Proteins or "NAPs". "NAP domain" refers to a sequence of the isolated protein, or NAP, believed to have the inhibitory activity, as further defined herein below. The anticoagulant activity of these proteins may be assessed by their activities in increasing clotting time of human plasma in the prothrombin time (PT) and activated partial thromboplastin time (aPTT) assays, as well as by their ability to inhibit the blood coagulation enzymes factor Xa or factor VIIa/TF. It is believed that the NAP domain is responsible for the observed anticoagulant activity of these proteins. Certain of these proteins have at least one NAP domain which is an amino acid sequence containing less than about 120 amino acid residues, and including 10 cysteine amino acid residues.

In another aspect, the present invention is directed to a method of preparing and isolating a cDNA molecule encoding a protein exhibiting anticoagulant activity and having a NAP domain, and to a recombinant cDNA molecule made by this method. This method comprises the steps of:
(a) constructing a cDNA library from a species of nematode;
(b) ligating said cDNA library into an appropriate cloning vector; (c) introducing said cloning vector containing said cDNA library into an appropriate host cell; (d) contacting the cDNA molecules of said host cell with a solution containing a hybridization probe having a nucleic acid sequence comprising AAR GCi TAY CCi GAR TGY GGi GAR AAY GAR TGG, [SEQ. ID. NO. 94] wherein R is A or G, Y is T or C, and i is inosine; (e) detecting a recombinant cDNA molecule which hybridizes to said probe; and (f) isolating said recombinant cDNA molecule.

In another aspect, the present invention is directed to a method of making a recombinant protein encoded by said cDNA which has anticoagulant activity and which includes a NAP domain and to recombinant proteins made by this method. This method comprises the steps of: (a) constructing a cDNA library from a species of nematode;
(b) ligating said cDNA library into an appropriate cloning vector; (c) introducing said cloning vector containing said cDNA library into an appropriate host cell; (d) contacting the cDNA molecules of said host cell with a solution containing a hybridization probe having a nucleic acid sequence comprising AAR GCi TAY CCi GAR TGY GGi GAR AAY GAR TGG, wherein R is A or G, Y is T or C, and i is inosine [SEQ. ID. NO. 94]; (e) detecting a recombinant cDNA molecule which hybridizes to said probe; (f) isolating said recombinant cDNA molecule; (g) ligating the nucleic acid sequence of said cDNA molecule which encodes said recombinant protein into an appropriate expression cloning vector; (h) transforming a second host cell with said expression cloning vector containing said nucleic acid sequence of said cDNA molecule which encodes said recombinant protein; (i) culturing the transformed second host cell; and (j) isolating said recombinant protein expressed by said second host cell. It is noted that when describing production of recombinant proteins in certain expression systems such as COS cells, the term "transfection" is conventionally used in place of (and sometimes interchangeably with) "transformation".

In another aspect, the present invention is directed to a method of making a recombinant cDNA encoding a recombinant protein having anticoagulant activity and having a NAP domain, comprising the steps of: (a) isolating a cDNA library from a nematode;
(b) ligating said cDNA library into a cloning vector;
(c) introducing said cloning vector containing said cDNA library into a host cell; (d) contacting the cDNA molecules of said host cells with a solution comprising first and second hybridization probes, wherein said first hybridization probe has the nucleic acid sequence comprising

```
AAG GCA TAC CCG GAG TGT GGT GAG AAT GAA TGG CTC          [SEQ. ID. NO. 1]

GAC GAC TGT GGA ACT CAG AAG CCA TGC GAG GCC AAG TGC AAT

GAG GAA CCC CCT GAG GAG GAA GAT CCG ATA TGC CGC TCA CGT

GGT TGT TTA TTA CCT CCT GCT TGC GTA TGC AAA GAC GGA TTC

TAC AGA GAC ACG GTG ATC GGC GAC TGT GTT AGG GAA GAA GAA

TGC GAC CAA CAT GAG ATT ATA CAT GTC TGA,
``` and said second hybridization probe has the nucleic acid sequence comprising

```
AAG GCA TAC CCG GAG TGT GGT GAG AAT                      [SEQ. ID. NO. 2]

GAA TGG CTC GAC GTC TGT GGA ACT AAG AAG CCA TGC GAG GCC

AAG TGC AGT GAG GAA GAG GAG GAA GAT CCG ATA TGC CGA TCA

TTT TCT TGT CCG GGT CCC GCT GCT TGC GTA TGC GAA GAC GGA

TTC TAC AGA GAC ACG GTG ATC GGC GAC TGT GTT AAG GAA GAA

GAA TGC GAC CAA CAT GAG ATT ATA CAT GTC TGA;
```

(e) detecting a recombinant cDNA molecule which hybridizes to said mixture of said probes; and (f) isolating said recombinant cDNA molecule.

In yet another aspect, the present invention is directed to a method of making a recombinant cDNA encoding a protein having anticoagulant activity and which encodes a NAP domain, comprising the steps of: (a) isolating a cDNA library from a nematode; (b) ligating said cDNA library into an appropriate phagemid expression cloning vector; (c) transforming host cells with said vector containing said cDNA library; (d) culturing said host cells; (e) infecting said host cells with a helper phage; (f) separating phage containing said cDNA library from said host cells; (g) combining a solution of said phage containing said cDNA library with a solution of biotinylated human factor Xa; (h) contacting a streptavidin-coated solid phase with said solution containing said phages containing said cDNA library, and said biotinylated human factor Xa; (i) isolating phages which bind to said streptavidin-coated solid phase; and (j) isolating the recombinant cDNA molecule from phages which bind to said streptavidin-coated solid phase.

In one preferred aspect, the present invention is directed to a recombinant cDNA having a nucleic acid sequence selected from the nucleic acid sequences depicted in FIG. 1, FIG. 3, FIGS. 7A to 7F, FIG. 9, FIGS. 13A to 13H, and FIG. 14.

The present invention also is directed to NAPs that inhibit the catalytic activity of FXa, to NAPs that inhibit the catalytic activity of the FVIIa/TF complex, and to NAPs that inhibit the catalytic activity of a serine protease, as well as nucleic acids encoding such NAPs and their methods of use.

Definitions.

The term "amino acid" refers to the natural L-amino acids; D-amino acids are included to the extent that a protein including such D-amino acids retains biological activity. Natural L-amino acids include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr) and valine (Val).

The term "amino acid residue" refers to radicals having the structure: (1)—NH—CH(R)C(=O)—, wherein R is the alpha-carbon side-chain group of an L-amino acid, except for L-proline; or (2)

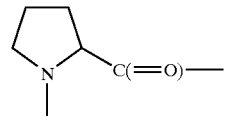

for L-proline.

The term "peptide" refers to a sequence of amino acids linked together through their alpha-amino and carboxylate groups by peptide bonds. Such sequences as shown herein are presented in the amino to carboxy direction, from left to right.

The term "protein" refers to a molecule comprised of one or more peptides.

The term "cDNA" refers to complementary DNA.

The term "nucleic acid" refers to polymers in which bases (e.g., purines or pyrimidines) are attached to a sugar phosphate backbone. Nucleic acids include DNA and RNA.

The term "nucleic acid sequence" refers to the sequence of nucleosides comprising a nucleic acid. Such sequences as shown herein are presented in the 5' to 3' direction, from left to right.

The term "recombinant DNA molecule" refers to a DNA molecule created by ligating together pieces of DNA that are not normally continguous.

The term "mRNA" refers to messenger ribonucleic acid.

The term "homology" refers to the degree of similarity of DNA or peptide sequences.

The terms "Factor Xa" or "fXa" or "FXa" are synonymous and are commonly known to mean a serine protease within the blood coagulation cascade of enzymes that functions as part of the prothrombinase complex to form the enzyme thrombin.

The phrase "Factor Xa inhibitory activity" means an activity that inhibits the catalytic activity of fXa toward its substrate.

The phrase "Factor Xa selective inhibitory activity" means inhibitory activity that is selective toward Factor Xa compared to other related enzymes, such as other serine proteases.

The phrase "Factor Xa inhibitor" is a compound having Factor Xa inhibitory activity.

The terms "Factor VIIa/Tissue Factor" or "fVIIa/TF" or "FVIIa/TF" are synonymous and are commonly known to mean a catalytically active complex of the serine protease coagulation factor VIIa (fVIIa) and the non-enzymatic protein Tissue Factor (TF), wherein the complex is assembled on the surface of a phospholipid membrane of defined composition.

The phrase "fVIIa/TF inhibitory activity" means an activity that inhibits the catalytic activity of the fVIIa/TF complex in the presence of fXa or catalytically inactive fXa derivative.

The phrase "fVIIa/TF selective inhibitory activity" means fVIIa/TF inhibitory activity that is selective toward fVIIa/TF compared to other related enzymes, such as other serine proteases, including FVIIa and fXa.

The phrase a "fVIIa/TF inhibitor" is a compound having fVIIa/TF inhibitory activity in the presence of fXa or catalytically inactive fXa derivatives.

The phrase "serine protease" is commonly known to mean an enzyme, comprising a triad of the amino acids histidine, aspartic acid and serine, that catalytically cleaves an amide bond, wherein the serine residue within the triad is involved in a covalent manner in the catalytic cleavage. Serine proteases are rendered catalytically inactive by covalent modification of the serine residue within the catalytic triad by diisopropylfluorophosphate (DFP).

The phrase "serine protease inhibitory activity" means an activity that inhibits the catalytic activity of a serine protease.

The phrase "serine protease selective inhibitory activity" means inhibitory activity that is selective toward one serine protease compared to other serine proteases.

The phrase "serine protease inhibitor" is a compound having serine protease inhibitory activity.

The term "prothrombinase" is commonly known to mean a catalytically active complex of the serine protease coagulation Factor Xa (fXa) and the non-enzymatic protein Factor Va (fva), wherein the complex is assembled on the surface of a phospholipid membrane of defined composition.

The phrase "anticoagulant activity" means an activity that inhibits the clotting of blood, which includes the clotting of plasma.

The term "selective", "selectivity", and permutations thereof, when referring to NAP activity toward a certain enzyme, mean the NAP inhibits the specified enzyme with at least 10-fold higher potency than it inhibits other, related enzymes. Thus, the NAP activity is selective toward that specified enzyme.

The term "substantially the same" when used to refer to proteins, amino acid sequences, cDNAs, nucleotide sequences and the like refers to proteins, cDNAs or sequences having at least about 90% homology with the other protein, cDNA, or sequence.

The term "NAP" or "NAP protein" means an isolated protein which includes at least one NAP domain and having serine protease inhibitory activity and/or anticoagulant activity.

BRIEF DESCRIPTION OF THE DRAWINGS

FIG. 1 depicts the nucleotide sequence of the AcaNAP5 cDNA [SEQ. ID. NO. 3]. The numbering starts at the first nucleotide of the cDNA. Translation starts at the first ATG codon (position 14); a second in frame ATG is present at position 20.

FIG. 2 depicts the amino acid sequence of mature AcaNAP5 [SEQ. ID. NO. 4].

FIG. 3 depicts the nucleotide sequence of the AcaNAP6 cDNA [SEQ. ID. NO. 5]. The numbering starts at the first nucleotide of the cDNA. Translation starts at the first ATG codon (position 14); a second in frame ATG is present at position 20.

FIG. 4 depicts the amino acid sequence of mature AcaNAP6 [SEQ. ID. NO. 6]. Amino acids that differ from AcaNAP5 are underlined. In addition to these amino acid substitutions, AcaNAP6 contains a two amino acid deletion (Pro—Pro) when compared to AcaNAP5.

FIG. 5 depicts the amino acid sequence of Pro-AcaNAP5 [SEQ. ID. NO. 7].

FIG. 6 depicts the amino acid sequence of Pro-AcaNAP6 [SEQ. ID. NO. 8]. Amino acids that differ from Pro-AcaNAP5 are underlined. In addition to these amino acid substitutions, Pro-AcaNAP6 contains a two amino acid deletion (Pro—Pro) when compared to Pro-AcaNAP5.

FIGS. 7A through 7F depict the nucleotide sequences of the cDNAs and deduced amino acid sequences of certain NAP proteins isolated from *Ancylostoma ceylanicum*, *Ancylostoma duodenale*, and *Heligmosomoides polygyrus*. FIG. 7A depicts sequences for the recombinant cDNA molecule, AceNAP4, isolated from *Ancylostoma ceylanicum* [SEQ. ID. NO. 9]. FIG. 7B depicts sequences for the recombinant cDNA molecule, AceNAP5, isolated from *Ancylostoma ceylanicum* [SEQ. ID. NO. 10]. FIG. 7C depicts sequences for the recombinant cDNA molecule, AceNAP7, isolated from *Ancylostoma ceylanicum* [SEQ. ID. NO. 11]. FIG. 7D depicts sequences for the recombinant cDNA molecule, AduNAP4, isolated from *Ancylostoma duodenale* [SEQ. ID. NO. 12]. FIG. 7E depicts sequences for the recombinant cDNA molecule, AduNAP7, isolated from *Ancylostoma duodenale* [SEQ. ID. NO. 13]. FIG. 7F depicts sequences for the recombinant cDNA molecule, HpoNAP5, isolated from *Heligmosomoides polygyrus* [SEQ. ID. NO. 14]. The EcoRI site, corresponding to the 5'-end of the recombinant cDNA molecule, is indicated in all cases (underlined). Numbering of each sequence starts at this EcoRI site. AceNAP4 and AduNAP7, each encode a protein which has two NAP domains; all other clones in this Figure code for a protein having a single NAP domain. The AduNAP4 cDNA clone is not full-length, i.e., the recombinant cDNA molecule lacks the 5'-terminal part of the coding region based on comparison with other isoforms.

FIGS. 8A through 8C depict the nucleotide sequence of the vectors, pDONG61 (FIG. 8A) [SEQ. ID. NO. 15], pDONG62 (FIG. 8B) [SEQ. ID. NO. 16], and pDONG63 (FIG. 5C) [SEQ. ID. NO. 17]. The HidIII-BamHI fragment which is shown is located between the HindIII and BamHI sites of pUC119. The vectors allow the cloning of cDNAs, as SfiI-NotI fragments, in the three different reading frames downstream of the filamentous phage gene 6. All relevant restriction sites are indicated. The AAA Lys-encoding triplet at position 373–375 is the last codon of gene 6. The gene 6 encoded protein is followed by a Gly-Gly-Gly-Ser-Gly-Gly [SEQ. ID. NO. 18] linker sequence.

FIG. 9 depicts the nucleotide sequence of the recombinant cDNA molecule, AcaNAPc2 cDNA [SEQ. ID. NO. 19]. The EcoRI site, corresponding to the 5'-end of the cDNA, is indicated (underlined). Numbering starts at this EcoRI site. The deduced amino acid sequence is also shown; the translational reading frame was determined by the gene 6 fusion partner. The AcaNAPc2 cDNA lacks a portion of the 5'-terminal part of the coding region; the homology with AcaNAP5 and AcaNAP6 predicts that the first seven amino acid residues belong to the secretion signal.

FIGS. 10A and 10B depict the comparative effects of certain NAP proteins on the prothrombin time (PT) measurement (FIG. 10A) and the activated partial thromboplastin time (aPTT) (FIG. 10B) of normal citrated human plasma. Solid circles, (●), represent Pro-AcaNAP5; open triangles, (Δ), represent AcaNAP5 (AcaNAP5$^a$ in Table 2); and open circles, (○), represent native AcaNAP5.

FIG. 11 depicts the alignment of the amino acid sequences encoded by certain NAP cDNAs isolated from various nematodes. AcaNAP5 [SEQ. ID. NO. 20], AcaNAP6 [SEQ. ID. NO. 21], and AcaNAPc2 [SEQ. ID. NO. 128] were isolated from *Ancylostoma caninum*. AceNAP5 [SEQ. ID. NO. 22], AceNAP7 [SEQ. ID. NO. 23], and AceNAP4 (AceNAP4d1 [SEQ. ID. NO. 24] and AceNAP4d2 [SEQ. ID. NO. 25] were isolated from *Ancylostoma ceylanicum*. AduNAP4 [SEQ. ID. NO. 26] and AdaNAP7 (AduNAP7d1 [SEQ. ID. NO. 27] and AduNAP7d2 [SEQ. ID. NO. 28]) were isolated from *Ancylostoma duodenale*. HpoNAP5 [SEQ. ID. NO. 29] was isolated from *Heligmosomoides polygyrus*. The amino acid sequences shown in this figure are as given in FIGS. 1, 3, 7A through 7F, and 9. The sequences of mature AcaNAP5 [SEQ. ID. NO. 4] and AcaNAP6 [SEQ. ID. NO. 6] (see FIGS. 2 and 4) are characterized, in part, by ten cysteine residues (numbered one through ten and shown in bold). All of the amino acid sequences in this Figure contain at least one NAP domain. The AceNAP4 cDNA consists of two adjacent regions, named AceNAP4d1 [SEQ. ID. NO. 24] and AceNAP4d2 [SEQ. ID. NO. 25], which encode a first (d1) and second (d2) NAP-domain; similarly, the AduNAP7 cDNA contains two adjacent regions, AduNAP7d1[SEQ. ID. NO. 27] and AduNAP7d2 [SEQ. ID. NO. 28], encoding a first (d1) and second (d2) NAP-domain. The alignment of the amino acid sequences of all NAP-domains is guided by the cysteines; dashes (—) were introduced at certain positions to maintain the cysteine alignment and indicate the absence of an amino acid at that position. The carboxy-terminal residue of a cDNA encoded protein is followed by the word "end".

FIGS. 12A and 12B depict a map of the *P. pastoris* pYAM7SP8 expression/secretion vector (FIG. 12A) and sequences included in the vector (FIG. 12B) [SEQ. ID. NO. 30]. As depicted in FIG. 12A, this plasmid contains the following elements inserted between the methanol-induced AOX1 promoter (dark arrow in the 5'AOX untranslated region) and the AOX1 transcription termination signal (3'T): a synthetic DNA fragment encoding the acid phosphatase secretion signal (S), a synthetic 19-amino acid pro sequence (P) ending with a Lys-Arg processing site for the KEX2 protease and a multicloning site. The HIS4 gene which serves as a selection marker in GS115 transformation was modified by site directed mutagenesis to eliminate the Stu1 recognition sequence (HIS4*). pBR322 sequences, including the Bla gene and origin (ori) for propagation in *E. coli* are represented by a single line. FIG. 12B depicts the following contiquous DNA sequences which are incorporated in pYAM7SP8: the acid phosphatase (PH01) secretion signal sequence, pro sequence and multicloning site (MCS) sequence. The ATG start codon of the PHO1 secretion signal is underlined.

FIGS. 13A through 13H depict the nucleotide sequences of the cDNAs and deduced amino acid sequences of certain NAP proteins isolated from *Ancylostoma caninum*. FIG. 13A depicts sequences for the recombinant cDNA molecule AcaNAP23 [SEQ. ID. NO. 31]. FIG. 13B depicts sequences for the recombinant cDNA molecule AcaNAP24 [SEQ. ID. NO. 32]. FIG. 13C depicts sequences for the recombinant cDNA molecule AcaNAP25 [SEQ. ID. NO. 33]. FIG. 13D depicts sequences for the recombinant cDNA molecules AcaNAP31, AcaNAP42, and AcaNAP46, all of which are identical [SEQ. ID. NO. 34]. FIG. 13E depicts sequences for the recombinant cDNA molecule AcaNAP44 (SEQ. ID. NO. 35]. FIG. 13F depicts sequences for the recombinant cDNA molecule AcaNAP45 [SEQ. ID. NO. 36].

FIG. 13G depicts sequences for the recombinant cDNA molecule AcaNAP47 [SEQ. ID. NO. 37]. FIG. 13H depicts sequences for the recombinant cDNA molecule AcaNAP48 [SEQ. ID. NO. 38]. The EcoRI site, corresponding to the 5'-end of the recombinant cDNA molecule, is indicated in all cases (underlined). Numbering of each sequence starts at this EcoRI site. AcaNAP45 and AcaNAP47, each encode a protein which has two NAP domains; all other clones in this Figure code for a protein having a single NAP domain.

FIG. 14 depicts the nucleotide, and deduced amino acid, sequence of the recombinant cDNA molecule NamNAP [SEQ. ID. NO. 39].

FIG. 16 presents the alignment of amino acid sequences corresponding to mature NAPs isolated according to the procedures disclosed herein: namely AcaNAP5 [SEQ. ID. NO. 40], AcaNAP6 [SEQ. ID. NO. 41], AcaNAP48 [SEQ. ID. NO. 42], AcaNAP23 [SEQ. ID. NO. 43], AcaNAP24 [SEQ. ID. NO. 44], AcaNAP25 [SEQ. ID. NO. 45], AcaNAP44 [SEQ. ID. NO. 46], AcaNAP31, 42, 46 [SEQ. ID. NO. 47], AceNAP4d1 [SEQ. ID. NO. 48], AceNAP4d2 [SEQ. ID. NO. 49], AcaNAP45d1 [SEQ. ID. NO. 50], AcaNAP47d1 [SEQ. ID. NO. 51], AduNAP7d1 [SEQ. ID. NO. 52], AcaNAP45d2 [SEQ. ID. NO. 53], AcaNAP47d2

Figure 15:
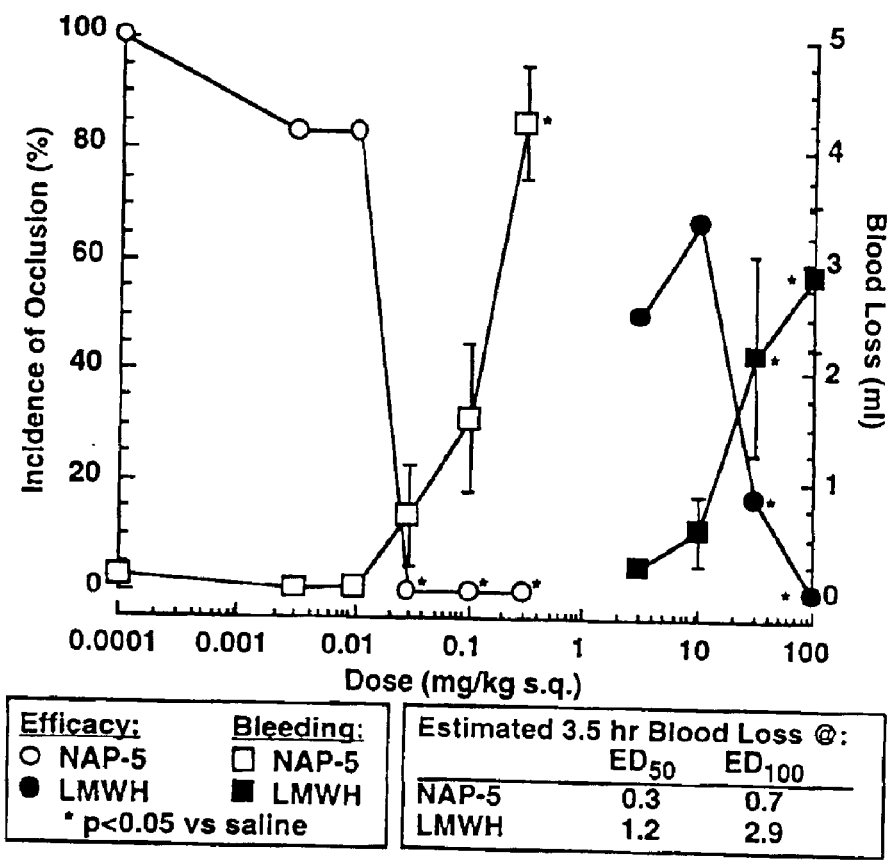
FIG. 15 presents the antithrombotic activity of AcaNAP5 and Low Molecular weight Heparin (LMWH; Enoxaparin™) evaluated in the $FeCl_3$ model of arterial thrombosis. Activity data is represented as the percent incidence of occlusive thrombus formation in the carotid artery (circles). Thrombus formation began 150 minutes after subcutaneous (s.c.) administration of test agent. Deep wound bleeding was quantified in a separate group of animals that were treated in an identical manner but without addition of $FeCl_3$ (squares). Blood loss at a deep surgical wound in the neck was quantified over a total of 210 minutes after subcutaneous compound administration.

[SEQ. ID. NO. 54], AduNAP4 [SEQ. ID. NO. 55], AduNAP7d2 [SEQ. ID. NO. 56], AceNAP5 [SEQ. ID. NO. 57], AceNAP7 [SEQ. ID. NO. 58], AcaNAPc2 [SEQ. ID. NO. 59], HpoNAP5 [SEQ. ID. NO. 60], and NamNAP [SEQ. ID. NO. 61]. Each NAP domain comprises ten cysteine residues, which are used to align the sequences, and amino acid sequences between the cysteines. A1 through A10 represent the amino acid sequences between the cysteine residues.

FIG. 17 depicts the amino acid sequence of mature AceNAP4 [SEQ. ID. NO. 62] having two NAP domains.

FIG. 18 depicts the amino acid sequence of mature AcaNAP45 [SEQ. ID. NO. 63] having two NAP domains.

FIG. 19 depicts the amino acid sequence of mature AcaNAP47 [SEQ. ID. NO. 64] having two NAP domains.

FIG. 20 depicts the amino acid sequence for mature AduNAP7 [SEQ. ID. NO. 65] having two NAP domains.

DETAILED DESCRIPTION OF THE INVENTION

This invention provides a family of proteins, collectively referred to as Nematode-extracted Anticoagulant Proteins (NAPs). These proteins are so designated because the first member originally isolated was extracted from a nematode, the canine hookworm, *Ancyclostoma caninum*. However, the designation NAP or NAP domain should not be considered to limit the proteins of the present invention by this or other natural source.

Individual NAP proteins are characterized by having at least one NAP domain and by having serine protease inhibitory and/or anticoagulant activity. Such anticoagulant activity may be assessed by increases in clotting time in both the PT and aPTT assays described herein, by the inhibition of factor Xa or factor VIIa/TF activity, or by demonstration of activity in vivo. Preferably, blood or plasma used in such assays derives from species known to be infected by nematodes, such as pigs, humans, primates, and the like. The NAP domain is an amino acid sequence. It is believed that the NAP domain is responsible for the observed inhibitory and/or anticoagulant activity. Certain representative NAP domains include the amino acid sequences depicted in FIGS. 11 and 16, particularly the sequences between the cysteines designated as Cysteine 1 and Cysteine 10 in the Figures and the sequence following Cysteine 10. The characteristics broadly defining this family of proteins, as well as the nucleic acid molecules, including mRNAs sequences and DNA sequences which encode such proteins, are provided. Methods of making these proteins, as well as methods of making nucleic acid molecules encoding such proteins, are also provided. The specific examples provided are exemplary only and other members of the NAP family of proteins, as well as nucleic acid sequences encoding them, can be obtained by following the procedures outlined in these examples and described herein.

The proteins of the present invention include isolated NAPs which comprise proteins having anticoagulant activity and including at least one NAP domain.

With respect to "anticoagulant activity", the purified proteins of the present invention are active as anticoagulants, and as such, are characterized by inhibiting the clotting of blood which includes the clotting of plasma. In one aspect, the preferred isolated proteins of the present invention include those which increase the clotting time of human plasma as measured in both the prothrombin time (PT) and activated partial thromboplastin time (aPTT) assays.

In the PT assay, clotting is initiated by the addition of a fixed amount of tissue factor-phospholipid micelle complex (thromboplastin) to human plasma. Anticoagulants interfere with certain interactions on the surface of this complex and increase the time required to achieve clotting relative to the clotting observed in the absence of the anticoagulant. The measurement of PT is particularly relevant for assessing NAP anticoagulant activity because the series of specific biochemical events required to cause clotting in this assay are similar to those that must be overcome by the hookworm in nature to facilitate feeding. Thus, the ability of NAP to act as an inhibitor in this assay can parallel its activity in nature, and is predictive of anticoagulant activity in vivo. In both the assay and in nature, the coagulation response is initiated by the formation of a binary complex of the serine protease factor VIIa (fVIIa) and the protein tissue factor (TF) (fVIIa/TF), resulting in the generation of fXa. The subsequent assembly of fXa into the prothrombinase complex is the key event responsible for the formation of thrombin and eventual clot formation.

In the aPTT assay, clotting is initiated by the addition of a certain fixed amount of negatively charged phospholipid micelle (activator) to the human plasma. Substances acting as anticoagulants will interfere with certain interactions on the surface of the complex and again increase the time to achieve a certain amount of clotting relative to that observed in the absence of the anticoagulant. Example B describes such PT and aPTT assays. These assays can be used to assess anticoagulant activity of the isolated NAPs of the present invention.

The preferred isolated NAPs of the present invention include those which double the clotting time of human plasma in the PT assay when present at a concentration of about 1 to about 500 nanomolar and which also double the clotting time of human plasma in the aPTT assay when present at a concentration of about 1 to about 500 nanomolar. Especially preferred are those proteins which double the clotting time of human plasma in the PT assay when present at a concentration of about 5 to about 100 nanomolar, and which also double the clotting time of human plasma in the aPTT assay when present at a concentration of about 5 to about 200 nanomolar. More especially preferred are those proteins which double the clotting time of human plasma in the PT assay when present at a concentration about 10 to about 50 nanomolar, and which also double the clotting time of human plasma in the aPTT assay when present at a concentration of about 10 to about 100 nanomolar.

Anticoagulant, or antithrombotic, activity of NAPs of the present invention also can be evaluated using the in vivo models presented in Example F. The rat $FeCl_3$ model described in part A of that Example is a model of platelet dependent, arterial thrombosis that is commonly used to assess antithrombotic compounds. The model evaluates the ability of a test compound to prevent the formation of an occlusive thrombus induced by $FeCl_3$ in a segment of the rat carotid artery. NAPs of the present invention are effective anticoagulants in this model when administered intravenously or subcutaneously. The deep wound bleeding assay described in part B of Example F allows measurement of blood loss after administration of an anticoagulant compound. A desired effect of an anticoagulant is that it inhibits blood coagulation, or thrombus formation, but not so much as to prevent clotting altogether and thereby potentiate bleeding. Thus, the deep wound bleeding assay measures the amount of blood loss over the 3.5 hour period after administration of anticoagulant. The data presented in FIG. 15 show NAP of the present invention to be an effective antithrombotic compound at a dose that does not cause excessive bleeding. In contrast, the dose of low molecular weight heparin (LMWH) that correlated with 0% occlusion caused about three times more bleeding than the effective dose of NAP.

General NAP Domain [FORMULA I]

With respect to "NAP domain", the isolated proteins (or NAPs) of the present invention include at least one NAP domain in their amino acid sequence. Certain NAP domains have an amino acid sequence having a molecular weight of about 5.0 to 10.0 kilodaltons, preferably from about 7.0 to 10.0 kilodaltons, and containing 10 cysteine amino acid residues.

Certain preferred isolated NAPs of the present invention include those which contain at least one NAP domain, wherein each such NAP domain is further characterized by including the amino acid sequence: Cys-$A_1$-Cys-$A_2$-Cys-$A_3$-Cys-$A_4$-Cys-$A_5$-Cys-$A_6$-Cys-$A_7$-Cys-$A_8$-Cys-$A_9$-Cys ("FORMULA I"), wherein: (a) $A_1$ is an amino acid sequence containing 7 to 8 amino acid residues; (b) $A_2$ is an amino acid sequence containing 2 to 5 amino acid residues; (c) $A_3$ is an amino acid sequence containing 3 amino acid residues; (d) $A_4$ is an amino acid sequence containing 6 to 17 amino acid residues; (e) $A_5$ is an amino acid sequence containing 3 to 4 amino acid residues; (f) $A_6$ is an amino acid sequence containing 3 to 5 amino acid residues. (g) $A_7$ is an amino acid residue; (h) $A_8$ is an amino acid sequence containing 10 to 12 amino acid residues; and (i) $A_9$ is an amino acid sequence containing 5 to 6 amino acid residues. Other NAPs having slightly different NAP domains (See FORMULAS II to V) are encompassed within the present invention.

Especially preferred NAP domains include those wherein $A_2$ is an amino acid sequence containing 4 to 5 amino acid residues and $A_4$ is an amino acid sequence containing 6 to 16 amino acid residues. More preferred are NAP domains wherein: (a) $A_1$ has Glu as its fourth amino acid residue; (b) $A_2$ has Gly as its first amino acid residue; (c) $A_8$ has Gly as its third amino acid residue and Arg as its sixth amino acid residue; and (d) $A_9$ has Val as its first amino acid residue. More preferably, $A_3$ has Asp or Glu as its first amino acid residue and Lys or Arg as its third amino acid residue and $A_7$ is Val or Gln. Also, more preferably $A_8$ has Leu or Phe as its fourth amino acid residue and Lys or Tyr as its fifth amino acid residue. Also preferred are NAP domains where, when $A_8$ has 11 or 12 amino acid residues, Asp or Gly is its penultimate amino acid residue, and, where when $A_8$ has 10 amino acids, Gly is its tenth amino acid residue. For expression of recombinant protein in certain expression systems, a recombinant NAP may additionally include an amino acid sequence for an appropriate secretion signal. Certain representative NAP domains include the sequences depicted in FIG. 11 and FIG. 16, particularly the sequences between (and including) the cysteines designated as Cysteine 1 and Cysteine 10 and following Cysteine 10.

According to a preferred aspect, provided are NAPs which include at least one NAP domain of Formula I wherein the NAP domain includes the amino acid sequence: Cys-A1-Cys-A2-Cys-A3-Cys-A4-Cys-A5-Cys-A6-Cys-A7-Cys-A8-Cys-A9-Cys-A10 wherein (a) Cys-A1 is selected from SEQ. ID. NOS. 66 and 129; (b) Cys-A2-Cys is selected from one of SEQ. ID. NOS. 130 to 133; (c) A3-Cys-A4 is selected from one of SEQ. ID. NOS. 134 to 145; (d) Cys-A5 is selected from SEQ. ID. NOS. 146 and 147; (e) Cys-A6 is selected from one of SEQ. ID. NOS. 148 to 150; (f) Cys-A7-Cys-A8 is selected from one of SEQ. ID. NOS. 151 to 153; and (g) Cys-A9-Cys is selected from SEQ. ID. NOS. 154 and 155. Also preferred are such proteins wherein Cys-A2-Cys is selected from SEQ. ID. NOS. 130 and 131 and A3-Cys-A4 is selected from one of SEQ. ID. NOS. 135 to 145. More preferred are those proteins having NAP domains wherein SEQ. ID. NOS. 66 and 129 have Glu at location 5; SEQ. ID. NOS. 130 and 131 have Gly at location 2; SEQ. ID. NOS. 151 to 153 have Gly at location 6 and Arg at location 9; and SEQ. ID. NOS. 154 and 155 have Val at location 2. More preferably SEQ. ID. NOS. 151 to 153 have Val or Glu at location 2; Leu or Phe at location 7 and/or Lys or Tyr at location 8. It is further preferred that SEQ. ID. NO. 151 has Asp or Gly at location 14; SEQ. ID. NO. 152 has Asp or Gly at location 13; and SEQ. ID. NO. 153 has Gly at location 13.

Certain NAPs of the present invention demonstrate specificity toward inhibiting a particular component in the coagulation cascade, such as fXa or the fVIIa/TF complex. The specificity of a NAP's inhibitory activity toward a component in the coagualtion cascade can be evaluated using the protocol in Example D. There, the ability of a NAP to inhibit the activity of a variety of serine proteases involved in coagulation is measured and compared. The ability of a NAP to inhibit the fVIIa/TF complex also can be assessed using the protocols in Example E, which measure the ability of a NAP to bind fXa in either an inhibitory or noninhibitory manner and to inhibit FVIIa when complexed with TF. AcaNAP5 and AcaNAP6 are examples of proteins having NAP domains that specifically inhibit fXa. AcaNAPc2 is a protein having a NAP domain that demonstrates selective inhibition of the fVIIa/TF complex when fXa, or a catalytically active or inactive derivative thereof, is present.

NAPs having Anticoagulant Activity, including NAPs having Factor Xa Inhibitory Activity (FORMULA II)

Thus, in one aspect NAPs of the present invention also include an isolated protein having anticoagulant activity, including an isolated protein having Factor Xa inhibitory activity, and having one or more NAP domains, wherein each NAP domain includes the sequence: Cys-A1-Cys-A2-Cys-A3-Cys-A4-Cys-A5-Cys-A6-Cys-A7-Cys-A8-Cys-A9-Cys-A10 ("FORMULA II"), wherein
(a) A1 is an amino acid sequence of 7 to 8 amino acid residues;
(b) A2 is an amino acid sequence;
(c) A3 is an amino acid sequence of 3 amino acid residues;
(d) A4 is an amino acid sequence;
(e) A5 is an amino acid sequence of 3 to 4 amino acid residues;
(f) A6 is an amino acid sequence;
(g) A7 is an amino acid;
(h) A8 is an amino acid sequence of 11 to 12 amino acid residues;
(i) A9 is an amino acid sequence of 5 to 7 amino acid residues; and
(j) A10 is an amino acid sequence;

wherein each of A2, A4, A6 and A10 has an independently selected number of independently selected amino acid residues and each sequence is selected such that each NAP domain has in total less than about 120 amino acid residues.

Pharmaceutical compositions comprising NAP proteins according to this aspect, and methods of inhibiting blood coagulation comprising administering NAP proteins according to this aspect also are contemplated by this invention.

NAP proteins within this aspect of the invention have at least one NAP domain. Preferred are NAPs having one or two NAP domains. NAP proteins AcaNAP5 [SEQ. ID. NOS.

4 and 40] and AcaNAP6 [SEQ. ID. NOS. 6 and 41] have one NAP domain and are preferred NAPs according to this aspect of the invention.

Preferred NAP proteins according to one embodiment of this aspect of the invention are those in which A2 is an amino acid sequence of 3 to 5 amino acid residues, A4 is an amino acid sequence of 6 to 19 amino acid residues, A6 is an amino acid sequence of 3 to 5 amino acid residues, and A10 is an amino acid sequence of 5 to 25 amino acid residues.

Thus, according to one preferred aspect, provided are isolated proteins having anticoagulant activity, including isolated proteins having activity as Factor Xa inhibitors, having at least one NAP domain of formula II which includes the following sequence:

Cys-A1-Cys-A2-Cys-A3-Cys-A4-Cys-A5-Cys-A6-Cys-A7-Cys-A8-Cys-A9-Cys-A10 wherein (a) Cys-A1 is selected from SEQ. ID. NOS. 67 and 156; (b) Cys-A2-Cys is selected from one of SEQ. ID. NOS. 157 to 159; (c) A3-Cys-A4 is selected from one of SEQ. ID. NOS. 160 to 173; (d) Cys-A5 is selected from SEQ. ID. NOS. 174 and 175; (e) Cys-A6 is selected from one of SEQ. ID. NOS. 176 to 178; (f) Cys-A7-Cys-A8 is selected from SEQ. ID. NOS. 179 and 180; (g) Cys-A9 is selected from one of SEQ. ID. NOS. 181 to 183; and (h) Cys-A10 is selected from one of SEQ. ID. NOS. 184 to 204.

In another preferred embodiment of this aspect of the invention, A3 has the sequence Glu-$A3_a$-$A3_b$, wherein $A^3_a$ and $A3_b$ are independently selected amino acid residues. More preferably, $A3_a$ is selected from the group consisting of Ala, Arg, Pro, Lys, Ile, His, Leu, and Thr, and $A3_b$ is selected from the group consisting of Lys, Thr, and Arg. Especially preferred A3 sequences are selected from the group consisting of Glu-Ala-Lys, Glu-Arg-Lys, Glu-Pro-Lys, Glu-Lys-Lys, Glu-Ile-Thr, Glu-His-Arg, Glu-Leu-Lys, and Glu-Thr-Lys.

In an additional preferred embodiment of this aspect of the invention, A4 is an amino acid sequence having a net anionic charge.

According to this aspect of the invention, a preferred A7 amino acid residue is Val or Ile.

Another preferred embodiment of this aspect of the invention is one in which A8 includes the amino acid sequence $A8_a$-$A8_b$-$A8_c$-$A8_d$-$A8_e$-$A^8_f$-$A8_g$ [SEQ. ID. NO. 68], wherein (a) $A8_a$ is the first amino acid residue in A8, (b) at least one of $A8_a$ and $A8_b$ is selected from the group consisting of Glu or Asp, and (c) $A8_c$ through $A8_g$ are independently selected amino acid residues.

Preferably, $AB_c$ is Gly, $A8_d$ is selected from the group consisting of Phe, Tyr, and Leu, $A8_e$ is Tyr, $A8_f$ is Arg, and $A8_g$ is selected from Asp and Asn. An especially preferred $A8_c$-$A8_d$-$A8_e$-$A8_f$-$A^8_g$ sequence is selected from the group consisting of Gly-Phe-Tyr-Arg-Asp [SEQ. ID. NO. 69], Gly-Phe-Tyr-Arg-Asn [SEQ. ID. NO. 70], Gly-Tyr-Tyr-Arg-Asp [SEQ, ID. NO. 71], Gly-Tyr-Tyr-Arg-Asn [SEQ. ID. NO. 72], and Gly-Leu-Tyr-Arg-Asp [SEQ. ID. NO. 73].

An additional preferred embodiment is one in which A10 includes an amino sequence selected from the group consisting of Glu-Ile-Ile-His-Val [SEQ. ID. NO. 74], Asp-Ile-Ile-Met-Val [SEQ. ID. NO. 75], Phe-Ile-Thr-Phe-Ala-Pro [SEQ. ID. NO. 76], and Met-Glu-Ile-Ile-Thr [SEQ. ID. NO. 77].

NAP proteins AcaNAP5 and AcaNAP6 include the amino acid sequence Glu-Ile-Ile-His-Val [SEQ. ID. NO. 74] in A10, and are preferred NAPs according to this embodiment of the invention.

In one embodiment of this aspect of the invention, a preferred NAP molecule is one wherein (a) A3 has the sequence Glu-$A3_a$-$A3_b$, wherein $A3_a$ and $A3_b$ are independently selected amino acid residues;

(b) A4 is an amino acid sequence having a net anionic charge;

(c) A7 is selected from the group consisting of Val and Ile;

(d) A8 includes an amino acid sequence selected from the group consisting of Gly-Phe-Tyr-Arg-Asp [SEQ. ID. NO. 69], Gly-Phe-Tyr-Arg-Asn [SEQ. ID. NO. 70], Gly-Tyr-Tyr-Arg-Asp [SEQ. ID. NO. 71], Gly-Tyr-Tyr-Arg-Asn [SEQ. ID. NO. 72], and Gly-Leu-Tyr-Arg-Asp [SEQ. ID. NO. 73]; and (e) A10 includes an amino sequence selected from the group consisting of Glu-Ile-Ile-His-Val [SEQ. ID. NO. 74], Asp-Ile-Ile-Met-Val [SEQ. ID. NO. 75], Phe-Ile-Thr-Phe-Ala-Pro [SEQ. ID. NO. 76], and Met-Glu-Ile-Ile-Thr [SEQ. ID. NO. 77].

Pharmaceutical compositions comprising NAP proteins according to this embodiment, and methods of inhibiting blood coagulation comprising administering NAP proteins according to this embodiment also are contemplated by this invention. NAP proteins within this embodiment of the invention have at least one NAP domain. Preferred are NAPs having one or two NAP domains. NAP proteins AcaNAP5 and AcaNAP6 have one NAP domain and are preferred NAPs according to this embodiment of the invention.

In another preferred embodiment, a NAP molecule is one wherein (a) A3 is selected from the group consisting of Glu-Ala-Lys, Glu-Arg-Lys, Glu-Pro-Lys, Glu-Lys-Lys, Glu-Ile-Thr, Glu-His-Arg, Glu-Leu-Lys, and Glu-Thr-Lys;

(b) A4 is an amino acid sequence having a net anionic charge;

(c) A7 is Val or Ile;

(d) A8 includes an amino acid sequence selected from the group consisting of $A8_a$-$A8_b$-Gly-Phe-Tyr-Arg-Asp [SEQ. ID. NO. 78], $A8_a$-$A8_b$-Gly-Phe-Tyr-Arg-Asn [SEQ. ID. NO. 79], $A8_a$-$A8_b$-Gly-Tyr-Tyr-Arg-Asp [SEQ. ID. NO. 80], $A8_a$-$A8_b$-Gly-Tyr-Tyr-Arg-Asn [SEQ. ID. NO. 81], and $A8_a$-$A8_b$-Gly-Leu-Tyr-Arg-Asp [SEQ. ID. NO. 82], wherein at least one of $A8_a$ and $A8_b$ is Glu or Asp;

(e) A9 is an amino acid sequence of five amino acid residues; and (f) A10 includes an amino acid sequence selected from the group consisting of Glu-Ile-Ile-His-Val [SEQ. ID. NO. 74], Asp-Ile-Ile-Met-Val [SEQ. ID. NO. 75], Phe-Ile-Thr-Phe-Ala-Pro [SEQ. ID. NO. 76], and Met-Glu-Ile-Ile-Thr [SEQ. ID. NO. 77]. Pharmaceutical compositions comprising NAP proteins according to this embodiment, and methods of inhibiting blood coagulation comprising administering NAP proteins according to this embodiment also are contemplated by this invention. NAP proteins within this embodiment of the invention have at least one NAP domain. Preferred are NAPs having one or two NAP domains. Preferred are proteins having at least one NAP domain that is substantially the same as that of either AcaNAP5 [SEQ. ID. NO. 40] or AcaNAP6 [SEQ. ID. NO. 41]. NAP proteins AcaNAP5 [SEQ. ID. NOS. 4 and 40] and AcaNAP6 [SEQ. ID. NOS. 6 and 41] have one NAP domain and are especially preferred NAPs according to this embodiment of the invention.

Preferred NAP proteins having anticoagulant activity, including those having Factor Xa inhibitory activity, according to all the embodiments recited above for this aspect of the invention, can be derived from a nematode species. A preferred nematode species is selected from the group consisting of Ancylostoma caninum, Ancylostoma ceylanicum, Ancylostoma duodenale, Necator americanus, and Heligomosomoides polygyrus. Particularly preferred are NAP proteins AcaNAP5 and AcaNAP6 derived from Ancylostoma caninum.

This aspect of the invention also contemplates isolated recombinant cDNA molecules encoding a protein having anticoagulant and/or Factor Xa inhibitory activity, wherein the protein is defined according to each of the embodiments recited above for isolated NAP protein having anticoagulant and/or Factor Xa inhibitory activity. Preferred cDNAs according to this aspect of the invention code for AcaNAP5 and AcaNAP6.

The Factor Xa inhibitory activity of NAPs within this aspect of the invention can be determined using protocols described herein. Example A describes one such method. In brief, a NAP is incubated with factor Xa for a period of time, after which a factor Xa substrate is added. The rate of substrate hydrolysis is measured, with a slower rate compared to the rate in the absence of NAP indicative of NAP inhibition of factor Xa. Example C provides another method of detecting a NAP's inhibitory activity toward factor Xa when it is assembled into the prothrombinase complex, which more accurately reflects the normal physiological function of fxa in vivo. As described therein, factor Xa assembled in the prothrombinase complex is incubated with NAP, followed by addition of substrate. Factor Xa-mediated thrombin generation by the prothrombinase complex is measured by the rate of thrombin generation from this mixture.

NAPs having Anticoaculant Activity, including NAPs having Factor VIIa/TF Inhibitory Activity (FORMULA III)

In another aspect, NAPs of the present invention also include an isolated protein having anticoagulant activity, including and isolated protein having Factor VIIa/TF inhibitory activity and having one or more NAP domains, wherein each NAP domain includes the sequence:
Cys-A1-Cys-A2-Cys-A3-Cys-A4-Cys-A5-Cys-A6-Cys-A7-Cys-A8-Cys-A9-Cys-A10 ("FORMULA III"),
wherein
(a) A1 is an amino acid sequence of 7 to 8 amino acid residues;
(b) A2 is an amino acid sequence;
(c) A3 is an amino acid sequence of 3 amino acid residues;
(d) A4 is an amino acid sequence;
(e) A5 is an amino acid sequence of 3 to 4 amino acid residues;
(f) A6 is an amino acid sequence;
(g) A7 is an amino acid;
(h) A8 is an amino acid sequence of 11 to 12 amino acid residues;
(i) A9 is an amino acid sequence of 5 to 7 amino acid residues; and
(j) A10 is an amino acid sequence;
wherein each of A2, A4, A6 and A10 has an independently selected number of independently selected amino acid residues and each sequence is selected such that each NAP domain has in total less than about 120 amino acid residues.

Pharmaceutical compositions comprising NAP proteins according to this aspect, and methods of inhibiting blood coagulation comprising administering NAP proteins according to this aspect also are contemplated by this invention.

NAP proteins within this aspect of the invention have at least one NAP domain. Preferred are NAPs having one or two NAP domains Preferred are proteins having at least one NAP domain substantially the same as that of AcaNAPc2 [SEQ. ID. NO. 59]. NAP protein AcaNAPc2 [SEQ. ID. NO. 59] has one NAP domain and is an especially preferred NAP according to this aspect of the invention.

Preferred NAP proteins according to this aspect of the invention are those in which A2 is an amino acid sequence of 3 to 5 amino acid residues, A4 is an amino acid sequence of 6 to 19 amino acid residues, A6 is an amino acid sequence of 3 to 5 amino acid residues, and A10 is an amino acid sequence of 5 to 25 amino acid residues.

Accordingly, in one preferred aspect, provided are NAPs having anticoagulant activity, including factor VIIa/TF inhibitory activity, and having at least one NAP domain of formula III wherein the NAP domain includes the amino acid sequence:
Cys-A1-Cys-A2-Cys-A3-Cys-A4-Cys-A5-Cys-A6-Cys-A7-Cys-A8-Cys-A9-Cys-A10 wherein (a) Cys-A1 is selected from SEQ. ID. NOS. 83 and 205; (b) Cys-A2-Cys is selected from one of SEQ. ID. NOS. 206 to 208; (c) A3-Cys-A4 is selected from one of SEQ. ID. NOS. 209 to 222; (d) Cys-A5 is selected from SEQ. ID. NOS. 223 and 224; (e) Cys-A6 is selected from one of SEQ. ID. NOS. 225 to 227; (f) Cys-A7-Cys-A8 is selected from SEQ. ID. NOS. 228 and 229; (g) Cys-A9 is selected from SEQ. ID. NOS. 230 to 232; and (h) Cys-A10 is selected from one of SEQ. ID. NOS. 233 to 253.

In another preferred embodiment according to this aspect of the invention, A3 has the sequence Asp-A3$_a$-A3$_b$, wherein A3$_a$ and A3$_b$ are independently selected amino acid residues. More preferably, A3 is Asp-Lys-Lys.

In an additional preferred embodiment, A4 is an amino acid sequence having a net anionic charge.

In another preferred embodiment of this aspect of the invention, A5 has the sequence A5$_a$-A5$_b$-A5$_c$-A5$_d$ [SEQ. ID. NO. 84], wherein A5$_a$ through A5$_d$ are independently selected amino acid residues. Preferably, A5$_a$ is Leu and A5$_c$ is Arg.

According to this aspect of the invention, a preferred A7 amino acid residue is Val or Ile, more preferably Val.

An additional preferred embodiment of this aspect of the invention is one in which A8 includes the amino acid sequence A8$_a$-A8$_b$-A8$_c$-A8$_d$-A8$_e$-A8$_f$-A8$_g$ [SEQ. ID. NO. 68],
wherein
(a) A8$_a$ is the first amino acid residue in A8,
(b) at least one of A8$_a$ and A8$_b$ is selected from the group consisting of Glu or Asp, and
(c) A8$_c$ through A8$_g$ are independently selected amino acid residues.

Preferably, A8$_c$ is Gly, A8$_d$ is selected from the group consisting of Phe, Tyr, and Leu, A8$_e$ is Tyr, A8$_f$ is Arg, and A8$_g$ is selected from Asp and Asn. A preferred A8$_c$-A8$_d$-A8$_e$-A8$_f$-A8$_g$ sequence is Gly-Phe-Tyr-Arg-Asn [SEQ. ID. NO. 70].

In one embodiment, a preferred NAP molecule is one wherein:
(a) A3 has the sequence Asp-A3$_a$-A3$_b$, wherein A3$_a$ and A3$_b$ are independently selected amino acid residues;
(b) A4 is an amino acid sequence having a net anionic charge;
(c) A5 has the sequence A5$_a$-A5$_b$-A5$_c$-A5$_d$, wherein A5$_a$ through A5$_d$ are independently selected amino acid residues; and (d) A7 is selected from the group consisting of Val and Ile.
Pharmaceutical compositions comprising NAP proteins according to this embodiment, and methods of inhibiting blood coagulation comprising administering NAP proteins according to this embodiment also are contemplated by this invention. NAP proteins within this embodiment of the invention have at least one NAP domain. Preferred are NAPs having one or two NAP domains. NAP protein AcaNAPc2 has one NAP domain and is a preferred NAP according to this embodiment of the invention.

In another preferred embodiment, a NAP molecule is one wherein (a) A3 is Asp-Lys-Lys;

(b) A4 is an amino acid sequence having a net anionic charge;

(c) A5 has the sequence $A5_a$-$A5_b$-$A5_c$-$A5_d$ [SEQ. ID. NO. 85], wherein $A5_a$ through $A5_d$ are independently selected amino acid residues;

(d) A7 is Val; and (e) A8 includes an amino acid sequence $A8_a$-$A8_b$-Gly-Phe-Tyr-Arg-Asn [SEQ. ID. NO. 79], wherein at least one of $A8_a$ and $A8_b$ is Glu or Asp. Pharmaceutical compositions comprising NAP proteins according to this embodiment, and methods of inhibiting blood coagulation comprising administering NAP proteins according to this embodiment also are contemplated by this invention. NAP proteins within this embodiment of the invention have at least one NAP domain. Preferred are NAPs having one or two NAP domains. NAP protein AcaNAPc2 [SEQ. ID. NO. 59] has one NAP domain and is a preferred NAP according to this embodiment of the invention.

Preferred NAP proteins having anticoagulant activity, including those having Factor VIIa/TF inhibitory activity, according to all the embodiments recited above for this aspect of the invention, can be derived from a nematode species. A preferred nematode species is selected from the group consisting of *Ancylostoma caninum, Ancylostoma ceylanicum, Ancylostoma duodenale, Necator americanus*, and *Heligomosomoides polygyrus*. Particularly preferred is NAP protein AcaNAPc2 derived from *Ancylostoma caninum*.

This aspect of the invention also contemplates isolated recombinant cDNA molecules encoding a protein having anticoagulant aid/or Factor VIIa/TF inhibitory activity, wherein the protein is defined according to each of the embodiments recited above for isolated NAP protein having anticoagulant and/or Factor VIIa/TF inhibitory activity. A preferred cDNA according to this aspect has a nucleotide sequence [SEQ. ID. NO. 19] and codes for AcaNAPc2 [SEQ. ID. NO. 59].

The fVIIa/TF inhibitory activity of NAPs within this aspect of the invention can be determined using protocols described herein. Example E describes fVIIa/TF assays. There, the fVIIa/TF-mediated cleavage and liberation of the tritiated activation peptide from radiolabeled human factor IX ($^3$H-FIX) or the amidolytic hydrolysis of a chromogenic peptidyl substrate are measured. Interestingly, NAP fVIIa/TF inhibitors of the present invention require the presence of fXa in order to be active fVIIa/TF inhibitors. However, NAP fVIIa/TF inhibitors were equally effective in the presence of fXa in which the active site had been irreversibly occupied with the peptidyl chloromethyl ketone H-Glu-Gly-Arg-CMK (EGR), and thereby rendered catalytically inactive (EGR-fXa). While not wishing to be bound by any one explanation, it appears that a NAP having fVIIa/TF inhibition activity forms a binary complex with fXa by binding to a specific recognition site on the enzyme that is distinct from the primary recognition sites $P_4$–$P_1$, within the catalytic center of the enzyme. This is followed by the formation of a quaternary inhibitory complex with the fVIIa/TF complex. Consistent with this hypothesis is that EGR-fXa can fully support the inhibition of fVIIa/TF by NAPs inhibitory for fVIIa/TF despite covalent occupancy of the primary recognition sites ($P_4$–$P_1$) within the catalytic site of fXa by the tripeptidyl-chloromethyl ketone (EGR-CMK).

The fVIIa/TF inhibitory activity of NAPs also can be determined using the protocols in Example D, as well as the fXa assays described in Examples A and C. There, the ability of a NAP to inhibit the catalytic activity of a variety of enzymes is measured and compared to its inhibitory activity toward the fVIIa/TF complex. Specific inhibition of fVIIa/TF by a NAP is a desired characteristic for certain applications.

A further aspect of the invention includes an isolated protein having anticoagulant activity, and cDNAs coding for the protein, wherein said protein specifically inhibits the catalytic activity of the fVIIa/TF complex in the presence of fXa or catalytically inactive fXa derivative, but does not specifically inhibit the activity of FVIIa in the absence of TF and does not specifically inhibit prothrombinase. Preferred proteins according to this aspect of the invention have the characteristics described above for an isolated protein having Factor VIIa/TF inhibitory activity and having one or more NAP domains. A preferred protein according to this aspect of the invention is AcaNAPc2.

NAPs within this aspect of the invention are identified by their fVIIa/TF inhibitory activity in the presence of fXa or a fXa derivative, whether the derivative is catalytically active or not. The protocols described in Examples B, C, and F are useful in determining the anticoagulant activity of such NAPs. The protocol in Example A can detect a NAP's inactivity toward free fXa or prothrombinase. Data generated using the protcols in Example E will identify NAPs that require either catalytically active or inactive fXa to inhibit fVIIa/TF complex.

NAPs having Serine Protease Inhibitory Activity (FORMULA IV)

In an additional aspect, NAPs of the present invention also include an isolated protein having serine protease inhibitory activity and having one or more NAP domains, wherein each NAP domain includes the sequence:

Cys-A1-Cys-A2-Cys-A3-Cys-A4-Cys-A5-Cys-A6-Cys-A7-Cys-A8-Cys-A9-Cys-A10, ("FORMULA IV")

wherein (a) A1 is an amino acid sequence of 7 to 8 amino acid residues;

(b) A2 is an amino acid sequence;

(c) A3 is an amino acid sequence of 3 amino acid residues;

(d) A4 is an amino acid sequence;

(e) A5 is an amino acid sequence of 3 to 4 amino acid residues;

(f) A6 is an amino acid sequence;

(g) A7 is an amino acid;

(h) A8 is an amino acid sequence of 10 to 12 amino acid residues;

(i) As is an amino acid sequence of 5 to 7 amino acid residues; and (j) A10 is an amino acid sequence; wherein each of A2, A4, A6 and A10 has an independently selected number of independently selected amino acid residues and each sequence is selected such that each NAP domain has in total less than about 120 amino acid residues. Pharmaceutical compositions comprising NAP proteins according to this aspect, and methods of inhibiting blood coagulation comprising administering NAP proteins according to this aspect also are contemplated by this invention. NAP proteins within this aspect of the invention have at least one NAP domain. Preferred are NAPs having one or two NAP domains. Preferred are NAP domains that have amino acid sequences that are substantially the same as the NAP domains of HpoNAP5 [SEQ. ID. NO. 60] or NamNAP [SEQ. ID. NO. 61]. NAP proteins HpoNAP5 [SEQ. ID. NO. 60] and NamNAP [SEQ. ID. NO. 61] have one NAP domain and are preferred NAPs according to this aspect of the invention.

Preferred NAP proteins according to this aspect of the invention are those in which A2 is an amino acid sequence of 3 to 5 amino acid residues, A4 is an amino acid sequence of 6 to 19 amino acid residues, A6 is an amino acid sequence of 3 to 5 amino acid residues, and A10 is an amino acid sequence of 1 to 25 amino acid residues.

Thus, in one preferred aspect, NAPs exhibiting serine protease activity have at least one NAP domain of Formula IV which includes the amino acid sequence:

Cys-A1-Cys-A2-Cys-A3-Cys-A4-Cys-A5-Cys-A6-Cys-A7-Cys-A8-Cys-A9-Cys-A10 wherein (a) Cys-A1 is selected from SEQ. ID. NOS. 86 and 254; (b) Cys-A2-Cys is selected from one of SEQ. ID. NOS. 255 to 257; (c) A3-Cys-A4 is selected from one of SEQ. ID. NOS. 258 to 271; (d) Cys-A5 is selected from SEQ. ID. NOS. 272 and 273; (e) Cys-A6 is selected from one of SEQ. ID. NOS. 274 to 276; (f) Cys-A7-Cys-A8 is selected from one of SEQ. ID. NOS. 277 to 279; (g) Cys-A9 is selected from one of SEQ. ID. NOS. 280 to 282; and (h) Cys-A10 is selected from one of SEQ. ID. NOS. 283 to 307.

In another preferred embodiment, A3 has the sequence Glu-A3$_a$-A3$_b$, wherein A3$_a$ and A3$_b$ are independently selected amino acid residues. More preferably, A3 is Glu-Pro-Lys.

In an additional preferred embodiment, A4 is an amino acid sequence having a net anionic charge.

In another preferred embodiment, A5 has the sequence A5$_a$-A5$_b$-A5$_c$, wherein A5$_a$ through A5$_c$ are independently selected amino acid residues. Preferably, A5$_a$ is Thr and A5$_c$ is Asn. An especially preferred A5 sequence includes Thr-Leu-Asn or Thr-Met-Asn.

According to this aspect of the invention, a preferred A7 amino acid residue is Gln.

In one embodiment of this aspect of the invention, a preferred NAP molecule is one wherein (a) A3 has the sequence Glu-A3$_a$-A3$_b$, wherein A3$_a$ and A3$_b$ are independently selected amino acid residues;

(b) A4 is an amino acid sequence having a net anionic charge;

(c) A5 has the sequence A5$_a$-A5$_b$-A5$_c$, wherein A5$_a$ through A5$_c$ are independently selected amino acid residues, and (d) A7 is Gln. Pharmaceutical compositions comprising NAP proteins according to this embodiment, and methods of inhibiting blood coagulation comprising administering NAP proteins according to this embodiment also are contemplated by this invention. NAP proteins within this embodiment of the invention have at least one NAP domain. Preferred are NAPs having one or two NAP domains. NAP proteins HpoNAP5 [SEQ. ID. NO. 60] and NamNAP [SEQ. ID. NO. 61] have one NAP domain and are preferred NAPs according to this embodiment of the invention.

In another preferred embodiment, a NAP molecule is one wherein (a) A3 is Glu-Pro-Lys;

(b) A4 is an amino acid sequence having a net anionic charge;

(c) A5 is selected from Thr-Leu-Asn and Thr-Met-Asn; and (d) A7 is Gln. Pharmaceutical compositions comprising NAP proteins according to this embodiment, and methods of inhibiting blood coagulation comprising administering NAP proteins according to this embodiment also are contemplated by this invention. NAP proteins within this embodiment of the invention have at least one NAP domain. Preferred are NAPs having one or two NAP domains. NAP proteins HpoNAP5 [SEQ. ID. NO. 60] and Na NAP [SEQ. ID. NO. 61] have one NAP domain and are preferred NAPs according to this embodiment of the invention.

Preferred NAP proteins having serine protease inhibitory activity, according to all the embodiments recited above for this aspect of the invention, can be derived from a nematode species. A preferred nematode species is selected from the group consisting of *Ancylostoma caninum, Ancylostoma ceylanicum, Ancylostoma duodenale, Necator americanus,* and *Heligomosomoides polygyrus.* Particularly preferred are NAP proteins HpoNAP5 and NamNAP derived from *Heligomosomoides polygyrus* and *Necator americanus*, respectively.

This aspect of the invention also contemplates isolated recombinant cDNA molecules encoding a protein having serine protease inhibitory activity, wherein the protein is defined according to each of the embodiments recited above for isolated NAP protein having serine protease inhibitory activity. Preferred cDNAs according to this aspect have nucleotide sequences [SEQ. ID. NO. 14] (HpoNAP5) and [SEQ. ID. NO. 39] (NamNAP) and code for HpoNAP5 [SEQ. ID. NO. 60] and NamNAP [SEQ. ID. NO. 61].

The serine protease inhibitory activity can be determined using any of the assays disclosed in Examples A through F, or any commonly used enzymatic assay for measuring inhibition of serine protease activity. Procedures for a multitude of enzymatic assays can be found in the volumes of *Methods of Enzymology* or similar reference materials. Preferred NAPs have serine protease inhibitory activity directed toward enzymes in the blood coagulation cascade or toward trypsin/elastase.

NAPs having Anticoagulant Activity (FORMULA V)

In another aspect of the invention, NAPs of the present invention also include an isolated protein having anticoagulant activity and having one or more NAP domains, wherein each NAP domain includes the sequence:

Cys-A1-Cys-A2-Cys-A3-Cys-A4-Cys-A5-Cys-A6-Cys-A7-Cys-A8-Cys-A9-Cys-A10 ("FORMULA V"), wherein (a) A1 is an amino acid sequence of 7 to 8 amino acid residues;

(b) A2 is an amino acid sequence;

(c) A3 is an amino acid sequence of 3 amino acid residues;

(d) A4 is an amino acid sequence;

(e) A5 is an amino acid sequence of 3 to 4 amino acid residues;

(f) A6 is an amino acid sequence;

(g) A7 is an amino acid;

(h) A8 is an amino acid sequence of 11 to 12 amino acid residues;

(i) A9 is an amino acid sequence of 5 to 7 amino acid residues; AND (j) A10 is an amino acid sequence;

wherein each of A2, A4, A6 and A10 has an independently selected number of independently selected amino acid residues and each sequence is selected such that each NAP domain has in total less than about 120 amino acid residues. Pharmaceutical compositions comprising NAP proteins according to this aspect, and methods of inhibiting blood coagulation comprising administering NAP proteins according to this aspect also are contemplated by this invention. NAP proteins within this aspect of the invention have at least one NAP domain. Preferred are NAPs having one or two NAP domains. Preferred NAPs include those having at least one NAP domain having an amino acid sequence substantially the same as any of [SEQ. ID. NOS. 40 to 58]. NAP proteins AcaNAP5 [SEQ. ID. NO. 40], AcaNAP6 [SEQ. ID. NO. 41], AcaNAP48 [SEQ. ID. NO. 42], AcaNAP23 [SEQ. ID. NO. 43], AcaNAP24 [SEQ. ID. NO. 44], AcaNAP25 [SEQ. ID. NO. 45], AcaNAP44 [SEQ. ID. NO. 46], AcaNAP31 [SEQ. ID. NO. 47], AduNAP4 [SEQ. ID. NO. 55], AceNAP5 [SEQ. ID. NO. 57], and AceNAP7 [SEQ. ID. NO. 58] have one NAP domain and are preferred NAPs according to this aspect of the invention. NAP proteins AceNAP4 [SEQ. ID. NO. 62], AcaNAP45 [SEQ. ID. NO. 63], AcaNAP47 [SEQ. ID. NO. 64], and AduNAP7 [SEQ. ID. NO. 65] have two NAP domains and are preferred NAPs according to this aspect of the invention.

Preferred NAP proteins according to this aspect of the invention are those in which A2 is an amino acid sequence of 3 to 5 amino acid residues, A4 is an amino acid sequence of 6 to 19 amino acid residues, A6 is an amino acid sequence of 3 to 5 amino acid residues, and A10 is an amino acid sequence of 5 to 25 amino acid residues.

Preferred NAPs of the present invention according to this aspect include isolated proteins having anticoagulant activity and having at least one NAP domain of formula V which includes the following sequence:

Cys-A1-Cys-A2-Cys-A3-Cys-A4-Cys-A5-Cys-A6-Cys-A7-Cys-A8-Cys-A9-Cys-A10 wherein (a) Cys-A1 is selected from SEQ. ID. NOS. 87 and 308; (b) Cys-A2-Cys is selected from one of SEQ. ID. NOS. 309 to 311; (c) A3-Cys-A4 is selected from one of SEQ. ID. NOS. 312 to 325; (d) Cys-A5 is selected from SEQ. ID. NOS. 326 and 327; (e) Cys-A6 is selected from one of SEQ. ID. NOS. 328 to 330; (f) Cys-A7-Cys-A8 is selected from SEQ. ID. NOS. 331 to 332; (g) Cys-A9 is selected from one of SEQ. ID. NOS. 333 to 335; and (h) Cys-A10 is selected from one of SEQ. ID. NOS. 336 to 356.

In another preferred embodiment, A3 has the sequence Glu-$A3_a$-$A3_b$, wherein $A3_a$ and $A3_b$ are independently selected amino acid residues. More preferably, $A3_a$ is selected from the group consisting of Ala, Arg, Pro, Lys, Ile, His, Leu, and Thr, and A3b is selected from the group consisting of Lys, Thr, and Arg. Especially preferred A3 sequences are selected from the group consisting of Glu-Ala-Lys, Glu-Arg-Lys, Glu-Pro-Lys, Glu-Lys-Lys, Glu-Ile-Thr, Glu-His-Arg, Glu-Leu-Lys, and Glu-Thr-Lys.

In an additional preferred embodiment, A4 is an amino acid sequence having a net anionic charge.

According to this aspect of the invention, a preferred A7 amino acid residue is Val or Ile.

Another preferred embodiment of the invention is one in which A8 includes the amino acid sequence $A8_a$-$A8_b$-$A8_c$-$A8_d$-$A8_e$-$A8_f$-$A8_g$ [SEQ. ID. NO. 68], wherein (a) $A8_a$ is the first amino acid residue in A8, (b) at least one of $A8_a$ and $A8_b$ is selected from the group consisting of Glu or Asp, and (c) $A8_c$ through $A8_g$ are independently selected amino acid residues.

Preferably, $A8_c$ is Gly, $A8_d$ is selected from the group consisting of Phe, Tyr, and Leu, $A8_e$ is Tyr, $A8_f$ is Arg, and $A8_g$ is selected from Asp and Asn. A preferred $A8_c$-$A8_d$-$A8_e$-$A8_f$-$A8_g$ sequence is selected from the group consisting of Gly-Phe-Tyr-Arg-Asp [SEQ. ID. NO. 69], Gly-Phe-Tyr-Arg-Asn [SEQ. ID. NO. 70], Gly-Tyr-Tyr-Arg-Asp [SEQ. ID. NO. 71], Gly-Tyr-Tyr-Arg-Asn [SEQ. ID. NO. 72], and Gly-Leu-Tyr-Arg-Asp [SEQ. ID. NO. 73].

Another preferred embodiment is one in which A10 includes an amino sequence selected from the group consisting of Glu-Ile-Ile-His-Val [SEQ. ID. NO. 74], Asp-Ile-Ile-Met-Val [SEQ. ID. NO. 75], Phe-Ile-Thr-Phe-Ala-Pro [SEQ. ID. NO. 76], and Met-Glu-Ile-Ile-Thr [SEQ. ID. NO. 77]. NAP proteins AcaNAP5 [SEQ. ID. NOS. 4 and 40] and AcaNAP 6 [SEQ. ID. NOS. 6 and 41] include the amino acid sequence Glu-Ile-Ile-His-Val [SEQ. ID. NO. 74] in A10, and are preferred NAPs according to this embodiment of the invention. NAP protein AcaNAP48 [SEQ. ID. NO. 42] includes the amino acid sequence Asp-Ile-Ile-Met-Val [SEQ. ID. NO. 75] in A10 and is a preferred NAP according to this embodiment of the invention. NAP proteins AcaNAp23 [SEQ. ID. NO. 43], AcaNAP24 [SEQ. ID. NO. 44], AcaNAP25 [SEQ. ID. NO. 45], AcaNAP44 [SEQ. ID. NO. 46], AcaNAP31 [SEQ. ID. NO. 47], and AceNAP4 [SEQ. ID. NO. 48, 49 AND 62] include the amino acid sequence Phe-Ile-Thr-Phe-Ala-Pro [SEQ. ID. NO. 76] and are preferred NAPs according to this embodiment of the invention. NAP proteins AcaNAP45 [SEQ. ID. NOS. 50, 53 AND 63], AcaNAP47 [SEQ. ID. NO. 51, 54 AND 64], AduNAP7 [SEQ. ID. NO. 52, 56 AND 65], AduNAP4 [SEQ. ID. NO. 55], AceNAP5 [SEQ. ID. NO. 57], and AceNAP7 [SEQ. ID. NO. 58] include the amino acid sequence Met-Glu-Ile-Ile-Thr [SEQ. ID. NO. 77] and are preferred NAPs according to this embodiment of the invention.

In one embodiment, a preferred NAP molecule is one wherein (a) A3 has the sequence Glu-$A3_a$-$A3_b$, wherein $A3_a$ and $A3_b$ are independently selected amino acid residues;

(b) A4 is an amino acid sequence having a net anionic charge;

(c) A7 is selected from the group consisting of Val and Ile;

(d) AB includes an amino acid sequence selected from the group consisting of Gly-Phe-Tyr-Arg-Asp [SEQ. ID. NO. 69], Gly-Phe-Tyr-Arg-Asn [SEQ. ID. NO. 70], Gly-Tyr-Tyr-Arg-Asp [SEQ. ID. NO. 71], Gly-Tyr-Tyr-Arg-Asn [SEQ. ID. NO. 72], and Gly-Leu-Tyr-Arg-Asp [SEQ. ID. NO. 73]; and (e) A10 includes an amino sequence selected from the group consisting of Glu-Ile-Ile-His-Val [SEQ. ID. NO. 74], Asp-Ile-Ile-Met-Val [SEQ. ID. NO. 75], Phe-Ile-Thr-Phe-Ala-Pro [SEQ. ID. NO. 76], and Met-Glu-Ile-Ile-Thr [SEQ. ID. NO. 77]. Pharmaceutical compositions comprising NAP proteins according to this embodiment, and methods of inhibiting blood coagulation comprising administering NAP proteins according to this embodiment also are contemplated by this invention. NAP proteins within this aspect of the invention have at least one NAP domain. Preferred are NAPs having one or two NAP domains. NAP proteins AcaNAP5 [SEQ. ID. NOS. 4 and 40], AcaNAP6 [SEQ. ID. NOS. 6 and 41], AcaNAP48 [SEQ. ID. NO. 42], AcaNAP23 [SEQ. ID. NO. 43], AcaNAP24 [SEQ. ID. NO. 44], AcaNAP25 [SEQ. ID. NO. 45], AcaNAP44 [SEQ. ID. NO. 46], AcaNAP31 [SEQ. ID. NO. 47], AduNAP4 [SEQ. ID. NO. 55], AceNAP5 [SEQ. ID. NO. 57], and AceNAP7 [SEQ. ID. NO. 58] have one NAP domain and are preferred NAPs according to this embodiment. NAP proteins AceNAP4 [SEQ. ID. NO. 62], AcaNAP45 [SEQ. ID. NO. 63], AcaNAP47 [SEQ. ID. NO. 64], and AduNAP7 [SEQ. ID. NO. 65] have two NAP domains and are preferred NAPs according to this embodiment.

In another preferred embodiment, a NAP molecule is one wherein (a) A3 is selected from the group consisting of Glu-Ala-Lys, Glu-Arg-Lys, Glu-Pro-Lys, Glu-Lys-Lys, Glu-Ile-Thr, Glu-His-Arg, Glu-Leu-Lys, and Glu-Thr-Lys;

(b) A4 is an amino acid sequence having a net anionic charge;

(c) A7 is Val or Ile;

(d) A8 includes an amino acid sequence selected from the group consisting of $A8_a$-$A8_b$-Gly-Phe-Tyr-Arg-Asp [SEQ. ID. NO. 78], $A8_a$-$A8_b$-Gly-Phe-Tyr-Arg-Asn [SEQ. ID. NO. 79], $A8_a$-$A8_b$-Gly-Tyr-Tyr-Arg-Asp [SEQ. ID. NO. 80], $A8_a$-$A8_b$-Gly-Tyr-Tyr-Arg-Asn [SEQ. ID. NO. 81], and $A8_a$-$A8_b$-Gly-Leu-Tyr-Arg-Asp [SEQ. ID. NO. 82], wherein at least one of $A8_a$ and $A8_b$ is Glu or Asp;

(e) A9 is an amino acid sequence of five amino acid residues; and (f) A10 includes an amino acid sequence selected from the group consisting of Glu-Ile-Ile-His-Val [SEQ. ID. NO. 74], Asp-Ile-Ile-Met-Val [SEQ. ID. NO. 75], Phe-Ile-Thr-Phe-Ala-Pro [SEQ. ID. NO. 76], and Met-Glu-Ile-Ile-Thr [SEQ. ID. NO. 77]. Pharmaceutical compositions comprising NAP proteins according to this embodiment, and methods of inhibiting blood coagulation comprising administering NAP proteins according to this embodiment also are contemplated by this invention. NAP proteins within this embodiment of the invention have at least one NAP domain. Preferred are NAPs having one or two NAP domains. NAP proteins AcaNAP5 [SEQ. ID. NOS. 4 and 40], AcaNAP6 [SEQ. ID. NOS. 6 and 41], AcaNAP48 [SEQ. ID. NO. 42], AcaNAP23 [SEQ. ID. NO. 43], AcaNAP24 [SEQ. ID. NO. 44], AcaNAP25 [SEQ. ID. NO. 45], AcaNAP44 [SEQ. ID. NO. 46], AcaNAP31 [SEQ. ID. NO. 47], AduNAP4 [SEQ. ID. NO. 55], AceNAP5 [SEQ. ID. NO. 57], and AceNAP7 [SEQ. ID. NO. 58] have one NAP domain and are preferred NAPs according to this embodiment. NAP proteins AceNAP4 [SEQ. ID. NO. 62], AcaNAP45 [SEQ. ID. NO. 63], AcaNAP47 [SEQ. ID. NO. 64], and AduNAP7 [SEQ. ID. NO. 65] have two NAP domains and are preferred NAPs according to this embodiment.

Preferred NAP proteins having anticoagulant activity, according to all the embodiments recited above for this aspect of the invention, can be derived from a nematode species. A preferred nematode species is selected from the group consisting of *Ancylostoma caninum, Ancylostoma ceylanicum, Ancylostoma duodenale, Necator americanus,* and *Heligomosomoides polygyrus*. Particularly preferred are NAP proteins AcaNAP5 [SEQ. ID. NO. 4 and 40], AcaNAP6 [SEQ. ID. NO. 6 and 41], AcaNAP48 [SEQ. ID. NO. 42], AcaNAP23 [SEQ. ID. NO. 43], AcaNAP24 [SEQ. ID. NO. 44], AcaNAP25 [SEQ. ID. NO. 45], AcaNAP44 [SEQ. ID. NO. 46], AcaNAP45 [SEQ. ID. NO. 63], AcaNAP47 [SEQ. ID. NO. 64], and AcaNAP31 [SEQ. ID. NO. 47] derived from *Ancylostoma caninum*; AceNAP4 [SEQ. ID. NO. 62], AceNAP5 [SEQ. ID. NO. 57], and AceNAP7 [SEQ. ID. NO. 58] derived from *Ancylostoma ceylanicum*; and AduNAP7 [SEQ. ID. NO. 65] and AduNAP4 [SEQ. ID. NO. 55] derived from *Ancylostoma duodenale*.

This aspect of the invention also contemplates isolated recombinant cDNA molecules encoding a protein having anticoagulant activity, wherein the protein is defined according to each of the embodiments recited above for isolated NAP protein having anticoagulant activity. Preferred cDNAS according to this aspect include AcaNAP5 [SEQ. ID. NO. 3], AcaNAP6 [SEQ. ID. NO. 5], AcaNAP48 [SEQ. ID. NO. 38], AcaNAP23 [SEQ. ID. NO. 31], AcaNAP24 [SEQ. ID. NO. 32], AcaNAP25 [SEQ. ID. NO. 33], AcaNAP44 [SEQ. ID. NO. 35], AcaNAP31 [SEQ. ID. NO. 34], AduNAP4 [SEQ. ID. NO. 12], AceNAP5 [SEQ. ID. NO. 10], AceNAP7 [SEQ. ID. NO. 11], AceNAP4 [SEQ. ID. NO. 9], AcaNAP45 [SEQ. ID. NO. 36], AcaNAP47 [SEQ. ID. NO. 37], and AduNAP7 [SEQ. ID. NO. 13].

The anticoagulation activity of NAPs within this aspect of the invention can be determined using protocols described herein. Examples B and F present particulary useful methods for assessing a NAP's anticoagulation activity. The procedures described for detecting NAPs having fxa inhibitory activity (Examples A,C) and fVIIa/TF inhibitory activity (Example E) also are useful in evaluating a NAP's anticoagulation activity.

Oligonucleotides

Another aspect of this invention is an oligonucleotide comprising a sequence selected from

YG109: TCAGACATGT-ATAATCTCAT-GTTGG [SEQ. ID. NO. 88],

YG103: AAGGCATACC-CGGAGTGTGG-TG [SEQ. ID. NO. 89],

NAP-1: AAR-CCN-TGY-GAR-MGG-AAR-TGY [SEQ. ID. NO. 90], and

NAP-4.RC: TW-RWA-NCC-NTC-YTT-RCA-NAC-RCA [SEQ. ID. NO. 91].

These oligonucleotide sequences hybridize to nucleic acid sequences coding for NAP protein.

The isolated NAPs of the present invention include those having variations in the disclosed amino acid sequence or sequences, including fragments, naturally occurring mutations, allelic variants, randomly generated artificial mutants and intentional sequence variations, all of which conserve anticoagulant activity. The term "fragments" refers to any part of the sequence which contains fewer amino acids than the complete protein, as for example, partial sequences excluding portions at the amino-terminus, carboxy-terminus or between the amino-terminus and carboxy-terminus of the complete protein.

The isolated NAPs of the present invention also include proteins having a recombinant amino acid sequence or sequences which conserve the anticoagulant activity of the NAP domain amino acid sequence or sequences. Thus, as used herein, the phrase "NAP protein" or the term "protein" when referring to a protein comprising a NAP domain, means, without discrimination, native NAP protein and NAP protein made by recombinant means. These recombinant proteins include hybrid proteins, such as fusion proteins, proteins resulting from the expression of multiple genes within the expression vector, proteins resulting from expression of multiple genes within the chromosome of the host cell, and may include a polypeptide having anticoagulant activity of a disclosed protein linked by peptide bonds to a second polypeptide. The recombinant proteins also include variants of the NAP domain amino acid sequence or sequences of the present invention that differ only by conservative amino acid substitution. Conservative amino acid substitutions are defined as "sets" in Table 1 of Taylor, W. R., J. Mol. Biol., 188:233 (1986). The recombinant proteins also include variants of the disclosed isolated NAP domain amino acid sequence or sequences of the present invention in which amino acid substitutions or deletions are made which conserve the anticoagulant activity of the isolated NAP domain sequence or sequences.

One preferred embodiment of the present invention is a protein isolated by biochemical methods from the nematode, *Ancylostoma caninum*, as described in Example 1. This protein increases the clotting time of human plasma in the PT and aPTT assays, contains one NAP domain, and is characterized by an N-terminus having the amino acid sequence, Lys-Ala-Tyr-Pro-Glu-Cys-Gly-Glu-Asn-Glu-Trp-Leu-Asp [SEQ. ID. NO. 92], and a molecular weight of about 8.7 kilodaltons to about 8.8 kilodaltons as determined by mass spectrometry.

Further preferred embodiments of the present invention include the proteins having anticoagulant activity made by recombinant methods from the cDNA library isolated from the nematode, *Ancylostoma caninum*, for example, AcaNAP5 [SEQ. ID. NO. 4 or 40], AcaNAP6 [SEQ. ID. NO. 6 or 41], Pro-AcaNAP5 [SEQ. ID. NO. 7], Pro-AcaNAP6 [SEQ. ID. NO. 8], AcaNAP48 [SEQ. ID. NO. 42], AcaNAP23 [SEQ. ID. NO. 43], AcaNAP24 [SEQ. ID. NO. 44], AcaNAP25 [SEQ. ID. NO. 45], AcaNAP44 [SEQ. ID. NO. 46], AcaNAP31 [SEQ. ID. NO. 47], AcaNAP45 [SEQ. ID. NO. 63], AcaNAP47 [SEQ. ID. NO. 64], and AcaNAPc2 [SEQ. ID. NO. 59]; isolated from the nematode, *Ancyclostoma ceylanium*, for example, AceNAP4 [SEQ. ID. NO. 62], AceNAP5 [SEQ. ID. NO. 57], and AceNAP7 [SEQ. ID. NO. 58]; isolated from the nematode, *Ancyclostoma duodenale*, for example, AduNAP4 [SEQ. ID. NO. 55] and AduNAP7 [SEQ. ID. NO. 65]; isolated from the nematode *Heligmosmoides polygyrus*, for example, HpoNAP5 [SEQ. ID. NO 60]; and the nematode *Necator americanus*, for example, NamNAP [SEQ. ID. NO. 61]. The amino acid sequences of these proteins are shown in FIGS. 11 and 16 and elsewhere. Each such preferred embodiment increases the clotting time of human plasma in the PT and aPTT assays and contains at least one NAP domain.

With respect to "isolated proteins", the proteins of the present invention are isolated by methods of protein purification well known in the art, or as disclosed below. They may be isolated from a natural source, from a chemical mixture after chemical synthesis on a solid phase or in solution such as solid-phase automated peptide synthesis, or from a cell culture after production by recombinant methods.

As described further hereinbelow, the present invention also contemplates pharmaceutical compositions comprising NAP and methods of using NAP to inhibit the process of blood coagulation and associated thrombosis. Oligonucleotide probes useful for identifying NAP nucleic acid in a sample also are within the purview of the present invention, as described more fully hereinbelow.

1. NAP Isolated From Natural Sources.

The preferred isolated proteins (NAPs) of the present invention may be isolated and purified from natural sources. Preferred as natural sources are nematodes; suitable nematodes include intestinal nematodes such as *Ancylostoma caninum, Ancylostoma ceylanicum, Ancylostoma duodenale, Necator americanus* and *Heligmosomoides polygyrus*. Especially preferred as a natural source is the hematophagous nematode, the hookworm, *Ancylostoma caninum*.

The preferred proteins of the present invention are isolated and purified from their natural sources by methods known in the biochemical arts. These methods include preparing a soluble extract and enriching the extract using chromatographic methods on different solid support matrices. Preferred methods of purification would include preparation of a soluble extract of a nematode in 0.02 M Tris-HCl, pH 7.4 buffer containing various protease inhibitors, followed by sequential chromatography of the extract through columns containing Concanavalin-A Sepharose matrix, Poros20 HQ cation-ion exchange matrix, Superdex30 gel filtration matrix and a C18 reverse-phase matrix. The fractions collected from such chromatography columns may be selected by their ability to increase the clotting time of human plasma, as measured by the PT and aPTT assays, or their ability to inhibit factor Xa amidolytic activity as measured in a calorimetric amidolytic assay using purified enzyme, or by other methods disclosed in Examples A to F herein. An example of a preferred method of purification of an isolated protein of the present invention would include that as disclosed in Example 1.

The preferred proteins of the present invention, when purified from a natural source, such as *Ancylostoma caninum*, as described, include those which contain the amino acid sequence: Lys-Ala-Tyr-Pro-Glu-Cys-Gly-Glu-Asn-Glu-Trp-Leu-Asp [SEQ. ID. NO. 92]. Especially preferred are the purified proteins having this amino acid sequence at its amino terminus, such as shown in FIG. 2 (AcaNAP5 [SEQ. ID. NO. 4]) or FIG. 4 (AcaNAP6 [SEQ. ID. NO. 6]). One preferred protein of the present invention was demonstrated to have the amino acid sequence, Lys-Ala-Tyr-Pro-Glu-Cys-Gly-Glu-Asn-Glu-Trp-Leu-Asp [SEQ. ID. NO. 92] at its amino-terminus and a molecular weight of 8.7 to 8.8 kilodaltons, as determined by mass spectrometry.

2. NAP Made by Chemical Synthesis.

The preferred isolated NAPs of the present invention may be synthesized by standard methods known in the chemical arts.

The isolated proteins of the present invention may be prepared using solid-phase synthesis, such as that described by Merrifield, J. Amer. Chem. Soc., 85:2149 (1964) or other equivalent methods known in the chemical arts, such as the method described by Houghten in Proc. Natl. Acad. Sci., 82:5132 (1985).

Solid-phase synthesis is commenced from the C-terminus of the peptide by coupling a protected amino acid or peptide to a suitable insoluble resin. Suitable resins include those containing chloromethyl, bromomethyl, hydroxylmethyl, aminomethyl, benzhydryl, and t-alkyloxycarbonylhydrazide groups to which the amino acid can be directly coupled.

In this solid phase synthesis, the carboxy terminal amino acid, having its alpha amino group and, if necessary, its reactive side chain group suitably protected, is first coupled to the insoluble resin. After removal of the alpha amino protecting group, such as by treatment with trifluoroacetic acid in a suitable solvent, the next amino acid or peptide, also having its alpha amino group and, if necessary, any reactive side chain group or groups suitably protected, is coupled to the free alpha amino group of the amino acid coupled to the resin. Additional suitably protected amino acids or peptides are coupled in the same manner to the growing peptide chain until the desired amino acid sequence is achieved. The synthesis may be done manually, by using automated peptide synthesizers, or by a combination of these.

The coupling of the suitably protected amino acid or peptide to the free alpha amino group of the resin-bound amino acid can be carried out according to conventional coupling methods, such as the azide method, mixed anhydride method, DCC (dicyclohexylcarbodiimide) method, activated ester method (p-nitrophenyl ester or N-hydroxysuccinimide ester), BOP (benzotriazole-1-yloxy-tris (diamino) phosphonium hexafluorophosphate) method or Woodward reagent K method.

It is common in peptide synthesis that the protecting groups for the alpha amino group of the amino acids or peptides coupled to the growing peptide chain attached to the insoluble resin will be removed under conditions which do not remove the side chain protecting groups. Upon completion of the synthesis, it is also common that the peptide is removed from the insoluble resin, and during or after such removal, the side chain protecting groups are removed.

Suitable protecting groups for the alpha amino group of all amino acids and the omega amino group of lysine include benzyloxycarbonyl, isonicotinyloxycarbonyl, o-chlorobenzyloxycarbonyl, p-nitrophenyloxycarbonyl, p-methoxyphenyloxycarbonyl, t-butoxycarbonyl, t-amyloxycarbonyl, adamantyloxycarbonyl, 2-(4-biphenyl)-2-propyloxycarbonyl, 9-fluorenylmethoxycarbonyl, methylsulfonylethoxylcarbonyl, trifluroacetyl, phthalyl, formyl, 2-nitrophenylsulfphenyl, diphenylphosphinothioyl, dimethylphosphinothioyl, and the like.

Suitable protecting groups for the carboxy group of aspartic acid and glutamic acid include benzyl ester, cyclohexyl ester, 4-nitrobenzyl ester, t-butyl ester, 4-pyridylmethyl ester, and the like.

Suitable protecting groups for the guanidino group of arginine include nitro, p-toluenesulfonyl, benzyloxycarbonyl, adamantyloxycarbonyl, p-methoxybenzenesulfonyl, 4-methoxy-2,6-dimethylbenzenesulfonyl, 1,3,5-trimethylphenylsulfonyl, and the like.

Suitable protecting groups for the thiol group of cysteine include p-methoxybenzyl, triphenylmethyl, acetylaminomethyl, ethylcarbamoyl, 4-methylbenzyl, 2,4,6-trimethylbenzyl, and the like.

Suitable protecting groups for the hydroxy group of serine include benzyl, t-butyl, acetyl, tetrahydropyranyl, and the like.

The completed peptide may be cleaved from the resin by treatment with liquid hydrofluoric acid containing one or more thio-containing scavengers at reduced temperatures. The cleavage of the peptide from the resin by such treatment will also remove all side chain protecting groups from the peptide.

The cleaved peptide is dissolved in dilute acetic acid followed by filtration, then is allowed to refold and establish proper disulfide bond formation by dilution to a peptide concentration of about 0.5 mM to about 2 mM in a 0.1 M acetic acid solution. The pH of this solution is adjusted to about 8.0 using ammonium hydroxide and the solution is stirred open to air for about 24 to about 72 hours.

The refolded peptide is purified by chromatography, preferably by high pressure liquid chromatography on a reverse phase column, eluting with a gradient of acetonitrile in water (also containing 0.1% trifluoroacetic acid), with the preferred gradient running from 0 to about 80% acetonitrile in water. Upon collection of fractions containing the pure peptide, the fractions are pooled and lyophilized to the solid peptide.

3. NAP Made By Recombinant Methods.

Alternatively, the preferred isolated NAPs of the present invention may be made by recombinant DNA methods taught herein and well known in the biological arts. Sambrook, J., Fritsch, E. F. and Maniatis, T., *Molecular Cloning, A Laboratory Manual, Second Edition*, volumes 1 to 3, Cold Spring Harbor Laboratory Press (1989).

Recombinant DNA methods allow segments of genetic information, DNA, from different organisms, to be joined together outside of the organisms from which the DNA was obtained and allow this hybrid DNA to be incorporated into a cell that will allow the production of the protein for which the original DNA encodes.

Genetic information encoding a protein of the present invention may be obtained from the genomic DNA or mRNA of an organism by methods well known in the art. Preferred methods of obtaining this genetic information include isolating mRNA from an organism, converting it to its complementary DNA (cDNA), incorporating the cDNA into an appropriate cloning vector, and identifying the clone which contains the recombinant cDNA encoding the desired protein by means of hybridization with appropriate oligonucleotide probes constructed from known sequences of the protein.

The genetic information in the recombinant cDNA encoding a protein of the present invention may be ligated into an expression vector, the vector introduced into host cells, and the genetic information expressed as the protein for which it encodes.

(A) Preparation of cDNA Library.

Preferred natural sources of mRNA from which to construct a cDNA library are nematodes which include intestinal nematodes such as *Ancylostoma caninum, Ancylostoma ceylanicum, Ancylostoma duodenale, Necator americanus* and *Heligmosomoides polygyrus*. Especially preferred as a natural source of mRNA is the hookworm nematode, *Ancylostoma caninum*.

Preferred methods of isolating mRNA encoding a protein of the present invention, along with other mRNA, from an organism include chromatography on poly U or poly T affinity gels. Especially preferred methods of isolating the mRNA from nematodes include the procedure and materials provided in the QuickPrep mRNA Purification kit (Pharmacia).

Preferred methods of obtaining double-stranded cDNA from isolated mRNA include synthesizing a single-stranded cDNA on the mRNA template using a reverse transcriptase, degrading the RNA hybridized to the cDNA strand using a ribonuclease (RNase), and synthesizing a complementary DNA strand by using a DNA polymerase to give a double-stranded cDNA. Especially preferred methods include those wherein about 3 micrograms of mRNA isolated from a nematode is converted into double-stranded cDNA making use of Avian Myeloblastosis Virus reverse transcriptase, RNase H, and *E. coli* DNA polymerase I and T4 DNA polymerase.

cDNA encoding a protein of the present invention, along with the other cDNA in the library constructed as above, are then ligated into cloning vectors. Cloning vectors include a DNA sequence which accommodates the cDNA from the cDNA library. The vectors containing the cDNA library are introduced into host cells that can exist in a stable manner and provide a environment in which the cloning vector is replicated. Suitable cloning vectors include plasmids, bacteriophages, viruses and cosmids. Preferred cloning vectors include the bacteriophages. Cloning vectors which are especially preferred include the bacteriophage, lambda gt11 Sfi-Not vector.

The construction of suitable cloning vectors containing the cDNA library and control sequences employs standard ligation and restriction techniques which are well known in the art. Isolated plasmids, DNA sequences or synthesized oligonucleotides are cleaved, tailored and religated in the form desired.

With respect to restriction techniques, site-specific cleavage of cDNA is performed by treating with suitable restriction enzyme under conditions which are generally understood in the art, and the particulars of which are specified by the manufacturer of these commercially available restriction enzymes. For example, see the product catalogs of New England Biolabs, Promega and Stratagene Cloning Systems.

Generally, about 1 microgram of the cDNA is cleaved by treatment in about one unit of a restriction enzyme in about 20 microliters of buffer solution. Typically, an excess of restriction enzyme is used to ensure complete cleavage of the cDNA. Incubation times of about 1 to 2 hours at about 37° C. are usually used, though exceptions are known. After each cleavage reaction, the protein may be removed by extraction with phenol/chloroform, optionally followed by chromatography over a gel filtration column, such as Sephadex® G50. Alternatively, cleaved cDNA fragments may be separated by their sizes by electrophoresis in polyacrylamide or agarose gels and isolated using standard techniques. A general description of size separations is found in Methods of Enzymology, 65:499–560 (1980).

The restriction enzyme-cleaved cDMA fragments are then ligated into a cloning vector.

With respect to ligation techniques, blunt-end ligations are usually performed in about 15 to about 30 microliters of a pH 7.5 buffer comprising about 1 mM ATP and about 0.3 to 0.6 (Weiss) units of T4 DNA ligase at about 14° C. Intermolecular "sticky end" ligations are usually performed at about 5 to 100 nanomolar total-end DNA concentrations. Intermolecular blunt-end ligations (usually employing about 10 to 30-fold molar excess of linkers) are performed at about 1 micromolar total-end DNA concentrations.

(B) Preparation of cDNA Encoding NAP.

Cloning vectors containing the cDNA library prepared as disclosed are introduced into host cells, the host cells are cultured, plated, and then probed with a hybridization probe to identify clones which contain the recombinant cDNA encoding a protein of the present invention. Preferred host cells include bacteria when phage cloning vectors are used. Especially preferred host cells include *E. coli* strains such as strain Y1090.

Alternatively, the recombinant cDNA encoding a protein of the present invention may be obtained by expression of such protein on the outer surface of a filamentous phage and then isolating such phage by binding them to a target protein involved in blood coagulation.

An important and well known feature of the genetic code is its redundancy—more than one triplet nucleotide sequence codes for one amino acid. Thus, a number of different nucleotide sequences are possible for recombinant cDNA molecules which encode a particular amino acid sequence for a NAP of the present invention. Such nucleotide sequences are considered functionally equivalent since they can result in the production of the same amino acid sequence in all organisms. Occasionally, a methylated variant of a purine or pyrimidine may be incorporated into a given nucleotide sequence. However, such methylations do not affect the coding relationship in any way.

(1) Using Oligonucleotide Probes.

Hybridization probes and primers are oligonucleotide sequences which are complementary to all or part of the recombinant cDNA molecule that is desired. They may be prepared using any suitable method, for example, the phosphotriester and phosphodiester methods, described respectively in Narang, S. A. et al., Methods in Enzymology, 68:90 (1979) and Brown, E. L. et al., Methods in Enzymology, 68:109 (1979), or automated embodiments thereof. In one such embodiment, diethylphosphoramidites are used as starting materials and may be synthesized as described by Beaucage et al., Tetrahedron Letters, 22:1859–1862 (1981). One method for synthesizing oligonucleotides on a modified solid support is described in U.S. Pat. No. 4,458,066. Probes differ from primers in that they are labelled with an enzyme, such as horseradish peroxidase, or radioactive atom, such as $^{32}P$, to facilitate their detection. A synthesized probe is radiolabeled by nick translation using *E. coli* DNA polymerase I or by end labeling using alkaline phosphatase and T4 bacteriophage polynucleotide kinase.

Preferred hybridization probes include oligonucleotide sequences which are complementary to a stretch of the single-stranded cDNA encoding a portion of the amino acid sequence of a NAP purified from a nematode, such as the hookworm, *Ancylostoma caninum*. For example, a portion of the amino acid sequence shown in FIG. 2 (AcaNAP5) [SEQ. ID. NO. 4] or FIG. 4 (AcaNAP6 [SEQ. ID. NO. 6]) can be used. Especially preferred hybridization probes include those wherein their oligonucleotide sequence is complementary to the stretch of the single-stranded cDNA encoding the amino acid sequence: Lys-Ala-Tyr-Pro-Glu-Cys-Gly-Glu-Asn-Glu-Trp [SEQ. ID. NO. 93]. Such hybridization probes include the degenerate probe having the oligonucleotide sequence: AAR GCi TAY CCi GAR TGY GGi GAR AAY GAR TGG [SEQ. ID. NO. 94], wherein R is A or G, Y is T or C, and i is inosine. A preferred recombinant cDNA molecule encoding a protein of the present invention is identified by its ability to hybridize to this probe.

Preferred hybridization probes also include the pair NAP-1 [SEQ. ID. NO. 90] and NAP-4.RC [SEQ. ID. NO. 91], and the pair YG109 [SEQ. ID. NO. 88] and YG103 [SEQ. ID. NO. 89], both of which are described in Examples 13 and 12, respectively.

Upon identification of the clone containing the desired cDNA, amplification is used to produce large quantities of a gene encoding a protein of the present invention in the form of a recombinant cDNA molecule.

Preferred methods of amplification include the use of the polymerase chain reaction (PCR). See, e.g., *PCR Technology*, W. H. Freeman and Company, New York (Edit. Erlich, H. A. 1992). PCR is an in vitro amplification method for the synthesis of specific DNA sequences. In PCR, two oligonucleotide primers that hybridize to opposite strands and flank the region of interest in the cDNA of the clone are used. A repetitive series of cycles involving cDNA denaturation into single strands, primer annealing to the single-stranded cDNA, and the extension of the annealed primers by DNA polymerase results in number of copies of cDNA, whose termini are defined by the 5-ends of the primers, approximately doubling at every cycle. *Ibid.*, p.1. Through PCR amplification, the coding domain and any additional primer encoded information such as restriction sites or translational signals (signal sequences, start codons and/or stop codons) of the recombinant cDNA molecule to be isolated is obtained.

Preferred conditions for amplification of cDNA include those using Taq polymerase and involving 30 temperature cycles of: 1 minute at 95° C.; 1 minute at 50° C.; 1.5 minutes at 72° C. Preferred primers include the oligo(dT)-NotI primer, AATTCGCGGC CGC(T)₁₅ [SEQ. ID. NO. 95], obtained from Promega Corp. in combination with either (i) the degenerate primer having the oligonucleotide sequence: AAR GCi TAY CCi GAR TGY GGi GAR AAY GAR TGG [SEQ. ID. NO. 94], wherein R is A or G, Y is T or C, and i is inosine, or (ii) the lambda gt11 primer #1218, GGTG-GCGACG ACTCCTGGAG CCCG [SEQ. ID. NO. 96], obtained from New England Biolabs.

The nucleic acid sequence of a recombinant cDNA molecule made as disclosed is determined by methods based on the dideoxy method of Sanger, F. et al, Proc. Natl. Acad. Sci. USA, 74:5463 (1977) as further described by Messing, et al., Nucleic Acids Res., 9:309 (1981).

Preferred recombinant cDNA molecules made as disclosed include those having the nucleic acid sequences of FIGS. 1, 3, 7, 9, 13, and 14.

(2) Using NAP cDNAs As Probes.

Also especially preferred as hybridization probes are oligonucleotide sequences encoding substantially all of the amino acid sequence of a NAP purified from the nematode, the hookworm, *Ancylostoma caninum*. Especially preferred probes include those derived from the AcaNAP5 and AcaNAP6 genes and having the following nucleic acid sequences (AcaNAP5 gene):

the cDNAs through their 5'-end. Indeed, cDNA libraries of sufficient size may contain several cDNAs which derive from the same mRNA but which are 5'-terminally truncated at various positions such that some of them may be expressed as fusion products. A strategy along this line, which relies on the ability of the leucine zippers Jun and Fos to form heterodimers was recently described. See, Crameri, R. and Suter, M., Gene, 137:69–75 (1993).

We have found a novel alternative and direct way to convalently link cDNA gene products to the phage surface; the finding is based on the observation that proteins fused to the C-terminus of phage coat protein 6 can be functionally displayed. This observation has led to the development of a phagemid system as described herein which allows the expression of functionally displayed cDNA products, which in turn permits the affinity-selection of phage particles which contain the cDNA required for the production of the displayed cDNA product. This system provides the basis for the isolation of cDNAs which encode a protein of the present invention. Once isolated, recombinant cDNA molecules containing such cDNA can be used for expression of the proteins of the present invention in other expression systems. The recombinant cDNA molecules made in this way are considered to be within the scope of the present invention.

```
AAG GCA TAC CCG GAG TGT GGT GAG                          [SEQ. ID. NO. 1]

AAT GAA TGG CTC GAC GAC TGT GGA ACT CAG AAG CCA TGC GAG GCC

AAG TGC AAT GAG GAA CCC CCT GAG GAG GAA GAT CCG ATA TGC CGC

TCA CGT GGT TGT TTA TTA CCT CCT GCT TGC GTA TGC AAA GAC GGA

TTC TAC AGA GAC ACG GTG ATC GGC GAC TGT GTT AGG GAA GAA GAA

TGC GAC CAA CAT GAG ATT ATA CAT GTC TGA,
``` or FIG. 3 (AcaNAP6 gene):

```
AAG GCA TAC CCG GAG TGT GGT GAG                          [SEQ. ID. NO. 2]

AAT GAA TGG CTC GAC GTC TGT GGA ACT AAG AAG CCA TGC GAG GCC

AAG TGC AGT GAG GAA GAG GAG GAA GAT CCG ATA TGC CGA TCA TTT

TCT TGT CCG GGT CCC GCT GCT TGC GTA TGC GAA GAC GGA TTC TAC

AGA GAC ACG GTG ATC GGC GAC TGT GTT AAG GAA GAA GAA TGC GAC

CAA CAT GAG ATT ATA CAT GTC TGA.
```

Preferred hybridization probes also include sequences encoding a substantial part of the amino acid sequence of a NAP, such as the PCR fragment generated with the primer couple NAP-1 [SEQ. ID. NO. 90] and NAP-4.RC [SEQ. ID. NO. 91] as described in Example 13.

(3) Using Phage Display.

Disclosed herein is a method to select cDNAs encoding the proteins of the present invention from whole cDNA libraries making use of filamentous phage display technology. Current display technology with filamentous phage relies on the in-frame insertion of coding regions of interest into gene 3 or gene 8 which code for the attachment protein and major coat protein of the phage, respectively. Those skilled in the art will recognize that various difficulties are inherent in performing this with a vast mixture of cDNAs of unknown sequence and that the most practical way to obtain functional display of cDNA products would consist of fusing Recombinant cDNA molecules of the present invention are isolated by preparing a cDNA library from a natural source (as for example, a nematode such as a hookworm), ligating this cDNA library into appropriate phagemid vectors, transforming host cells with these vectors containing the cDNAs, culturing the host cells, infecting the transformed cells with an appropriate helper phage, separating phage from the host cell culture, separating phage expressing a protein of the present invention on its surface, isolating these phage, and isolating a recombinant cDNA molecule from such phage.

The phagemid vectors are constructed using the pUC119 expression vector described by Vieira, J. and Messing, J., Methods in Enzymology, 15:3–11 (1987). The filamentous phage gene 6 encoding a surface protein of the phage is modified on its 5' and 3' ends by the addition of HindIII and SfiI restriction sites, respectively, by use of three forward primers and one backward primer using PCR. This results in three DNA fragments which are further modified by addition to their 3' ends of NotI and BamHI restriction sites by PCR. After separate digestion of the three DNA fragments with HindIII and BamHI, the three DNA fragments are ligated into the pUC119 to give pDONG61, pDONG62 and pDONG63 expression vectors. These vectors permit the insertion of cDNA as SfiI-NotI fragments into them.

cDNA libraries are prepared from natural sources, such as nematodes, as described in Examples 2, 9, and 13. Preferred nematodes from which to make such libraries include the intestinal nematodes such as *Ancylostoma caninum, Ancylostoma ceylanicum, Ancylostoma duodenale, Necator americanus* and *Heligmosomoides polygyrus.*

A cDNA library as SfiI-NotI fragments may be directly directionally ligated into the phagemid vectors pDONG61, pDONG62 and pDONG63. Alternatively, a cDNA library which has been ligated into the lambda gt11 phage vector as described in Example 2 can be recovered by PCR, followed by isolation with electrophoresis and then directional ligation into these vectors. In the latter approach, preferred conditions for PCR use Taq polymerase; the primers, lambda gt11 primer #1218 having the sequence GGTGGCGACG ACTCCTGGAG CCCG (New England Biolabs, Beverly, Mass., USA) [SEQ. ID. NO. 96] and the oligo(dT)-NotI primer having the sequence, AATTCGCGGC CGC(T)$_{15}$, (Promega Corp.) [SEQ. ID. NO. 95]; and 20 temperature cycles of 1 minute at 95° C., 1 minute at 50° C., and 3 minutes at 72° C., followed by 10 minutes at 65° C.

Host cells are transformed with the pDONG expression vectors containing a cDNA library. Preferred host cells include *E. coli* strains, with strain TG1 being especially preferred. Preferred methods for the transformation of *E. coli* host cells include electroporation.

The transformed cells are cultured at 37° C. in LB medium supplemented with 1% glucose and 100 micrograms/ml carbenicillin until the optical absorbance at 600 nm reaches the value of 0.5 and then are infected with VCSM 13 helper phage (Stratagene) at a multiplicity of infection (moi) of 20.

The phage are separated from the culture by centrifugation, then are purified by precipitations with polyethylene glycol/sodium chloride.

The phage which express a NAP of the present invention on their surface are isolated by taking advantage of the ability of the NAP to bind to a target protein involved in blood coagulation, for example, Factor Xa.

Preferred methods of isolating such phage include a method comprising the steps of:
(1) combining a solution of factor Xa labelled to biotin with a solution of such phage;
(2) incubating this mixture;
(3) contacting a solid phase labelled with streptavidin with this mixture;
(4) incubating the solid phase with the mixture;
(5) removing the solid phase from the mixture and contacting the solid phase with buffer to remove unbound phage;
(6) contacting the solid phase with a second buffer to remove the bound phage from the solid phase;
(7) isolating such phage;
(8) transforming host cells with such phage;
(9) culturing the transformed host cells;
(10) infecting transformed host cells with VCSM13 helper phage;
(11) isolating the phage from the host cell culture; and
(12) repeating steps (1) to (11) four more times.

An especially preferred method of isolating such phage include the method as detailed in Example 10.

Single-stranded DNA was prepared from the isolated phages and their inserts 3' to the filamentous phage gene 6 sequenced.

FIG. 9 depicts the recombinant cDNA molecule, AcaNAPc2, isolated by the phage display method. The deduced amino acid sequence of the protein of the present invention encoded by AcaNAPc2 is also shown in this figure.

(C) Preparation of Recombinant NAP.

The recombinant cDNA molecules of the present invention when isolated as disclosed are used to obtain expression of the NAPs of the present invention. Generally, a recombinant cDNA molecule of the present invention is incorporated into an expression vector, this expression vector is introduced into an appropriate host cell, the host cell is cultured, and the expressed protein is isolated.

Expression vectors are DNA sequences that are required for the transcription of cloned copies of genes and translation of their mRNAs in an appropriate host. These vectors can express either procaryotic or eucaryotic genes in a variety of cells such as bacteria, yeast, mammalian, plant and insect cells. Proteins may also be expressed in a number of virus systems.

Suitably constructed expression vectors contain an origin of replication for autonomous replication in host cells, or are capable of integrating into the host cell chromosomes. Such vectors will also contain selective markers, a limited number of useful restriction enzyme sites, a high copy number, and strong promoters. Promoters are DNA sequences that direct RNA polymerase to bind to DNA and initiate RNA synthesis; strong promoters cause such initiation at high frequency. The preferred expression vectors of the present invention are operatively linked to a recombinant cDNA molecule of the present invention, i.e., the vectors are capable directing both replication of the attached recombinant cDNA molecule and expression of the protein encoded by the recombinant cDNA molecule. Expression vectors may include, but are not limited to cloning vectors, modified cloning vectors and specifically designed plasmids or viruses.

Suitable host cells for expression of the proteins of the present invention include bacteria, yeast, mammalian, plant and insect cells. With each type of cell and species therein certain expression vectors are appropriate as will be disclosed below.

Procaryotes may be used for expression of the proteins of the present invention. Suitable bacteria host cells include the various strains of *E. coli, Bacillus subtilis,* and various species of *Pseudomonas.* In these systems, plasmid vectors which contain replication sites and control sequences derived from species compatible with the host are used. Suitable vectors for *E. coli* are derivatives of pBR322, a plasmid derived from an *E. coli* species by Bolivar et al., Gene, 2:95 (1977). Common procaryotic control sequences, which are defined herein to include promoters for transcription, initiation, optionally with an operator, along with ribosome binding site sequences, include the beta-lactamase and lactose promoter systems (Chang et al., Nature, 198:1056 (1977)), the tryptophan promoter system (Goeddel et al., Nucleic Acids Res., 8:4057 (1980)) and the lambda-derived-$P_L$ promoter and N-gene ribosome binding site (Shimatake et al., Nature, 292:128 (1981)). However, any available promoter system compatible with procaryotes can be used. Preferred procaryote expression systems include *E. coli* and their expression vectors.

Eucaryotes may be used for expression of the proteins of the present invention. Eucaryotes are usually represented by the yeast and mammalian cells. Suitable yeast host cells include *Saccharomyces cerevisiae* and *Pichia pastoris*. Suitable mammalian host cells include COS and CHO (chinese hamster ovary) cells.

Expression vectors for the eucaryotes are comprised of promoters derived from appropriate eucaryotic genes. Suitable promoters for yeast cell expression vectors include promoters for synthesis of glycolytic enzymes, including those for 3-phosphoglycerate kinase gene in *Saccharomyces cerevisiae* (Hitzman et al., J. Biol. Chem., 255:2073 (1980)) and those for the metabolism of methanol as the alcohol oxidase gene in *Pichia pastoris* (Stroman et al., U.S. Pat. Nos. 4,808,537 and 4,855,231). Other suitable promoters include those from the enolase gene (Holland, M. J. et al., J. Biol. Chem., 256:1385 (1981)) or the Leu2 gene obtained from YEp13 (Broach, J. et al., Gene, 8:121 (1978)).

Preferred yeast expression systems include *Pichia pastoris* and their expression vectors. NAP-encoding cDNAs expressed in *Pichia pastoris* optionally may be mutated to encode a NAP protein that incorporates a proline residue at the C-terminus. In some instances the NAP protein is expressed at a higher level and can be more resistant to unwanted proteolysis. One such cDNA, and its expression in *Pichia pastoris*, is described in Example 17.

Suitable promoters for mammalian cell expression vectors include the early and late promoters from SV40 (Fiers, et al., Nature, 273:113 (1978)) or other viral promoters such as those derived from polyoma, adenovirus II, bovine papilloma virus or avian sarcoma viruses.

Suitable viral and mammalian enhancers may also be incorporated into these expression vectors.

Suitable promoters for plant cell expression vectors include the nopaline synthesis promoter described by Depicker, A. et al., Mol. Appl. Gen., 1:561 (1978).

Suitable promoters for insect cell expression vectors include modified versions of the system described by Smith et al., U.S. Pat. No. 4,745,051. The expression vector comprises a baculovirus polyhedrin promoter under whose control a cDNA molecule encoding a protein can be placed.

Host cells are transformed by introduction of expression vectors of the present invention into them. Transformation is done using standard techniques appropriate for each type of cell. The calcium treatment employing calcium chloride described in Cohen, S.N., Proc. Natl. Acad. Sci. USA, 692:2110 (1972), or the RbCl method described in Maniatis et al., *Molecular Cloning: A Laboratory Manual*, p. 254, Cold Spring Harbor Press (1982) is used for procaryotes or other cells which contain substantial cell wall barriers. The transformation of yeast is carried out as described in Van Solingen, P. et al., J. Bacter., 130:946 (1977) and Hsiao, C. L. et al., Proc. Natl. Acad. Sci. USA, 76:3829 (1979). Mammalian cells without much cell wall are transformed using the calcium phosphate procedure of Graham and van der Eb, Virology, 2:546 (1978). Plant cells are transformed by infection with *Agrobacterium tumefaciens* as described in Shaw, C. et al, Gene, 23:315 (1983). Preferred methods of transforming *E. coli*. and *Pichia pastoris* with expression vectors include electroporation.

Transformed host cells are cultured under conditions, such as type of media, temperature, oxygen content, fluid motion, etc., well known in the biological arts.

The recombinant proteins of the present invention are isolated from the host cell or media by standard methods well known in the biochemical arts, which include the use of chromatography methods. Preferred methods of purification would include sequential chromatography of an extract through columns containing Poros20 HQ anion-ion exchange matrix or Poros20 HS cation exchange matrix, Superdex30 gel filtration matrix and a C18 reverse-phase matrix. The fractions collected after one such chromatography column may be selected by their ability to increase the clotting time of human plasma, as measured by the PT and aPTT assays, or their ability to inhibit factor Xa amidolytic activity as measured in a colorimetric assay, or demonstration of activity in any of the other assays disclosed herein. Examples of preferred methods of purification of a recombinant protein of the present invention are disclosed in Examples 3, 4, 6, 8, 14 and 15.

4. Methods of Using NAP.

In one aspect, the present invention includes methods of collecting mammalian plasma such that clotting of said plasma is inhibited, comprising adding to a blood collection tube an amount of a protein of the present invention sufficient to inhibit the formation of a clot when mammalian blood is drawn into the tube, adding mammalian blood to said tube, separating the red blood cells from the mammalian plasma, and collecting the mammalian plasma.

Blood collection tubes include stoppered test tubes having a vacuum therein as a means to draw blood obtained by venipuncture into the tubes. Preferred test tubes include those which are made of borosilicate glass, and have the dimensions of, for example, 10.25×47 mm, 10.25×50 mm, 10.25×64 mm, 10.25×82 mm, 13×75 mm, 13×100 mm, 16×75 mm, 16×100 mm or 16×125 mm. Preferred stoppers include those which can be easily punctured by a blood collection needle and which when placed onto the test tube provide a seal sufficient to prevent leaking of air into the tube.

The proteins of the present invention are added to the blood collection tubes in a variety of forms well known in the art, such as a liquid composition thereof, a solid composition thereof, or a liquid composition which is lyophilized to a solid in the tube. The amount added to such tubes is that amount sufficient to inhibit the formation of a clot when mammalian blood is drawn into the tube. The proteins of the present invention are added to blood collection tubes in such amounts that, when combined with 2 to 10 ml of mammalian blood, the concentration of such proteins will be sufficient to inhibit clot formation. Typically, this effective concentration will be about 1 to 10,000 nM, with 10 to 1000 nM being preferred.

Alternatively, the proteins of the present invention may be added to such tubes in combination with other clot-inhibiting additives, such as heparin salts, EDTA salts, citrate salts or oxalate salts.

After mammalian blood is drawn into a blood collection tube containing either a protein of the present invention or the same in combination with other clot-inhibiting additives, the red blood cells ate separated from the mammalian plasma by centrifugation. The centrifugation is performed at g-forces, temperatures and times well known in the medical arts. Typical condition for separating plasma from red blood cells include centrifugation at a centrifugal force of about 100×g to abut 1500×g, at a temperatures of about 5 to about 25° C., tend for a time of about 10 to about 60 minutes.

The mammalian plasma may be collected by pouring it off into a separate container, by withdrawing it into a pipette or by other means well known to those skilled in the medical arts.

In another aspect, the present invention includes methods for preventing or inhibiting thrombosis (clot formation) or blood coagulation in a mammal, comprising administering to said mammal a therapeutically effective amount of a protein or a pharmaceutical composition of the present invention.

The proteins or pharmaceutical compositions of the present invention are administered in vivo, ordinarily in a mammal, preferably in a human. In employing them in vivo, the proteins or pharmaceutical compositions can be administered to a mammal in a variety of ways, including orally, parenterally, intravenously, subcutaneously, intramuscularly, colonically, rectally, nasally or intraperitoneally, employing a variety of dosage forms. Administration is preferably parenteral, such as intravenous on a daily basis. Alternatively, administration is preferably oral, such as by tablets, capsules or elixers taken on a daily basis.

In practicing the methods of the present invention, the proteins or pharmaceutical compositions of the present invention are administered alone or in combination with one another, or in combination with other therapeutic or in vivo diagnostic agents.

As is apparent to one skilled in the medical art, a therapeutically effective amount of the proteins or pharmaceutical compositions of the present invention will vary depending upon the age, weight and mammalian species treated, the particular proteins employed, the particular mode of administration and the desired affects and the therapeutic indication. Because these factors and their relationship to determining this amount are well known in the medical arts, the determination of therapeutically effective dosage levels, the amount necessary to achieve the desired result of preventing thrombosis, will be within the ambit of one skilled in these arts.

Typically, administration of the proteins or pharmaceutical composition of the present invention is commenced at lower dosage levels, with dosage levels being increased until the desired effect of preventing in vivo thrombosis is achieved which would define a therapeutically effective amount. For the proteins of the present invention, alone or as part of a pharmaceutical composition, such doses are between about 0.01 mg/kg and 100 mg/kg body weight, preferably between about 0.01 and 10 mg/kg, body weight, 5. Utility.

Proteins of the present invention when made and selected as disclosed are useful as potent inhibitors of blood coagulation in vitro and in vivo. As such, these proteins are useful as in vitro diagnostic reagents to prevent the clotting of blood and are also useful as in vivo pharmaceutical agents to prevent or inhibit thrombosis or blood coagulation in mammals.

The proteins of the present invention are useful as in vitro diagnostic reagents for inhibiting clotting in blood drawing tubes. The use of stoppered test tubes having a vacuum therein as a means to draw blood obtained by venipuncture into the tube is well known in the medical arts. Kasten, B. L., "Specimen Collection", *Laboratory Test Handbook,* 2nd Edition, Lexi-Comp Inc., Cleveland pp. 16–17 (Edits. Jacobs, D. S. et al. 1990). Such vacuum tubes may be free of clot-inhibiting additives, in which case, they are useful for the isolation of mammalian serum from the blood. They may alternatively contain clot-inhibiting additives (such as heparin salts, EDTA salts, citrate salts or oxalate salts), in which case, they are useful for the isolation of mammalian plasma from the blood. The proteins of the present invention are potent inhibitors of blood clotting and as such, can be incorporated into blood collection tubes to prevent clotting of the mammalian blood drawn into them.

The proteins of the present invention are used alone, in combination of other proteins of the present invention, or in combination with other known inhibitors of clotting, in the blood collection tubes, for example, with heparin salts, EDTA salts, citrate salts or oxalate salts.

The amount to be added to such tubes, or effective amount, is that amount sufficient to inhibit the formation of a blood clot when mammalian blood is drawn into the tube. The proteins of the present invention are added to blood collection tubes in such amounts that, when combined with 2 to 10 ml of mammalian blood, the concentration of such proteins will be sufficient to inhibit the formation of blood clots. Typically, this effective amount is that required to give a final concentration in the blood of about 1 to 10,000 nM, with 10 to 1000 nM being preferred.

The proteins of the present invention may also be used to prepare diagnostic compositions. In one embodiment, diagnostic compositions are prepared by dissolving the proteins of the present invention into diagnostically acceptable carriers, which carriers include phosphate buffered saline (0.01 M sodium phosphate +0.15 M sodium chloride, pH 7.2 or Tris buffered saline (0.05 M Tris-HCl +0.15 M sodium chloride, pH 8.0). In another embodiment, the proteins of the present invention may be blended with other solid diagnostically acceptable carriers by methods well known in the art to provide solid diagnostic compositions. These carriers include buffer salts.

The addition of the proteins of the present invention to blood collection tubes mast be accomplished by methods well known in the art, which methods include introduction of a liquid diagnostic composition thereof, a solid diagnostic composition thereof, or a liquid diagnostic composition which is lyophilized in such tubes to a solid plug of a solid diagnostic composition.

The use of blood collection tubes containing the diagnostic compositions of the present invention comprises contacting a effective amount of such diagnostic composition with mammalian blood drawn into the tube. Typically, when a sample of 2 to 10 ml of mammalian blood is drawn into a blood collection tube and contacted with such diagnostic composition therein; the effective amount to be used will include those concentrations of the proteins formulated as a diagnostic composition which in the blood sample are sufficient to inhibit the formation of blood clots. Preferred effective concentrations would be about 1 to 10,000 nM, with 10 to 1000 nM being especially preferred.

According to an alternate aspect of our invention, the proteins of the present invention are also useful as pharmaceutical agents for preventing or inhibiting thrombosis or blood coagulation in a mammal. This prevention or inhibition of thrombosis or blood coagulation includes preventing or inhibiting abnormal thrombosis.

Conditions characterized by abnormal thrombosis are well known in the medical arts and include those involving the arterial and venous vasculature of mammals. With respect to the coronary arterial vasculature, abnormal thrombosis (thrombus formation) characterizes the rupture of an established atherosclerotic plaque which is the major cause of acute myocardial infarction and unstable angina, and also characterizes the occlusive coronary thrombus formation resulting from either thrombolytic therapy or percutaneous transluminal coronary angioplasty (PTCA). With respect to the venous vasculature, abnormal thrombosis characterizes the condition observed in patients undergoing major surgery in the lower extremities or the abdominal area who often suffer from thrombus formation in the venous vasculature resulting in reduced blood flow to the affected extremity and a predisposition for pulmonary embolism. Abnormal thrombosis further characterizes disseminated intravascular coagulopathy which commonly occurs within both vascular systems during septic shock, certain viral infections and cancer, a condition wherein there is rapid consumption of coagulation factors and systemic coagulation which results in the formation of life-threatening thrombi occurring throughout the microvasculature leading to widespread organ failure.

The NAP proteins of the present invention also are useful immunogens against which antibodies are raised. Antibodies, both monoclonal and polyclonal, directed to a NAP are useful for diagnostic purposes and for the identification of concentration levels of NAP in various biological fluids. Immunoassay utilizing these antibodies may be used as a diagnostic test, such as to detect infection of a mammalian host by a parasitic worm or to detect NAP from a parasitic worm in a tissue of the mammalian host. Also, such immunoassays may be used in the detection and isolation of NAP from tissue homogenates, cloned cells and the like.

NAP can be used, with suitable adjuvants, as a vaccine against parasitic worm infections in mammals. Immunization with NAP vaccine may be used in both the prophylaxis and therapy of parasitic infections. Disease conditions caused by parasitic worms may be treated by administering to an animal infected with these parasites anti-NAP antibody.

NAP proteins of this invention having serine protease inhibitory activity also are useful in conditions or assays where the inhibition of serine protease is desired. For example, NAP proteins that inhibit the serine protease trypsin or elastase are useful for treatment of acute pancreatitis or acute inflammatory response mediated by leukocytes, respectively.

The recombinant cDNA molecules encoding the proteins of the present invention are useful in one aspect for isolating other recombinant cDNA molecules which also encode the proteins of the present invention. In another aspect, they are useful for expression of the proteins of the present invention in host cells.

The nucleotide probes of the present invention are useful to identify and isolate nucleic acid encoding NAPs from nematodes or other organisms. Additionally, the nucleotide probes are useful diagnostic reagents to detect the presence of nematode-encoding nucleic acid in a sample, such as a bodily fluid or tissue from a mammal suspected of infection by nematode. The probes can be used directly, with appropriate label for detection, to detect the presence of nematode nucleic acid, or can be used in a more indirect manner, such as in a PCR-type reaction, to amplify nematode nucleic acid that may be present in the sample for detection. The conditions of such methods and diagnostic assays are readily available in the art.

To assist in understanding, the present invention will now be be further illustrated by the following examples. These examples as they relate to this invention should not be construed as specifically limiting the invention and such variations of the invention, now known or later developed, which would be within the purview of one skilled in the art are considered to fall within the scope of the invention as described herein and hereinafter claimed.

EXAMPLES

Example 1

Isolation of Novel Anticoagulant Protein (NAP) from *Ancylostoma caninum*.

(A) Preparation of the *Ancylostoma caniumum* Lysate.

Frozen canine hookworms, *Ancylostoma caninum*, were obtained from Antibody Systems (Bedford, Tex.). Hookworms were stored at −80° C. until used for homogenate.

Hookworms were frozen in liquid nitrogen and ground in a mortar followed by a homogenaization on ice in homogenization buffer using a PotterS homogenizer with a teflon piston (B.Braun Melsungen AS, Germany). The homogenization buffer contained: 0.02 M Tris-HCl pH 7.4, 0.05 M NaCl, 0.001 M $MgCl_2$, 0.001 M $CaCl_2$, $1.0 \times 10_{-5}$ M E-64 protease inhibitor (Boehringer Mannheim, Germany), $1.0 \times 10^{-5}$ M pepstatin A (isovaleryl-Val-Val-4-amino-3-hydroxy-6-methyl-heptanoyl-Ala-4-amino-3-hydroxy-6-methylheptanoic acid, ICN Biomedicals, CA), $1.0 \times 10^{-5}$ M chymostatin (Boehringer), $1.0 \times 10^{-5}$ M leupeptin (ICN), $5 \times 10^{-5}$ M AEBSF (4-(2-aminoethyl)-benzenesulfonyl fluoride, ICN), and 5% (v/v) glycerol. Approximately 4 ml of homogenization buffer was used to homogenize each gram of frozen worms (approximately 500 worms). Insoluble material was pelleted by two sequential centrifugation steps: $19,000 \times g_{max}$ at 4° C. for 30 minutes followed by $110,000 \times g_{max}$ at 4° C. for 40 minutes. The supernatant solution was clarified by passage through a 0.45 micrometer cellulose acetate filter (Corning, N.Y.) to give *Ancylostoma caniumum* lysate.

(B) Concanavalin A Sepharose Chromatography.

*Ancylostoma caniumum* lysate (100 ml) was adsorbed onto 22 ml of Concanavalin A Sepharose (Pharmacia, Sweden) pre-equilibrated with Con A buffer (0.02 M Tris-HCl, pH 7.4, 1 M NaCl, 0.002 M $CaCl_2$) by loading it onto a 1.6×11 cm column of this gel at a flow rate of 3 ml/minute (90 cm/hour). The column was at ambient temperature while the reservoir of lysate was maintained at ice bath temperature throughout the procedure. The column was subsequently washed with 2 column volumes of Con A buffer. The column flow-through and wash were collected (approximately 150 ml) and stored at −80° C. until further processing was done.

(C) Anion-Exchange Chromatography.

The flow-through and wash of the Concanavalin A Sepharose column was buffered by adding solid sodium acetate to a final concentration of 12.5 mM. The conductivity was reduced by dilution with milliQ water and the pH was adjusted with HCl to pH 5.3. The precipitate formed during pH adjustment was pelleted by centrifugation $15,000 \times g_{max}$ at 4° C. for 15 minutes. The supernatant solution was clarified by passage through a 0.2 micrometer cellulose acetate filter (Corning, N.Y.).

This clarified solution (total volume approximately 600 ml) was loaded on to a Poros20 HQ (Perseptive Biosystems, MA) 1×2 cm column pre-equilibrated with Anion buffer (0.05 M Na acetate, pH 5.3, 0.1 M NaCl) at a flow rate of 10 ml/minute (800 cm/hour). The column and the solution added were at ambient temperature throughout this purification step. The column was subsequently washed with 10 column volumes of Anion buffer.

Material that had inhibitory activity, detected following the procedure below, in the factor Xa amidolytic assay was eluted with Cation buffer containing 0.55 M NaCl at a flow rate of 5 ml/minute (400 cm/hour).

A sample of solution was tested in a factor Xa amidolytic assay as follows. Reaction mixtures (150 microliters) were prepared in 96-well plates containing factor Xa and various dilutions of the sample in assay buffer (100 mM Tris-HCl pH 7.4; 140 mM NaCl; 0.1% BSA) Human factor X was purchased from Enzyme Research Laboratories (South Bend, Ind., USA) and activated with Russell's Viper venom using the procedure of Bock, P. E., Craig, P. A., Olson, S. T., and Singh P., Arch. Biochem. Biophys., 273:375–388 (1989). Following a 30 minute incubation at ambient temperature, the enzymatic reactions were initiated by addition of 50 microliters of a 1 mM substrate solution in water (N-alpha-benzyloxycarbonyl-D-arginyl-L-glycyl-L- arginine p-nitroanilide-dihydrochloride; S-2765; Chromogenix, Mölndal, Sweden) to yield final concentrations of 0.2 nM factor Xa and 0.25 mM S-2765. Substrate hydrolysis was monitored by continuously measuring absorbance at 405 nm using a Vmax kinetic plate reader (Molecular Devices, Menlo Park, Calif., USA).
(D) Heat Treatment.

Half of the 0.55 M NaCl elution pool (3 ml) from anion-exchange chromatography was neutralized by adding 1 M Tris-HCl, pH 7.5 to a final concentration of 50 mM, incubated for 5 minutes at 90° C. in a glass tube and subsequently cooled rapidly on ice. Insoluble material was pelleted by centrifugation 19,000×$g_{max}$ at 40° C. for 20 minutes. The supernatant contained material which inhibited factor Xa in the factor Xa amidolytic assay. About 89% of the factor Xa inhibitory activity was recovered in the supernatant, after this heat treatment after accounting for dilution.
(E) Molecular Sieve Chromatography using Superdex30 (alternative for the heat treatment step).

Half of the 0.55 M NaCl elution pool (3 ml) from anion-exchange chromatography was loaded on a Superdex30 PG (Pharmacia, Sweden) 1.6×66 cm column pre-equilibrated with 0.01 M sodium phosphate, pH 7.4, 0.15 M NaCl at 24° C.

The chromatography was conducted at a flow rate of 2 ml/minute. The factor Xa inhibitory activity (determined in the factor Xa amidolytic assay) eluted 56–64 ml into the run ($K_{av}$ of 0.207). This elution volume would be expected for a globular protein with a molecular mass of 14,000 daltons.
(F) Reverse Phase Chromatography.

Hookworm lysate which was fractionated by chromatography on Concanavalin A Sepharose, anion-exchange and Superdex30 (or with the alternative heat treatment step) was loaded on to a 0.46×25 cm C18 column (218TP54 Vydac; Hesperia, Calif.) which was then developed with a linear gradient of 10–35% acetonitrile in 0.1% (v/v) trifluoroacetic acid at a flow rate of 1 ml/minute with a rate of 0.625% change in acetonitrile/minute. FXa inhibitory activity (determined in the factor Xa amidolytic assay) eluted at approximately 30% acetonitrile. The HPLC runs were performed on a Vista 5500 connected with a Polychrom 9600 detector set at 215 nm (Varian, Calif.). Detector signals were integrated on a 4290 integrator obtained from the same company. Factor Xa inhibitory activity containing fractions were vacuum dried and then redissolved in PBS (0.01 M sodium phosphate, pH 7.4, 0.15 M NaCl).

These fractions were pooled and then loaded on to a 0.46×25 cm C18 column (218TP54 Vydac; Hesperia, Calif.) which was developed with a linear gradient of 10–35% acetonitrile in 0.1% trifluoroacetic acid at a flow rate of 1 ml/minute with a slower rate of 0.4% change in acetonitrile/minute. Factor Xa inhibitory activity containing fractions were pooled and subsequently vacuum dried.
(G) Molecular Weight Determination of NAP from *Ancylostoma caninum*.

The estimated mass for NAP isolated as described in this example was determined using electrospray ionisation mass spectrometry.

A vacuum-dried pellet of NAP was dissolved in 50% (v/v) acetonitrile, 1% (v/v) formic acid. Mass analysis was performed using a VG Bio-Q (Fisons Instruments, Manchester UK).

The NAP sample was pumped through a capillary and at its tip a high voltage of 4 kV was applied. Under the influence of the high electric field, the sample was sprayed out in droplets containing the protein molecules. Aided by the drying effect of a neutral gas ($N_2$) at 60° C., the droplets were further reduced in size until all the solvent had been evaporated and only the protein species remained in the gaseous form. A population of protein species arose which differed from each other in one charge. With a quadrupole analyzer, the different Dale (mass/charge)-values were detected. Calibration of the instrument was accomplished using Horse Heart Myoglobin (Sigma, Mo.).

The estimated mass of NAP isolated as described in sections A, B, C, D, and F of this example is 8734.60 daltons. The estimated mass of native NAP isolated as described in sections A, 3, C, E, and F is 8735.67 daltons.
(H) Amino Acid Sequencing of NAP from *Ancylostoma caninum*.

Amino acid determination was performed on a 476-A Protein/Peptide Sequencer with On Board Microgradient PTH Analyzer and Model 610A Data Analysis System (Applied Biosystems, CA). Quantification of the residues was performed by on-line analysis on the system computer (Applied Biosystems, CA); residue assignment was performed by visual analysis of the HPLC chromatograms. The first twenty amino acids of the amino-terminus of native NAP were determined to be:
Lys Ala Tyr Pro Glu Cys Gly Glu Asn Glu Trp Leu Asp Asp Cys Gly Thr Gln Lys Pro [SEQ. ID. NO. 97].

The cysteine residues were not directly detected in this analysis because the sample was not reduced and subsequently alkylated. Cysteines were assigned to the positions where no specific amino acid was identified.

Example 2

Cloning and Sequencing of NAP from *Ancylostoma caninum*.
(A) Preparation of Hybridization Probe.

Full-length cDNA clones encoding NAP were isolated by screening a cDNA library, prepared from the mRNA isolated from the nematode, *Ancylostoma caninum*, with a radiolabeled degenerate oligonucleotide whose sequence was based on the first eleven amino acids of the amino-terminus of NAP from *A. caninum*:
Lys Ala Tyr Pro Glu Cys Gly Glu Asn Glu Trp [SEQ. ID. NO. 93].

The 33-mer oligonucleotide hybridization probe, designated YG99, had the following sequence:
AAR GCi TAY CCi GAR TGY GGi GAR AAY GAR TGG [SEQ. ID. NO. 94]
where "R" refers to A or G; "Y" refers to T or C; and "i" refers to inosine. YG99 was radiolabeled by enzymatic 5'-end phosphorylation (5'-end labeling kit; Amersham, Buckinghamshire, England) using gamma-$^{32}$P-ATP (specific activity >7000Ci/mmole; ICN, Costa Mesa, Calif., USA) and subsequently passed over a NAP™10 column (Pharmacia, Uppsala, Sweden).
(B) Preparation of cDNA Library.

A cDNA library was constructed using described procedures (Promega Protocols and Applications Guide 2nd Ed.; Promega Corp., Madison, Wis., USA).

Adult hookworms, *Ancylostoma caninum*, were purchased from Antibody Systems (Bedford, Tex.). Poly(A+) RNA was prepared using the QuickPrep mRNA Purification Kit (Pharmacia). About 3 micrograms of mRNA were reverse transcribed using an oligo(dT)-NotI primer/adaptor, AATTCGCGGCCGC(T)15 [SEQ. ID. NO. 95], (Promega Corp.) and AMV (Avian Myeloblastosis Virus) reverse transcriptase (Boehringer, Mannheim, Germany). The enzymes used for double-stranded cDNA synthesis were the following: *E. coli* DNA polymerase I and RNaseH from Life Technologies (Gaithersburg, Md., USA) and T4 DNA polymerase from Pharmacia.

EcoRI linkers (pCGGAATTCCG) [SEQ. ID. NO. 98] were ligated onto the obtained cDNA after treatment with EcoRI methylase (RiboClone EcoRI Linker Ligation System; Promega).

The cDNAs were digested with NotI and EcoRI, passed over a 1.5% agarose gel (all sizeable material was eluted using the Geneclean protocol, BIO101 Inc., La Jolla, Calif.), and unidirectionally ligated into the EcoRI-NotI arms of the lambda gt11 Sfi-NotI vector (Promega). After in vitro packaging (GigapackII-Gold, Stratagene, La Jolla, Calif.) recombinant phage were obtained by infecting strain Y1090 (Promega).

The usefulness of the cDNA library was demonstrated by PCR analysis (Taq polymerase from Boehringer; 30 temperature cycles: 1 minute at 95° C.; 1 minute at 50° C.; 3 minutes at 72° C.) of a number of randomly picked clones using the lambda gt11 primer #1218, having the sequence, GGTGGCGACG ACTCCTGGAG CCCG (New England Biolabs, Beverly, Mass., USA) [SEQ. ID. NO. 96]; targeting sequences located upstream of the cDNA insert) in combination with the above-mentioned oligo(dT)-NotI primer/adaptor; the majority of the clones was found to contain cDNA inserts of variable size.

(C) Identification of Clones.

Approximately 1×10$^6$ cDNA clones (duplicate plaque-lift filters were prepared using Hybond™-N; Amersham) were screened with the radiolabeled YG99 oligonucleotide using the following pre-hybridization and hybridization conditions: 5×SSC(SSC: 150 mM NaCl, 15 mM trisodium citrate), 5× Denhardt's solution, 0.5% SDS, 100 micrograms/ml sonicated fish sperm DNA (Boehringer), overnight at 42° C. The filters were washed 4 times in 2×SSC, 0.1% SDS at 37° C. After exposure (about 72 hours) to X-ray film, a total of between 350 and 500 hybridization spots were identified.

Twenty-four positive clones, designated NAP1 through NAP24, were subjected to a second hybridization round at lower plaque-density; except for NAP24, single plaques containing a homogeneous population of lambda phage were identified. The retained clones were analyzed by PCR amplifications (Taq polymerase from Boehringer; 30 temperature cycles: 1 minute at 95° C.; 1 minute at 50° C.; 1.5 minutes at 72° C.) using the oligo(dT)-NotI primer (AATTCGCGGC CGC(T)$_{15}$) [SEQ. ID. NO. 95] in combination with either (i) YG99 or (ii) the lambda gt11 primer #1218. The majority of the clones (20 out of 23) yielded a fragment of about 400 bp when the oligo(dT)-NotI/YG99 primer set was used and a fragment of about 520 bp when the oligo(dT)-NotI/#1218 primer couple was used. Nineteen such possibly full-length clones were further characterized.

The cDNA inserts of five clones were subcloned as SfiI-NotI fragments on both pGEM-5Zf(−) and pGEM-9Zf (−) (Promega). Because the SfiI sites of lambda gt11 and pGEM-5Zf(−) are not compatible with one another, the cloning on this vector required the use of a small adaptor fragment obtained after annealing the following two 5'-end phosphorylated oligonucleotides: pTGGCCTAGCG TCAGGAGT [SEQ. ID. NO. 99] and PCCTGACGCTA GGCCATGG [SEQ. ID. NO. 100]. Following preparation of single-stranded DNA, the sequences of these cDNAs were determined with the dideoxy chain termination method using primer #1233 having the sequence, AGCGGATAAC AATTTCACAC AGGA (New England Biolabs) [SEQ. ID. NO. 101]. All five clones were found to be full-length including a complete secretion signal. Clones NAP5, NAP7 and NAP22 were found to have an identical coding region. Clones NAP6 and NAP11 are also identical but differ from the NAP5 type of coding region. FIG. 1 depicts the nucleotide sequence of the NAP5 gene and FIG. 2 depicts the amino acid sequence of the protein encoded, AcaNAP5. Likewise, FIG. 3 depicts the nucleotide sequence of the NAP6 [SEQ. ID. NO. 5] gene and FIG. 4 depicts the amino acid sequence of the protein encoded, AcaNAP6 [SEQ. ID. NO. 6].

Fourteen other possibly full-length clones were subjected to a restriction analysis. The above mentioned 400 bp PCR product obtained with the YG99/oligo(dT)-NotI primer couple, was digested with four different enzymes capable of discriminating between a NAP5- and NAP6-type of clone: Sau96I, Sau3AI, DdeI, and HpaII. The results were consistent with 10 out of the 14 clones being NAP5-type (e.g. NAP4, NAP8, NAP9, NAP15, NAP16, NAP17, NAP18, NAP20, NAP21, and NAP23) while the remaining four were NAP6-type (e.g. NAP10, NAP12, NAP14, and NAP19).

These clones were renamed to reflect origin from *Ancylostoma caninum* by placing the letters Aca immediately before the NAP designation. For example, NAP5 became AcaNAP5, NAPE became AcaNAP6 and so forth.

Example 3

Production and Purification of Recombinant AcaNAP5 in *P. pastoris*.

(A) Expression Vector Construction.

The *Pichia pastoris* yeast expression system, including the *E. coli*/*P. pastoris* shuttle vector, pHIL-D2, has been described in a number of United States Patents. See, e.g., U.S. Pat. Nos. 5,330,901; 5,268,273; 5,204,261; 5,166,329; 5,135,868; 5,122,465; 5,032,516; 5,004,688; 5,002,876; 4,895,800; 4,885,242; 4,882,279; 4,879,231; 4,857,467; 4,855,231; 4,837,148; 4,818,700; 4,812,405; 4,808,537; 4,777,242; and 4,683,293.

The pYAM7SP8 vector used to direct expression and secretion of recombinant AcaNAP5 in *P. pastoris* was a derivative of the pHIL-D2 plasmid (Despreaux, C. W. and Manning, R. F., Gene 131:35–41 (1993)), having the same general structure. In addition to the transcription and recombination elements of pHIL-D2 required for expression and chromosomal integration in *P. pastoris* (see Stroman, D. W. et al., U.S. Pat. No. 4,855,231), this vector contained a chimeric prepro leader sequence inserted downstream of the alcohol oxidase (AOX1) promoter. The prepro leader consisted of the *P. pastoris* acid phosphatase (PHO1) secretion signal fused to a synthetic 19-amino acid pro-sequence. This pro-sequence was one of the two 19-aa pro-sequences designed by Clements et al., Gene 106:267–272 (1991) on the basis of the *Saccharomyces cerevisiae* alpha-factor leader sequence. Engineered immediately downstream from the prepro leader sequence was a synthetic multi-cloning site with recognition sequences for the enzymes StuI, SacII, EcoRI, BglII, NotI, XhoI, SpeI and BamHI to facilitate the cloning of foreign genes. NAP as expressed from pYAM7SP8 in *Pichia pastoris* was first translated as a prepro-product and subsequently processed by the host cell to remove the pre- and pro-sequences.

The structure of this vector is shown in FIG. 12. The signal sequence (S) has the nucleic acid sequence: ATG TTC TCT CCA ATT TTG TCC TTG GAA ATT ATT TTA GCT TTG GCT ACT TTG CAA TCT GTC TTC GCT [SEQ. ID. NO. 102]. The pro sequence (P) has the nucleic acid sequence: CAG CCA GGT ATC TCC ACT ACC GTT GGT TCC GCT GCC GAG GGT TCT TTG GAC AAG AGG [SEQ. ID. NO. 103]. The multiple cloning site (MCS) has the nucleic acid sequence: CCT ATC CGC GGA ATT CAG ATC TGA ATG CGG CCG CTC GAG ACT AGT GGA TCC [SEQ. ID. NO. 104].

The pGEM-9Zf(-) vector (Promega) containing the AcaNAP5 cDNA was used to isolate by amplification ("PCR-rescue") the region encoding the mature AcaNAP5 protein (using Vent polymerase from New England Biolabs, Beverly, Mass.; 20 temperature cycles: 1 minute at 94° C., 1 minute at 50° C., and 1.5 minutes at 72° C.). The following oligonucleotide primers were used:

YG101: GCTCGC<u>TCTA-GAAGCTT</u>CAG-ACATGTATAA-TCTCATGTTG-G [SEQ. ID. NO. 105]

YG103: AAGGCATACC-CGGAGTGTGG-TG [SEQ. ID. NO. 89]

The YG101 primer, targeting C-terminal sequences, contained a non-annealing extension which included XbaI and HindIII restriction sites (underlined).

Following digestion with XbaI enzyme, the amplification product, having the expected size, was isolated from gel and subsequently enzymatically phosphorylated (T4 polynucleotide kinase from New England Biolabs, Beverly, Mass.). After heat-inactivation (10 minutes at at 70° C.) of the kinase, the blunt-ended/XbaI fragment was directionally cloned into the vector pYAM7SP8 for expression purposes. The recipient vector-fragment from pYAM7SP8 was prepared by StuI-SpeI restriction, and purified from agarose gel. The *E. coli* strain, WK6 [Zell, R. and Fritz, H.-J., EMBO J., 6: 1809–1815 (1987)], was transformed with the ligation mixture, and ampicillin resistant clones were selected.

Based on restriction analysis, a plasmid clone containing an insert of the expected size, designated pYAM7SP-NAP5, was retained for further characterization. Sequence determination of the clone pYAM7SP-NAP5 confirmed the precise insertion of the mature AcaNAP5 coding region in fusion with the prepro leader signal, as predicted by the construction scheme, as well as the absence of unwanted mutations in the coding region.

(B) Expression of Recombinant AcaNAP5 in *P. pastoris*.

The *Pichia pastoris* strain GTS115 (his4) has been described in Stroman, D. W. et al., U.S. Pat. No. 4,855,231. All of the *P. pastoris* manipulations were performed essentially as described in Stroman, D. W. et al., U.S. Pat. No. 4,855,231.

About 1 microgram of pYAM7SP-NAP5 plasmid DNA was electroporated into the strain GTS115 using a standard electroporation protocol. The plasmid was previously linearized by SalI digestion, which theoretically facilitates the targeting and integration of the plasmid into the his4 chromosomal locus.

The selection of a AcaNAP5 high-expressor strain was performed essentially as described hereinbelow. His+ transformants were recovered on MD plates (Yeast Nitrogen Base without amino acids (DIFCO), 13.4 g/l; Biotin, 400 micrograms/L; D-glucose, 20 g/l; agar, 15 g/l). Single colonies (n=60) originating from the electroporation were inoculated into 100 microliters of FM22-glycerol-PTM1 medium in wells of a 96-well plate and were allowed to grow on a plate-agitator at 30° C. for 24 hours. One liter of FM22-glycerol-PTM1 medium contained 42.87 g $KH_2PO_4$, 5 g $(NH_4)_2SO_4$, 1 g $CaSO_4.2H_2O$, 14.28 g $K_2SO_4$, 11.7 g $MgSO_4.7H_2O$, 50 g glycerol sterilized as a 100 ml solution, and 1 ml of PTM1 trace mineral mix filter-sterilized. The FM22 part of the medium was prepared as a 900 ml solution adjusted to pH 4.9 with KOH and sterile filtered. One liter of the PTM1 mix contained 6 g $CuSO_4.5H_2O$, 0.8 g KI, 3 g $MnSO_4.H_2O$, 0.2 g $NaMoO_4.2H_2O$, 0.02 g $H_3BO_3$, 0.5 g $COCl_2.6H_2O$, 20 g $ZnCl_2$, 5 ml $H_2SO_4$, 65 g $FeSO_4.7H_2O$, 0.2 g biotin.

The cells were then pelleted and resuspended in fresh FM22-methanol-PTM1 medium (same composition as above except that the 50 g glycerol was replaced by 0.5% (v/v) methanol in order to induce expression of the AOX1 promoter). After an additional incubation period of 24 hours at 30° C., the supernatants of the mini-cultures were tested for the presence of secreted AcaNAP5. Two clones that directed a high level of synthesis and secretion of AcaNAP5, as shown by the appearance of high factor Xa inhibitory activity in the culture medium (as measured by the amidolytic factor Xa assay described in Example 1), were selected. After a second screening round, using the same procedure, but this time at the shake-flask level, one isolated host cell was chosen and designated *P. pastoris* GTS115/7SP-NAP5.

The host cell, GTS115/7SP-NAP5, was shown to have a wild type methanol-utilisation phenotype (Mut+), which demonstrated that the integration of the expression cassette into the chromosome of GTS115 did not alter the functionality of the genomic AOX1 gene.

Subsequent production of recombinant AcaNAP5 material was performed in shake flask cultures, as described in Stroman, D. W. et al., U.S. Pat. No. 4,855,231. The recombinant product was purified from *Pichia pastoris* cell supernatant as described below.

(C) Purification of Recombinant AcaNAP5.

(1) Cation Exchange Chromatography.

Following expression, the culture supernatant from GTS115/7SSP-NAP5 (100 ml) was centrifuged at 16000 r.p.m. (about 30,000×g) for 20 minutes before the pH was adjusted with 1N HCl to pH 3. The conductivity of the supernatant was decreased to less than 10 mS/cm by adding MilliQ water. The diluted supernatant was clarified by passage through a 0.22 micrometer cellulose acetate filter (Corning Inc., Corning, N.Y., USA)

The total volume (approximately 500 ml) of supernatant was loaded on a Poros20 HS (Perseptive Biosystems,MA) 1×2 cm column pre-equilibrated with Cation Buffer (0.05 M sodium citrate, pH 3) at a flow rate of 5 ml/minute (400 cm/hour). The column and the sample were at ambient temperature throughout this purification step. The column was subsequently washed with 50 column volumes Cation Buffer. Material that had inhibitory activity in a factor Xa amidolytic assay was eluted with Cation Buffer containing 1M NaCl at a flow rate of 2 ml/minute.

(2) Molecular Sieve Chromatography Using Superdex30.

The 1M NaCl elution pool containing the inhibitory material (3 ml) from the cation-exchange column was loaded on a Superdex30 PG (Pharmacia, Sweden) 1.6×66 cm column pre-equilibrated with 0.01 M sodium phosphate, pH 7.4, 0.15 M NaCl at ambient temperature. The chromatography was conducted at a flow rate of 2 ml/minute. The factor Xa inhibitory activity eluted 56–64 ml into the run ($K_{av}$ of 0.207). This is the same elution volume as determined for the native molecule (Example 1, part E).

(3) Reverse Phase Chromatography.

1 ml of the pooled fractions from the gel filtration chromatography was loaded on to a 0.46×25 cm C18 column (218TP54 Vydac; Hesperia, Calif.) which was then developed with a linear gradient of 10–35% acetonitrile in 0.1% (v/v) trifluoroacetic acid at 1 ml/minute with a rate of 0.4% change in acetonitrile/minute. Factor Xa inhibitory activity, assayed as in Example 1, eluted around 30–35% acetonitrile and was present in several fractions. HPLC runs were performed on the same system as described in Example 1. Fractions from several runs on this column containing the factor Xa inhibitory activity were pooled and vacuum dried.

(4) Molecular Weight Determination of Recombinant AcaNAP5

The estimated mass for the main constituent isolated as described in sections (1) to (3) of this example were determined using the same electrospray ionisation mass spectrometry system as described in Example 1.

The estimated mass of recombinant AcaNAP5 was 8735.69 Daltons.

(5) Amino Acid Sequencing of Recombinant AcaNAP5.

Following purification by section (1) to (3) of this example, the recombinant AcaNAP5 from *Pichia pastoris* was subjected to amino acid sequence analysis as described in Example 1. The first five amino acids of the amino-terminus of AcaNAP5 were determined to be: Lys-Ala-Tyr-Pro-Glu [SEQ. ID. NO. 106]. The sequence was identical to the native NAP protein (see Example 1).

Example 4

Production and Purification Of Recombinant AcaNAP6 in *P. pastoris*.

(A) Expression Vector Construction.

The expression vector, pYAM7SP-NAP6, was made in the same manner as described for pYAM7SP-NAP5 in Example 3.

(B) Expression of Recombinant AcaNAP6 in *P. pastoris*.

The vector, pYAM7SP-NAP6, was used to transform the *Pichia* strain GTS115 (his4) as described in Example 3.

(C) Purification of AcaNAP6.

The recombinant AcaNAP6, expressed from *Pichia* strain GTS115 (his4) transformed with the expression vector, pYAM7SP-NAP6, was purified as described for recombinant AcaNAP5 in Example 3.

The estimated mass of recombinant AcaNAP6 was determined, as described in Example 3, to be 8393.84 Daltons.

The majority of the AcaNAP6 preparation had the following amino-terminus: Lys-Ala-Tyr-Pro-Glu [SEQ. ID. NO. 106].

Example 5

Expression of Recombinant Pro-AcaNAP5 in COS Cells.

(A) Expression Vector Construction.

The pGEM-9Zf(−) vector (Promega Corporation, Madison, Wis., USA) into which the AcaNAP5 cDNA was subcloned, served as target for PCR-rescue of the entire AcaNAP5 coding region, including the native secretion signal (using Vent polymerase from New England Biolabs, Beverly, Mass., USA; 20 temperature cycles: 1 minute at 95° C., 1 minute at 50° C., and 1.5 minutes at 72° C.). The oligonucleotide primers used were: (1) YG101, targeting the 3'-end of the gene encoding a NAP and having the sequence, GCTCGCTCTA GAAGCTTCAG ACATGTATAA TCTCATGTTG G [SEQ, ID. NO. 105], and (2) YG102, targeting the 5'-end of the gene encoding a NAP and having the sequence, GACCAG ACAATGAAG ATGCTTTACG CTATCG [SEQ. ID. NO. 107]. These primers contain non-annealing extensions which include XbaI restriction sites (underlined).

Following digestion with XbaI enzyme, the amplification product having the expected size was isolated from an agarose gel and subsequently substituted for the about 450 basepair XbaI stuffer fragment of the pEF-BOS vector [Mizushima, S. and Nagata, S., Nucl. Acids Res., 18:5322 (1990)] for expression purposes. The recipient vector-fragment was prepared by XbaI digestion and purified from an agarose gel.

*E. coli* strain WK6 [Zell, R. and Fritz, H.-J., EMBO J., 6: 1809–1815 (1987)] was transformed with the ligation mixture. Thirty randomly picked ampicillin-resistant transformants were subjected to PCR analysis (Taq polymerase from Life Technologies Inc., Gaithersburg, Md., USA; 30 cycles of amplification with the following temperature program: 1 minute at 95° C., 1 minute at 50° C., and 1 minute at 72° C.). Oligonucleotide primers used were: (i) YG103 having the sequence, AAGGCATACC CGGAGTGTGG TG [SEQ. ID. NO. 89], and matching the amino-terminus of the region encoding mature NAP, and (ii) YG60 having the sequence, GTGGGAGACC TGATACTCTC AAG [SEQ. ID. NO. 108], and targeting vector sequences downstream of the site of insertion, i.e., in the 3'-untranslated region of the pEF-BOS expression cassette. Only clones that harbor the insert in the desired orientation can yield a PCR fragment of predictable length (about 250 basepair). Two such clones were further characterized by sequence determination and were found to contain the desired XbaI insert. One of the clones, designated pEF-BOS-NAP5, was used to transfect COS cells.

(B) Transfection of COS Cells.

COS-7 cells (ATCC CRL 1651) were transfected with pEF-BOS-NAP5, pEF-BOS containing an irrelevant insert or with omission of DNA (mock transfections) using DEAE-dextran. The following media and stock solutions were used with the DEAE-dextran method:

(1) COS-medium: DMEM; 10% FBS (incubated for 30 minutes at 56° C.); 0.03% L-glutamine; penicillin (50 I.U./ml) and streptomycin (50 micrograms/ml) (all products from Life Technologies).

(2) MEM-HEPES: MEM medium from Life Technologies Inc., reconstituted according to the manufacturer's specifications; containing a 25 mM final concentration of HEPES; adjusted to pH 7.1 before filtration (0.22 micrometer).

(3) DNA solution: 6 micrograms DNA per 3 ml MEM-HEPES (4) DEAE-dextran solution: 30 microliters DEAE-dextran stock (Pharmacia, Uppsala, Sweden; 100 mg/ml in $H_2O$) per 3 ml MEM-HEPES.

(5) Transfection mixture: 3 ml of the DEAE-dextran solution is added to 3 ml of the DNA solution and the mixture is left to stand for 30 minutes at ambient temperature.

(6) Chloroquine solution: a 1:100 dilution of chloroquine stock (Sigma, St.Louis, Mo., USA; 10 mM in water; filtered through a 0.22 micrometer membrane) in COS medium.

Transient transfection of the COS cells was performed as follows. COS cells (about $3.5 \times 10^6$), cultured in a 175 $cm^2$ Nunc TC-flask (Life Technologies Inc.) were washed once with MEM-HEPES. Six ml of the transfection mixture were pipetted onto the washed cells. After incubation for 30 minutes at ambient temperature, 48 ml of the chloroquine solution were added and the cells were incubated for another 4 hours at 37° C. The cells were washed one time with fresh COS-medium and finally incubated in 50 ml of the same medium at 37° C.

(C) Culturing of Transfected COS Cells.

Three, four, and five days after transfection a sample of the culture Supernatants was tested in a factor Xa amidolytic assay according to the procedure in Example 1. The results clearly demonstrated that factor Xa inhibitory activity was accumulating in the culture supernatant of the cells transfected with pEF-BOS-NAP5.

The COS culture supernatant was harvested five days after transfection and the MAP protein purified as described in Example 6.

Example 6
Purification of Recombinant Pro-AcaNAP5.

(A) Anion Exchange Chromatography.

The COS culture supernatant containing Pro-AcaNAP5 was centrifuged at 1500 r.p.m. (about 500×g) for 10 minutes before adding solid sodium acetate to a final concentration of 50 mM. The following protease inhibitors were added (all protease inhibitors from ICN Biomedicals Inc, Costa Mesa, Calif., USA): $1.0 \times 10_{-5}$ M pepstatin A (isovaleryl-Val-Val-4-amino-3-hydroxy-6-methyl-heptanoyl-Ala-4-amino-3-hydroxy-6-methylheptanoic acid), $1.0 \times 10^{-5}$ M leupeptin, $5 \times 10^{-5}$ M AEBSF (4-(2-aminoethyl)-benzenesulfonyl fluoride). The pH was adjusted with HCl to pH 5.3. The supernatant was clarified by passage through a 0.2 micrometer cellulose acetate filter (Corning Inc., Corning, N.Y., USA).

The clarified supernatant (total volume approximately 300 ml) was loaded on a Poros20 HQ (Perseptive Biosystems, MA) 1×2 cm column pre-equilibrated with Anion buffer (0.05 M sodium acetate, pH 5.3, 0.1 M NaCl) at a flow rate of 10 ml/minute (800 cm/hour). The column and the sample were at ambient temperature throughout this purification step. The column was subsequently washed with at least 10 column volumes of Anion buffer. Material that had inhibitory activity in a factor Xa amidolytic assay was eluted with Anion buffer containing 0.55 M NaCl at a flow rate of 5 ml/minute (400 cm/hour) and was collected.

(B) Molecular Sieve Chromatography Using Superdex30.

The 0.55 M NaCl elution pool (3 ml) from the anion-exchange chromatography was loaded on a Superdex30 PG (Pharmacia, Sweden) 1.6×66 cm column pre-equilibrated with 0.01 M sodium phosphate, pH 7.4, 0.15 M NaCl at 24° C. The chromatography was conducted at a flow rate of 2 ml/minute. Material which was inhibitory in the Factor Xa amidolytic assay eluted 56–64 ml into the run ($K_{av}$ of 0.207). This was exactly the same elution volume as determined for the native molecule.

(C) Heat Treatment.

The total pool of fractions having factor Xa inhibitory activity was incubated for 5 minutes at 90° C. in a glass tube and subsequently cooled rapidly on ice. Insoluble material was pelleted by centrifugation 19,000×gmax at 4° C. for 20 minutes. The supernatant contained all of the factor Xa inhibitory activity.

(D) Reverse Phase HPLC Chromatography.

The supernatant of the beat-treated sample was loaded onto a 0.46×25 cm C18 column (218TP54 Vydac; Hesperia, CA) which was then developed with a linear gradient of 10–35% acektonitrile in 0.1% (v/v) trifluoroacetic acid at 1 ml/minute with a rate of 0.4% change in acetonitrile/minute. Factor Xa inhibitory activity eluted at approximately 30% acetonitrile. The HPLC runs were performed on the same system as described in Example 1. Factor Xa inhibitory activity-containing fractions were vacuum dried.

(E) Molecular Weight Determination.

The estimated mass for recombinant Pro-AcaNAP5, isolated as described in sections A–D of this example, was determined using the same electrospray ionisation mass spectrometry system as described in Example 1.

The estimated mass of recombinant Pro-AcaNAP5 was 9248.4 daltons.

(F) Amino Acid Sequencing.

Following purification, the recombinant Pro-AcaNAP5 from COS cells was subjected to amino acid analysis to determine its amino-terminus sequence, as described in Example 1. The first nine amino acids of the amino-terminus terminus of Pro-AcaNAP5 was determined to be: Arg Thr Val Arg Lys Ala Tyr Pro Glu [SEQ. ID. NO. 109]. Compared to the native AcaNAP5 protein (see Example 1), Pro-AcaNAP5 possesses four additional amino acids on its N-terminus. The amino acid sequence of Pro-AcaNAP5 is shown in FIG. 5.

Example 7
Expression of Recombinant Pro-AcaNAP6 in COS Cells.

Pro-AcaNAP6 was transiently produced in COS cells essentially as described for Pro-AcaNAP5 in Example 5.

The AcaNAP6 coding region, including the secretion signal, was PCR-rescued with the same two oligonucleotide primers used for AcaNAP5: (1) YG101 targeting the 3'-end of the gene and having the sequence, GCTCOCTCTA GAAGCTTCAG ACATGTATAA TCTCATGTTG G [SEQ. ID. NO. 105], and (2) YG102 targeting the 5'-end of the gene and having the sequence, GACCAGTCTA GACAATGAAG ATGCTTTACG CTATCG [SEQ. ID. NO. 107]. The YG101-primer contains a non-matching nucleotide when used with AcaNAP6 as target (underlined T-residue; compare with FIG. 1 and FIG. 3); this mismatch results in the replacement an ATT Ile-codon by an ATA Ile-codon. The mismatch did not markedly influence the amplification efficiency.

The following modification from Example 5 was introduced: twenty-four hours after transfection of the COS cells (which is described in Example 5, section B) the COS-medium containing 10% FBS was replaced with 50 ml of a medium consisting of a 1:1 mixture of DMEM and Nutrient Mixture Ham's F-12 (Life Technologies). The cells then were further incubated at 37° C. and the production of factor Xa inhibitory activity detected as described in Example 5.

Example 8
Purification of Recombinant Pro-AcaNAP6.

(A) Anion Exchange Chromatography.

The COS culture supernatant containing Pro-AcaNAP6 was centrifuged at 1500 r.p.m. for 10 minutes before adding solid sodium acetate to a final concentration of 50 mM. The following protease inhibitors were added (all protease inhibitors from ICN Biomedicals Inc, Costa Mesa, Calif., USA): $1.0 \times 10^{-5}$ M pepstatin A (isovaleryl-Val-Val-4-amino-3-hydroxy-6-methyl-heptanoyl-Ala-4-amino-3-hydroxy-6-methylheptanoic acid), $1.0 \times 10^{-5}$ M leupeptin, $5 \times 10^{-5}$ M AEBSF (4-(2-aminoethyl)-benzenesulfonyl fluoride). The pH was adjusted with HCl to pH 5.3. The supernatant was clarified by passage through a 0.2 micrometer cellulose acetate filter (Corning Inc., Corning, N.Y., USA).

The clarified supernatant (total volume approximately 450 ml) was loaded on a Poros20 HQ (Perseptive Biosystems,MA) 1×2 cm column pre-equilibrated with Anion buffer (0.05 M Na sodium acetate, pH 5.3, 0.1 M NaCl) at a flow rate of 10 ml/minute (800 cm/hour). The column and the sample were at ambient temperature throughout this purification step. The column was subsequently washed with at least 10 column volumes of Anion buffer. Material that had inhibitory activity in a factor Xa amidolytic assay was eluted with Anion buffer containing 0.55 M NaCl at a flow rate of 5 ml/minute (400 cm/hour) and was collected.

(B) Molecular Sieve Chromatography Using Superdex30.

The 0.55 M NaCl elution pool (3 ml) from the anion-exchange chromatography was loaded on a Superdex30 PG (Pharmacia, Sweden) 1.6×66 cm column pre-equilibrated with 0.01 M sodium phosphate, pH 7.4, 0.15 M NaCl at 24°

C. The chromatography was conducted at a flow rate of 2 ml/minute. Material which was inhibitory in the Factor Xa amidolytic assay eluted 56–64 ml into the run ($K_{av}$ of 0.207). This was exactly the same elution volume as determined for the native NAP.

(C) Reverse Phase HPLC Chromatography.

The pooled fractions from the gel filtration were loaded onto a 0.46×25 cm C18 column (218TP54 Vydac; Hesperia, Calif.) which then was developed with a linear gradient of 10–35% acetonitrile in 0.1% (v/v) trifluoroacetic acid at a flow rate of 1 ml/minute with a rate of 0.4% change in acetonitrile/minute. Factor Xa inhibitory activity (assayed according to Example 1) eluted at approximately 30% acetonitrile. The HPLC runs were performed on the same system as described in Example 1. Factor Xa inhibitory activity containing-fractions were vacuum dried.

(D) Molecular Weight Determination.

The estimated mass for recombinant Pro-AcaNAP6, isolated as described in sections A to C of this example, was determined using the same electrospray ionisation mass spectrometry system as described in Example 1.

The estimated mass of recombinant Pro-AcaNAP6 was 8906.9 daltons.

(E) Amino Acid Sequencing.

Following purification, the recombinant Pro-AcaNAP6 from COS cells was subjected to amino acid sequence analysis as described in Example 1. The first five amino acids of the N-terminus of Pro-AcaNAP6 were determined to be: Arg Thr Val Arg Lys [SEQ. ID. NO. 110]. Compared to the native NAP protein (see Example 1), Pro-AcaNAP6 possesses four additional amino acids on its amino-terminus. The amino acid sequence of Pro-AcaNAP6 is shown in FIG. 6 [SEQ. ID. NO. 8).

Example 9

The Use of NAP DNA Sequences to Isolate Genes Encoding Other NAP Proteins.

The AcaNAP5 and AcaNAP6 cDNA sequences (from Example 2) were used to isolate related molecules from other parasitic species by cross-hybridization.

The pGEM-9Zf(-) vectors (Promega) containing the AcaNAPS and AcaNAP6 cDNAs were used to PCR-rescue the regions encoding the mature NAP proteins (Taq polymerase from Life Technologies; 20 temperature cycles: 1 minute at 95° C., 1 minute at 50° C., and 1.5 minutes at 72° C.). The oligonucleotide primers used were: (1) YG109, targeting the C-terminal sequences of cDNA encoding NAP, and having the sequence, TCAGACATGT-ATAATCTCAT-GTTGG [SEQ. ID. NO. 88], and (2) YG103 having the sequence, AAGGCATACC-CGGAGTGTGG-TG [SEQ. ID. NO. 89]. The YG109 primer contains a single nucleotide mismatch (underlined T-residue; compare with the sequences shown in FIGS. 1 and 3) when used with AcaNAP6 as target. This did not markedly influence the amplification efficiency. The correctly sized PCR products (about 230 basepairs) were both isolated from a 1.5% agarose gel. An equimolar mixture was radiolabeled by random primer extension (T7 QuickPrime kit; Pharmacia) and subsequently passed over a Bio-Spin 30 column (Bio-Rad, Richmond, Calif., USA).

*Ancylostoma ceylanicum* (Ace), *Ancylostoma duodenale* (Adu), and *Heligmosomoides pblygyrus* (Hpo) cDNA libraries were prepared essentially as described for *Ancylostoma caninum* in Example 2.

*Ancylostoma ceylanicum* and *Heligmosomoides polygyrus* were purchased from Dr. D. I. Pritchard, Department of Life Science, University of Nottingham, Nottingham, UK. *Ancylostoma duodenale* was purchased from Dr. G. A. Schad, The School of Veterinary Medicine, Department of Pathobiology, University of Pennsylvania, Philadelphia, Pa., USA.

In each case, the cDNAs were directionally cloned as EcoRI-NotI fragments in lambda gt11. Approximately $2\times10^5$ cDNA clones from each library (duplicate plaque-lift filters were prepared using Hybond™-N; Amersham) were screened with the radiolabeled AcaNAP5 and AcaNAP6 fragments using the following prehybridization and hybridization conditions: 5×SSC(SSC: 150 mM NaCl, 15 mM trisodium citrate), 5× Denhardt's solution, 0.5% SDS, 20% formamide, 100 micrograms/ml sonicated fish sperm DNA (Boehringer), overnight at 42° C. The filters were washed 4 times for 30 minutes in 2×SSC, 0.1% SDS at 37° C. After exposure (about 60 hours) to X-ray film, a total of between 100 and 200 hybridization spots were identified in the case of Ace and Adu. A small number of very faint spots were visible in the case of the Hpo cDNA library. For each of the libraries, eight positives were subjected to a second hybridization round at lower plaque-density so as to isolate single plaques.

The retained clones were further characterized by PCR amplification of the cDNA-inserts using the oligo(dT)-NotI primer (Promega; this is the same primer used to prepare first strand cDNA; see Example 2) [SEQ. ID. NO. 95] in combination with the lambda-gtll primer #1218 having the sequence, GGTGGCGACG ACTCCTGGAG CCCG [SEQ. ID. NO. 96] (New England Biolabs; primer #1218 targets lambda sequences located upstream of the site of cDNA insertion). PCR amplifications were performed as follows: Taq polymerase from Boehringer; 30 temperature cycles: 1 minute at 95° C.; 1 minute at 50° C.; 1.5 minutes at 72° C. Gel-electrophoretic analysis of the PCR products clearly demonstrated that cDNAs of roughly the same size as the AcaNAP5 cDNA (e.g., 400 to 500 bp) were obtained for each species. In addition to these AcaNAP5-sized cDNAs, some Ace and Adu cDNAs were estimated to be about 700 bp long.

A number of clones, containing either a 500 bp or an 800 bp insert, were chosen for sequence determination. To that end the cDNA inserts were subcloned, as SfiI-NotI fragments, into pGEM-type phagemids (Promega; refer to Example 2 for details) which permit the preparation of single stranded DNA. The sequencing results led to the identification of six different new NAP-like proteins, designated as follows: AceNAP4, AceNAP5, AceNAP7, AduNAP4, AduNAP7, and HpoNAP5. The nucleotide sequences of the cDNAs as well as the deduced amino acid sequences of the encoded proteins are shown in FIG. 7A (AceNAP4 [SEQ. ID. NO. 9]), FIG. 7B (AceNAP5) [SEQ. ID. NO. 10], FIG. 7C (AceNAP7) [SEQ. ID. NO. 11], FIG. 7D (AduNAP4) [SEQ. ID. NO. 12], FIG. 7E (AduNAP7) [SEQ. ID. NO. 13], and FIG. 7F (HpoNAP5) [SEQ. ID. NO. 14]. The AceNAP4 [SEQ. ID. NO. 9] and AduNAP7 [SEQ. ID. NO. 13] cDNAs, each about 700 bp long, each encoded proteins which incorporated two NAP domains; the other cDNAs isolated coded for a protein having a single NAP domain. The AduNAP4 cDNA clone [SEQ. ID. NO. 12] was not full-length, i.e,. the clone lacked the 5'-terminal part of the coding region; the correct reading frame could, however, be assigned based on amino acid sequence homology with the NAP family of related molecules.

The identified cDNA sequences can be used to produce the encoded proteins as disclosed in Examples 3, 4, 5, and 7 using the same or alternative suitable expression systems. Conditioned media or cell lysates, depending on the system used, can be tested as such or after fractionation (using such methodology as outlined in Example 3, 4, 6 and 8) for protease inhibitory and anticoagulant activity. Proteins that are encoded by cDNAs which hybridize to probes derived from fragments of the AcaNAP5 gene (FIG. 1) [SEQ. ID. NO. 3] and/or the AcaNAP6 gene (FIG. 3) [SEQ. ID. NO. 5] and that possess serine protease inhibitory and/or anticoagulant properties are considered to belong to the NAP family of related molecules.

Example 10

Identification of NAP by Functional Display of cDNA Encoded Proteins.

(A) The pDONG Series of Vectors.

The nucleotide sequences of the pDONG vectors, pDONG61 [SEQ. ID. NO. 15], pDONG62 [SEQ. ID. NO. 16] and pDONG63 [SEQ. ID. NO. 17], derivatives of pUC119 [Vieira, J. and Messing, J., Methods in Enzymology, 15:3–11 (1987)), are depicted in FIGS. 8A to 8C respectively.

To construct these three vectors, HindIII and SfiI restriction sites were added at the 5'-end and 3'-end of the filamentous phage gene 6 by PCR amplification of the M13K07 single stranded DNA [Vieira, J. and Messing, J., Ibid] with the G6BACKHIND backward primer and G6FORSFI61, G6FORSFI62 or G6FORSFI63 as forward primers. In a second PCR, the three obtained fragments were re-amplified with G6BACKHIND and G6FORNOTBAMH as forward primer to append NotI and BamHI sites at the 3'-end of the fragments. The sequences of the above mentioned PCR-primers are as follows (restriction sites are underlined):

cycles: 1 minute at 95° C., 1 minute at 50° C., and 3 minutes at 72° C. followed by 10 minutes at 65° C.), with the lambda gt11 primer #1218 having the sequence, GGTGGCGACG ACTCCTGGAGCCCG [SEQ. ID. NO. 96] (New England Biolabs, Beverly, Mass., USA; targeting sequences located upstream of the cDNA insert) in combination with the oligo(dT)-NotI primer/adaptor (Promega) used for first strand cDNA synthesis. Following digestion with the restriction enzymes SfiI and NotI, the whole size-range of amplification products were recovered from agarose gel.

All fragments were directionally cloned into the pDONG61, pDONG62, and pDONG63 vectors. The recipient vector-fragments were prepared by digestion of the CsCl purified vectors with SfiI and NotI and purification with the "Wizard™ PCR Preps DNA Purification System" (Promega Corp, Madison, Wis., USA).

*E. coli* strain TG1 [Sambrook, J., Fritsch, E. F. and Maniatis, T., *Molecular Cloning, A Laboratory Manual, Second Edition*, volumes 1 to 3, Cold Spring Harbor Laboratory Press (1989)] was transformed by electroporation with the pDONG/cDNA ligation mixtures. Electrotransformed cells were incubated 1 hour at 37° C. in SOC medium [Sambrook, J. et al., Ibid.] and plated on LB-agar containing 0.1% glucose and 100 micrograms/ml carbenicillin (245×245×25 mm plates; Nunc). $2.2 \times 10^6$, $1.6 \times 10^6$, and $1.4 \times 10^6$ carbenicillin resistant transformants were obtained with pDONG61, pDONG62, and pDONG63, respectively. From each respective library, designated 20L, 21L and 22L, a number of randomly picked transformants were subjected to PCR analysis (Taq polymerase from Life Technologies; 30 cycles of amplification with the following

```
G6BACKHIND:      ATCCGAAGCT TTGCTAACAT ACTGCGTAAT AAG                          [SEQ. ID. NO. 111]

G6FORSFI61:      TATGGGATGG CCGACTTGGC CTCCGCCTGA GCCTCCACCT TTATCCCAAT CCAAATAAGA [SEQ. ID. NO. 112]

G6FORSFI62:      ATGGGATGGC CGACTTGGCC CTCCGCCTGA GCCTCCACCT TTATCCCAAT CCAAATAAGA [SEQ. ID. NO. 113]

G6FORSFI63:      TATGGGATGG CCGACTTGGC CGATCCGCCT GAGCCTCCAC CTTTATCCCA ATCCAAATAA [SEQ. ID. NO. 114]

GAG6FORNOTBAMH:  AGGAGGGGAT CCGCGGCCGC GTGATATGGG ATGGCCGACT TGGCC           [SEQ. ID. NO. 115]
```

Finally, the PCR products were gel-purified, individually digested with HindIII and BamHI and inserted between the corresponding sites of pUC119. Sequence determination confirmed that pDONG61, pDONG62, and pDONG63 all contained the intended insert.

The pDONG series of vectors permit the cloning of cDNAs, as SfiI-NotI fragments. This cloning fuses the cDNAs in each of the three reading (translation) frames to the 3'-end of filamentous phage gene 6 which encodes one of the phage's coat proteins. Infection of a male-specific *E. coli* strain harboring a pDONG-derivative, with VCSM13 helper phage (Stratagene, La Jolla, Calif.), results in the rescuing of pseudo-virions which encapsidate one specific single strand of the pDONG-derivative and which may also incorporate a recombinant protein 6 (p6) fusion protein in their coat. cDNAs which are such that the encoded protein is functionally displayed on the phage surface as a recombinant p6 fusion protein become identifiable by means of a panning experiment described below.

(B) Transfer of the *Ancylostoma caninum* cDNA Library from Lambda gt11 to the pDONG Series of Vectors.

A phage lambda preparation of the pooled *A. caninum* cDNA clones (about $1 \times 10^6$ plaques, see Example 2) was used to PCR-rescue the cDNA inserts (Taq polymerase from Life Technologies, Gaithersburg, Md., USA; 20 temperature temperature program: 1 minute at 95° C., 1 minute at 50° C., and 1 to 3 minutes at 72° C.) using two primers that match with sequences flanking the multiple cloning site of pUC119 (primers #1224 having the sequence, CGCCAGGGTTTTC-CCAGTCA CGAC [SEQ. ID. No. 116], and #1233 having the sequence, AGCGGATAAC AATTTCACAC AGGA [SEQ. ID. NO. 101]; New England Biolabs). The results showed that the vast majority of the clones contained a cDNA-insert of variable size.

(C) Factor Xa Based Affinity-Selection of cDNA Clones Encoding a NAP Protein.

Phage particles from the 20L, 21L and 22L libraries were rescued as follows: each library was scraped from the plates and grown at 37° C. in 100 ml LB medium supplemented with 1% glucose and 100 micrograms/ml carbenicillin until the optical absorbance at 600 nm reaches the value of 0.5. After addition of VCSM13 helper phage (Stratagene) at a multiplicity of infection (moi) of 20, the culture was left to stand for 30 minutes at 37° C. and then slowly shaken for another 30 minutes. The cells were pelleted by centrifugation and resuspended in 250 ml LB medium supplemented with 100 micrograms/ml carbenicillin and 50 micrograms/ml kanamycin. These cultures were allowed to grow overnight at 30° C. under vigorous agitation. The resulting phage particles were purified by two consecutive precipitations with polyethylene glycol/NaCl and resuspended at $1\times10^{13}$ virions per ml in TRIS-buffered saline (0.05M Tris, 0.15 M sodium chloride, pH 7.4) (TBS).

Equal amounts of phage particles from the 20L, 21L and 22L were then mixed together.

Human factor Xa (see Example 1 for preparation) was biotinylated with biotin-XX-NHS according to manufacturer's instructions (Pierce). The amidolytic activity of the protease was not affected by this modification as shown by an enzymatic assay using the chromogenic substrate S-2765 (Chromogenix; see Example 1). Streptavidin-coated magnetic beads (Dynal; 1 mg per panning round) were washed three times with TBS and blocked in TBS supplemented with 2% skim milk (Difco) at ambient temperature. After one hour, the magnetic beads were washed twice with TBS before use.

For the first round of panning, $1\times10^{13}$ phage from the pooled libraries were incubated for 75 minutes at 4° C. in 200 microliters of TBS buffer supplemented with 250 nM biotinylated factor Xa, 5 mM $CaCl_2$ and 2% skim milk. After this time, 1 mg blocked streptavidin-coated magnetic beads, resuspended in 200 microliters of TBS containing 5 mM CaCl2 and 2% skim milk, was added to the phage solution and incubated for 1 hour at 4° C. with gentle agitation. With a magnet (Dynal), the magnetic beads were then rinsed ten times with 500 microliters of TBS containing 0.1% Tween-20. Bound phage were eluted from the magnetic beads by incubating them with 500 microliters of 0.1 M glycine-HCl buffer (pH 2.0) for 10 minutes. The supernatant was neutralized with 150 microliters 1 M Tris-HCl buffer (pH 8.0).

For phage propagation, *E. coli* strain TG1 [Sambrook, J., Fritsch, E. F. and Maniatis, T., *Molecular Cloning, A Laboratory Manual, Second Edition*, volumes 1 to 3, Cold Spring Harbor Laboratory Press (1989)] was grown at 37° C. in 10 ml LB medium until the optical absorbance at 600 nm reached the value of 0.5. The culture was infected with 650 microliters of phage eluted from the magnetic beads and briefly incubated at 37° C. with no shaking. After centrifugation, the infected cells were resuspended in 2 ml LB medium and plated onto 245×245×25 mm plates filled with LB-agar containing 1% glucose and 100 micrograms/ ml carbenicillin. After overnight incubation at 37° C., the cells were scraped from the plates and resuspended in 40 ml LB medium supplemented with 1% glucose and 100 micrograms/ml carbenicillin. A cell aliquot corresponding to 15 optical densities at 600 nm was then used to inoculate 100 ml LB medium containing 1% glucose and 100 micrograms/ ml carbenicillin. Phage rescue for the next panning round was done as outlined above.

For the second panning round, $6\times10^{12}$ phage were incubated during 90 minutes with 1 mg blocked streptavidin-coated magnetic beads in 200 microliters of TBS containing 2.5 mM $Ca^{2+}$ and 2% skim milk (this step was introduced in the procedure to avoid selection of streptavidin-binding clones). After removal of the beads, the same protocol was followed as for round 1. Rounds 3, 4 and 5 were accomplished as round 2, except that the phage input was lowered to $2\times10^{12}$ phage.

Twenty-four individual carbenicillin resistant clones that were isolated after five rounds of panning against biotinylated factor Xa, were then analyzed by ELISA. Streptavidin-coated 96-well plates (Pierce) were blocked for 1 hour with 200 microliters of TBS containing 2% skim milk per well, then were incubated for 1 hour with 100 microliters of 20 nM biotinylated factor Xa in TBS per well. For each clone, about $10^{10}$ phage diluted in 100 microliters TBS containing 2% skim milk and 0.1% Tween-20 were added to the wells. After a 2-hour incubation, the wells were rinsed four times with 200 microliters TBS containing 0.1% Tween-20. Bound phage were visualized by consecutively incubating with a rabbit anti-M13 antiserum (see Example 11), an alkaline phosphatase conjugated anti-rabbit serum (Sigma), and p-nitrophenylphosphate as substrate (Sigma). Absorbances were taken at 405 nm after 20 minutes. Out of the 24 clones, five bound strongly to factor Xa. No significant non-specific binding was observed with these phage when tested in the same ELISA with omission of biotinylated factor Xa.

Single stranded DNA was then prepared from the five positive clones and the inserts 3' to the gene 6 were submitted to automated DNA sequencing using the primer #1224 having the sequence, CGCCAGGGTT TTC-CCAGTCA CGAC [SEQ. ID. NO. 116] (New England Biolabs). All five clones were found to contain the same 470 bp 5'-truncated cDNA fused in frame to gene 6 in pDONG63. The nucleotide sequence of this cDNA as well as the deduced amino acid sequence are depicted in FIG. 9 [SEQ. ID. NO. 19]. The cDNA, designated AcaNAPc2, encodes a protein, designated NAP isoform c2, that belongs to the NAP family of related proteins.

Example 11

Preparation of Antiserum Against M13 Phage.

Antiserum against M13 phage was prepared in rabbits by subcutaneous injections of about $10^{13}$ M13K07 phage in 500 microliters of PBS (0.01 M sodium. phosphate, pH 7.4+0.15 M sodium chloride) combined with ea equal volume of adjuvant. The M13KO7 phage were CsCl-purified essentially as described by Glaser-Wuttke, G., Keppner, J., and Rasched, I., Biochim. Biophys. Acta, 9: 239–247 (1989). The initial injection was done with Complete Freunds adjuvant on day 0, followed by subsequent injections with Incomplete Freunds adjuvant on days 7, 14 and 35. Antiserum was harvested on day 42.

The IgG fraction of the antiserum was enriched by passage over a Protein A-Sepharose column using conditions well known in the art.

Example 12

The Use of AcaNAP5 and AcaNAP6 DNA Sequences to Isolate Additional NAP-Encoding Sequences from *A. caninum*.

The AcaNAP5 and AcaNAP6 cDNA sequences (from Example 2) were used to isolate related molecules from the same parasitic species by cross-hybridization.

The pGEM-9Zf(-) vectors (Promega, Madison, Wis.) containing the AcaNAP5 and AcaNAP6 cDNAs were used to PCR-rescue the regions encoding the mature NAP proteins (Taq polymerase from Life Technologies (Gaithersburg, Md.); 20 temperature cycles: 1 minute at 95° C., 1 minute at 50° C., and 1.5 minutes at 72° C.). The oligonucleotide primers used were: (1) YG109, targeting the C-terminal-encoding sequences of cDNA encoding AcaNAP5 and AcaNAP6, and having the sequence, TCAGACATGT-ATAATCTCAT-GTTGG [SEQ. ID. NO. 88], and (2) YG103, targeting the N-terminal-encoding sequences of mature AcaNAP5 and AcaNAP6, having the sequence, AAGGCATACC-CGGAGTGTGG-TG [SEQ. ID. NO. 89]. The YG109 primer contains a single nucleotide mismatch when used with AcaNAP6 as target (underlined T-residue; compare with the sequence shown in FIG. 3 [SEQ. ID. NO. 5]).

This mismatch did not markedly influence the amplification efficiency. The correctly sized PCR products (about 230 basepairs) for AcaNAP5 and AcaNAP6 were both isolated from a 1.5% agarose gel. An equimolar mixture was radiolabeled by random primer extension (T7 QuickPrime kit; Pharmacia (Sweden) and subsequently passed over a Bio-Spin 30 column (Bio-Rad, Richmond, Calif., USA).

Approximately 750,000 *Ancylostoma caninum* (Aca) cDNA clones (refer to Example 2 (B); duplicate plaque-lift filters were prepared using Hybond™-N; Amersham (Buckinghamshire, England) were screened with the radiolabeled AcaNAP5 and AcaNAP6 cDNA fragments using the following prehybridization and hybridization conditions: 5×SSC(SSC: 150 mM NaCl, 15 mM trisodium citrate), 5× Denhardt's solution, 0.5% SDS, 20% formamide, 100 micrograms/ml sonicated fish sperm DNA (Boehringer), overnight at 42° C. The filters were washed 4 times for 30 minutes in 2×SSC, 0.1% SDS at 37° C. After exposure to X-ray film, a total of about 300 positives were identified.

48 of the 300 positives were subjected to PCR-amplification (Taq polymerase from Boehringer Mannheim, Germany; 30 temperature cycles: 1 minute at 95° C.; 1 minute at 50° C.; 1.5 minutes at 72° C.) using the above mentioned YG109 primer, specific for the C-terminus-encoding sequence of AcaNAP5 and AcaNAP6 cDNAs, and primer #1218 which targets lambda-gtll sequences located upstream of the site of cDNA insertion (New England Biolabs, Beverly, Mass.; GGTGGCGACG ACTCCTGGAG CCCG [SEQ. ID. NO. 96]). 31 out of the 48 positives yielded a PCR product of a size similar to that expected for a AcaNAP5/6-type cDNA.

The remaining 17 positives were used as template for amplification with primer #1218 and an AcaNAPc2 specific primer (e.g., LJ189, targeting the AcaNAPc2 C-terminus and having the sequence GTTTCGAGTT CCGGGATATA TAAAGTCC [SEQ. ID. NO. 117]; refer to Example 10 and FIG. 9). None of the clones yielded a PCR product. All 17 positives were then subjected to a second hybridization round at lower plaque-density; single isolated clones were identified in all cases. The 17 isolated cDNA clones were re-analyzed by PCR using the primer couples #1218/YG109 and #1218/LJ189. Three out of the 17 clones yielded an amplification product with the #1218/YG109 primers.

The remaining 14 clones were further analyzed by PCR amplification with the primers #1218 and oligo(dT)-Not (Promega, Madison, Wis.; this is the same primer used to prepare first strand cDNA; see Example 2). All 14 clones yielded a PCR product. Gel-electrophoretic analysis of the PCR products indicated that some cDNAs were considerably longer than the AcaNAP5 cDNA insert.

Ten clones, including those having the largest cDNA inserts, were chosen for sequence determination. To that end the cDNA inserts were subcloned as SfiI-NotI fragments onto pGEM-type phagemids (Promega, Madison, Wis.), as described in Example 2. The sequencing identified eight additional NAP protein sequences, designated as follows: AcaNAP23, AcaNAP24, AcaNAP25, AcaNAP31, AcaNAP44, AcaNAP45, AcaNAP47, and AcaNAP48. Two additional cDNA clones, designated AcaNAP42 and AcaNAP46, encoded proteins identical to those encoded by AcaNAP31 [SEQ. ID. NO. 34]. The nucleotide sequences of the cDNAs as well as the deduced amino acid sequences of the encoded proteins are shown in FIG. 13A (AcaNAP23 [SEQ. ID. NO. 31]), FIG. 13B (AcaNAP24 [SEQ. ID. NO. 32]), FIG. 13C (AcaNAP25 [SEQ. ID. NO. 33]), FIG. 13D (AcaNAP31 [SEQ. ID. NO. 34]), FIG. 13E (AcaNAP44 [SEQ. ID. NO. 35]), FIG. 13F (AcaNAP45 [SEQ. ID. NO. 36]), FIG. 13G (AcaNAP47 [SEQ. ID. NO. 37]), and FIG. 13H (AcaNAP48 [SEQ. ID. NO. 38]). All clones were full-length and included a complete secretion signal. The AcaNAP45 [SEQ. ID. NO. 36] and AcaNAP47 [SEQ. ID. NO. 37] cDNAs, each encode proteins which incorporate two NAP domains; the other cDNAs code for a protein having a single NAP domain.

Example 13

The Use of NAP DNA Sequences to Isolate Sequences Encoding a NAP Protein from *Necator americanus*

The sequences of AcaNAP5 [SEQ. ID. NO. 3], AcaNAP6 [SEQ. ID. NO. 5], AcaNAPc2 [SEQ. ID. NO. 19], AcaNAP23 [SEQ. ID. NO. 31], AcaNAP24 [SEQ. ID. NO. 32], AcaNAP25 [SEQ. ID. NO. 33], AcaNAP31 [SEQ. ID. NO. 34], AcaNAP44 [SEQ. ID. NO. 35], AcaNAP45 [SEQ. ID. NO. 36], AcaNAP47 [SEQ. ID. NO. 37], AcaNAP48 [SEQ. ID. NO. 38], AceNAP4 [SEQ. ID. NO. 9], AceNAP5 [SEQ. ID. NO. 10], AceNAP7 [SEQ. ID. NO. 11], AduNAP4 [SEQ. ID. NO. 12], AduNAP7 [SEQ. ID. NO. 13], and HpoNAP5 [SEQ. ID. NO. 14] (see FIGS. 1, 3, 7, and 13) were used to isolate related molecules from the hematophageous parasite *Necator americanus* by PCR-cloning.

Consensus amino acid sequences were generated from regions of homology among the NAP proteins. These consensus sequences were then used to design the following degenerate PCR primers: NAP-1,5'-AAR-CCN-TGY-GAR-MGG-AAR-TGY-3' [SEQ. ID. NO. 90] corresponding to the amino acid sequence NH2-Lys-Pro-Cys-Glu-(Arg/Pro/Lys)-Lys-Cys [SEQ. ID. NO. 118]; NAP-4.RC, 5'-TW-RWA-NCC-NTc-YTT-RCA-NAC-RCA-3' [SEQ. ID. NO. 91], corresponding to the sequence $NH_2$-Cys-(Val/Ile/Gln)-Cys-(Lys/Asp/Glu/Gln)-(Asp/Glu)-Gly-(Phe/Tyr)-Tyr [SEQ. ID. NO. 119]. These primers were used pairwise to generate NAP-specific probes by PCR using *N. americanus* cDNA as template.

Adult worms, *N. americanus*, were purchased from Dr. David Pritchard, University of Nottingham. Poly(A+) RNA was prepared using the QuickPrep mRNA Purification Kit (Pharmacia, Piscataway, N.J.). One microgram of mRNA was reverse transcribed using AMV reverse transcriptase and random hexamer primers (Amersham, Arlington Hills, Ill.). One fiftieth of the single-stranded cDNA reaction product was used as template for ~400 pmole of each of NAP-1 and NAP-4.RC, with PCR GeneAmp (Perkin Elmer, Norwalk, Conn.) reagents, on a Perkin-Elmer DNA thermal cycler. PCR conditions were: cycles 1–3, denaturation at 96° C. for 2 minutes, annealing at 37° C. for 1 minute, and elongation at 72° C. for 3 minutes (ramp time between 37° C. and 72° C. was 2 minutes); cycles 4–5, denaturation at 94° C. for 1 minute, annealing at 37° C. for 1 minute, and elongation at 72° C. for 2 minutes (ramp time between 37° C. and 72° C. was 2 minutes); cycles 6–45, denaturation at 94° C. for 1 minutes, annealing at 37° C. for 1 minute, and elongation at 72° C. for 2 minutes. Elongation times were incremented by 3 seconds/cycle for cycles 6–45.

PCR amplification of *N. americanus* cDNA with NAP-1 and NAP-4.RC resulted in an approximately 100 bp amplification product. The PCR product was labeled with [a-32P]-dCTP (Amersham) using random primer labeling (Stratagene, La Jolla, Calif.), and labeled DNA was separated from unincorporated nucleotides using a Chromaspin-10 column (Clonetech, Palo Alto, Calif.).

A cDNA library was constructed using the following procedure. Double stranded cDNA was synthesized from 1 µg of *N. americanus* poly(A+) RNA using AMV reverse transcriptase and random hexamer primers (Amersham, Arlington Hills, Ill.). cDNA fragments larger than approximately 300 bp were purified on a 6% polyacrylamide gel and ligated to EcoRI linkers (Stratagene, San Diego, Calif.) using standard procedures. Linkered cDNA was ligated into EcoRI-cut and dephosphorylated lambda gt10 (Stratagene, San Diego, Calif.) and packaged using a Gigapack Gold II packaging kit (Stratagene, San Diego, Calif.).

Prehybridization and hybridization conditions were 6×SSC(SSC: 150 mM NaCl, 15 mM trisodium citrate, pH 7.0), 0.02 M sodium phosphate pH 6.5, 5× Denhardt's solution, 100 µg/ml sheared, denatured salmon sperm DNA, 0.23% dextran sulfate. Prehybridization and hybridization were at 42° C., and the filters were washed for 30 minutes at 45° C. with 2×SSC after two prewashes with 2×SSC for 20 minutes. The filters were exposed overnight to X-ray film with two intensifying screens at −70° C.

Approximately 400,000 recombinant phage of the random primed *N. americanus* library (unamplified) were screened with the NAP-1/NAP-4.RC PCR fragment. About eleven recombinant phage hybridized to this probe, of which four were isolated for nucleotide sequencing analysis. Double stranded sequencing was effected by subcloning the EcoRI cDNA fragments contained in these phage isolates into pBluescript II KS+ vector (Stratagene, San Diego, Calif.). DNA was sequenced using the Sequenase version 2.0 kit (Amersham, Arlington Hills, Ill.)) and M13 oligonucleotide primers (Stratagene, San Diego, Calif.).

The four lambda isolates contained DNA that encoded a single 79 amino acid NAP polypeptide that resembles NAP sequences from *Ancylostoma* spp. and *H. polygyrus*. The NAP polypeptide from *N. americanus* has a calculated molecular weight of 8859.6 Daltons. The nucleotide and deduced amino acid sequences are shown in FIG. 14.

Example 14
Expression of Recombinant AceNAP4 in COS Cells.
A. Expression

AceNAP4 was transiently produced in COS cells essentially as described for Pro-AcaNAP5 in Example 5 and Pro-AcaNAP6 in Example 7.

A pGEM-type phagemid that harbors the AceNAP4 cDNA (from Example 9), served as target for PCR-rescue of the entire AceNAP4 coding region, including the secretion signal, using two XbaI-appending oligonucleotide primers. The primers used were: (1) SHPCR4, targeting the 5'-end of the gene and having the sequence, GACCAGTCTA GAC-CACCATG GCGGTGCTTT ATTCAGTAGC AATA [SEQ. ID. NO. 120], and (2) SHPCR5, targeting the 3'-end of the gene and having the sequence, GCTCGCTCTA GAT-TATCGTG AGGTTTCTGG TGCAAAAGTG [SEQ. ID. NO. 121]. The XbaI restriction sites included in the primers are underlined. The primers were used to amplify the AceNAP4 sequence according to the conditions described in Example 5.

Following digestion with XbaI enzyme, the amplification product, having the expected size, was isolated from an agarose gel and subsequently substituted for the about 450 basepair XbaI stuffer fragment of the pEF-BOS vector [Mizushima, S. and Nagata, S., Nucl. Acids Res., 18: 5322 (1990)]. The protocol described in Example 5 was followed to yield clone pEF-BOS-AceNAP4, which was first shown to harbor the XbaI-insert in the desired orientation by PCR using primers SHPCR4 and YG60, and subsequently confirmed by sequence determination. This clone was used to transfect COS cells according to the methods in Example 5.

Twenty-four hours after transfection of the COS cells (refer to Example 5, section B) the COS-medium containing 10% FBS was replaced with 50 ml of a medium consisting of a 1:1 mixture of DMEM and Nutrient Mixture Ham's F-12 (Life Technologies (Gaithersburg, Md.). The cells were then further incubated at 37° C. and the production of EGR-factor Xa dependent TF/factor VIIa inhibitory activity detected as described in Example E.
B. Purification of AceNAP4
1. Anion-Exchange Chromatography The COS culture supernatant from the AceNAP4-expressing cells was centrifuged at 1500 r.p.m. (about 500× g) for 10 minutes before the following protease inhibitors (ICN Biomedicals Inc., Costa Mesa, Calif.) were added ($1.0 \times 10^{-5}$M pepstatinA (isovaleryl-Val-Val-4-amino-3-hydroxy-6-methyl-heptanoyl-Ala-4-amino-3hydroxy-6-methylheptanoic acid), $1.0 \times 10^{-5}$M AEBSF (4-(2-amonoethyl)-benzenesulfonyl fluoride). Solid sodium acetate was added to a final concentration of 50 mM before the pH was adjusted with 1N HCl to pH 5.3. The supernatant was clarified by passage through a 0.22 micrometer cellulose acetate filter (Corning Inc., Corning, N.Y., USA).

The clarified supernatant (total volume aproximaterly 450 ml) was loaded on a Poros20 HQ (Perseptive Biosystems, MA) 1×2 cm column preequilibrated with Anion Buffer (0.05M sodium acetate 0.1M NaCl, pH 5.3) at a flow rate of 5 ml/minute. The column and the sample were at ambient temperature throughout this purification step. The column was subsequently washed with 10 column volumes of Anion Buffer and 10 column volumes of 50 mM sodium acetate, 0.37M NaCl, pH5.3

Material that had EGR-FXa dependent fVIIa/TF amidolytic inhibitory activity (see Example E) was eluted with 50 mM sodium acetate, 1M NaCl, pH5.3 at a flow of 2 ml/minute.
2. Reverse-Phase Chromatography An aliqout of the pool of fractions collected after anion exchange chromatography was loaded onto a 0.46×25 cm C18 column (218TP54 Vydac; Hesperia, Calif.) which was then developed with a linear gradient of 10–35% acetonitrile in 0.1% (v/v) trifluoroacetic acid at 1 ml/minute with a rate of 0.4% change in acetonitrile/minute. EGR-FXa dependent TF/FVIIa amidolytic inhibitory activity (see Example E) was monitored and fractions containing this inhibitory activity were isolated and vacuum-dried.
3. Characterization of Recombinant AceNAP4

The AceNAP4 compound demonstrated SDS-PAGE mobility on a 4–20% gel, consistent with its size predicted from the sequence of the cDNA (Coomassie stained gel of material after RP-chromatography).

Example 15
Production and Purification of Recombinant AcaNAPc2 in *P. pastoris*.
A. Expression Vector Construction.

Expression of the AcaNAPc2 gene in *P. pastoris* was accomplished using the protocol detailed in Example 3 for the expression of AcaNAP5 with the following modifications.

The pDONG63 vector containing the AcaNAPc2 cDNA, described in Example 10, was used to isolate by amplification ("PCR-rescue") the region encoding mature AcaNAPc2 protein (using Vent polymerase from New England Biolabs, Beverly, Mass.; 20 temperature cycles: 1 minute at 94° C., 1 minute at 50° C., and 1.5 minutes at 72° C.). The following oligonucleotide primers were used:
LJ190: AAAGCAACGA-TGCAGTGTGG-TGAG [SEQ. ID. NO. 122]
LJ191: GCTCGCTCTA-GAAGCTTCAG-TTCGAGTTC-CGGGATATAT-AAAGTCC [SEQ. ID. NO. 123]

The LJ191 primer, targeting C-terminal sequences, contained a non-annealing extension which included XbaI and HindIII restriction sites (underlined).

Following digestion with XbaI enzyme, the amplification product, having the expected size, was isolated from gel and subsequently enzymatically phosphorylated (T4 polynucleotide kinase from New England Biolabs, Beverly, Mass.). After heat-inactivation (10 minutes at at 70° C.) of the kinase, the blunt-ended/XbaI fragment was directionally cloned into the vector pYAM7SP8 for expression purposes. The recipient vector-fragment from pYAM7SP8 was prepared by StuI-SpeI restriction, and purified from agarose gel. The *E. coli* strain, WK6 [Zell, R. and Fritz, H.-J., EMBO J., 6: 1809–1815 (1987)], was transformed with the ligation mixture, and ampicillin resistant clones were selected.

Based on restriction analysis, a plasmid clone containing an insert of the expected size, designated pYAM7SP-NAPC2, was retained for further characterization. Sequence determination of the clone pYAM7SP-NAPC2 confirmed the precise insertion of the mature AcaNAPc2 coding region in fusion with the prepro leader signal, as predicted by the construction scheme, as well as the absence of unwanted mutations in the coding region.

B. Expression of Recombinant AcaNAPc2 in *P. pastoris.*

The *Pichia* strain GTS115 (his4) has been described in Stroman, D. W. et al., U.S. Pat. No. 4,855,231. All of the *P. pastoris* manipulations were performed essentially as described in Stroman, D. W. et al., U.S. Pat. No. 4,855,231.

About 1 microgram of pYAM7SP-NAPC2 plasmid DNA was electroporated into the strain GTS115 using a standard electroporation protocol. The plasmid was previously linearized by SalI digestion, theoretically targeting the integration event into the his4 chromosomal locus.

The selection of a AcaNAPc2 high-expresser strain was performed as described in Example 3 for NAP isoform 5 (AcaNAP5) using mini-culture screening. The mini-cultures were tested for the presence of secreted AcaNAPc2 using the fVIIa/TF-EGR-fxa assay (Example E) resulting in the selection of two clones. After a second screening round, using the same procedure, but this time at the shake-flask level, one isolated host cell was chosen and designated *P. pastoris* GTS115/7SP-NAPc2.

The host cell, GTS115/7SP-NAPc2, was shown to have a wild type methanol-utilisation phenotype (Mut⁺), which demonstrated that the integration of the expression cassette into the chromosome of GTS115 did not alter the functionality of the genomic AOX1 gene.

Subsequent production of recombinant AcaNAPc2 material was performed in shake flask cultures, as described in Stroman, D. W. et al., U.S. Pat. No. 4,855,231. The recombinant product was purified from *Pichia pastoris* cell supernatant as described below.

C. Purification of Recombinant AcaNAPc2

1. Cation Exchange Chromatography

The culture supernatant (100 ml) was centrifuged at 16000 rpm (about 30,000×g) for 20 minutes before the pH was adjusted with 1N HCl to pH 3. The conductivity of the supernatant was decreased to less than 10 mS/cm by adding MilliQ water. The diluted supernatant was clarified by passage through a 0.22 micrometer cellulose acetate filter (Corning Inc., Corning, N.Y., USA).

The total volume (approximately 500 ml) of the supernatant was loaded onto a Porcs20HS (Perseptive Biosystems, MA) 1×2 cm column pre-equilibrated with Cation Buffer (50 mM sodium citrate pH 3) at a flow-rate of 5 ml/minute. The column and the diluted fermentation supernatant were at room temperature througout this purification step. The column was subsequently washed with 50 column volumes Cation Buffer and 10 column volumes Cation Buffer containing 0.1M NaCl. Material that had inhibitory activity in a prothrombinase assay was eluted with Cation Buffer containing 1M NaCl at a flow rate of 2 ml/min.

2. Molecular Sieve Chromatography using Superdex30

The 1M NaCl elution pool containing the EGR-fXa-fVIIa/TF inhibitory material (3 ml; see Example C) from the cation-exchange column was loaded onto a Superdex30 PG (Pharmacia, Sweden) 1.6×60 cm column pre-equilibrated with 0.1 M sodium phosphate pH7.4, 0.15 M NaCl at ambient temperature. The chromatography was conducted at a flow-rate of 2 ml/minute. The prothrombinase inhibitory activity (Example C) eluted 56–64 ml into the run and was pooled.

3. Reverse Phase Chromatography

One ml of the pooled fractions from the gel filtration chromatography was loaded onto a 0.46×25 cm C18 column (218TP54 Vydac; Hesperia, Calif.) which was then developed with a linear gradient 10–30% acetonitrile in 0.1% (v/v) trifluoroacetic acid with a rate of 0.5% change in acetonitrile/minute. The major peak which eluted around 20–25% acetonitrile, was manually collected and displayed prothrombinate inhibitory activity.

4. Molecular Mass Determination

The estimated mass for the main constituent isolated as described in section (1) to (3) of this example was determined using electrospray ionisation mass spectrometry. The estimated mass of the recombinant AcaNAPc2 was 9640 daltons, fully in agreement with the calculated molecular mass of this molecule derived from the cDNA sequence.

Example 16

Expression of AcaNAP42 in *P. pastoris.*

The pGEM-9zf(−) vector (Promega) containing the caNAP42 cDNA (Example 12) was used to isolate the region encoding the mature AcaNAP42 protein by PCR amplification (using Taq polymerase from Perkin Elmer, Branchburg, N.J.; 25 temperature cycles: 1 minute at 94° C., 1 minute at 50° C., and 1 minute at 72° C.). The following oligonucleotide primers were used:

```
oligo3: 5'GAG ACT TTT AAA TCA CTG TGG GAT CAG AAG3'    [SEQ. ID. NO. 124]

oligo2: 5'TTC AGG ACT AGT TCA TGG TGC GAA AGT AAT AAA3'[SEQ. ID. NO. 125]
```

The oligo 3 primer, targeting the N-terminal sequence, contained a non-annealing extension which includes DraI restriction site (underlined). The oligo 2 primer, targeting the C-terminal sequence, contained SpeI restriction site.

The NAP amplification product, having the expected approximately 250 bp size, was digested with DraI and SpeI enzymes, purified by extraction with phenol: chloroform: iso-amyl alcohol (25:24:1, volume/volume) and precipitated in ethyl alcohol. The recipient vector-fragment from pYAM7SP8 (Example 3) was prepared by StuI-SpeI restriction, purified by extraction with phenol: chloroform:iso-amyl alcohol (25:24:1, volume/volume) and precipitated in ethyl alcohol. The *E. coli* strain, XL1-Blue (Bullock, W.O., Fernande, J. M., and Short, J. M. Biotechniques 5: 376–379 (1987)], was transformed with the ligation mixture that contained the above DNA fragments, and ampicillin resistant clones were selected.

Based on restriction analysis, a plasmid clone containing an insert of the expected size, designated pYAM7SP8-NAP42, was retained for further characterization. Sequence determination of the clone confirmed correct insertion of the mature coding region in fusion with the PHO1/alpha-factor prepro leader signal, as predicted by the construction scheme, as well as the absence of unwanted mutations in the coding region.

About 10 micrograms of pYAM 7SP-NAP 42 plasmid were electroporated into *Pichia* strain GTS115 (his4), described in Example 3. The plasmid was previously digested by NotI enzyme, targeting the integration event at the AOX1 chromosomal locus.

The His+ transformants were selected as described in Example 3. Single colonies (n=90) from the electroporation were grown in wells of a 96-well plate containing 100 microliters of glycerol-minimal medium for 24 hours on a plate-shaker at room temperature. One liter of the glycerol-minimal medium contained 13.4 g Yeast Nitrogen Base without amino acids (DIFCO); 400 micrograms biotin; 10 ml glycerol; and 10 mM potassium phosphate (pH 6.0).

The cells were pelleted and resuspended in fresh methanol-minimal medium (same composition as above except that the 10 ml glycerol was replaced by 5 ml methanol) to induce the AOX1 promoter. After an additional incubation period of 24 hours with agitation at room temperature, 10 microliters of culture supernatants were tested by the Prothrombin Time Assay (Example B). The presence of secreted AcaNAP42 was detected by the prolongation of the coagulation time of human plasma.

Example 17
Expression of AcaNAPc2/Proline in *P. pastoris*.

To enhance stability and the expression level of AcaNAPc2, a mutant cDNA was constructed that encoded an additional proline residue at the C-terminus of the protein (AcaNAPc2/Proline or "AcaNAPc2P"). The expression vector, pYAM7SP8-NAPc2/Proline, was made in the same manner as described in Example 16. The oligo 8 primer is the N-terminal primer with DraI restriction site and the oligo 9 primer is the C-terminal primer containing XbaI site and the amino acid codon, TGG, to add one Proline residue to the C-terminal of the natural form of AcaNAPc2.

Example 18
Alternative Methods of Purifying AcaNAP5, AcaNAPc2 and AcaNAPc2P.
(A) AcaNAp5

An alternative method of purifying AcaNAP5 from fermentation media is as follows. Cells were removed from a fermentation of a *Pichia pastoris* strain expressing AcaNAP5, and the media was frozen. The purification protocol was initiated by thawing frozen media overnight at 4° C., then diluting it with approximately four parts Milli Q water to lower the conductivity below 8 mS. The pH was adjusted to 3.5, and the media was filtered using a 0.22 μm cellulose acetate filter (Corning Inc., Corning, N.Y.).

The activity of the NAP-containing material was determined in the prothrombin time clotting assay at the beginning of the purification procedure and at each step in the procedure using the protocol in Example B.

The filtered media was applied to a Pharmacia SP-Fast Flow column, at a flow rate of 60 ml/min at ambient temperature, and the column was washed with 10 column volumes of 50 mM citrate/phosphate, pH 3.5. Step elution was performed with 100 mM NaCl, 250 mM NaCl, and then 1000 mM NaCl, all in 50 mM citrate/phosphate, pH 3.5. PT activity was detected in the 250 mM NaCl eluate. The total eluate was dialyzed until the conductivity was below 8 mS.

The pH of the material was adjusted to 4.5 with acetic acid, and then applied to a sulfoethyl aspartamide column at ambient temperature. Approximately 10 column volumes of 50 mM ammonium acetate, pH 4.5/40% acetonitrile, were used to wash the column. The column was eluted with 50 mM ammonium acetate, pH 4.5/40% acetonitrile/200 mM NaCl, and the eluate was dialyzed or diafiltered as before.

The eluate was adjusted to 0.1% TFA, applied to a Vydac C18 protein/peptide reverse phase column at ambient temperature, and eluted using 0.1% TFA/19% acetonitrile, followed by 0.1% TFA/25% acetonitrile, at a flow rate of 7 ml/min. NAP was detected in and recovered from the 0.1% TFA/25% acetonitrile elution.
(B) AcaNAPc2 and AcaNAPc2P AcaNAPc2 or AcaNhPc2P can be purified as described above with the following protocol modifications. After thawing and diluting the media to achieve a conductivity below 8 mS, the pH of the AcaNAPc2-containing media was adjusted to pH 5.0 using NaOH. The filtered media was applied to a Pharmacia Q Fast Flow column, at a flow rate

```
oligo 8: 5'GCG TTT AAA GCA ACG ATG CAG TGT GGT G3'                              [SEQ. ID. NO. 126]

oligo 9: 5'C GCT CTA GAA GCT TCA TGG GTT TCG AGT TCC GGG ATA TAT AAA GTC3' [SEQ. ID. NO. 127]
```

Following digestion of the amplification product (approximately 270 bp) with DraI and XbaI, the amplification product was purified and ligated with the vector-fragment from pYAM7SP8 prepared by StuI-SpeI restriction. A plasmid clone containing the AcaNAPc2/Proline insert was confirmed by DNA sequencing and designated pYAM7SP8-NAPc2/Proline.

The vector, pYAM7SP8-NAPc2/Proline, was used to transform strain GTS115 (his) as described in Example 16. Transformants were selected and grown according to Example 16. The presence of secreted AcaNAPc2/proline in the growth media was detected by the prolongation of the coagulation time of human plasma (see Example B).

of 60 ml/min at ambient temperature, and the column was washed with 10 column volumes of 50 mM acetic acid, pH 5.0. Step elution was performed with 100 mM NaCl, 250 mM NaCl, and then 1000 ml NaCl, all in 50 mM acetic acid, pH 5.0. PT activity was detected in the 250 mM NaCl eluate. The total eluate was dialyzed until the conductivity was below 8 mS, and the protocol outlined above was followed using sulfoethyl aspartamide and RP-HPLC chromatography.

Example A
Factor Xa Amidolytic Assay.

The ability of NAPs of the present invention to act as inhibitors of factor Xa catalytic activity was assessed by determining the NAP-induced inhibition of amidolytic activity catalyzed by the human enzyme, as represented by $K_i^*$ values.

The buffer used for all assays was HBSA (10 mM HEPES, pH 7.5, 150 mM sodium chloride, 0.1% bovine serum albumin). All reagents were from Sigma Chemical Co. (St. Louis, Mo.), unless otherwise indicated.

The assay was conducted by combining in appropriate wells of a Corning microtiter plate, 50 microliters of HBSA, 50 microliters of the test NAP compound diluted (0.025–25 nM) in HBSA (or HBSA alone for uninhibited velocity measurement), and 50 microliters of the Factor Xa enzyme diluted in HBSA (prepared from purified human factor X obtained from Enzyme Research Laboratories (South Bend, Ind.) according to the method described by Bock, P. E. et al., Archives of Biochem. Biophys. 273:375 (1989). The enzyme was diluted into HBSA prior to the assay in which the final concentration was 0.5 nM). Following a 30 minute incubation at ambient temperature, 50 microliters of the substrate S2765 (N-alpha-benzyloxycarbonyl-D-argininyl-L-glycyl-L-arginine-p-nitroanilide dihydrochloride, obtained from Kabi Diagnostica (or Kabi Pharmacia Hepar Inc., Franklin, Ohio) and made up in deionized water followed by dilution in HBSA prior to the assay) were added to the wells yielding a final total volume of 200 microliters and a final concentration of 250 micromolar (about 5-times Km). The initial velocity of chromogenic substrate hydrolysis was measured by the change in absorbance at 405 nm using a Thermo Max® Kinetic Microplate Reader (Molecular Devices, Palo alto, CA) over a 5 minute period in which less than 5% of the added substrate was utilized.

Ratios of inhibited pre-equilibrium, steady-state velocities containing NAP (Vi) to the uninhibited velocity of free fXa alone ($V_o$) were plotted against the corresponding concentrations of NAP. These data were then directly fit to an equation for tight-binding inhibitors (Morrison, J. F., and Walsh, C. T., Adv. Enzymol. 61:201–300 (1988)], from which the apparent equilibrium dissociation inhibitory constant $K_i^*$ was calculated.

Table 1 below gives the $K_i^*$ values for the test compounds AcaNAP5 [SEQ. ID. NO. 4], AcaNAP6 [SEQ. ID. NO. 6], and AcaNAPc2 [SEQ, ID. NO. 59], prepared as described in Examples 3, 4, and 15, respectively. The data show the utility of AcaNAP5 and AcaNAP6 as potent in vitro inhibitors of human FXa. In contrast, AcaNAPc2 did not effectively inhibit FXa amidolytic activity indicating that it does not affect the catalytic activity of free fXa.

TABLE 1

| Compound | $K_i^*$ (pM) |
| --- | --- |
| AcaNAP5 | 43 ± 5 |
| AcaNAP6 | 996 ± 65 |
| AcaNAPc2 | NI[a] |

[a]NI = no inhibition; a maximum of 15% inhibition was observed up to 1 μM.

Example B
Prothrombin Time (PT) and Activated Partial Thromboplastin Time (aPTT) Assays.

The ex vivo anticoagulant effects of NAPs of the present invention in human plasma were evaluated by measuring the prolongation of the activated partial thromboplastin time (aPTT) and prothrombin time (PT) over a broad concentration range of each inhibitor.

Fresh frozen pooled normal citrated human plasma was obtained from George King Biomedical, Overland Park, Kans. Respective measurements of aPTT and PT were made using the Coag-A-Mate RA4 automated coagulometer (General Diagnostics, Organon Technica, Oklahoma City, Okla.) using the Automated aPTT Platelin® L reagent (Organon Technica, Durham, N.C.) and Simplastin® Excel (Organon Technica, Durham, N.C.) respectively, as initiators of clotting according to the manufacturer's instructions.

The assays were conducted by making a series of dilutions of each tested NAP in rapidly thawed plasma followed by adding 200 microliters or 100 microliters of the above referenced reagents to the wells of the assay carousel for the aPTT or PT measurements, respectively. Alternatively, the NAPs were serially diluted into HBSA and 10 μl of each dilution were added to 100 μl of normal human plasma in the wells of the Coag-A-Mate assay carousel, followed by addition of reagent.

Concentrations of NAP were plotted against clotting time, and a doubling time concentration was calculated, i.e., a specified concentration of NAP that doubled the control clotting time of either the PT or the aPTT. The control clotting times (absence of NAP) in the PT and APTT were 12.1 seconds and 28.5 seconds, respectively.

Table 2 below shows the ex vivo anticoagulant effects of AcaNAP5 [SEQ. ID. NO. 4], AcaNAP6 [SEQ. ID. NO. 6], AcaNAPc2 [SEQ. ID. NO. 59], and AceNAP4 [SEQ. ID. NO. 62] and Pro-AcaNAPS [SEQ. ID. NO. 7] represented by the concentration of each that doubled (doubling concentration) the control clotting time of normal human plasma in the respective PT and APTT clotting assays relative to a control assay where no such NAP was present. The data show the utility of these compounds as potent anticoagulants of clotting human plasma. The data also demonstrate the equivalency of native NAP and recombinant NAP.

TABLE 2

| Compound | Doubling Concentration (nM) in the PT | Doubling Concentration (nM) in the aPTT |
| --- | --- | --- |
| AcaNAP5[a] | 43 ± 8 | 87 ± 4 |
| AcaNAP6[a] | 37 ± 3 | 62 ± 0 |
| AcaNAPc2[a] | 15 ± 1 | 105 ± 11 |
| ACeNAP4[a] | 40 ± 4 | 115 ± 12 |
| AcaNAP5[b] | 26.9 | 76.2 |
| AcaNAP5[c] | 39.2 | 60.0 |
| Pro-AcaNAP5[d] | 21.9 | 31.0 |

[a]Made in *Pichia pastoris*.
[b]Native protein.
[c]Made in *Pichia pastoris* (different recombinant batch than (a)).
[d]Made in COS cells.

FIGS. 10A and 10B also show NAP-induced prolongation of the PT (FIG. 10A) and aPTT (FIG. 10B) in a dose-dependent manner.

Example C
Prothrombinase Inhibition Assay.

The ability of NAP of the present invention to act as an inhibitor of the activation of prothrombin by Factor Xa that has been assembled into a physiologic prothrombinase complex was assessed by determining the respective inhibition constant, $K_i^*$.

Prothrombinase activity was measured using a coupled amidolytic assay, where a preformed complex of human FXa, human Factor Va (FVa), and phospholipid vesicles first activates human prothrombin to thrombin. The amidolytic activity of the generated thrombin is measured simultaneously using a chromogenic substrate. Purified human FVa was obtained from Haematologic Technologies, Inc. (Essex Junction, VT). Purified human prothrombin was purchased from Celsus Laboratories, Inc. (Cincinnati, Ohio). The chromogenic substrate Pefachrome t-PA ($CH_3SO_2$-D-hexahydrotyrosine-glycyl-L-arginine-p-nitroanilide) from Pentapharm Ltd (Basel, Switzerland) was purchased from Centerchem, Inc. (Tarrytown, N.Y.). The substrate was reconstituted in deionized water prior to use.

Phospholipid vesicles were made, consisting of phosphotidyl choline (67%, w/v), phosphatidyl glycerol (16%, w/v), phosphatidyl ethanolamine (10%, w/v), and phosphatidyl serine (7%, w/v) in the presence of detergent, as described by Ruf et al. [Ruf, W., Miles, D. J., Rehemtulla, A., and Edgington, T. S. Methods in Enzymology 222: 209–224 (1993)]. The phospholipids were purchased from Avanti Polar Lipids, (Alabaster, Ala.).

The prothrombinase complex was formed in a polypropylene test tube by combining FVa, FXa, and phospholipid vesicles (PLV) in HBSA containing 3 mM $CaCl_2$ for 10 min. In appropriate wells of a microtiter plate, 50 μl of the complex were combined with 50 μl of NAP diluted in HBSA, or HBSA alone (for $V_o$ (uninhibited velocity) measurement). Following an incubation of 30 min at room temperature, the triplicate reactions were initiated by the addition of a substrate solution, containing human prothrombin and the chromogenic substrate for thrombin, Pefachrome tPA. The final concentration of reactants in a total volume of 150 μL of HBSA was: NAP (0.025–25 nM), FXa (25.0 fM), PLV (5 μM), prothrombin (250 nM), Pefachrome tPA (250 μM, 5×Km), and $CaCl_2$ (3 mM).

The prothrombinase activity of fXa was measured as an increase in the absorbance at 405 nm over 10 min (velocity); exactly as described in Example A, under steady-state conditions. The absorbance increase was sigmoidal over time, reflecting the coupled reactions of the activation of prothrombin by the FXa-containing prothrombinase complex, and the subsequent hydrolysis of Pefachrome tPA by the generated thrombin. The data from each well of a triplicate were combined and fit by reiterative, linear least squares regression analysis, as a function of absorbance versus $time^2$, as described (Carson, S.D. Comput. Prog. Biomed. 19: 151–157 (1985)) to determine the initial velocity ($V_i$) of prothrombin activation. Ratios of inhibited steady-state initial velocities containing NAP (Vi) to the uninhibited velocity of prothrombinase fXa alone ($V_o$) were plotted against the corresponding concentrations of NAP. These data were directly fit to the equation for tight-binding inhibitors, as in Example A above, and the apparent equilibrium dissociation inhibitory constant $K_i^*$ was calculated.

Table 3 below gives the dissociation inhibitor constant ($Ki^*$) of recombinant AcaNAP5 [SEQ. ID. NO. 4], AcaNAP6 [SEQ. ID. NO. 6] and AcaNAPc2 [SEQ. ID. NO. 59] (all made in *Pichia pastoris* as described) against the activation of prothrombin by human fXa incorporated into a prothrombinase complex. These data show the utility of these compounds as inhibitors of human FXa incorporated into the prothrombinase complex.

TABLE 3

| Compound | Ki* (pM) |
| --- | --- |
| AcaNAP5 | 144 ± 15 |
| AcaNAP6 | 207 ± 40 |
| AcaNAPc2 | 2385 ± 283 |

The data presented in Examples A, B, and C suggest that AcaNAP5 and AcaNAP6 may be interacting with FXa in a similar manner that involves directly restricting access of both the peptidyl and macromolecular substrate (prothrombin) to the catalytic center of the enzyme. In contrast, AcaNAPc2 appears to be interacting with FXa in a way that only perturbs the macromolecular interactions of this enzyme with either the substrate and/or cofactor (Factor Va), while not directly inhibiting the catalytic turnover of the peptidyl substrate (see Table 1).

Example D
In Vitro Enzyme Assays for Activity Specificity Determination.

The ability of NAP of the present invention to act as a selective inhibitor of FXa catalytic activity or TF/VIIa activity was assessed by determining whether the test NAP would inhibit other enzymes in an assay at a concentration that was 100-fold higher than the concentration of the following related serine proteases: thrombin, Factor Xa, Factor XIa, Factor XIIa, kallikrein, activated protein C, plasmin, recombinant tissue plasminogen activator (rt-PA), urokinase, chymotrypsin, and trypsin. These assays also are used to determine the specificity of NAPs having serine protease inhibitory activity.

(1) General Protocol for Enzyme Inhibition Assays

The buffer used for all assays was HBSA (Example A). All substrates were reconstituted in deionized water, followed by dilution into HBSA prior to the assay. The amidolytic assay for determining the specificity of inhibition of serine proteases was conducted by combining in appropriate wells of a Corning microtiter plate, 50 μl of HBSA, 50 μl of NAP at a specified concentration diluted in HBSA, or HBSA alone (uninhibited control velocity, Vo), and 50 μl of a specified enzyme (see specific enzymes below). Following a 30 minute incubation at ambient temperature, 50 μl of substrate were added to triplicate wells. The final concentration of reactants in a total volume of 200 μl of HBSA was: NAP (75 nM), enzyme (750 pM), and chromogenic substrate (as indicated below). The initial velocity of chromogenic substrate hydrolysis was measured as a change in absorbance at 405 nm over a 5 minute period, in which less than 5% of the added substrate was hydrolyzed. The velocities of test samples, containing NAP (vi) were then expressed as a percent of the uninhibited control velocity (Vo) by the following formula: Vi/Vo X 100, for each of the enzymes.

(2) Specific Enzyme Assays (a) Thrombin Assay

Thrombin catalytic activity was determined using the chromogenic substrate Pefachrome t-PA ($CH_3SO_2$-D-hexahydrotyrosine-glycyl-L-arginine-p-nitroaniline, obtained from Pentapharm Ltd., Basel, Switzerland). The final concentration of Pefachrome t-PA was 250 μM (about 5-times Km). Purified human alpha-thrombin was obtained from Enzyme Research Laboratories, Inc.(South Bend, Ind.).

(b) Factor Xa Assay

Factor Xa catalytic activity was determined using the chromogenic substrate S-2765 (N-benzyloxycarbonyl-D-arginine-L-glycine-L-arginine-p-nitroaniline), obtained from Kabi Pharmacia Hepar, Inc. (Franklin, Ohio). All substrates were reconstituted in deionized water prior to use. The final concentration of S-2765 was 250 μM (about 5-times Km). Purified human Factor X was obtained from Enzyme Research Laboratories, Inc. (South Bend, Ind.) and Factor Xa (FXa) was activated and prepared from Factor X as described [Bock, P. E., Craig, P. A., Olson, S. T., and Singh, P. Arch. Biochem. Biophys. 273:375–388 (1989)].

(c) Factor XIa Assay

Factor FXIa catalytic activity was determined using the chromogenic substrate S-2366 (L-Pyroglutamyl-L-prolyl-L- arginine-p-nitroaniline, obtained from Kabi Pharmacia Hepar, Franklin, Ohio). The final concentration of S-2366 was 750 µM. Purified human FXIa was obtained from Enzyme Research Laboratories, Inc.(South Bend, Ind.).

(d) Factor XIIa Assay

Factor FXIIa catalytic activity was determined using the chromogenic substrate Spectrozyme FXIIa (H-D-CHT-L-glycyl-L-arginine-p-nitroaniline), obtained from American Diagnostica, Greenwich,Conn.). The final concentration of Spectrozyme FXIIa was 100 µM. Purified human FXIIa was obtained from Enzyme Research Laboratories, Inc. (South Bend, Ind.).

(e) Kallikrein Assay

Kallikrein catalytic activity was determined using the chromogenic substrate S-2302 (H-D-prolyl-L-phenylalanyl-L-arginine-p-nitroaniline, obtained from Kabi Pharmacia Hepar, Franklin, Ohio). The final concentration of S-2302 was 400 µM. Purified human kallikrein was obtained from Enzyme Research Laboratories, Inc. (South Bend, Ind.).

(f) Activated Protein C (aPC)

Activated Protein C catalytic activity was determined using the chromogenic substrate Spectrozyme PCa (H-D-lysyl(-Cbo)-L-prolyl-L-arginine-p-nitroaniline) obtained from American Diagnostica Inc. (Greenwich, Conn.). The final concentration was 400 µM (about 4 times Km). Purified human aPC was obtained from Hematologic Technologies, Inc.(Essex Junction, Vt.)

(g) Plasmin Assay

Plasmin catalytic activity was determined using the chromogenic substrate S-2366 (L-Pyroglutamyl-L-prolyl-L-arginine-p-nitroaniline, obtained from Kabi Pharmacia Hepar, Franklin, Ohio). The final concentration of S-2366 was 300 µM (about 4 times Km). Purified human plasmin was obtained from Enzyme Research Laboratories, Inc. (South Bend, Ind.).

(h) Recombinant tissue Plasminogen Activator (rt-PA)

rt-PA catalytic activity was determined using the substrate, Pefachrome t-PA ($CH_3SO_2$-D-hexahydrotyrosine-glycyl-L-arginine-p-nitroaniline, obtained from Pentapharm Ltd., Basel, Switzerland). The final concentration was 500 µM (about 3 times Km). Human rt-PA (Activase®) was obtained from Genentech, Inc. (So. San Fransisco, Calif.).

(i) Urokinase

Urokinase catalytic activity was determined using the substrate S-2444 (L-Pyroglutamyl-L-glycyl-L-arginine-p-nitroaniline, obtained from Kabi Pharmacia Hepar, Franklin, Ohio). The final concentration of S-2444 was 150 µM (about 7 times Km). Human urokinase (Abbokinase®), purified from cultured human kidney cells, was obtained from Abbott Laboratories (North Chicago, Ill.).

(j) Chymotrypsin

Chymotrypsin catalytic activity was determined using the chromogenic substrate, S-2586 (Methoxy-succinyl-L-argininyl-L-prolyl-L-tyrosine-p-nitroaniline, which was obtained from Kabi Pharmacia Hepar, Franklin, Ohio). The final concentration of S-2586 was 100 µM. (about 8 times Km). Purified (3X-crystallized;CDI) bovine pancreatic-chymotrypsin was obtained from Worthington Biochemical Corp. (Freehold, N.J.).

(k) Trypsin

Trypsin catalytic activity was determined using the chromogenic substrate S-2222 (N-benzoyl-L-isoleucyl-L-glutamyl [-methyl ester]-L-arginine-p-nitroaniline, which was obtained from Kabi Pharmacia Hepar, Franklin, Ohio). The final concentration of S-2222 was 300 µM (about S times Km). Purified human pancreatic trypsin was obtained from Scripps Laboratories (San Diego, Calif.).

Table 4 lists the inhibition of the amidolytic acativity of FXa and 10 additional serine proteases by either recombinant AcaNAP-5 [SEQ. ID. NO. 4] or recombinant AcaNAP-6 [SEQ. ID. NO. 6] (both expressed in *Pichia pastoris*, as described), expressed as percent of control velocity. These NAPs demonstrate a high degree of specificity for the inhibition of FXa compared to the other, related serine proteases.

TABLE 4

| Enzyme | % Control Velocity +AcaNAP5 | % Control Velocity +AcaNAP6 |
|---|---|---|
| FXa | 1 ± 1 | 14 ± 1 |
| FIIa | 104 ± 5 | 98 ± 3 |
| FXIa | 34 ± 12 | 98 ± 3 |
| FXIIa | 103 ± 6 | 100 ± 4 |
| kallikrein | 102 ± 4 | 101 ± 3 |
| aPC | 95 ± 2 | 98 ± 1 |
| plasmin | 111 ± 6 | 113 ± 12 |
| r-tPA | 96 ± 9 | 96 ± 7 |
| urokinase | 101 ± 14 | 96 ± 2 |
| chymotrypsin | 105 ± 0 | 100 ± 11 |
| trypsin | 98 ± 6 | 93 ± 4 |

Table 5 lists the inhibitory effect of recombinant AcaNAPc2 [SEQ. ID. NO. 59] and recombinant AceNAP4 [SEQ. ID. NO. 62] (both expressed in *Pichia pastoris*, as described) on the amidolytic activity of 11 selected serine proteases. Inhibition is expressed as percent of control velocity. These data demonstrate that these NAPs possess a high degree of specificity for the serine proteases in Table 5.

TABLE 5

| Enzyme | % Control Velocity +AcaNAPc2 | % Control Velocity +AceNAP4 |
|---|---|---|
| Fxa | 84 ± 3 | 76 ± 3 |
| FIIa | 99 ± 3 | 93 ± 3 |
| FXIa | 103 ± 4 | 96 ± 1 |
| FXIIa | 97 ± 1 | 102 ± 2 |
| kallikrein | 101 ± 1 | 32 ± 1 |
| aPC | 97 ± 3 | 103 ± 1 |
| plasmin | 107 ± 9 | 100 ± 1 |
| r-tPA | 96 ± 2 | 108 ± 3 |
| urokinase | 97 ± 1 | 103 ± 4 |
| chymotrypsin | 99 ± 0 | 96 ± 4 |
| trypsin | 93 ± 4 | 98 ± 4 |

Example E

Assays for measuring the inhibition of the fVIIa/TF complex by NAP.

(1) fVIIa/TF fIX Activation Assay

This Example measures the ability of NAPs of the present invention to act as an inhibitor of the catalytic complex of fVIIa/TF, which has a primary role in initiation of the coagulation response in the ex vivo prothrombin time assay (Example B). Activation of tritiated Factor IX by the rFVIIa/rTF/PLV complex was assessed by determining the respective intrinsic inhibition constant, $Ki^*$.

Lyophilized, purified, recombinant human factor VIIa was obtained from BiosPacific, Inc. (Emeryville, Calif.), and reconstituted in HBS (10 mM HEPES, pH 7.5, 150 mM sodium chloride) prior to use. Purified human Factor X was obtained from Enzyme Research Laboratories, Inc. (South Bend, Ind.) and Factor Xa (free FXa) was activated and prepared from Factor X as described (Bock, P. E., Craig, P. A., Olson, S. T., and Singh, P. Arch. Biochem. Biophys.

273:375–388 (1989)). Active site-blocked human Factor Xa (EGR-FXa), which had been irreversibly inactivated with L-Glutamyl-L-glycyl-L-arginyl chloromethylketone, was obtained from Haematologic Technologies, Inc. (Essex Junction, Vt.). Recombinant human tissue factor (rTF) was produced by a baculovirus-expression system, and purified to homogeneity by monoclonal antibody affinity chromatography (Corvas International, Inc., San Diego, Calif.).

The purified rTF apoprotein was incorporated into phospholipid vesicles (rTF/PLV), consisting of phosphotidyl choline (75%, w/v) and phosphotidyl serine (25%, w/v) in the presence of detergent, as described by Ruf et al. (Ruf, W., Miles, D. J., Rehemtulla, A., and Edgington, T. S. Methods in Enzymology 222: 209–224 (1993)). The phospholipids were purchased from Avanti Polar Lipids, (Alabaster, Ala.). The buffer used for all assays was HBSA, HBS containing 0.1% (w/v) bovine serum albumin. All reagents were obtained from Sigma Chemical Co. (St. Louis, Mo.), unless otherwise indicated.

The activation of human $^3$H-Factor IX (FIX) by the rFVIIa/rTF complex was monitored by measuring the release of the radiolabelled activation peptide. Purified human fIX was obtained from Haematologic Technologies, Inc. (Essex Junction, Vt.), and radioactively labelled by reductive tritiation as described (Van Lenten & Ashwell, 1971, JBC 246, 1889–1894). The resulting tritiated preparation of FIX had a specific activity of 194 clotting units/mg as measured in immuno-depleted FIX deficient plasma (Ortho), and retained 97% of its activity. The radiospecific activity was 2.7×10$^8$ dpm/mg. The Km for the activation of $^3$H-FIX by rFVIIa/rTF/PLV was 25 nM, which was equivalent to the Km obtained for untreated (unlabelled) FIX.

The assay for Ki* determinations was conducted as follows: rFVIIa and rTF/PLV were combined in a polypropylene test tube, and allowed to form a complex for 10 min in HBSA, containing 5 mM CaCl$_2$. Aliquots of rFVIIa/rTF/PLV complex were combined in the appropriate polypropylene microcentrifuge tubes with EGR-FXa or free FXa, when included, and either the NAP test compound at various concentrations, after dilution into HBSA, or HBSA alone (as $V_o$ (uninhibited velocity) control). Following an incubation of 60 min at ambient temperature, reactions were initiated by the addition of $^3$H-FIX. The final concentration of the reactants in 420 µl of HBSA was:

rFVIIa [50 pM], rTF [2.7 nM], PLV [6.4 micromolar], either EGR-FXa or free FXa [300 pM], recombinant NAP [5–1,500 pM], $^3$H-FIX [200 nM], and CaCl$_2$[5 mM]. In addition, a background control reaction was run that included all of the above reactants, except rFVIIa.

At specific time points (8, 16, 24, 32, and 40 min), 80 µl of the reaction mixture was added to an eppendorf tube that contained an equal volume of 50 mM EDTA in HBS with 0.5% BSA to stop the reaction; this was followed by the addition of 160 µL of 6% (w/v) trichloroacetic acid. The protein was precipitated, and separated from the supernatant by centrifugation at 16,000×g for 6 min at 4° C. The radioactivity contained in the resulting supernatant was measured by removing triplicate aliquots that were added to Scintiverse BD (Fisher Scientific, Fairlawn, N.J.), and quantitated by liquid scintillation counting. The control rate of activation was determined by linear regression analysis of the soluble counts released over time under steady-state conditions, where less than 5% of the tritiated FIX was consumed. The background control (<1.0% of control velocity) was subtracted from all samples. Ratios of inhibited steady-state velocities (Vi), in the presence of a NAP, to the uninhibited control velocity of rFVIIa/TF alone ($V_o$) were plotted against the corresponding concentrations of NAP. These data were then directly fit to an equation for tight-binding inhibitors [Morrison, J. F., and Walsh, C. T., Adv. Enzymol. 61:201–300 (1988)], from which the apparent equilibrium dissociation inhibitory constant Ki* was calculated.

The data for recombinant AcaNAP5, AcaNAP6, AcaNAPc2, and AceNAP4 (prepared as described) is presented in Table 6 following Section B, below.

(2) Factor VIIa/Tissue Factor Amidolytic Assay

The ability of NAPs of the present invention to act as an inhibitor of the amidolytic activity of the fVIIa/TF complex was assessed by determining the respective inhibition constant, Ki*, in the presence and absence of active site-blocked human Factor Xa (EGR-fXa).

rFVIIa/rTF amidolytic activity was determined using the chromogenic substrate S-2288 (H-D-isoleucyl-L-prolyl-L-arginine-p-nitroaniline), obtained from Kabi Pharmacia Hepar, Inc. (Franklin, Ohio). The substrate was reconstituted in deionized water prior to use. rFVIIa and rTF/PLV were combined in a polypropylene test tube, and allowed to form a complex for 10 min in HBSA, containing 3 mM CaCl$_2$. The assay for Ki* determinations was conducted by combining in appropriate wells of a Corning microtiter plate 50 µL of the rFVIIa/rTF/PLV complex, 50 µL of EGR-FXa, and 50 µL of either the NAP test compound at various concentrations, after dilution into HBSA, or HBSA alone (for $V_o$ (uninhibited velocity) measurement). Following an incubation of 30 min at ambient temperature, the triplicate reactions were initiated by adding 50 µL of S-2288. The final concentration of reactants in a total volume of 200 µL of HBSA was: recombinant NAP (0.025–25 mM), rFVIIa (750 pM), rTF (3.0 nM), PLV (6.4 micromolar), EGR-FXa (2.5 nM), and S-228B (3.0 mM, 3×Km).

The amidolytic activity of rFVIIa/rTF/PLV was measured as a linear increase in the absorbance at 405 nm over 10 min (velocity), using a Thermo Max® Kinetic Microplate Reader (Molecular Devices, Palo Alto, Calif.), under steady-state conditions, where less than 5% of the substrate was consumed. Ratios of inhibited pre-equilibrium, steady-state velocities (Vi), in the presence of NAP, to the uninhibited velocity in the presence of free fXa alone ($V_o$) were plotted against the corresponding concentrations of NAP. These data were then directly fit to the same equation for tight-binding inhibitors, used in Example E.1., from which the apparent equilibrium dissociation inhibitory constant $K_i$* was calculated.

Table 6 below gives the Ki* values of recombinant AcaNAPc2 [SEQ. ID. NO. 59], AceNAP4 [SEQ. ID. NO. 62], AcaNAP5 [SEQ. ID. NO. 4], and AcaNAP6 [SEQ. ID. NO. 6] (prepared in *Pichia pastoris*, as described) in inhibitory assays of rFVIIa/rTF activity. The data shows the utility of AcaNAPc2 and AceNAP4 as potent inhibitors of the human rFVIIa/rTF/PLV complex in the absence and presence of either free FXa or active site-blocked FXa. The in vitro activity of AcaNAPc2P (see Example 17) was substantially the same as AcaNAPc2.

TABLE 6

| | Ki* (pM) | | | | |
|---|---|---|---|---|---|
| | Amidolytic Assay | | $3_H$-FIX Activation | | |
| NAP Compound | No FXa Addition | Plus EGR-FXa | No FXa Addition | +free FXa | +EGR-FXa |
| AcaNAPc2 | NI | 36 ± 20 | NI | 35 ± 5 | 8.4 ± 1.5 |
| AceNAP4 | 59,230 ± 3,600 | 378 ± 37 | ND | ND | ND |

TABLE 6-continued

| | Ki* (pM) | | | | |
|---|---|---|---|---|---|
| | Amidolytic Assay | | $3_H$-FIX Activation | | |
| NAP Compound | No FXa Addition | Plus EGR-FXa | No FXa Addition | +free FXa | +EGR-FXa |
| AcaNAP5 | NI | NI | NI | NI | NI |
| AcaNAP6 | NI | NI | NI | NI | NI |

NI = no inhibition
ND = not determined

Example F
In Vivo Models of NAP Activity.

(1) Evaluation of the Antithrombotic Activity of NAP in the Rat Model of FeCl$_3$-induced Platelet-Dependent Arterial Thrombosis The antithrombotic (prevention of thrombus formation) properties of NAP were evaluated using the established experimental rat model of acute vascular thrombosis.

The rat FeCl$_3$ model is a well characterized model of platelet dependent, arterial thrombosis which has been used to evaluate potential antithrombotic compounds. Kurz, R. D., Main, B. W., and Sandusky, G. E., *Thromb. Res.*, 60: 269–280 (1990). In this model a platelet-rich, occlusive thrombus is formed in a segment of the rat carotid artery treated locally with a fresh solution of FeCl$_3$ absorbed to a piece of filter paper. The FeCl$_3$ is thought to diffuse into the treated segment of artery and cause de-endothelialization of the affected vessel surface. This results in the exposure of blood to subendothelial structures which in turn cause platelet adherence, thrombin formation and platelet aggregation. The net result is occlusive thrombus formation. The effect of a test compound on the incidence of occlusive thrombus formation following application of FeCl$_3$ is monitored by ultrasonic flowtometry and is used as the primary end point. The use of flowtometry to measure carotid artery blood flow, is a modification of the original procedure in which thermal detection of clot formation was employed. Kurz, K. D., Main, B. W., and Sandusky, G. E., *Thromb. Res.*, 60: 269–280 (1990).

(a) Intravenous Administration

Male Harlan Sprague Dawley rats (420–450 g) were acclimated at least 72 hours prior to use and fasted for 12 hours prior to surgery with free access to water. The animals were prepared, anesthetized with Nembutal followed by the insertion of catheters for blood pressure monitoring, drug and anesthesia delivery. The left carotid artery was isolated by making a midline cervical incision followed by blunt dissection and spreading techniques to separate a 2 cm segment of the vessel from the carotid sheath. A silk suture is inserted under the proximal and distal ends of the isolated vessel to provide clearance for the placement of a ultrasonic flow probe (Transonic) around the proximal end of the vessel. The probe is then secured with a stationary arm.

Following surgery the animals were randomized in either a control (saline) or treatment (recombinant AcabP5) group. The test compound (prepared in *P. pastoris* according to Example 3) was administered as a single intravenous bolus at the doses outlined in Table 7 after placement of the flow probe and 5 min prior to the thrombogenic stimulus. At t=0, a 3 mm diameter piece of filter paper (Whatman #3) soaked with 10 µL of a 35% solution of fresh FeCl$_3$ (made up in water) was applied to the segment of isolated carotid artery distal to the flow probe. Blood pressure, blood flow, heart rate, and respiration were monitored for 60 minutes. The incidence of occlusion (defined as the attainment of zero blood flow) was recorded as the primary end point.

The efficacy of AcaNAP5 [SEQ. ID. NO. 4] as an antithrombotic agent in preventing thrombus formation in this in vivo model was demonstrated by the dose-dependent reduction in the incidence of thrombotic occlusion, as shown in Table 7 below.

TABLE 7

| Treatment Group | Dose (mg/kg) | n | Incidence of Occlusion |
|---|---|---|---|
| Saline | — | 8 | 8/8 |
| AcaNAP5 | 0.001 | 8 | 7/8 |
| AcaNAP5 | 0.003 | 8 | 5/8 |
| AcaNAP5 | 0.01 | 8 | 3/8* |
| AcaNAP5 | 0.03 | 8 | 1/8* |
| AcaNAP5 | 0.1 | 8 | 0/8* |
| AcaNAP5 | 0.3 | 4 | 0/4* |
| AcaNAP5 | 1.0 | 2 | 0/2* |

*p ≤ 0.05 from saline control by Fishers test

The effective dose which prevents 50% of thrombotic occlusions in this model (ED$_{50}$) can be determined from the above data by plotting the incidence of occlusion versus the dose administered. This allows a direct comparison of the antithrombotic efficacy of AcaNAP5 with other antithrombotic agents which have also been evaluated in this model as described above. Table 8 below lists the ED$_{50}$ values for several well known anticoagulant agents in this model compared to AcaNAP5.

TABLE 8

| Compound | ED$_{50}$[a] |
|---|---|
| Standard Heparin | 300 U/kg |
| Argatroban | 3.8 mg/kg |
| Hirulog ™ | 3.0 mg/kg |
| rTAP[b] | 0.6 mg/kg |
| AcaNAP5 | 0.0055 mg/kg |

[a]ED$_{50}$ is defined as the dose that prevents the incidence of complete thrombotic occlusion in 50% of animals tested
[b]recombinant Tick Anticoagulant Peptide, Vlasuk et al. Thromb. Haemostas. 70:212–216 (1993)

(b) Subcutaneous Administration

The antithrombotic effect of AcaNAP5 compared to Low Molecular Weight heparin (Enoxaparin; Lovenox, Rhone-Poulenc Rorer) after subcutaneous administration was evaluated in rats using the FeCl$_3$ model. The model was performed in an identical manner to that described above with the exception that the compound was administered subcutaneously and efficacy was determined at two different times: 30 and 150 minutes after administration. To accomplish this, both carotid arteries were employed in a sequential manner. The results of these experiments indicate that AcaNAP5 [SEQ. ID. NO. 4] is an effective antithrombotic agent in vivo after subcutaneous administration. The results are shown below in Table 9.

TABLE 9

| Compound | 30" ED$_{50}$[a] (mg/kg) | 150" ED$_{50}$[a] (mg/kg) |
|---|---|---|
| Low Molecular Weight Heparin | 30.0 | 15.0 |
| AcaNAP5 | 0.07 | 0.015 |

[a]ED$_{50}$ is defined as the dose that prevents the incidence of complete thrombotic occlusion in 50% of animals tested.

(2) Deep Wound Bleeding Measurement

A model of deep wound bleeding was used to measure the effect of NAP on bleeding and compare the effect with that of Low Molecular Weight Heparin.

Male rats were anesthetized and instrumented in an identical manner to those undergoing the $FeCl_3$ model. However, $FeCl_3$ was not applied to the carotid artery. The deep surgical wound in the neck that exposes the carotid artery was employed to quantify blood loss over time. Blood loss was measured over a period of 3.5 hours following subcutaneous administration of either AcaNAP5 or LMWH. The wound was packed with surgical sponges which were removed every 30 minutes. The sponges were subsequently immersed in Drabkin's reagent (sigma Chemical Co., St. Louis, Mo.) which lyses the red blood cells and reacts with hemoglobin in a calorimetric fashion. The calorimetric samples were then quantified by measuring absorbance at 550 nM, which provides a determination of the amount of blood in the sponge.

The dose response characteristics for both test compounds are shown in FIG. 15 along with efficacy data for both compounds. AcaNAP5 [SEQ. ID. NO. 4] was much more potent than Low Molecular Weight heparin in preventing occlusive arterial thrombus formation in this model. Furthermore, animals treated with NAP bled less than those treated with Low Molecular Weight heparin.

The data presented in Tables 7 and 9 and FIG. 15 clearly demonstrate the effectiveness of NAP in preventing occlusive thrombus formation in this experimental model. The relevance of this data to preventing human thrombosis is clear when compared to the other anticoagulant agents, listed in Table 8. These agents were been evaluated in the same experimental models described therein, in an identical manner to that described for NAPs, and in this experimental model and have demonstrated antithrombotic efficacy in preventing thrombus formation clinically, as described in the following literature citations: Heparin-Hirsh, J. N. Engl. J. Med 324:1565–1574 1992, Cairns, J. A. et al. Chest 102: 456S–481S (1992); Argatroban-Gold, H. K. et al. J. Am. Coll. Cardiol. 21: 1039–1047 (1993); and Hirulog™- Sharma, G.V.R.K. et al. Am. J. Cardiol. 72: 1357–1360 (1993) and Lidón, R. M. et al. Circulation 88: 1495–1501 (1993).

Example G

Pig Model of Acute Coronary Artery Thrombosis.

The protocol used in these studies is a modification of a thrombosis model which has been reported previously (Lucchesi, B. R., et al., (1994), Brit. J. Pharmacol. 113:1333–1343).

Animals were anesthetized and instrumented with arterial and venous catheters (left common carotid and external jugular, respectively). A thoracotomy was made in the 4th intercostal space and the heart was exposed. The left anterior descending (LAD) coronary artery was isolated from the overlying connective tissue and was instrumented with a Doppler flow probe and a 17 gauge ligature stenosis. An anodal electrode also was implanted inside the vessel.

Baseline measurements were taken and the NAP or placebo to be tested was administered via the external jugular vein. Five minutes after administration, a direct current (300 $\mu$A, DC) was applied to the stimulating electrode to initiate intimal damage to the coronary endothelium and begin thrombus formation. Current continued for a period of 3 hours. Animals were observed until either 1 hour after the cessation of current or the death of the animal, whichever came first.

Table 10 presents data demonstrating the incidence of occlusion in animals administered AcaNAP5 or AcaNAPc2p (see Example 17) at three increasing doses of NAP. The incidence of occlusion in the animals receiving placebo was 8/8 (100%). Time to occlusion in placebo treated animals was 66.6±7.5 min. (mean±sem). Vessels in AcaNAP treated pigs that failed to occlude during the 4 hour period of observation were assigned an arbitrary time to occlusion of 240 minutes in order to facilitate statistical comparisons.

The data demonstrate AcaNAP5 and AcaNAPc2P were similarly efficacious in this setting; both prolonged the time to coronary artery occlusion in a dose dependent manner. Furthermore, both molecules significantly prolonged in time to occlusion at a dose (0.03 mg/kg i.v.) that did not produce significant elevations in bleeding. These data, and other, suggest AcaNAP5 and AcaNAPc2P have favorable therapeutic indices.

Table 10. Comparision of primary endpoints between AcaNAPc2P and AcaNAP5 after intravenous dosing in the pig model of acute coronary artery thrombosis.

| Dose (i.v.) | Incidence of Occlusion | | Time of Occlusion (min) | | Total Blood Loss (ml) | |
|---|---|---|---|---|---|---|
| (mg/kg) | AcaNAP5 | AcaNAPc2P | AcaNAP5 | AcaNAPc2P | AcaNAP5 | AcaNAPc2P |
| 0.01 | 6/6 | 6/6 | 107 ± 13.0 | 105 ± 6.2 | 2.8 ± 0.8 | 1.6 ± 0.3 |
| 0.03 | 5/6 | 4/6 | 150 ± 23.2 | 159 ± 27 | 5.6 ± 1.4 | 4.9 ± 1.4 |
| 0.10 | 4/6 | 2/6† | 187 ± 22.9* | 215 ± 25* | 43.5 ± 18* | 17.6 ± 7.9* |

†p < 0.05 vs saline (8/8), Fisher's Exact;
*p < 0.05 vs saline, ANOVA, Dunnett's multiple comparison test.

What is claimed is:

1. An isolated protein having anticoagulant activity and having one or more Nematode Anticoagulant Protein (NAP) domains, wherein each NAP domain includes the sequence:

Cys-A1-Cys-A2-Cys-A3-Cys-A4-Cys-A5-Cys-A6-Cys-A7-Cys-A8-Cys-A9-Cys-A10 (FORMULA III), wherein (a) A1 is an amino acid sequence of 7 to 8 amino acid residues;
(b) A2 is an amino acid sequence;
(c) A3 is an amino acid sequence of 3 amino acid residues and has the sequence Asp-A3$_a$-A3$_b$, wherein A3$_a$ and A3$_b$ are independently selected;
(d) A4 is an amino acid sequence having a net anionic charge;
(e) A5 is an amino acid sequence of 4 amino acid residues and has the sequence A5$_a$-A5$_b$-, A5$_c$-A5$_6$ (SEQ ID NO: 85), wherein A5$_a$ through A5$_d$ are independently selected amino acid residues;
(f) A6 is an amino acid sequence;
(g) A7 is an amino acid residue selected from the group consisting of Val and Ile;
(h) A8 is an amino acid sequence of 11 to 12 amino acid residues;
(i) A9 is amino acid sequence of 5 to 7 amino acid residues; and
(j) A10 is an amino acid sequence;

when each of A2, A4, A6 and A10 has an independently selected number of independently selected amino acid residues and each sequence is selected such that each NAP domain has in total less than 120 amino acid residues, and wherein said protein has a NAP domain with an amino acid sequence having at least 90% sequence identity with the NAP domain of AcaNAPc2, wherein AcaNAPc2 has the amino acid sequence sat forth in SEQ ID NO: 59.

2. An isolated protein having anticoagulant activity and having one or more NAP domains, wherein each NAP domain includes the sequence:

Cys-A1-Cys-A2-Cys-A3-Cys-A4-Cys-A5-Cys-A6-Cys-A7-Cys-A8-Cys-A9-Cys-A10 (FORMULA III), wherein (a) A1 is an amino acid sequence of 7 to 8 amino acid residues;
(b) A2 is an amino acid sequence;
(c) A3 is an amino acid sequence of 3 amino acid residues and has the sequence Asp-Lys-Lys;
(d) A4 is an amino acid sequence having a net anionic charge;
(e) A5 is an amino acid sequence of 4 amino acid residues and has the sequence $A5_a$-$A5_b$-$A5_c$-$A5_d$, wherein $A5_a$ is Leu, $A5_c$ is Arg, and $A5_b$ and $A5_d$ are independently selected amino acid residues (SEQ ID NO: 357);
(f) A6 is an amino acid sequence;
(g) A7 is Val;
(h) A8 is an amino acid sequence of 11 to 12 amino acid residues and include the amino acid sequence $A8_a$-$A8_b$-Gly-Phe-Tyr-Arg-Asn (SEQ ID NO: 79), wherein at least one of $A8_a$ and $A8_b$ is Glu or Asp;
(i) A9 is an amino acid sequence of 5 to 7 amino acid residues; and
(j) A10 is an amino acid sequence;
wherein each of A2, A4, A6 and A10 has an independently selected number of independently selected amino acid residues and each sequence is selected such that each NAP domain has in total less than 120 amino acid residues, and wherein said protein has a NAP domain with an amino acid sequence having at least 90% sequence identity with the NAP domain of AcaNAPc2, wherein the amino acid sequence of AcaNAPc2 is set forth in SEQ ID NO: 59.

3. An isolated protein having Factor VIIa/TF inhibitory activity having a NAP domain with an amino acid sequence having at least 90% sequence identity with the NAP domain of AcaNAPc2, wherein the amino acid sequence of AcAPc2 is set forth in SEQ ID NO: 59.

4. An isolated protein having an amino acid sequence having at least 90% sequence identity with AcaNAPc2, wherein the amino acid sequence of AcaNAPc2 is set forth in SEQ ID NO: 59.

5. An isolated protein having an amino acid sequence having at least 90% sequence identity with AcaNAPc2/proline, wherein AcaNAPc2/proline has the amino acid sequence of AcaNAPc2 as set forth in SEQ ID NO:59 with the addition of a proline at the carboxy terminus of SEQ ID NO:59.

6. A method of treating a pathologic condition characterized by abnormal thrombosis by preventing or decreasing the abnormal thrombosis which comprises administering a protein of claim 1.

7. A method of treating a pathologic condition characterized by abnormal thrombosis by preventing or decreasing the abnormal thrombosis which comprises administering a protein of claim 2.

8. A method of treating a pathologic condition characterized by abnormal thrombosis by preventing or decreasing the abnormal thrombosis which comprises administering a protein of claim 2.

9. A method of treating a pathologic condition characterized by abnormal thrombosis by preventing or decreasing the abnormal thrombosis which comprises administering a protein of claim 3.

10. A method of treating a pathologic condition characterized by abnormal thrombosis by preventing or decreasing the abnormal thrombosis which comprises administering a protein of claim 5.

11. A method according to any one of claims 6 to 10 wherein said pathologic condition is disseminated intravascular coagulopathy.

12. A method according to any one of claims 6 to 10 wherein said abnormal thrombosis occurs in the venous vasculature of patients undergoing major surgery in the lower extremities or abdominal area.

13. A pharmaceutical composition comprising a protein of any one of claims 1 to 5 and a pharmaceutically acceptable carrier.

* * * * *

SEQUENCE LISTING

<160> NUMBER OF SEQ ID NOS: 357

<210> SEQ ID NO 1
<211> LENGTH: 234
<212> TYPE: DNA
<213> ORGANISM: Ancyclostoma caninum

<400> SEQUENCE: 1

```
aaggcatacc cggagtgtgg tgagaatgaa tggctcgacg actgtggaac tcagaagcca      60
tgcgaggcca agtgcaatga ggaaccccct gaggaggaag atccgatatg ccgctcacgt     120
ggttgtttat tacctcctgc ttgcgtatgc aaagacggat tctacagaga cacggtgatc     180
ggcgactgtg ttagggaaga agaatgcgac caacatgaga ttatacatgt ctga           234
```

<210> SEQ ID NO 2
<211> LENGTH: 228
<212> TYPE: DNA
<213> ORGANISM: Ancyclostoma caninum

<400> SEQUENCE: 2

```
aaggcatacc cggagtgtgg tgagaatgaa tggctcgacg tctgtggaac taagaagcca      60
tgcgaggcca agtgcagtga ggaagaggag aagatccgga tatgccgatc attttcttgt    120
ccgggtcccg ctgcttgcgt atgcgaagac ggattctaca gagacacggt gatcggcgac    180
tgtgttaagg aagaagaatg cgaccaacat gagattatac atgtctga                 228
```

<210> SEQ ID NO 3
<211> LENGTH: 461
<212> TYPE: DNA
<213> ORGANISM: Ancyclostoma caninum
<220> FEATURE:
<221> NAME/KEY: CDS
<222> LOCATION: (22)..(321)
<220> FEATURE:
<221> NAME/KEY: MOD_RES
<223> OTHER INFORMATION: AcaNAPs cDNA sequence

<400> SEQUENCE: 3

```
gaattccgct actactcaac a atg aag atg ctt tac gct atc gct ata atg        51
                        Met Lys Met Leu Tyr Ala Ile Ala Ile Met
                         1               5                  10 ttt ctc ctg gta tca tta tgc agc gca aga aca gtg agg aag gca tac        99
Phe Leu Leu Val Ser Leu Cys Ser Ala Arg Thr Val Arg Lys Ala Tyr
             15                  20                  25 ccg gag tgt ggt gag aat gaa tgg ctc gac gac tgt gga act cag aag       147
Pro Glu Cys Gly Glu Asn Glu Trp Leu Asp Asp Cys Gly Thr Gln Lys
         30                  35                  40 cca tgc gag gcc aag tgc aat gag gaa ccc cct gag gag gaa gat ccg       195
Pro Cys Glu Ala Lys Cys Asn Glu Glu Pro Pro Glu Glu Glu Asp Pro
     45                  50                  55 ata tgc cgc tca cgt ggt tgt tta tta cct cct gct tgc gta tgc aaa       243
Ile Cys Arg Ser Arg Gly Cys Leu Leu Pro Pro Ala Cys Val Cys Lys
 60                  65                  70 gac gga ttc tac aga gac acg gtg atc ggc gac tgt gtt agg gaa gaa       291
Asp Gly Phe Tyr Arg Asp Thr Val Ile Gly Asp Cys Val Arg Glu Glu
 75                  80                  85                  90 gaa tgc gac caa cat gag att ata cat gtc tgaacgagaa gcaacaataacc       344
Glu Cys Asp Gln His Glu Ile Ile His Val
                 95                 100 aaaggttcca actctcgctc tgcaaaatcg ctagttggat gtctcttttg cgtccgaata    404
gttttagttg atgttaagta agaactcctg ctggagagaa taaagctttc caactcc       461
```

<210> SEQ ID NO 4
<211> LENGTH: 77
<212> TYPE: PRT
<213> ORGANISM: Ascyclostoma caninum

```
<400> SEQUENCE: 4

Lys Ala Tyr Pro Glu Cys Gly Glu Asn Glu Trp Leu Asp Asp
1               5                  10

Cys Gly Thr Gln Lys Pro Cys Glu Ala Lys Cys Asn Glu Glu
 15              20                  25

Pro Pro Glu Glu Glu Asp Pro Ile Cys Arg Ser Arg Gly Cys
     30              35                  40

Leu Leu Pro Ala Cys Val Cys Lys Asp Gly Phe Tyr Arg
         45              50              55

Asp Thr Val Ile Gly Asp Cys Val Arg Glu Glu Glu Cys Asp
             60              65              70

Gln His Glu Ile Ile His Val
                75

<210> SEQ ID NO 5
<211> LENGTH: 455
<212> TYPE: DNA
<213> ORGANISM: Ancyclostoma caninum
<220> FEATURE:
<221> NAME/KEY: CDS
<222> LOCATION: (22)..(315)
<220> FEATURE:
<221> NAME/KEY: MOD_RES
<223> OTHER INFORMATION: AcaNAP6 cDNA sequence

<400> SEQUENCE: 5
gaattccgct actactcaac a atg aag atg ctt tac gct atc gct ata atg    51
                       Met Lys Met Leu Tyr Ala Ile Ala Ile Met
                         1               5                  10 ttt ctc ctg gtg tca tta tgc agc aca aga aca gtg agg aag gca tac    99
Phe Leu Leu Val Ser Leu Cys Ser Thr Arg Thr Val Arg Lys Ala Tyr
             15                  20                  25 ccg gag tgt ggt gag aat gaa tgg ctc gac gtc tgt gga act aag aag   147
Pro Glu Cys Gly Glu Asn Glu Trp Leu Asp Val Cys Gly Thr Lys Lys
                 30                  35                  40 cca tgc gag gcc aag tgc agt gag gaa gag gag gaa gat ccg ata tgc   195
Pro Cys Glu Ala Lys Cys Ser Glu Glu Glu Glu Glu Asp Pro Ile Cys
             45                  50                  55 cga tca ttt tct tgt ccg ggt ccc gct gct tgc gta tgc gaa gac gga   243
Arg Ser Phe Ser Cys Pro Gly Pro Ala Ala Cys Val Cys Glu Asp Gly
         60                  65                  70 ttc tac aga gac acg gtg atc ggc gac tgt gtt aag gaa gaa gaa tgc   291
Phe Tyr Arg Asp Thr Val Ile Gly Asp Cys Val Lys Glu Glu Glu Cys
75                  80                  85                  90 gac caa cat gag att att cat gtc tgaacgagag agcagtaata accaaaggttc 346
Asp Gln His Glu Ile Ile His Val
                95 caactttcgc tctacaaaat cgctagttgg atttctcctt tgcgtgcgaa tagttttagt   406 tgatattaag taaaacctcc tgttgaagag aataaagctt tccaacttc              455

<210> SEQ ID NO 6
<211> LENGTH: 75
<212> TYPE: PRT
<213> ORGANISM: Ascyclostoma caninum

<400> SEQUENCE: 6

Lys Ala Tyr Pro Glu Cys Gly Glu Asn Glu Trp Leu Asp Val Cys Gly
1               5                  10                  15

Thr Lys Lys Pro Cys Glu Ala Lys Cys Ser Glu Glu Glu Glu Glu Asp
             20                  25                  30
```

```
Pro Ile Cys Arg Ser Phe Ser Cys Pro Gly Pro Ala Ala Cys Val Cys
        35                  40                  45

Glu Asp Gly Phe Tyr Arg Asp Thr Val Ile Gly Asp Cys Val Lys Glu
    50                  55                  60

Glu Glu Cys Asp Gln His Glu Ile Ile His Val
65                  70                  75

<210> SEQ ID NO 7
<211> LENGTH: 81
<212> TYPE: PRT
<213> ORGANISM: Ascyclostoma caninum

<400> SEQUENCE: 7

Arg Thr Val Arg Lys Ala Tyr Pro Glu Cys Gly Glu Asn Glu Trp Leu
1               5                  10                  15

Asp Asp Cys Gly Thr Gln Lys Pro Cys Glu Ala Lys Cys Asn Glu Glu
            20                  25                  30

Pro Pro Glu Glu Glu Asp Pro Ile Cys Arg Ser Arg Gly Cys Leu Leu
        35                  40                  45

Pro Pro Ala Cys Val Cys Lys Asp Gly Phe Tyr Arg Asp Thr Val Ile
    50                  55                  60

Gly Asp Cys Val Arg Glu Glu Glu Cys Asp Gln His Glu Ile Ile His
65                  70                  75                  80

Val

<210> SEQ ID NO 8
<211> LENGTH: 79
<212> TYPE: PRT
<213> ORGANISM: Ascyclostoma caninum

<400> SEQUENCE: 8

Arg Thr Val Arg Lys Ala Tyr Pro Glu Cys Gly Glu Asn Glu Trp Leu
1               5                  10                  15

Asp Val Cys Gly Thr Lys Lys Pro Cys Glu Ala Lys Cys Ser Glu Glu
            20                  25                  30

Glu Glu Glu Asp Pro Ile Cys Arg Ser Phe Ser Cys Pro Gly Pro Ala
        35                  40                  45

Ala Cys Val Cys Glu Asp Gly Phe Tyr Arg Asp Thr Val Ile Gly Asp
    50                  55                  60

Cys Val Lys Glu Glu Glu Cys Asp Gln His Glu Ile Ile His Val
65                  70                  75

<210> SEQ ID NO 9
<211> LENGTH: 711
<212> TYPE: DNA
<213> ORGANISM: Ancyclostoma ceylanicum
<220> FEATURE:
<221> NAME/KEY: CDS
<222> LOCATION: (21)..(590)
<220> FEATURE:
<221> NAME/KEY: MOD_RES
<223> OTHER INFORMATION: Rcombinant cDNA Molecule AceNAP4 sequence

<400> SEQUENCE: 9
gaattcacta ttatccaaca atg gcg gtg ctt tat tca gta gca ata gcg       50
                     Met Ala Val Leu Tyr Ser Val Ala Ile Ala
                      1               5                  10 tta cta ctg gta tca caa tgc agt ggg aaa ccg aac aat gtg atg act    98
Leu Leu Leu Val Ser Gln Cys Ser Gly Lys Pro Asn Asn Val Met Thr
            15                  20                  25
```

```
aac gct tgt ggt ctt aat gaa tat ttc gct gag tgt ggc aat atg aag        146
Asn Ala Cys Gly Leu Asn Glu Tyr Phe Ala Glu Cys Gly Asn Met Lys
             30                  35                  40 gaa tgc gag cac aga tgc aat gag gag gaa aat gag gaa agg gac gag        194
Glu Cys Glu His Arg Cys Asn Glu Glu Glu Asn Glu Glu Arg Asp Glu
         45                  50                  55 gaa aga ata acg gca tgc ctc atc cgt gtg tgt ttc cgt cct ggt gct        242
Glu Arg Ile Thr Ala Cys Leu Ile Arg Val Cys Phe Arg Pro Gly Ala
 60                  65                  70 tgc gta tgc aaa gac gga tta tat aga aac aga aca ggc agc tgt gtg        290
Cys Val Cys Lys Asp Gly Phe Tyr Arg Asn Arg Thr Gly Ser Cys Val
 75                  80                  85                  90 gaa gaa gat gac tgc gag tac gag aat atg gag ttc att act ttt gca        338
Glu Glu Asp Asp Cys Glu Tyr Glu Asn Met Glu Phe Ile Thr Phe Ala
                 95                 100                 105 cca gaa gta ccg ata tgt ggt tcc aac gaa agg tac tcc gac tgc ggc        386
Pro Glu Val Pro Ile Cys Gly Ser Asn Glu Arg Tyr Ser Asp Cys Gly
             110                 115                 120 aat gac aaa caa tgc gag cgc aaa tgc aac gag gac gat tat gag aag        434
Asn Asp Lys Gln Cys Glu Arg Lys Cys Asn Glu Asp Asp Tyr Glu Lys
         125                 130                 135 gga gat gag gca tgc cgc tca cat gtt tgt gaa cgt cct ggt gcc tgt        482
Gly Asp Glu Ala Cys Arg Ser His Val Cys Glu Arg Pro Gly Ala Cys
140                 145                 150 gta tgc gaa gac ggg ttc tac aga aac aaa aaa ggt agc tgt gtg gaa        530
Val Cys Glu Asp Gly Phe Tyr Arg Asn Lys Lys Gly Ser Cys Val Glu
155                 160                 165                 170 agc gat gac tgc gaa tac gat aat atg gat ttc atc act ttt gca cca        578
Ser Asp Asp Cys Glu Tyr Asp Asn Met Asp Phe Ile Thr Phe Ala Pro
                 175                 180                 185 gaa acc tca cga taaccaaga tgctacctct cgtacgcaac tccgctgatt gaggtt     636
Glu Thr Ser Arg
             190 gattcactcc cttgcatctc aacatttttt ttgtgatgct gtgcatctga gcttaacctg    696 ataaagccta tggtg                                                      711

<210> SEQ ID NO 10
<211> LENGTH: 425
<212> TYPE: DNA
<213> ORGANISM: Ancyclostoma ceylanicum
<220> FEATURE:
<221> NAME/KEY: CDS
<222> LOCATION: (10)..(291)
<220> FEATURE:
<221> NAME/KEY: MOD_RES
<223> OTHER INFORMATION: Recombinant cDNA Molecule AceNAP5 sequence

<400> SEQUENCE: 10 gaattccgc atg cgg acg ctc tac ctc att tct atc tgg ttg ttc ctc atc     51
           Met Arg Thr Leu Tyr Leu Ile Ser Ile Trp Leu Phe Leu Ile
            1               5                  10 tcg caa tgt aat gga aaa gca ttc ccg aaa tgt gac gtc aat gaa aga       99
Ser Gln Cys Asn Gly Lys Ala Phe Pro Lys Cys Asp Val Asn Glu Arg
 15                  20                  25                  30 ttc gag gtg tgt ggc aat ctg aag gag tgc gag ctc aag tgc gat gag     147
Phe Glu Val Cys Gly Asn Leu Lys Glu Cys Glu Leu Lys Cys Asp Glu
                 35                  40                  45 gac cct aag ata tgc tct cgt gca tgt att cgt ccc cct gct tgc gta     195
Asp Pro Lys Ile Cys Ser Arg Ala Cys Ile Arg Pro Pro Ala Cys Val
             50                  55                  60
```

```
tgc gat gac gga ttc tac aga gac aaa tat ggc ttc tgt gtt gaa gaa      243
Cys Asp Asp Gly Phe Tyr Arg Asp Lys Tyr Gly Phe Cys Val Glu Glu
             65                  70                  75 gac gaa tgt aac gat atg gag att att act ttt cca cca gaa acc aaa tg   293
Asp Glu Cys Asn Asp Met Glu Ile Ile Thr Phe Pro Pro Glu Thr Lys
 80                  85                  90 atgaccgaag cttccacctt tctatacata tcttcactgc ttgacaggct tctcgacaat    353
ttagaagttc tgcttgactt tgtctatttg aaattgttca cactaatggg ggaagtaaag    413
cattttcacg ac                                                        425

<210> SEQ ID NO 11
<211> LENGTH: 471
<212> TYPE: DNA
<213> ORGANISM: Ancyclostoma ceylanicum
<220> FEATURE:
<221> NAME/KEY: CDS
<222> LOCATION: (23)..(237)
<220> FEATURE:
<221> NAME/KEY: MOD_RES
<223> OTHER INFORMATION: Recombinant cDNA Molecule AceNAP7 sequence

<400> SEQUENCE: 11
gaattccgct acattttcaa ca atg tcg acg ctt tat gtt atc gca ata tgt     52
                         Met Ser Thr Leu Tyr Val Ile Ala Ile Cys
                          1               5                  10 ttg ctg ctt gtt tcg caa tgc aat gga aga acg gtg aag aag tgt ggc      100
Leu Leu Leu Val Ser Gln Cys Asn Gly Arg Thr Val Lys Lys Cys Gly
                 15                  20                  25 aag aat gaa aga tac gac gac tgt ggc aat gca aag gac tgc gag acc      148
Lys Asn Glu Arg Tyr Asp Asp Cys Gly Asn Ala Lys Asp Cys Glu Thr
             30                  35                  40 aag tgc ggt gaa gag gaa aag gtg tgc cgt tcg cgt gag tgt act agt      196
Lys Cys Gly Glu Glu Glu Lys Val Cys Arg Ser Arg Glu Cys Thr Ser
         45                  50                  55 cct ggt gcc tgc gta tgc gaa caa gga ttc tac aga gat ccg gct ggc      244
Pro Gly Ala Cys Val Cys Glu Gln Gly Phe Tyr Arg Asp Pro Ala Gly
     60                  65                  70 gac tgt gtc act gat gaa gaa tgt gat gaa tgg aac aat atg gag atc      292
Asp Cys Val Thr Asp Glu Glu Cys Asp Glu Trp Asn Asn Met Glu Ile
 75                  80                  85                  90 att act atg cca aaa cag tagtgcgaag ttccttctt tctccaaatc tgctccgtg    349
Ile Thr Met Pro Lys Gln
                 95 ctcaattatc acacacctcc actagttaag attgactgac tctcttgcat tgtagtattt    409 tcgcttgact ctgtgcattt aagcatgaga tactactagg gagaataaaa attactaact    469 ac                                                                   471

<210> SEQ ID NO 12
<211> LENGTH: 396
<212> TYPE: DNA
<213> ORGANISM: Ancyclostoma duodenale
<220> FEATURE:
<221> NAME/KEY: CDS
<222> LOCATION: (10)..(237)
<220> FEATURE:
<221> NAME/KEY: MOD_RES
<223> OTHER INFORMATION: Recombinant cDNA Molecule AduNAP4 sequence

<400> SEQUENCE: 12 gaattccgg aaa tgt cct acc gat gaa tgg ttc gat tgg tgt gga act tac    51
          Lys Cys Pro Thr Asp Glu Trp Phe Asp Trp Cys Gly Thr Tyr
           1               5                  10
```

```
aag cat tgc gaa ctc aag tgc gat agg gag cta act gag aaa gaa gag      99
Lys His Cys Glu Leu Lys Cys Asp Arg Glu Leu Thr Glu Lys Glu Glu
 15                  20                  25                  30 cag gca tgt ctc tca cgt gtt tgt gag aag tcc gct tgc gta tgc aat     147
Gln Ala Cys Leu Ser Arg Val Cys Glu Lys Ser Ala Cys Val Cys Asn
                 35                  40                  45 gac gga tta tac aga gac aag ttt ggc aac tgt gtt gaa aaa gac gaa     195
Asp Gly Leu Tyr Arg Asp Lys Phe Gly Asn Cys Val Glu Lys Asp Glu
             50                  55                  60 tgc aac gat atg gag att att act ttt gca cca gaa acc aaa taatggcta   247
Cys Asn Asp Met Glu Ile Ile Thr Phe Ala Pro Glu Thr Lys
         65                  70                  75 aggttccaaa ccttgctaca caccgtcagt gctttactgt ttcctctacg tgttagtagt   307
tttgcttgac tctgtgtatt taagcattgt ctactaatgg gcaaagtaaa gcattgtaag   367
gacataataa tgagtaaacc ttctgattt                                     396

<210> SEQ ID NO 13
<211> LENGTH: 688
<212> TYPE: DNA
<213> ORGANISM: Ancyclostoma ceylanicum
<220> FEATURE:
<221> NAME/KEY: CDS
<222> LOCATION: (21)..(560)
<220> FEATURE:
<221> NAME/KEY: MOD_RES
<223> OTHER INFORMATION: Recombinant cDNA Molecule AduNAP7 sequence

<400> SEQUENCE: 13
gaattccggg cggcagaaag atg cga atg ctc tac ctt gtt cct atc tgg        50
                       Met Arg Met Leu Tyr Leu Val Pro Ile Trp
                        1               5                   10 ttg ctg ctc att tcg cta tgc agt gga aaa gct gcg aag aaa tgt ggt      98
Leu Leu Leu Ile Ser Leu Cys Ser Gly Lys Ala Ala Lys Lys Cys Gly
                 15                  20                  25 ctc aat gaa agg ctg gac tgt ggc aat ctg aag caa tgc gag ccc aag     146
Leu Asn Glu Arg Leu Asp Cys Gly Asn Leu Lys Gln Cys Glu Pro Lys
             30                  35                  40 tgc agc gac ttg gaa agt gag gag tat gag gag gaa gat gag tcg aaa     194
Cys Ser Asp Leu Glu Ser Glu Glu Tyr Glu Glu Glu Asp Glu Ser Lys
         45                  50                  55 tgt cga tca cgt gaa tgt tct cgt cgt gtt tgt gta tgc gat gaa gga     242
Cys Arg Ser Arg Glu Cys Ser Arg Arg Val Cys Val Cys Asp Glu Gly
     60                  65                  70 ttc tac aga aac aag aag ggc aag tgt gtt gca aaa gat gtt tgc gag     290
Phe Tyr Arg Asn Lys Lys Gly Lys Cys Val Ala Lys Asp Val Cys Glu
 75                  80                  85                  90 gac gac aat atg gag att atc act ttt cca cca gaa gac gaa tgt ggt     338
Asp Asp Asn Met Glu Ile Ile Thr Phe Pro Pro Glu Asp Glu Cys Gly
                 95                 100                 105 ccc gat gaa tgg ttc gac tac tgt gga aat tat aag aag tgc gaa cgc     386
Pro Asp Glu Trp Phe Asp Tyr Cys Gly Asn Tyr Lys Lys Cys Glu Arg
            110                 115                 120 aag tgc agt gag gag aca agt gag aaa aat gag gag gca tgc ctc tct     434
Lys Cys Ser Glu Glu Thr Ser Glu Lys Asn Glu Glu Ala Cys Leu Ser
        125                 130                 135 cgt gct tgt act ggt cgt gct tgc gta tgc aaa gac gga ttg tac aga     482
Arg Ala Cys Thr Gly Arg Ala Cys Val Cys Lys Asp Gly Leu Tyr Arg
    140                 145                 150 gac gac ttt ggc aac tgt gtt cca cat gac gaa tgc aac gat atg gag     530
Asp Asp Phe Gly Asn Cys Val Pro His Asp Glu Cys Asn Asp Met Glu
```

-continued

```
                  155                 160                 165                 170
atc atc act ttt cca ccg gaa acc aaa cat tgaccagagg ctccaactct cgct              584
Ile Ile Thr Phe Pro Pro Glu Thr Lys His
                  175                 180 acacaacgtc agggctagaa tggcccctct gcgagttagt agttttgctt gactctgctt              644
atttgagcac tttctattga tggcgaaaat aaagcattta aaac                                688

<210> SEQ ID NO 14
<211> LENGTH: 349
<212> TYPE: DNA
<213> ORGANISM: Heligmosomoides polygyrus
<220> FEATURE:
<221> NAME/KEY: CDS
<222> LOCATION: (49)..(276)
<220> FEATURE:
<221> NAME/KEY: MOD_RES
<223> OTHER INFORMATION: Recmobinant cDNA Molecule HpoNAP5 sequence

<400> SEQUENCE: 14
gaattccgcg cacctgagag gtgagctacg caagtcttcg ctggtaca atg atc cga               57
                                                     Met Ile Arg
                                                      1 aag ctc gtt ctg ctg act gct atc gtc acg gtg gtg cta agt gcg aag              105
Lys Leu Val Leu Leu Thr Ala Ile Val Thr Val Val Leu Ser Ala Lys
  5                  10                  15 acc tgt gga cca aac gag gag tac act gaa tgc ggg acg cca tgc gag              153
Thr Cys Gly Pro Asn Glu Glu Tyr Thr Glu Cys Gly Thr Pro Cys Glu
 20                  25                  30                  35 ccg aag tgc aat gaa ccg atg cca gac atc tgt act ctg aac tgc atc              201
Pro Lys Cys Asn Glu Pro Met Pro Asp Ile Cys Thr Leu Asn Cys Ile
                 40                  45                  50 gtg aac gtg tgt cag tgc aaa ccc ggc ttc aag cgc gga ccg aaa gga              249
Val Asn Val Cys Gln Cys Lys Pro Gly Phe Lys Arg Gly Pro Lys Gly
     55                  60                  65 tgc gtc gcc ccc gga cca ggc tgt aaa tagttctcca cctgcccttt cgttggaa           304
Cys Val Ala Pro Gly Pro Gly Cys Lys
 70                  75 caaatggctg tcttttaca ttctgaatca ataaagccga acggt                              349

<210> SEQ ID NO 15
<211> LENGTH: 432
<212> TYPE: DNA
<213> ORGANISM: Heligmosomoides polygyrus
<220> FEATURE:
<221> NAME/KEY: CDS
<222> LOCATION: (40)..(393)
<220> FEATURE:
<221> NAME/KEY: MOD_RES
<223> OTHER INFORMATION: pDONG61 vector sequence

<400> SEQUENCE: 15
aagctttgct aacatactgc gtaataagga gtcttaatc atg cca gtt ctt ttg                54
                                             Met Pro Val Leu Leu
                                              1               5 ggt att ccg tta tta ttg cgt ttc ctc ggt ttc ctt ctg gta act ttg              102
Gly Ile Pro Leu Leu Leu Arg Phe Leu Gly Phe Leu Leu Val Thr Leu
                 10                  15                  20 ttc ggc tat ctg ctt act ttc ctt aaa aag ggc ttc ggt aag ata gct              150
Phe Gly Tyr Leu Leu Thr Phe Leu Lys Lys Gly Phe Gly Lys Ile Ala
         25                  30                  35 att gct att tca ttg ttt ctt gct ctt att att ggg ctt aac tca att              198
Ile Ala Ile Ser Leu Phe Leu Ala Leu Ile Ile Gly Leu Asn Ser Ile
     40                  45                  50
```

```
ctt gtg ggt tat ctc tct gat att agc gca caa tta ccc tct gat ttt        246
Leu Val Gly Tyr Leu Ser Asp Ile Ser Ala Gln Leu Pro Ser Asp Phe
    55                  60                  65 gtt cag ggc gtt cag tta att ctc ccg tct aat gcg ctt ccc tgt ttt        294
Val Gln Gly Val Gln Leu Ile Leu Pro Ser Asn Ala Leu Pro Cys Phe
 70                  75                  80                  85 tat gtt att ctc tct gta aag gct gct att ttc att ttt gac gtt aaa        342
Tyr Val Ile Leu Ser Val Lys Ala Ala Ile Phe Ile Phe Asp Val Lys
                 90                  95                 100 caa aaa atc gtt tct tat ttg gat tgg gat aaa ggt gga ggc tca ggc        390
Gln Lys Ile Val Ser Tyr Leu Asp Trp Asp Lys Gly Gly Gly Ser Gly
            105                 110                 115 gga ggccaagtcg gccatcccat atcacgcggc cgcggatcc                         432
Gly
```

<210> SEQ ID NO 16
<211> LENGTH: 433
<212> TYPE: DNA
<213> ORGANISM: Heligmosomoides polygyrus
<220> FEATURE:
<221> NAME/KEY: CDS
<222> LOCATION: (40)..(393)
<220> FEATURE:
<221> NAME/KEY: MOD_RES
<223> OTHER INFORMATION: pDONG62 vector sequence

<400> SEQUENCE: 16

```
aagctttgct aacatactgc gtaataagga gtcttaatc atg cca gtt ctt ttg         54
                                            Met Pro Val Leu Leu
                                             1               5 ggt att ccg tta tta ttg cgt ttc ctc ggt ttc ctt ctg gta act ttg        102
Gly Ile Pro Leu Leu Leu Arg Phe Leu Gly Phe Leu Leu Val Thr Leu
                 10                  15                  20 ttc ggc tat ctg ctt act ttc ctt aaa aag ggc ttc ggt aag ata gct        150
Phe Gly Tyr Leu Leu Thr Phe Leu Lys Lys Gly Phe Gly Lys Ile Ala
             25                  30                  35 att gct att tca ttg ttt ctt gct ctt att att ggg ctt aac tca att        198
Ile Ala Ile Ser Leu Phe Leu Ala Leu Ile Ile Gly Leu Asn Ser Ile
        40                  45                  50 ctt gtg ggt tat ctc tct gat att agc gca caa tta ccc tct gat ttt        246
Leu Val Gly Tyr Leu Ser Asp Ile Ser Ala Gln Leu Pro Ser Asp Phe
    55                  60                  65 gtt cag ggc gtt cag tta att ctc ccg tct aat gcg ctt ccc tgt ttt        294
Val Gln Gly Val Gln Leu Ile Leu Pro Ser Asn Ala Leu Pro Cys Phe
 70                  75                  80                  85 tat gtt att ctc tct gta aag gct gct att ttc att ttt gac gtt aaa        342
Tyr Val Ile Leu Ser Val Lys Ala Ala Ile Phe Ile Phe Asp Val Lys
                 90                  95                 100 caa aaa atc gtt tct tat ttg gat tgg gat aaa ggt gga ggc tca ggc        390
Gln Lys Ile Val Ser Tyr Leu Asp Trp Asp Lys Gly Gly Gly Ser Gly
            105                 110                 115 gga gggccaagtc ggccatccca tatcacgcgg ccgcggatcc                        433
Gly
```

<210> SEQ ID NO 17
<211> LENGTH: 434
<212> TYPE: DNA
<213> ORGANISM: Heligmosomoides polygyrus
<220> FEATURE:
<221> NAME/KEY: CDS
<222> LOCATION: (140)..(291)
<220> FEATURE:
<221> NAME/KEY: MOD_RES
<223> OTHER INFORMATION: pDONG63 vector sequence

<400> SEQUENCE: 17

```
aagctttgct aacatactgc gtaataagga gtcttaatc atg cca gtt ctt ttg          54
                                             Met Pro Val Leu Leu
                                               1               5 ggt att ccg tta tta ttg cgt ttc ctc ggt ttc ctt ctg gta act ttg        102
Gly Ile Pro Leu Leu Leu Arg Phe Leu Gly Phe Leu Leu Val Thr Leu
             10                  15                  20 ttc ggc tat ctg ctt act ttc ctt aaa aag ggc ttc ggt aag ata gct        150
Phe Gly Tyr Leu Leu Thr Phe Leu Lys Lys Gly Phe Gly Lys Ile Ala
             25                  30                  35 att gct att tca ttg ttt ctt gct ctt att att ggg ctt aac tca att        198
Ile Ala Ile Ser Leu Phe Leu Ala Leu Ile Ile Gly Leu Asn Ser Ile
         40                  45                  50 ctt gtg ggt tat ctc tct gat att agc gca caa tta ccc tct gat ttt        246
Leu Val Gly Tyr Leu Ser Asp Ile Ser Ala Gln Leu Pro Ser Asp Phe
55                  60                  65 gtt cag ggc gtt cag tta att ctc ccg tct aat gcg ctt ccc tgt ttt        294
Val Gln Gly Val Gln Leu Ile Leu Pro Ser Asn Ala Leu Pro Cys Phe
70                  75                  80                  85 tat gtt att ctc tct gta aag gct gct att ttc att ttt gac gtt aaa        342
Tyr Val Ile Leu Ser Val Lys Ala Ala Ile Phe Ile Phe Asp Val Lys
                 90                  95                 100 caa aaa atc gtt tct tat ttg gat tgg gat aaa ggt gga ggc tca ggc        390
Gln Lys Ile Val Ser Tyr Leu Asp Trp Asp Lys Gly Gly Gly Ser Gly
             105                 110                 115 gga tcggccaagt cggccatccc atatcacgcg gccgcggatc c                      434
Gly
```

```
<210> SEQ ID NO 18
<211> LENGTH: 6
<212> TYPE: PRT
<213> ORGANISM: Artificial Sequence
<220> FEATURE:
<221> NAME/KEY: misc_feature
<223> OTHER INFORMATION: Description of Artificial Sequence: pDONG
      vector linker sequence
```

<400> SEQUENCE: 18

```
Gly Gly Gly Ser Gly Gly
  1               5
```

```
<210> SEQ ID NO 19
<211> LENGTH: 430
<212> TYPE: DNA
<213> ORGANISM: Ancyclostoma ceylanicum
<220> FEATURE:
<221> NAME/KEY: CDS
<222> LOCATION: (10)..(282)
<220> FEATURE:
<221> NAME/KEY: MOD_RES
<223> OTHER INFORMATION: "w" stands for a or t
```

<400> SEQUENCE: 19

```
gaattccgg ctg gtw tcc tac tgc agt gga aaa gca acg atg cag tgt ggt       51
          Leu Val Ser Tyr Cys Ser Gly Lys Ala Thr Met Gln Cys Gly
            1               5                  10 gag aat gaa aag tac gat tcg tgc ggt agc aag gag tgc gat aag aag         99
Glu Asn Glu Lys Tyr Asp Ser Cys Gly Ser Lys Glu Cys Asp Lys Lys
15                  20                  25                  30 tgc aaa tat gac gga gtt gag gag gaa gac gac gag gaa cct aat gtg        147
Cys Lys Tyr Asp Gly Val Glu Glu Glu Asp Asp Glu Glu Pro Asn Val
                 35                  40                  45
```

```
cca tgc cta gta cgt gtg tgt cat caa gat tgc gta tgc gaa gaa gga      195
Pro Cys Leu Val Arg Val Cys His Gln Asp Cys Val Cys Glu Glu Gly
             50                  55                  60 ttc tat aga aac aaa gat gac aaa tgt gta tca gca gaa gag tgc gaa      243
Phe Tyr Arg Asn Lys Asp Asp Lys Cys Val Ser Ala Glu Glu Cys Glu
     65                  70                  75 ctt gac aat atg gac ttt ata tat ccc gga act cga aac tgaacgaaggctc    295
Leu Asp Asn Met Asp Phe Ile Tyr Pro Gly Thr Arg Asn
 80                  85                  90 cattcttgct gcacaagatc gattgtctct cccctgcatc tcagtagttt tgctacattg    355
tatatggtag caaaaaatta gcttagggag aataaaatct ttacctatat ttaatcaatg    415
aagtattctc tttct                                                     430
```

```
<210> SEQ ID NO 20
<211> LENGTH: 100
<212> TYPE: PRT
<213> ORGANISM: Ancyclostoma caninum

<400> SEQUENCE: 20

Met Lys Met Leu Tyr Ala Ile Ala Ile Met Phe Leu Leu Val Ser Leu
 1               5                  10                  15

Cys Ser Ala Arg Thr Val Arg Lys Ala Tyr Pro Glu Cys Gly Glu Asn
            20                  25                  30

Glu Trp Leu Asp Asp Cys Gly Thr Gln Lys Pro Cys Glu Ala Lys Cys
         35                  40                  45

Asn Glu Glu Pro Pro Glu Glu Glu Asp Pro Ile Cys Arg Ser Arg Gly
     50                  55                  60

Cys Leu Leu Pro Pro Ala Cys Val Cys Lys Asp Gly Phe Tyr Arg Asp
 65                  70                  75                  80

Thr Val Ile Gly Asp Cys Val Arg Glu Glu Cys Asp Gln His Glu
                 85                  90                  95

Ile Ile His Val
            100
```

```
<210> SEQ ID NO 21
<211> LENGTH: 98
<212> TYPE: PRT
<213> ORGANISM: Ancyclostoma caninum

<400> SEQUENCE: 21

Met Lys Met Leu Tyr Ala Ile Ala Ile Met Phe Leu Leu Val Ser Leu
 1               5                  10                  15

Cys Ser Thr Arg Thr Val Arg Lys Ala Tyr Pro Glu Cys Gly Glu Asn
            20                  25                  30

Glu Trp Leu Asp Val Cys Gly Thr Lys Lys Pro Cys Glu Ala Lys Cys
         35                  40                  45

Ser Glu Glu Glu Glu Asp Pro Ile Cys Arg Ser Phe Ser Cys Pro
     50                  55                  60

Gly Pro Ala Ala Cys Val Cys Glu Asp Gly Phe Tyr Arg Asp Thr Val
 65                  70                  75                  80

Ile Gly Asp Cys Val Lys Glu Glu Cys Asp Gln His Glu Ile Ile
                 85                  90                  95

His Val
```

```
<210> SEQ ID NO 22
<211> LENGTH: 94
```

```
<212> TYPE: PRT
<213> ORGANISM: Ancyclostoma ceylanicum

<400> SEQUENCE: 22

Met Arg Thr Leu Tyr Leu Ile Ser Ile Trp Leu Phe Leu Ile Ser Gln
1               5                   10                  15

Cys Asn Gly Lys Ala Phe Pro Lys Cys Asp Val Asn Glu Arg Phe Glu
            20                  25                  30

Val Cys Gly Asn Leu Lys Glu Cys Glu Leu Lys Cys Asp Glu Asp Pro
        35                  40                  45

Lys Ile Cys Ser Arg Ala Cys Ile Arg Pro Ala Cys Val Cys Asp
    50                  55                  60

Asp Gly Phe Tyr Arg Asp Lys Tyr Gly Phe Cys Val Glu Glu Asp Glu
65                  70                  75                  80

Cys Asn Asp Met Glu Ile Ile Thr Phe Pro Pro Glu Thr Lys
                85                  90

<210> SEQ ID NO 23
<211> LENGTH: 96
<212> TYPE: PRT
<213> ORGANISM: Ancyclostoma ceylanicum

<400> SEQUENCE: 23

Met Ser Thr Leu Tyr Val Ile Ala Ile Cys Leu Leu Leu Val Ser Gln
1               5                   10                  15

Cys Asn Gly Arg Thr Val Lys Lys Cys Gly Lys Asn Glu Arg Tyr Asp
            20                  25                  30

Asp Cys Gly Asn Ala Lys Asp Cys Glu Thr Lys Cys Gly Glu Glu Glu
        35                  40                  45

Lys Val Cys Arg Ser Arg Glu Cys Thr Ser Pro Gly Ala Cys Val Cys
    50                  55                  60

Glu Gln Gly Phe Tyr Arg Asp Pro Ala Gly Asp Cys Val Thr Asp Glu
65                  70                  75                  80

Glu Cys Asp Glu Trp Asn Asn Met Glu Ile Ile Thr Met Pro Lys Gln
                85                  90                  95

<210> SEQ ID NO 24
<211> LENGTH: 108
<212> TYPE: PRT
<213> ORGANISM: Ancyclostoma ceylanicum

<400> SEQUENCE: 24

Met Ala Val Leu Tyr Ser Val Ala Ile Ala Leu Leu Leu Val Ser Gln
1               5                   10                  15

Cys Ser Gly Lys Pro Asn Asn Val Met Thr Asn Ala Cys Gly Leu Asn
            20                  25                  30

Glu Tyr Phe Ala Glu Cys Gly Asn Met Lys Glu Cys Glu His Arg Cys
            35                  40                  45

Asn Glu Glu Asn Glu Glu Arg Asp Glu Glu Arg Ile Thr Ala Cys
    50                  55                  60

Leu Ile Arg Val Cys Phe Arg Pro Gly Ala Cys Val Cys Lys Asp Gly
65                  70                  75                  80

Phe Tyr Arg Asn Arg Thr Gly Ser Cys Val Glu Glu Asp Asp Cys Glu
                85                  90                  95

Tyr Glu Asn Met Glu Phe Ile Thr Phe Ala Pro Glu
            100                 105
```

```
<210> SEQ ID NO 25
<211> LENGTH: 82
<212> TYPE: PRT
<213> ORGANISM: Ancyclostoma ceylanicum

<400> SEQUENCE: 25

Val Pro Ile Cys Gly Ser Asn Glu Arg Tyr Ser Asp Cys Gly Asn Asp
 1               5                  10                  15

Lys Gln Cys Glu Arg Lys Cys Asn Glu Asp Asp Tyr Glu Lys Gly Asp
            20                  25                  30

Glu Ala Cys Arg Ser His Val Cys Glu Arg Pro Gly Ala Cys Val Cys
        35                  40                  45

Glu Asp Gly Phe Tyr Arg Asn Lys Lys Gly Ser Cys Val Glu Ser Asp
    50                  55                  60

Asp Cys Glu Tyr Asp Asn Met Asp Phe Ile Thr Phe Ala Pro Glu Thr
65                  70                  75                  80

Ser Arg

<210> SEQ ID NO 26
<211> LENGTH: 75
<212> TYPE: PRT
<213> ORGANISM: Ancyclostoma duodenale

<400> SEQUENCE: 26

Lys Cys Pro Thr Asp Glu Trp Phe Asp Trp Cys Gly Thr Tyr Lys His
 1               5                  10                  15

Cys Glu Leu Lys Cys Asp Arg Glu Leu Thr Glu Glu Gln Ala Cys
            20                  25                  30

Leu Ser Arg Val Cys Glu Lys Ser Ala Cys Val Cys Asn Asp Gly Leu
        35                  40                  45

Tyr Arg Asp Lys Phe Gly Asn Cys Val Glu Lys Asp Glu Cys Asn Asp
    50                  55                  60

Met Glu Ile Ile Thr Phe Ala Pro Glu Thr Lys
65                  70                  75

<210> SEQ ID NO 27
<211> LENGTH: 102
<212> TYPE: PRT
<213> ORGANISM: Ancyclostoma duodenale

<400> SEQUENCE: 27

Met Arg Met Leu Tyr Leu Val Pro Ile Trp Leu Leu Leu Ile Ser Leu
 1               5                  10                  15

Cys Ser Gly Lys Ala Ala Lys Lys Cys Gly Leu Asn Glu Arg Leu Asp
            20                  25                  30

Cys Gly Asn Leu Lys Gln Cys Glu Pro Lys Cys Ser Asp Leu Glu Ser
        35                  40                  45

Glu Glu Tyr Glu Glu Asp Glu Ser Lys Cys Arg Ser Arg Glu Cys
    50                  55                  60

Ser Arg Arg Val Cys Val Cys Asp Gly Phe Tyr Arg Asn Lys Lys
65                  70                  75                  80

Gly Lys Cys Val Ala Lys Asp Val Cys Glu Asp Asp Asn Met Glu Ile
                85                  90                  95

Ile Thr Phe Pro Pro Glu
                100

<210> SEQ ID NO 28
<211> LENGTH: 78
```

<210> SEQ ID NO 28
<212> TYPE: PRT
<213> ORGANISM: Ancyclostoma duodenale

<400> SEQUENCE: 28

```
Asp Glu Cys Gly Pro Asp Glu Trp Phe Asp Tyr Cys Gly Asn Tyr Lys
1               5                   10                  15
Lys Cys Glu Arg Lys Cys Ser Glu Glu Thr Ser Glu Lys Asn Glu Glu
            20                  25                  30
Ala Cys Leu Ser Arg Ala Cys Thr Gly Arg Ala Cys Val Cys Lys Asp
        35                  40                  45
Gly Leu Tyr Arg Asp Asp Phe Gly Asn Cys Val Pro His Asp Glu Cys
    50                  55                  60
Asn Asp Met Glu Ile Ile Thr Phe Pro Pro Glu Thr Lys His
65                  70                  75
```

<210> SEQ ID NO 29
<211> LENGTH: 76
<212> TYPE: PRT
<213> ORGANISM: Helogmosomoides polygyrus

<400> SEQUENCE: 29

```
Met Ile Arg Lys Leu Val Leu Leu Thr Ala Ile Val Thr Val Val Leu
1               5                   10                  15
Ser Ala Lys Thr Cys Gly Pro Asn Glu Glu Tyr Thr Glu Cys Gly Thr
            20                  25                  30
Pro Cys Glu Pro Lys Cys Asn Glu Pro Met Pro Asp Ile Cys Thr Leu
        35                  40                  45
Asn Cys Ile Val Asn Val Cys Gln Cys Lys Pro Gly Phe Lys Arg Gly
    50                  55                  60
Pro Lys Gly Cys Val Ala Pro Gly Pro Gly Cys Lys
65                  70                  75
```

<210> SEQ ID NO 30
<211> LENGTH: 187
<212> TYPE: DNA
<213> ORGANISM: Ancyclostoma caninum

<400> SEQUENCE: 30

```
ttattcgaaa cgatgttctc tccaattttg tccttggaaa ttattttagc tactttgcaa    60
tctgtcttcg cccagccagt tatctccact accgttggtt ccgctgccga gggttctttg   120
gacaagaggc ctatccgcgg aattcagatc tgaatgcggc cgctcgagac tagtggatcc   180
ttagaca                                                             187
```

<210> SEQ ID NO 31
<211> LENGTH: 495
<212> TYPE: DNA
<213> ORGANISM: Ancyclostoma caninum
<220> FEATURE:
<221> NAME/KEY: CDS
<222> LOCATION: (36)..(356)
<220> FEATURE:
<221> NAME/KEY: MOD_RES
<223> OTHER INFORMATION: Recombinant cDNA Molecule AcaNAP23 sequence

<400> SEQUENCE: 31

```
gaattccgcg gaattccgct tgctactact caacg atg aag acg ctc tat att       53
                                      Met Lys Thr Leu Tyr Ile
                                      1               5 gtc gct ata tgc tcg ctc ctc att tcg ctg tgt act gga aaa cct tcg     101
Val Ala Ile Cys Ser Leu Leu Ile Ser Leu Cys Thr Gly Lys Pro Ser
```

-continued

```
              10                  15                  20
gag aaa gaa tgt ggt ccc cat gaa aga ctc gac tgt ggc aac aag aag    149
Glu Lys Glu Cys Gly Pro His Glu Arg Leu Asp Cys Gly Asn Lys Lys
         25                  30                  35 cca tgc gag cgc aag tgc aaa ata gag aca agt gag gag gag gat gac    197
Pro Cys Glu Arg Lys Cys Lys Ile Glu Thr Ser Glu Glu Glu Asp Asp
 40                  45                  50 tac gaa gag gga acc gaa cgt ttt cga tgc ctc tta cgt gtg tgt gat    245
Tyr Glu Glu Gly Thr Glu Arg Phe Arg Cys Leu Leu Arg Val Cys Asp
 55                  60                  65                  70 cag cct tat gaa tgc ata tgc gat gat gga tac tac aga aac aag aaa    293
Gln Pro Tyr Glu Cys Ile Cys Asp Asp Gly Tyr Tyr Arg Asn Lys Lys
                 75                  80                  85 ggc gaa tgt gtg act gat gat gta tgc cag gaa gac ttt atg gag ttt    341
Gly Glu Cys Val Thr Asp Asp Val Cys Gln Glu Asp Phe Met Glu Phe
                     90                  95                 100 att act ttc gca cca taaacccaat aatgaccaat gactcccatt cttcgtgatcag  398
Ile Thr Phe Ala Pro
            105 cgtcggtggt tgacagtctc ccctacatct tagtagtttt gcttgataat gtatacataa  458 actgtacttt ctgagataga ataaagctct caactac                           495
```

```
<210> SEQ ID NO 32
<211> LENGTH: 478
<212> TYPE: DNA
<213> ORGANISM: Ancyclostoma caninum
<220> FEATURE:
<221> NAME/KEY: CDS
<222> LOCATION: (24)..(341)
<220> FEATURE:
<221> NAME/KEY: MOD_RES
<223> OTHER INFORMATION: Recombinant cDNA Molecule AcaNAP24 sequence

<400> SEQUENCE: 32
```

```
gaattccgcg gaattccgca acg atg aag acg ctc tat att atc gct ata tgc     53
                         Met Lys Thr Leu Tyr Ile Ile Ala Ile Cys
                           1               5                  10 tcg ctc ctc att tcg ttg tgt act gga aga ccg gaa aaa aag tgc ggt    101
Ser Leu Leu Ile Ser Leu Cys Thr Gly Arg Pro Glu Lys Lys Cys Gly
             15                  20                  25 ccc ggt gaa aga ctc gcc tgt ggc aat aag aag cca tgc gag cgc aag    149
Pro Gly Glu Arg Leu Ala Cys Gly Asn Lys Lys Pro Cys Glu Arg Lys
         30                  35                  40 tgc aaa ata gag aca agt gag gag gag gat gac tac cca gag gga acc    197
Cys Lys Ile Glu Thr Ser Glu Glu Glu Asp Asp Tyr Pro Glu Gly Thr
 45                  50                  55 gaa cgt ttt cga tgc ctc tta cgt gtg tgt gat cag cct tat gaa tgc    245
Glu Arg Phe Arg Cys Leu Leu Arg Val Cys Asp Gln Pro Tyr Glu Cys
 60                  65                  70 ata tgc gat gat gga tac tac aga aac aag aaa ggc gaa tgt gtg act    293
Ile Cys Asp Asp Gly Tyr Tyr Arg Asn Lys Lys Gly Glu Cys Val Thr
 75                  80                  85                  90 gat gat gta tgc cag gaa gac ttt atg gag ttt att act ttc gca cca    341
Asp Asp Val Cys Gln Glu Asp Phe Met Glu Phe Ile Thr Phe Ala Pro
                 95                 100                 105 taaacccaat aatgaccact ggctcccatt cttcgtgacc agcgtcggtg gttgacagtc  401
tcccctgcat cttagtagtt tgcttgata atgtatccat aaacagtact ttctgagata   461
gaataaagct ctcaact                                                 478
```

```
<210> SEQ ID NO 33
<211> LENGTH: 472
<212> TYPE: DNA
<213> ORGANISM: Ancyclostoma caninum
<220> FEATURE:
<221> NAME/KEY: CDS
<222> LOCATION: (21)..(335)
<220> FEATURE:
<221> NAME/KEY: MOD_RES
<223> OTHER INFORMATION: Recombinant cDNA Molecule AcaNAP25 sequence

<400> SEQUENCE: 33
gaattccgta ctactcaacg atg aag acg ctc tat att atc gct ata tgc          50
                     Met Lys Thr Leu Tyr Ile Ile Ala Ile Cys
                      1               5                  10 tcg ctg ctc ttt tca ctg tgt act gga aga ccg gaa aaa aag tgc ggt        98
Ser Leu Leu Phe Ser Leu Cys Thr Gly Arg Pro Glu Lys Lys Cys Gly
             15                  20                  25 ccc ggt gaa aga ctc gac tgt gcc aac aag aag cca tgc gag ccc aag       146
Pro Gly Glu Arg Leu Asp Cys Ala Asn Lys Lys Pro Cys Glu Pro Lys
         30                  35                  40 tgc aaa ata gag aca agt gag gag gag gat gac gac gta gag gat acc       194
Cys Lys Ile Glu Thr Ser Glu Glu Glu Asp Asp Asp Val Glu Asp Thr
     45                  50                  55 gat gtg aga tgc ctc gta cgt gtg tgt gaa cgt cct ctt aaa tgc ata       242
Asp Val Arg Cys Leu Val Arg Val Cys Glu Arg Pro Leu Lys Cys Ile
 60                  65                  70 tgc aag gat gga tac tac aga aac aag aaa ggc gaa tgt gtg act gat       290
Cys Lys Asp Gly Tyr Tyr Arg Asn Lys Lys Gly Glu Cys Val Thr Asp
 75                  80                  85                  90 gat gta tgc cag gaa gac ttt atg gag ttt att act ttc gca cca taaacc    341
Asp Val Cys Gln Glu Asp Phe Met Glu Phe Ile Thr Phe Ala Pro
                 95                 100                 105 caataatgac cactggctcc cattcttcgt gatcagcgtc ggtggttgac agtctcccct     401
gcatcttagt tgctttgctt gataatctat acataaacag tactttctga gatagaataa     461
agctctcaac t                                                          472

<210> SEQ ID NO 34
<211> LENGTH: 487
<212> TYPE: DNA
<213> ORGANISM: Ancyclostoma caninum
<220> FEATURE:
<221> NAME/KEY: CDS
<222> LOCATION: (57)..(347)
<220> FEATURE:
<221> NAME/KEY: MOD_RES
<223> OTHER INFORMATION: Recombinant cDNA Molecule AcaNAP31, AcaNAP42
      and AcaNAP46 sequence

<400> SEQUENCE: 34
gaattccgga cttactagta ctcagcgaat caaatacgac ttactactac tcaacg atg      59
                                                              Met
                                                               1 aag acg ctc tct gct atc cct ata atg ctg ctc ctg gta tcg caa tgc       107
Lys Thr Leu Ser Ala Ile Pro Ile Met Leu Leu Leu Val Ser Gln Cys
             5                  10                  15 agt gga aaa tca ctg tgg gat cag aag tgt ggt gag aat gaa agg ctc       155
Ser Gly Lys Ser Leu Trp Asp Gln Lys Cys Gly Glu Asn Glu Arg Leu
         20                  25                  30 gac tgt ggc aat cag aag gac tgt gag cgc aag tgc gat gat aaa aga       203
Asp Cys Gly Asn Gln Lys Asp Cys Glu Arg Lys Cys Asp Asp Lys Arg
     35                  40                  45 agt gaa gaa gaa att atg cag gca tgt ctc aca cgt caa tgt ctt cct       251
```

```
Ser Glu Glu Glu Ile Met Gln Ala Cys Leu Thr Arg Gln Cys Leu Pro
 50                  55                  60                  65 cct gtt tgc gta tgt gaa gat gga ttc tac aga aat gac aac gac caa          299
Pro Val Cys Val Cys Glu Asp Gly Phe Tyr Arg Asn Asp Asn Asp Gln
                 70                  75                  80 tgt gtt gat gaa gaa gaa tgc aat atg gag ttt att act ttc gcr cca tg       349
Cys Val Asp Glu Glu Glu Cys Asn Met Glu Phe Ile Thr Phe Ala Pro
             85                  90                  95 aagcaaatga cagccgatgg tttggactct cgctacagat cacagcttta ctgtttccct        409
tgcatcatag tagttttgct agatagtgta tatattagca tgattttctg ataggagaa         469 taaagctttc caattttc                                                      487

<210> SEQ ID NO 35
<211> LENGTH: 477
<212> TYPE: DNA
<213> ORGANISM: Ancyclostoma caninum
<220> FEATURE:
<221> NAME/KEY: CDS
<222> LOCATION: (24)..(338)
<220> FEATURE:
<221> NAME/KEY: MOD_RES
<223> OTHER INFORMATION: Recombinant cDNA Molecule AcaNAP44 sequence

<400> SEQUENCE: 35
gaattccgcg gaattccgca acg atg aag acg ctc tat att atc gct ata tgc        53
                         Met Lys Thr Leu Tyr Ile Ile Ala Ile Cys
                           1               5                  10 tcg ctc ctc att tcg ctg tgt act gga aga ccg gaa aaa aag tgc ggt          101
Ser Leu Leu Ile Ser Leu Cys Thr Gly Arg Pro Glu Lys Lys Cys Gly
                15                  20                  25 ccc ggt gaa aga ctc gac tgt gcc aac aag aag cca tgc gag ccc aag          149
Pro Gly Glu Arg Leu Asp Cys Ala Asn Lys Lys Pro Cys Glu Pro Lys
             30                  35                  40 tgc aaa ata gag aca agt gag gag gag gat gac gac gta gag gaa acc          197
Cys Lys Ile Glu Thr Ser Glu Glu Glu Asp Asp Asp Val Glu Glu Thr
         45                  50                  55 gat gtg aga tgc ctc gta cgt gtg tgt gaa cgg cct ctt aaa tgc ata          245
Asp Val Arg Cys Leu Val Arg Val Cys Glu Arg Pro Leu Lys Cys Ile
     60                  65                  70 tgc aag gat gga tac tac aga aac aag aaa ggc gaa tgt gtg act gat          293
Cys Lys Asp Gly Tyr Tyr Arg Asn Lys Lys Gly Glu Cys Val Thr Asp
 75                  80                  85                  90 gat gta tgc cag gaa gac ttt atg gag ttt att act ttc gca cca taaacc       344
Asp Val Cys Gln Glu Asp Phe Met Glu Phe Ile Thr Phe Ala Pro
                 95                 100                 105 caataatgac cactggctcc cattcttcgt gatcagcgtc ggtggttgac agtctcccct        404
gcatcttagt tgctttgctt gataatctat acataaacag tactttctga gatagaataa        464
agctctcaac tac                                                           477

<210> SEQ ID NO 36
<211> LENGTH: 685
<212> TYPE: DNA
<213> ORGANISM: Ancyclostoma caninum
<220> FEATURE:
<221> NAME/KEY: CDS
<222> LOCATION: (14)..(556)
<220> FEATURE:
<221> NAME/KEY: MOD_RES
<223> OTHER INFORMATION: Recombinant cDNA Molecule AcaNAP45 sequence

<400> SEQUENCE: 36
```

```
aattccgga aaa atg ctg atg ctc tac ctt gtt cct atc tgg ttg cta          48
            Met Leu Met Leu Tyr Leu Val Pro Ile Trp Leu Leu
              1               5                  10 ctc att tcg caa tgc agt gga aaa tcc gcg aag aaa tgt ggt ctc aat        96
Leu Ile Ser Gln Cys Ser Gly Lys Ser Ala Lys Lys Cys Gly Leu Asn
         15                  20                  25 gaa aaa ttg gac tgt ggc aat ctg aag gca tgc gag aaa aag tgc agc       144
Glu Lys Leu Asp Cys Gly Asn Leu Lys Ala Cys Glu Lys Lys Cys Ser
     30                  35                  40 gac ttg gac aat gag gag gat tat aag gag gaa gat gag tcg aaa tgc       192
Asp Leu Asp Asn Glu Glu Asp Tyr Lys Glu Glu Asp Glu Ser Lys Cys
45                  50                  55                  60 cga tca cgt gaa tgt agt cgt cgt gtt tgt gta tgc gat gaa gga ttc       240
Arg Ser Arg Glu Cys Ser Arg Arg Val Cys Val Cys Asp Glu Gly Phe
                 65                  70                  75 tac aga aac aag aag ggc caa tgt gtg aca aga gat gat tgc gag tat       288
Tyr Arg Asn Lys Lys Gly Gln Cys Val Thr Arg Asp Asp Cys Glu Tyr
             80                  85                  90 gac aat atg gag att atc act ttt cca cca gaa gat aaa tgt ggt ccc       336
Asp Asn Met Glu Ile Ile Thr Phe Pro Pro Glu Asp Lys Cys Gly Pro
         95                  100                 105 gat gaa tgg ttc gac tgg tgt gga act tac aag cag tgt gag cgc aag       384
Asp Glu Trp Phe Asp Trp Cys Gly Thr Tyr Lys Gln Cys Glu Arg Lys
     110                 115                 120 tgc aat aag gag cta agt gag aaa gat gaa gag gca tgc ctc tca cgt       432
Cys Asn Lys Glu Leu Ser Glu Lys Asp Glu Glu Ala Cys Leu Ser Arg
125                 130                 135                 140 gct tgt act ggt cgt gct tgt gtt tgc aac gac gga ctg tac aga gac       480
Ala Cys Thr Gly Arg Ala Cys Val Cys Asn Asp Gly Leu Tyr Arg Asp
                 145                 150                 155 gat ttt ggc aat tgt gtt gag aaa gac gaa tgt aac gat atg gag att       528
Asp Phe Gly Asn Cys Val Glu Lys Asp Glu Cys Asn Asp Met Glu Ile
             160                 165                 170 atc act ttt cca ccg gaa acc aaa cac tgaccaaagg ctctaactct cgctacat    583
Ile Thr Phe Pro Pro Glu Thr Lys His
         175                 180 aacgtcagtg cttgaattgc ccctttacga gttagtaatt ttgactaact ctgtgtaatt     643
gagcattgtc tactgatggt gaaaatgaag tgttcaatgt ct                        685
```

<210> SEQ ID NO 37
<211> LENGTH: 707
<212> TYPE: DNA
<213> ORGANISM: Ancyclostoma caninum
<220> FEATURE:
<221> NAME/KEY: CDS
<222> LOCATION: (34)..(576)
<220> FEATURE:
<221> NAME/KEY: MOD_RES
<223> OTHER INFORMATION: Recombinant cDNA Molecule AcaNAP47 sequence

<400> SEQUENCE: 37

```
gaattccgcg gaattccggt tggcggcaga aaa atg ctg atg ctc tac ctt gtt       54
                                 Met Leu Met Leu Tyr Leu Val
                                   1               5 cct atc tgg ttc ctg ctc att tcg caa tgc agt gga aaa tcc gcg aag       102
Pro Ile Trp Phe Leu Leu Ile Ser Gln Cys Ser Gly Lys Ser Ala Lys
         10                  15                  20 aaa tgt ggc ctc aat gaa aaa ttg gac tgt ggc aat ctg aag gca tgc       150
Lys Cys Gly Leu Asn Glu Lys Leu Asp Cys Gly Asn Leu Lys Ala Cys
 25                  30                  35 gag aaa aag tgc agc gac ttg gac aat gag gag gat tat ggg gag gaa       198
Glu Lys Lys Cys Ser Asp Leu Asp Asn Glu Glu Asp Tyr Gly Glu Glu
```

```
Glu Lys Lys Cys Ser Asp Leu Asp Asn Glu Glu Asp Tyr Gly Glu Glu
 40              45                  50                  55 gat gag tcg aaa tgc cga tca cgt gaa tgt att ggt cgt gtt tgc gta       246
Asp Glu Ser Lys Cys Arg Ser Arg Glu Cys Ile Gly Arg Val Cys Val
                 60                  65                  70 tgc gat gaa gga ttc tac aga aac aag aag ggc caa tgt gtg aca aga       294
Cys Asp Glu Gly Phe Tyr Arg Asn Lys Lys Gly Gln Cys Val Thr Arg
             75                  80                  85 gac gat tgc gag tat gac aat atg gag att atc act ttt cca cca gaa       342
Asp Asp Cys Glu Tyr Asp Asn Met Glu Ile Ile Thr Phe Pro Pro Glu
         90                  95                 100 gat aaa tgt ggt ccc gat gaa tgg ttc gac tgg tgt gga act tac aag       390
Asp Lys Cys Gly Pro Asp Glu Trp Phe Asp Trp Cys Gly Thr Tyr Lys
     105                 110                 115 cag tgt gag cgc aag tgc agt gag gag cta agt gag aaa aat gag gag       438
Gln Cys Glu Arg Lys Cys Ser Glu Glu Leu Ser Glu Lys Asn Glu Glu
120                 125                 130                 135 gca tgc ctc tca cgt gct tgt act ggt cgt gct tgc gtt tgc aac gac       486
Ala Cys Leu Ser Arg Ala Cys Thr Gly Arg Ala Cys Val Cys Asn Asp
                140                 145                 150 gga ttg tat aga gac gat ttt ggc aat tgt gtt gag aaa gac gaa tgt       534
Gly Leu Tyr Arg Asp Asp Phe Gly Asn Cys Val Glu Lys Asp Glu Cys
            155                 160                 165 aac gat atg gag att atc act ttt cca ccg gaa acc aaa cac tgaccaaagg   586
Asn Asp Met Glu Ile Ile Thr Phe Pro Pro Glu Thr Lys His
        170                 175                 180 ctctagctct cgctacataa cgtcagtgct tgaattgtcc ctttacgtgt tagtaattttt    646 gactaactct gtgtatttga gcattgtcta ctaatggtga aaatgaagct tttcaatgac     706
t                                                                     707

<210> SEQ ID NO 38
<211> LENGTH: 529
<212> TYPE: DNA
<213> ORGANISM: Ancyclostoma caninum
<220> FEATURE:
<221> NAME/KEY: CDS
<222> LOCATION: (31)..(309)
<220> FEATURE:
<221> NAME/KEY: MOD_RES
<223> OTHER INFORMATION: Recombinant cDNA Molecule AcaNAP48 sequence

<400> SEQUENCE: 38
gaattccgta cgacctacta ctactcaacg atg aag gcg ctc tat gtt atc tct     54
                                  Met Lys Ala Leu Tyr Val Ile Ser
                                   1               5 ata acg ttg ctc ctg gta tgg caa tgc agt gca aga aca gcg agg aaa      102
Ile Thr Leu Leu Leu Val Trp Gln Cys Ser Ala Arg Thr Ala Arg Lys
         10                  15                  20 ccc cca acg tgt ggt gaa aat gaa agg gtc gaa tgg tgt ggc aag cag      150
Pro Pro Thr Cys Gly Glu Asn Glu Arg Val Glu Trp Cys Gly Lys Gln
 25                  30                  35                  40 tgc gag atc aca tgt gac gac cca gat aag ata tgc cgc tca ctc gct      198
Cys Glu Ile Thr Cys Asp Asp Pro Asp Lys Ile Cys Arg Ser Leu Ala
                 45                  50                  55 tgt cct ggt cct cct gct tgc gta tgc gac gac gga tac tac aga gac      246
Cys Pro Gly Pro Pro Ala Cys Val Cys Asp Asp Gly Tyr Tyr Arg Asp
             60                  65                  70 acg aac gtt ggc ttg tgt gta caa tat gac gaa tgc aac gat atg gat      294
Thr Asn Val Gly Leu Cys Val Gln Tyr Asp Glu Cys Asn Asp Met Asp
         75                  80                  85
```

```
att att atg gtt tca tagggttgac tgaagaatcg aacaaccggt gcacaacttc    349
Ile Ile Met Val Ser
         90 tatgcttgac tatctctctt gcatcatgca agtttagcta gatagtgtat atattagcaa    409 gacccttgg ggagaatgaa gcttcccaac tatattaaat caataacgtt ttcgcttcat    469 gtacacgtgc tcagcacatt catatccact cctcacactc catgaaagca gtgaaatgtt    529
```

<210> SEQ ID NO 39
<211> LENGTH: 361
<212> TYPE: DNA
<213> ORGANISM: Necator americanus
<220> FEATURE:
<221> NAME/KEY: CDS
<222> LOCATION: (16)..(252)
<220> FEATURE:
<221> NAME/KEY: MOD_RES
<223> OTHER INFORMATION: Recombinant cDNA Molecule NamNAP sequence

<400> SEQUENCE: 39

```
gccaactctt cgaac atg att cga ggc ctc gtt ctt ctt tct ctc ctg ttt     51
              Met Ile Arg Gly Leu Val Leu Leu Ser Leu Leu Phe
                1               5                  10 tgc gtc act ttt gca gcg aag aga gat tgt cca gca aat gag gaa tgg     99
Cys Val Thr Phe Ala Ala Lys Arg Asp Cys Pro Ala Asn Glu Glu Trp
         15                  20                  25 agg gaa tgt ggc act cca tgt gaa cca aaa tgc aat caa ccg atg cca    147
Arg Glu Cys Gly Thr Pro Cys Glu Pro Lys Cys Asn Gln Pro Met Pro
 30                  35                  40 gat ata tgt act atg aat tgt atc gtc gat gtg tgt caa tgc aag gag    195
Asp Ile Cys Thr Met Asn Cys Ile Val Asp Val Cys Gln Cys Lys Glu
 45                  50                  55                  60 gga tac aag cgt cat gaa acg aag gga tgc tta aag gaa gga tca gct    243
Gly Tyr Lys Arg His Glu Thr Lys Gly Cys Leu Lys Glu Gly Ser Ala
                 65                  70                  75 gat tgt aaa taagttatca gaacgctcgt tttgtcttac attagatggg tgagctgatg    302
Asp Cys Lys tatctgtcag ataaactctt tcttctaaaa aaaaaaaaa aaaaaaaaaa aaaaaaaa    361
```

<210> SEQ ID NO 40
<211> LENGTH: 77
<212> TYPE: PRT
<213> ORGANISM: Ancyclostoma caninum

<400> SEQUENCE: 40

```
Lys Ala Tyr Pro Glu Cys Gly Glu Asn Glu Trp Leu Asp Asp Cys Gly
  1               5                  10                  15

Thr Gln Lys Pro Cys Glu Ala Lys Cys Asn Glu Glu Pro Pro Glu Glu
             20                  25                  30

Glu Asp Pro Ile Cys Arg Ser Arg Gly Cys Leu Leu Pro Pro Ala Cys
         35                  40                  45

Val Cys Lys Asp Gly Phe Tyr Arg Asp Thr Val Ile Gly Asp Cys Val
     50                  55                  60

Arg Glu Glu Glu Cys Asp Gln His Glu Ile Ile His Val
 65                  70                  75
```

<210> SEQ ID NO 41
<211> LENGTH: 75
<212> TYPE: PRT
<213> ORGANISM: Ancyclostoma caninum

<400> SEQUENCE: 41

```
Lys Ala Tyr Pro Glu Cys Gly Glu Asn Glu Trp Leu Asp Val Cys Gly
1               5                   10                  15

Thr Lys Lys Pro Cys Glu Ala Lys Cys Ser Glu Glu Glu Glu Glu Asp
            20                  25                  30

Pro Ile Cys Arg Ser Phe Ser Cys Pro Gly Pro Ala Ala Cys Val Cys
            35                  40                  45

Glu Asp Gly Phe Tyr Arg Asp Thr Val Ile Gly Asp Cys Val Lys Glu
        50                  55                  60

Glu Glu Cys Asp Gln His Glu Ile Ile His Val
65                  70                  75
```

<210> SEQ ID NO 42
<211> LENGTH: 74
<212> TYPE: PRT
<213> ORGANISM: Ancyclostoma caninum
<400> SEQUENCE: 42

```
Arg Thr Ala Arg Lys Pro Pro Thr Cys Gly Glu Asn Glu Arg Val Glu
1               5                   10                  15

Trp Cys Gly Lys Gln Cys Glu Ile Thr Cys Asp Asp Pro Asp Lys Ile
            20                  25                  30

Cys Arg Ser Leu Ala Cys Pro Gly Pro Pro Ala Cys Val Cys Asp Asp
            35                  40                  45

Gly Tyr Tyr Arg Asp Thr Asn Val Gly Leu Cys Val Gln Tyr Asp Glu
        50                  55                  60

Cys Asn Asp Met Asp Ile Ile Met Val Ser
65                  70
```

<210> SEQ ID NO 43
<211> LENGTH: 88
<212> TYPE: PRT
<213> ORGANISM: Ancyclostoma caninum
<400> SEQUENCE: 43

```
Lys Pro Ser Glu Lys Glu Cys Gly Pro His Glu Arg Leu Asp Cys Gly
1               5                   10                  15

Asn Lys Lys Pro Cys Glu Arg Lys Cys Lys Ile Glu Thr Ser Glu Glu
            20                  25                  30

Glu Asp Asp Tyr Glu Glu Gly Thr Glu Arg Phe Arg Cys Leu Leu Arg
            35                  40                  45

Val Cys Asp Gln Pro Tyr Glu Cys Ile Cys Asp Asp Gly Tyr Tyr Arg
        50                  55                  60

Asn Lys Lys Gly Glu Cys Val Thr Asp Val Cys Gln Glu Asp Phe
65                  70                  75                  80

Met Glu Phe Ile Thr Phe Ala Pro
                85
```

<210> SEQ ID NO 44
<211> LENGTH: 87
<212> TYPE: PRT
<213> ORGANISM: Ancyclostoma caninum
<400> SEQUENCE: 44

```
Arg Pro Glu Lys Lys Cys Gly Pro Gly Glu Arg Leu Ala Cys Gly Asn
1               5                   10                  15

Lys Lys Pro Cys Glu Arg Lys Cys Lys Ile Glu Thr Ser Glu Glu Glu
            20                  25                  30
```

Asp Asp Tyr Pro Glu Gly Thr Glu Arg Phe Arg Cys Leu Leu Arg Val
        35                  40                  45

Cys Asp Gln Pro Tyr Glu Cys Ile Cys Asp Asp Gly Tyr Tyr Arg Asn
 50                  55                  60

Lys Lys Gly Glu Cys Val Thr Asp Asp Val Cys Gln Glu Asp Phe Met
 65                  70                  75                  80

Glu Phe Ile Thr Phe Ala Pro
                85

<210> SEQ ID NO 45
<211> LENGTH: 86
<212> TYPE: PRT
<213> ORGANISM: Ancyclostoma caninum

<400> SEQUENCE: 45

Arg Pro Glu Lys Lys Cys Gly Pro Gly Glu Arg Leu Asp Cys Ala Asn
 1               5                  10                  15

Lys Lys Pro Cys Glu Pro Lys Cys Lys Ile Glu Thr Ser Glu Glu Glu
                20                  25                  30

Asp Asp Val Glu Asp Thr Asp Val Arg Cys Leu Val Arg Val Cys
        35                  40                  45

Glu Arg Pro Leu Lys Cys Ile Cys Lys Asp Gly Tyr Tyr Arg Asn Lys
 50                  55                  60

Lys Gly Glu Cys Val Thr Asp Asp Val Cys Gln Glu Asp Phe Met Glu
 65                  70                  75                  80

Phe Ile Thr Phe Ala Pro
                85

<210> SEQ ID NO 46
<211> LENGTH: 86
<212> TYPE: PRT
<213> ORGANISM: Ancyclostoma caninum

<400> SEQUENCE: 46

Arg Pro Glu Lys Lys Cys Gly Pro Gly Glu Arg Leu Asp Cys Ala Asn
 1               5                  10                  15

Lys Lys Pro Cys Glu Pro Lys Cys Lys Ile Glu Thr Ser Glu Glu Glu
                20                  25                  30

Asp Asp Val Glu Glu Thr Asp Val Arg Cys Leu Val Arg Val Cys
        35                  40                  45

Glu Arg Pro Leu Lys Cys Ile Cys Lys Asp Gly Tyr Tyr Arg Asn Lys
 50                  55                  60

Lys Gly Glu Cys Val Thr Asp Asp Val Cys Gln Glu Asp Phe Met Glu
 65                  70                  75                  80

Phe Ile Thr Phe Ala Pro
                85

<210> SEQ ID NO 47
<211> LENGTH: 78
<212> TYPE: PRT
<213> ORGANISM: Ancyclostoma caninum

<400> SEQUENCE: 47

Lys Ser Leu Trp Asp Gln Lys Cys Gly Glu Asn Glu Arg Leu Asp Cys
 1               5                  10                  15

Gly Asn Gln Lys Asp Cys Glu Arg Lys Cys Asp Asp Lys Arg Ser Glu
                20                  25                  30

Glu Glu Ile Met Gln Ala Cys Leu Thr Arg Gln Cys Leu Pro Pro Val

```
              35                  40                  45
Cys Val Cys Glu Asp Gly Phe Tyr Arg Asn Asp Asn Asp Gln Cys Val
 50                  55                  60

Asp Glu Glu Glu Cys Asn Met Glu Phe Ile Thr Phe Ala Pro
 65                  70                  75
```

<210> SEQ ID NO 48
<211> LENGTH: 89
<212> TYPE: PRT
<213> ORGANISM: Ancyclostoma ceylanicum

<400> SEQUENCE: 48

```
Lys Pro Asn Asn Val Met Thr Asn Ala Cys Gly Leu Asn Glu Tyr Phe
 1               5                  10                  15

Ala Glu Cys Gly Asn Met Lys Glu Cys Glu His Arg Cys Asn Glu Glu
             20                  25                  30

Glu Asn Glu Glu Arg Asp Glu Glu Arg Ile Thr Ala Cys Leu Ile Arg
         35                  40                  45

Val Cys Phe Arg Pro Gly Ala Cys Val Cys Lys Asp Gly Phe Tyr Arg
 50                  55                  60

Asn Arg Thr Gly Ser Cys Val Glu Glu Asp Cys Glu Tyr Glu Asn
 65                  70                  75                  80

Met Glu Phe Ile Thr Phe Ala Pro Glu
                 85
```

<210> SEQ ID NO 49
<211> LENGTH: 82
<212> TYPE: PRT
<213> ORGANISM: Ancyclostoma ceylanicum

<400> SEQUENCE: 49

```
Val Pro Ile Cys Gly Ser Asn Glu Arg Tyr Ser Asp Cys Gly Asn Asp
 1               5                  10                  15

Lys Gln Cys Glu Arg Lys Cys Asn Glu Asp Asp Tyr Glu Lys Gly Asp
             20                  25                  30

Glu Ala Cys Arg Ser His Val Cys Glu Arg Pro Gly Ala Cys Val Cys
         35                  40                  45

Glu Asp Gly Phe Tyr Arg Asn Lys Lys Gly Ser Cys Val Glu Ser Asp
 50                  55                  60

Asp Cys Glu Tyr Asp Asn Met Asp Phe Ile Thr Phe Ala Pro Glu Thr
 65                  70                  75                  80

Ser Arg
```

<210> SEQ ID NO 50
<211> LENGTH: 84
<212> TYPE: PRT
<213> ORGANISM: Ancyclostoma caninum

<400> SEQUENCE: 50

```
Lys Ser Ala Lys Lys Cys Gly Leu Asn Glu Lys Leu Asp Cys Gly Asn
 1               5                  10                  15

Leu Lys Ala Cys Glu Lys Lys Cys Ser Asp Leu Asp Asn Glu Glu Asp
             20                  25                  30

Tyr Lys Glu Glu Asp Glu Ser Lys Cys Arg Ser Arg Gly Cys Ser Arg
         35                  40                  45

Arg Val Cys Val Cys Asp Glu Gly Phe Tyr Arg Asn Lys Lys Gly Gln
 50                  55                  60
```

```
Cys Val Thr Arg Asp Asp Cys Glu Tyr Asp Asn Met Glu Ile Ile Thr
 65                  70                  75                  80

Phe Pro Pro Glu

<210> SEQ ID NO 51
<211> LENGTH: 84
<212> TYPE: PRT
<213> ORGANISM: Ancyclostoma caninum

<400> SEQUENCE: 51

Lys Ser Ala Lys Lys Cys Gly Leu Asn Glu Lys Leu Asp Cys Gly Asn
 1               5                  10                  15

Leu Lys Ala Cys Glu Lys Lys Cys Ser Asp Leu Asp Asn Glu Glu Asp
                20                  25                  30

Tyr Gly Glu Glu Asp Glu Ser Lys Cys Arg Ser Arg Glu Cys Ile Gly
            35                  40                  45

Arg Val Cys Val Cys Asp Glu Gly Phe Tyr Arg Asn Lys Lys Gly Gln
        50                  55                  60

Cys Val Thr Arg Asp Asp Cys Glu Tyr Asp Asn Met Glu Ile Ile Thr
 65                  70                  75                  80

Phe Pro Pro Glu

<210> SEQ ID NO 52
<211> LENGTH: 83
<212> TYPE: PRT
<213> ORGANISM: Ancyclostoma duodenale

<400> SEQUENCE: 52

Lys Ala Ala Lys Lys Cys Gly Leu Asn Glu Arg Leu Asp Cys Gly Asn
 1               5                  10                  15

Leu Lys Gln Cys Glu Pro Lys Cys Ser Asp Leu Glu Ser Glu Glu Tyr
                20                  25                  30

Glu Glu Glu Asp Glu Ser Lys Cys Arg Ser Arg Glu Cys Ser Arg Arg
            35                  40                  45

Val Cys Val Cys Asp Glu Gly Phe Tyr Arg Asn Lys Lys Gly Lys Cys
        50                  55                  60

Val Ala Lys Asp Val Cys Glu Asp Asp Asn Met Glu Ile Ile Thr Phe
 65                  70                  75                  80

Pro Pro Glu

<210> SEQ ID NO 53
<211> LENGTH: 78
<212> TYPE: PRT
<213> ORGANISM: Ancyclostoma caninum

<400> SEQUENCE: 53

Asp Lys Cys Gly Pro Asp Glu Trp Phe Asp Trp Cys Gly Thr Tyr Lys
 1               5                  10                  15

Gln Cys Glu Arg Lys Cys Asn Lys Glu Leu Ser Glu Lys Asp Glu Glu
                20                  25                  30

Ala Cys Leu Ser Arg Ala Cys Thr Gly Arg Ala Cys Val Cys Asn Asp
            35                  40                  45

Gly Leu Tyr Arg Asp Asp Phe Gly Asn Cys Val Glu Lys Asp Glu Cys
        50                  55                  60

Asn Asp Met Glu Ile Ile Thr Phe Pro Pro Glu Thr Lys His
 65                  70                  75
```

<210> SEQ ID NO 54
<211> LENGTH: 78
<212> TYPE: PRT
<213> ORGANISM: Ancyclostoma caninum

<400> SEQUENCE: 54

Asp Lys Cys Gly Pro Asp Glu Trp Phe Asp Trp Cys Gly Thr Tyr Lys
1               5                   10                  15

Gln Cys Glu Arg Lys Cys Ser Glu Glu Leu Ser Glu Lys Asn Glu Glu
            20                  25                  30

Ala Cys Leu Ser Arg Ala Cys Thr Gly Arg Ala Cys Val Cys Asn Asp
        35                  40                  45

Gly Leu Tyr Arg Asp Asp Phe Gly Asn Cys Val Glu Lys Asp Glu Cys
    50                  55                  60

Asn Asp Met Glu Ile Ile Thr Phe Pro Pro Glu Thr Lys His
65                  70                  75

<210> SEQ ID NO 55
<211> LENGTH: 77
<212> TYPE: PRT
<213> ORGANISM: Ancyclostoma duodenale

<400> SEQUENCE: 55

Lys Cys Pro Thr Asp Glu Trp Phe Asp Trp Cys Gly Thr Tyr Lys His
1               5                   10                  15

Cys Glu Leu Lys Cys Asp Arg Glu Leu Thr Glu Lys Glu Glu Gln Ala
            20                  25                  30

Cys Leu Ser Arg Val Cys Glu Lys Ser Ala Cys Val Cys Asn Asp Gly
        35                  40                  45

Leu Tyr Arg Asp Lys Phe Gly Asn Cys Val Glu Lys Asp Glu Cys Asn
    50                  55                  60

Asp Met Glu Ile Ile Thr Phe Ala Pro Glu Glu Thr Lys
65                  70                  75

<210> SEQ ID NO 56
<211> LENGTH: 78
<212> TYPE: PRT
<213> ORGANISM: Ancyclostoma duodenale

<400> SEQUENCE: 56

Asp Glu Cys Gly Pro Asp Glu Trp Phe Asp Tyr Cys Gly Asn Tyr Lys
1               5                   10                  15

Lys Cys Glu Arg Lys Cys Ser Glu Glu Thr Ser Glu Lys Asn Glu Glu
            20                  25                  30

Ala Cys Leu Ser Arg Ala Cys Thr Gly Arg Ala Cys Val Cys Lys Asp
        35                  40                  45

Gly Leu Tyr Arg Asp Asp Phe Gly Asn Cys Val Pro His Asp Glu Cys
    50                  55                  60

Asn Asp Met Glu Ile Ile Thr Phe Pro Pro Glu Thr Lys His
65                  70                  75

<210> SEQ ID NO 57
<211> LENGTH: 75
<212> TYPE: PRT
<213> ORGANISM: Ancyclostoma ceylanicum

<400> SEQUENCE: 57

Lys Ala Phe Pro Lys Cys Asp Val Asn Glu Arg Phe Glu Val Cys Gly
1               5                   10                  15

```
Asn Leu Lys Glu Cys Glu Leu Lys Cys Asp Glu Asp Pro Lys Ile Cys
             20                  25                  30

Ser Arg Ala Cys Ile Arg Pro Pro Ala Cys Val Cys Asp Asp Gly Phe
         35                  40                  45

Tyr Arg Asp Lys Tyr Gly Phe Cys Val Glu Glu Asp Glu Cys Asn Asp
 50                  55                  60

Met Glu Ile Ile Thr Phe Pro Pro Glu Thr Lys
 65                  70                  75

<210> SEQ ID NO 58
<211> LENGTH: 77
<212> TYPE: PRT
<213> ORGANISM: Ancyclostoma ceylanicum

<400> SEQUENCE: 58

Arg Thr Val Lys Lys Cys Gly Lys Asn Glu Arg Tyr Asp Asp Cys Gly
 1               5                  10                  15

Asn Ala Lys Asp Cys Glu Thr Lys Cys Gly Glu Glu Lys Val Cys
             20                  25                  30

Arg Ser Arg Glu Cys Thr Ser Pro Gly Ala Cys Val Cys Glu Gln Gly
         35                  40                  45

Phe Tyr Arg Asp Pro Ala Gly Asp Cys Val Thr Asp Glu Glu Cys Asp
 50                  55                  60

Glu Trp Asn Asn Met Glu Ile Ile Thr Met Pro Lys Gln
 65                  70                  75

<210> SEQ ID NO 59
<211> LENGTH: 84
<212> TYPE: PRT
<213> ORGANISM: Ancyclostoma caninum

<400> SEQUENCE: 59

Lys Ala Thr Met Gln Cys Gly Glu Asn Glu Lys Tyr Asp Ser Cys Gly
 1               5                  10                  15

Ser Lys Glu Cys Asp Lys Lys Cys Lys Tyr Asp Gly Val Glu Glu Glu
             20                  25                  30

Asp Asp Glu Glu Pro Asn Val Pro Cys Leu Val Arg Val Cys His Gln
         35                  40                  45

Asp Cys Val Cys Glu Glu Gly Phe Tyr Arg Asn Lys Asp Asp Lys Cys
 50                  55                  60

Val Ser Ala Glu Asp Cys Glu Leu Asp Asn Met Asp Phe Ile Tyr Pro
 65                  70                  75                  80

Gly Thr Arg Asn

<210> SEQ ID NO 60
<211> LENGTH: 58
<212> TYPE: PRT
<213> ORGANISM: Heligmosomoides polygyrus

<400> SEQUENCE: 60

Lys Thr Cys Gly Pro Asn Glu Glu Tyr Thr Glu Cys Gly Thr Pro Cys
 1               5                  10                  15

Glu Pro Lys Cys Asn Glu Pro Met Pro Asp Ile Cys Thr Leu Asn Cys
             20                  25                  30

Ile Val Asn Val Cys Gln Cys Lys Pro Gly Phe Lys Arg Gly Pro Lys
         35                  40                  45

Gly Cys Val Ala Pro Gly Pro Gly Cys Lys
 50                  55
```

<210> SEQ ID NO 61
<211> LENGTH: 61
<212> TYPE: PRT
<213> ORGANISM: Necator americanus

<400> SEQUENCE: 61

```
Lys Arg Asp Cys Pro Ala Asn Glu Glu Trp Arg Glu Cys Gly Thr Pro
 1               5                  10                  15

Cys Glu Pro Lys Cys Asn Gln Pro Met Pro Asp Ile Cys Thr Met Asn
            20                  25                  30

Cys Ile Val Asp Val Cys Gln Cys Lys Glu Gly Tyr Lys Arg His Glu
        35                  40                  45

Thr Lys Gly Cys Leu Lys Glu Gly Ser Ala Asp Cys Lys
    50                  55                  60
```

<210> SEQ ID NO 62
<211> LENGTH: 171
<212> TYPE: PRT
<213> ORGANISM: Ancyclostoma ceylanicum

<400> SEQUENCE: 62

```
Lys Pro Asn Asn Val Met Thr Asn Ala Cys Gly Leu Asn Glu Tyr Phe
 1               5                  10                  15

Ala Glu Cys Gly Asn Met Lys Glu Cys Glu His Arg Cys Asn Glu Glu
            20                  25                  30

Glu Asn Glu Glu Arg Asp Glu Arg Ile Thr Ala Cys Leu Ile Arg
        35                  40                  45

Val Cys Phe Arg Pro Gly Ala Cys Val Cys Lys Asp Gly Phe Tyr Arg
    50                  55                  60

Asn Arg Thr Gly Ser Cys Val Glu Glu Asp Cys Glu Tyr Glu Asn
65                  70                  75                  80

Met Glu Phe Ile Thr Phe Ala Pro Glu Val Pro Ile Cys Gly Ser Asn
                85                  90                  95

Glu Arg Tyr Ser Asp Cys Gly Asn Asp Lys Gln Cys Glu Arg Lys Cys
                100                 105                 110

Asn Glu Asp Asp Tyr Glu Lys Gly Asp Glu Ala Cys Arg Ser His Val
            115                 120                 125

Cys Glu Arg Pro Gly Ala Cys Val Cys Glu Asp Gly Phe Tyr Arg Asn
        130                 135                 140

Lys Lys Gly Ser Cys Val Glu Ser Asp Cys Glu Tyr Asp Asn Met
145                 150                 155                 160

Asp Phe Ile Thr Phe Ala Pro Glu Thr Ser Arg
                165                 170
```

<210> SEQ ID NO 63
<211> LENGTH: 162
<212> TYPE: PRT
<213> ORGANISM: Ancyclostoma caninum

<400> SEQUENCE: 63

```
Lys Ser Ala Lys Lys Cys Gly Leu Asn Glu Lys Leu Asp Cys Gly Asn
 1               5                  10                  15

Leu Lys Ala Cys Glu Lys Lys Cys Ser Asp Leu Asp Asn Glu Glu Asp
            20                  25                  30

Tyr Lys Glu Glu Asp Glu Ser Lys Cys Arg Ser Arg Glu Cys Ser Arg
        35                  40                  45
```

-continued

```
Arg Val Cys Val Cys Asp Glu Gly Phe Tyr Arg Asn Lys Lys Gly Gln
 50                  55                  60

Cys Val Thr Arg Asp Asp Cys Glu Tyr Asp Asn Met Glu Ile Ile Thr
 65                  70                  75                  80

Phe Pro Pro Glu Asp Lys Cys Gly Pro Asp Glu Trp Phe Asp Trp Cys
                 85                  90                  95

Gly Thr Tyr Lys Gln Cys Glu Arg Lys Cys Asn Lys Glu Leu Ser Glu
                100                 105                 110

Lys Asp Glu Glu Ala Cys Leu Ser Arg Ala Cys Thr Gly Arg Ala Cys
            115                 120                 125

Val Cys Asn Asp Gly Leu Tyr Arg Asp Asp Phe Gly Asn Cys Val Glu
    130                 135                 140

Lys Asp Glu Cys Asn Asp Met Glu Ile Ile Thr Phe Pro Pro Glu Thr
145                 150                 155                 160

Lys His
```

<210> SEQ ID NO 64
<211> LENGTH: 162
<212> TYPE: PRT
<213> ORGANISM: Ancyclostoma caninum

<400> SEQUENCE: 64

```
Lys Ser Ala Lys Lys Cys Gly Leu Asn Glu Lys Leu Asp Cys Gly Asn
 1               5                  10                  15

Leu Lys Ala Cys Glu Lys Lys Cys Ser Asp Leu Asp Asn Glu Glu Asp
                 20                  25                  30

Tyr Gly Glu Glu Asp Glu Ser Lys Cys Arg Ser Arg Glu Cys Ile Gly
             35                  40                  45

Arg Val Cys Val Cys Asp Glu Gly Phe Tyr Arg Asn Lys Lys Gly Gln
 50                  55                  60

Cys Val Thr Arg Asp Asp Cys Glu Tyr Asp Asn Met Glu Ile Ile Thr
 65                  70                  75                  80

Phe Pro Pro Glu Asp Lys Cys Gly Pro Asp Glu Trp Phe Asp Trp Cys
                 85                  90                  95

Gly Thr Tyr Lys Gln Cys Glu Arg Lys Cys Ser Glu Glu Leu Ser Glu
                100                 105                 110

Lys Asn Glu Glu Ala Cys Leu Ser Arg Ala Cys Thr Gly Arg Ala Cys
            115                 120                 125

Val Cys Asn Asp Gly Leu Tyr Arg Asp Asp Phe Gly Asn Cys Val Glu
    130                 135                 140

Lys Asp Glu Cys Asn Asp Met Glu Ile Ile Thr Phe Pro Pro Glu Thr
145                 150                 155                 160

Lys His
```

<210> SEQ ID NO 65
<211> LENGTH: 161
<212> TYPE: PRT
<213> ORGANISM: Ancyclostoma duodenale

<400> SEQUENCE: 65

```
Lys Ala Ala Lys Lys Cys Gly Leu Asn Glu Arg Leu Asp Cys Gly Asn
 1               5                  10                  15

Leu Lys Gln Cys Glu Pro Lys Cys Ser Asp Leu Glu Ser Glu Glu Tyr
                 20                  25                  30

Glu Glu Glu Asp Glu Ser Lys Cys Arg Ser Arg Glu Cys Ser Arg Arg
             35                  40                  45
```

```
Val Cys Val Cys Asp Glu Gly Phe Tyr Arg Asn Lys Lys Gly Lys Cys
 50                  55                  60

Val Ala Lys Asp Val Cys Glu Asp Asp Asn Met Glu Ile Ile Thr Phe
 65                  70                  75                  80

Pro Pro Glu Asp Glu Cys Gly Pro Asp Glu Trp Phe Asp Tyr Cys Gly
                 85                  90                  95

Asn Tyr Lys Lys Cys Glu Arg Lys Cys Ser Glu Glu Thr Ser Glu Lys
            100                 105                 110

Asn Glu Glu Ala Cys Leu Ser Arg Ala Cys Thr Gly Arg Ala Cys Val
            115                 120                 125

Cys Lys Asp Gly Leu Tyr Arg Asp Asp Phe Gly Asn Cys Val Pro His
    130                 135                 140

Asp Glu Cys Asn Asp Met Glu Ile Ile Thr Phe Pro Pro Glu Thr Lys
145                 150                 155                 160

His

<210> SEQ ID NO 66
<211> LENGTH: 9
<212> TYPE: PRT
<213> ORGANISM: Ancyclostoma caninum
<220> FEATURE:
<221> NAME/KEY: MISC_FEATURE
<222> LOCATION: (2)
<223> OTHER INFORMATION: Xaa is any amino acid
<220> FEATURE:
<221> NAME/KEY: MISC_FEATURE
<222> LOCATION: (3)
<223> OTHER INFORMATION: Xaa is any amino acid
<220> FEATURE:
<221> NAME/KEY: MISC_FEATURE
<222> LOCATION: (4)
<223> OTHER INFORMATION: Xaa is any amino acid
<220> FEATURE:
<221> NAME/KEY: MISC_FEATURE
<222> LOCATION: (5)
<223> OTHER INFORMATION: Xaa is any amino acid
<220> FEATURE:
<221> NAME/KEY: MISC_FEATURE
<222> LOCATION: (6)
<223> OTHER INFORMATION: Xaa is any amino acid
<220> FEATURE:
<221> NAME/KEY: MISC_FEATURE
<222> LOCATION: (7)
<223> OTHER INFORMATION: Xaa is any amino  acid
<220> FEATURE:
<221> NAME/KEY: MISC_FEATURE
<222> LOCATION: (8)
<223> OTHER INFORMATION: Xaa is any amino  acid
<220> FEATURE:
<221> NAME/KEY: MISC_FEATURE
<222> LOCATION: (9)
<223> OTHER INFORMATION: Xaa is any amino  acid

<400> SEQUENCE: 66

Cys Xaa Xaa Xaa Xaa Xaa Xaa Xaa Xaa
 1               5

<210> SEQ ID NO 67
<211> LENGTH: 9
<212> TYPE: PRT
<213> ORGANISM: Ancyclostoma caninum
<220> FEATURE:
<221> NAME/KEY: MISC_FEATURE
<222> LOCATION: (2)
<223> OTHER INFORMATION: Xaa is any amino  acid
<220> FEATURE:
<221> NAME/KEY: MISC_FEATURE
<222> LOCATION: (3)
```

```
<223> OTHER INFORMATION: Xaa is any amino acid
<220> FEATURE:
<221> NAME/KEY: MISC_FEATURE
<222> LOCATION: (4)
<223> OTHER INFORMATION: Xaa is any amino acid
<220> FEATURE:
<221> NAME/KEY: MISC_FEATURE
<222> LOCATION: (5)
<223> OTHER INFORMATION: Xaa is any amino acid
<220> FEATURE:
<221> NAME/KEY: MISC_FEATURE
<222> LOCATION: (6)
<223> OTHER INFORMATION: Xaa is any amino acid
<220> FEATURE:
<221> NAME/KEY: MISC_FEATURE
<222> LOCATION: (7)
<223> OTHER INFORMATION: Xaa is any amino acid
<220> FEATURE:
<221> NAME/KEY: MISC_FEATURE
<222> LOCATION: (8)
<223> OTHER INFORMATION: Xaa is any amino acid
<220> FEATURE:
<221> NAME/KEY: MISC_FEATURE
<222> LOCATION: (9)
<223> OTHER INFORMATION: Xaa is any amino acid

<400> SEQUENCE: 67

Cys Xaa Xaa Xaa Xaa Xaa Xaa Xaa Xaa
1               5

<210> SEQ ID NO 68
<211> LENGTH: 7
<212> TYPE: PRT
<213> ORGANISM: Ancyclostoma caninum
<220> FEATURE:
<221> NAME/KEY: MISC_FEATURE
<222> LOCATION: (1)
<223> OTHER INFORMATION: Xaa is any amino acid, provided that at least
      one of Xaa at location 1 is Glu or Asp
<220> FEATURE:
<221> NAME/KEY: MISC_FEATURE
<222> LOCATION: (2)
<223> OTHER INFORMATION: Xaa is any amino acid, provided that at least
      one of Xaa at location 1 is Glu or Asp
<220> FEATURE:
<221> NAME/KEY: MISC_FEATURE
<222> LOCATION: (3)
<223> OTHER INFORMATION: Xaa is any amino acid
<220> FEATURE:
<221> NAME/KEY: MISC_FEATURE
<222> LOCATION: (4)
<223> OTHER INFORMATION: Xaa is any amino acid
<220> FEATURE:
<221> NAME/KEY: MISC_FEATURE
<222> LOCATION: (5)
<223> OTHER INFORMATION: Xaa is any amino acid
<220> FEATURE:
<221> NAME/KEY: MISC_FEATURE
<222> LOCATION: (6)
<223> OTHER INFORMATION: Xaa is any amino acid
<220> FEATURE:
<221> NAME/KEY: MISC_FEATURE
<222> LOCATION: (7)
<223> OTHER INFORMATION: Xaa is any amino acid

<400> SEQUENCE: 68

Xaa Xaa Xaa Xaa Xaa Xaa Xaa
1               5

<210> SEQ ID NO 69
<211> LENGTH: 5
<212> TYPE: PRT
<213> ORGANISM: Ancyclostoma caninum

<400> SEQUENCE: 69
```

```
Gly Phe Tyr Arg Asp
1               5

<210> SEQ ID NO 70
<211> LENGTH: 5
<212> TYPE: PRT
<213> ORGANISM: Ancyclostoma caninum

<400> SEQUENCE: 70

Gly Phe Tyr Arg Asn
1               5

<210> SEQ ID NO 71
<211> LENGTH: 5
<212> TYPE: PRT
<213> ORGANISM: Ancyclostoma caninum

<400> SEQUENCE: 71

Gly Tyr Tyr Arg Asp
1               5

<210> SEQ ID NO 72
<211> LENGTH: 5
<212> TYPE: PRT
<213> ORGANISM: Ancyclostoma caninum

<400> SEQUENCE: 72

Gly Tyr Tyr Arg Asn
1               5

<210> SEQ ID NO 73
<211> LENGTH: 5
<212> TYPE: PRT
<213> ORGANISM: Ancyclostoma caninum

<400> SEQUENCE: 73

Gly Leu Tyr Arg Asp
1               5

<210> SEQ ID NO 74
<211> LENGTH: 5
<212> TYPE: PRT
<213> ORGANISM: Ancyclostoma caninum

<400> SEQUENCE: 74

Glu Ile Ile His Val
1               5

<210> SEQ ID NO 75
<211> LENGTH: 5
<212> TYPE: PRT
<213> ORGANISM: Ancyclostoma caninum

<400> SEQUENCE: 75

Asp Ile Ile Met Val
1               5

<210> SEQ ID NO 76
<211> LENGTH: 6
<212> TYPE: PRT
<213> ORGANISM: Ancyclostoma caninum

<400> SEQUENCE: 76

Phe Ile Thr Phe Ala Pro
```

```
1               5
```

<210> SEQ ID NO 77
<211> LENGTH: 5
<212> TYPE: PRT
<213> ORGANISM: Ancyclostoma caninum

<400> SEQUENCE: 77

```
Met Glu Ile Ile Thr
1               5
```

<210> SEQ ID NO 78
<211> LENGTH: 7
<212> TYPE: PRT
<213> ORGANISM: Ancyclostoma caninum
<220> FEATURE:
<221> NAME/KEY: MISC_FEATURE
<222> LOCATION: (1)
<223> OTHER INFORMATION: Xaa is any amino acid, provided that at least
      one Xaa is Glu or Asp
<220> FEATURE:
<221> NAME/KEY: MISC_FEATURE
<222> LOCATION: (2)
<223> OTHER INFORMATION: Xaa is any amino acid, provided that at least
      one Xaa is Glu or Asp

<400> SEQUENCE: 78

```
Xaa Xaa Gly Phe Tyr Arg Asp
1               5
```

<210> SEQ ID NO 79
<211> LENGTH: 7
<212> TYPE: PRT
<213> ORGANISM: Ancyclostoma caninum
<220> FEATURE:
<221> NAME/KEY: MISC_FEATURE
<222> LOCATION: (1)
<223> OTHER INFORMATION: Xaa is any amino acid, provided that at least
      one Xaa is Glu or Asp
<220> FEATURE:
<221> NAME/KEY: MISC_FEATURE
<222> LOCATION: (2)
<223> OTHER INFORMATION: Xaa is any amino acid, provided that at least
      one Xaa is Glu or Asp

<400> SEQUENCE: 79

```
Xaa Xaa Gly Phe Tyr Arg Asn
1               5
```

<210> SEQ ID NO 80
<211> LENGTH: 7
<212> TYPE: PRT
<213> ORGANISM: Ancyclostoma caninum
<220> FEATURE:
<221> NAME/KEY: MISC_FEATURE
<222> LOCATION: (1)
<223> OTHER INFORMATION: Xaa is any amino acid, provided that at least
      one Xaa is Glu or Asp
<220> FEATURE:
<221> NAME/KEY: MISC_FEATURE
<222> LOCATION: (2)
<223> OTHER INFORMATION: Xaa is any amino acid, provided that at least
      one Xaa is Glu or Asp

<400> SEQUENCE: 80

```
Xaa Xaa Gly Tyr Tyr Arg Asp
1               5
```

<210> SEQ ID NO 81
<211> LENGTH: 7

```
<212> TYPE: PRT
<213> ORGANISM: Ancyclostoma caninum
<220> FEATURE:
<221> NAME/KEY: MISC_FEATURE
<222> LOCATION: (1)
<223> OTHER INFORMATION: Xaa is any amino acid, provided that at least
      one Xaa is Glu or Asp
<220> FEATURE:
<221> NAME/KEY: MISC_FEATURE
<222> LOCATION: (2)
<223> OTHER INFORMATION: Xaa is any amino acid, provided that at least
      one Xaa is Glu or Asp

<400> SEQUENCE: 81

Xaa Xaa Gly Tyr Tyr Arg Asn
1               5

<210> SEQ ID NO 82
<211> LENGTH: 7
<212> TYPE: PRT
<213> ORGANISM: Ancyclostoma caninum
<220> FEATURE:
<221> NAME/KEY: MISC_FEATURE
<222> LOCATION: (1)
<223> OTHER INFORMATION: Xaa is any amino acid, provided that at least
      one Xaa is Glu or Asp
<220> FEATURE:
<221> NAME/KEY: MISC_FEATURE
<222> LOCATION: (2)
<223> OTHER INFORMATION: Xaa any amino acid, provided that at least one
      Xaa is Glu or Asp

<400> SEQUENCE: 82

Xaa Xaa Gly Leu Tyr Arg Asp
1               5

<210> SEQ ID NO 83
<211> LENGTH: 9
<212> TYPE: PRT
<213> ORGANISM: Ancyclostoma caninum
<220> FEATURE:
<221> NAME/KEY: MISC_FEATURE
<222> LOCATION: (2)
<223> OTHER INFORMATION: Xaa is any amino acid
<220> FEATURE:
<221> NAME/KEY: MISC_FEATURE
<222> LOCATION: (3)
<223> OTHER INFORMATION: Xaa is any amino acid
<220> FEATURE:
<221> NAME/KEY: MISC_FEATURE
<222> LOCATION: (4)
<223> OTHER INFORMATION: Xaa is any amino acid
<220> FEATURE:
<221> NAME/KEY: MISC_FEATURE
<222> LOCATION: (5)
<223> OTHER INFORMATION: Xaa is any amino acid
<220> FEATURE:
<221> NAME/KEY: MISC_FEATURE
<222> LOCATION: (6)
<223> OTHER INFORMATION: Xaa is any amino acid
<220> FEATURE:
<221> NAME/KEY: MISC_FEATURE
<222> LOCATION: (7)
<223> OTHER INFORMATION: Xaa is any amino acid
<220> FEATURE:
<221> NAME/KEY: MISC_FEATURE
<222> LOCATION: (8)
<223> OTHER INFORMATION: Xaa is any amino acid
<220> FEATURE:
<221> NAME/KEY: MISC_FEATURE
<222> LOCATION: (9)
<223> OTHER INFORMATION: Xaa is any amino acid

<400> SEQUENCE: 83
```

```
Cys Xaa Xaa Xaa Xaa Xaa Xaa Xaa Xaa
1               5
```

<210> SEQ ID NO 84
<211> LENGTH: 4
<212> TYPE: PRT
<213> ORGANISM: Ancyclostoma caninum
<220> FEATURE:
<221> NAME/KEY: MISC_FEATURE
<222> LOCATION: (1)
<223> OTHER INFORMATION: Xaa is Leu
<220> FEATURE:
<221> NAME/KEY: MISC_FEATURE
<222> LOCATION: (2)
<223> OTHER INFORMATION: Xaa is any amino acid
<220> FEATURE:
<221> NAME/KEY: MISC_FEATURE
<222> LOCATION: (3)
<223> OTHER INFORMATION: Xaa is Arg
<220> FEATURE:
<221> NAME/KEY: MISC_FEATURE
<222> LOCATION: (4)
<223> OTHER INFORMATION: Xaa is any amino acid

<400> SEQUENCE: 84

```
Xaa Xaa Xaa Xaa
1
```

<210> SEQ ID NO 85
<211> LENGTH: 4
<212> TYPE: PRT
<213> ORGANISM: Ancyclostoma caninum
<220> FEATURE:
<221> NAME/KEY: MISC_FEATURE
<222> LOCATION: (1)
<223> OTHER INFORMATION: Xaa is any amino acid
<220> FEATURE:
<221> NAME/KEY: MISC_FEATURE
<222> LOCATION: (2)
<223> OTHER INFORMATION: Xaa is any amino acid
<220> FEATURE:
<221> NAME/KEY: MISC_FEATURE
<222> LOCATION: (2)
<223> OTHER INFORMATION: Xaa is any amino acid
<220> FEATURE:
<221> NAME/KEY: MISC_FEATURE
<222> LOCATION: (2)
<223> OTHER INFORMATION: Xaa is any amino acid

<400> SEQUENCE: 85

```
Xaa Xaa Xaa Xaa
1
```

<210> SEQ ID NO 86
<211> LENGTH: 9
<212> TYPE: PRT
<213> ORGANISM: Ancyclostoma caninum
<220> FEATURE:
<221> NAME/KEY: MISC_FEATURE
<222> LOCATION: (2)
<223> OTHER INFORMATION: Xaa is any amino acid
<220> FEATURE:
<221> NAME/KEY: MISC_FEATURE
<222> LOCATION: (3)
<223> OTHER INFORMATION: Xaa is any amino acid
<220> FEATURE:
<221> NAME/KEY: MISC_FEATURE
<222> LOCATION: (4)
<223> OTHER INFORMATION: Xaa is any amino acid
<220> FEATURE:
<221> NAME/KEY: MISC_FEATURE
<222> LOCATION: (5)
<223> OTHER INFORMATION: Xaa is any amino acid
<220> FEATURE:

```
<221> NAME/KEY: MISC_FEATURE
<222> LOCATION: (6)
<223> OTHER INFORMATION: Xaa is any amino acid
<220> FEATURE:
<221> NAME/KEY: MISC_FEATURE
<222> LOCATION: (7)
<223> OTHER INFORMATION: Xaa is any amino acid
<220> FEATURE:
<221> NAME/KEY: MISC_FEATURE
<222> LOCATION: (8)
<223> OTHER INFORMATION: Xaa is any amino acid
<220> FEATURE:
<221> NAME/KEY: MISC_FEATURE
<222> LOCATION: (9)
<223> OTHER INFORMATION: Xaa is any amino acid

<400> SEQUENCE: 86

Cys Xaa Xaa Xaa Xaa Xaa Xaa Xaa Xaa
  1               5

<210> SEQ ID NO 87
<211> LENGTH: 9
<212> TYPE: PRT
<213> ORGANISM: Ancyclostoma caninum
<220> FEATURE:
<221> NAME/KEY: MISC_FEATURE
<222> LOCATION: (2)
<223> OTHER INFORMATION: Xaa is any amino acid
<220> FEATURE:
<221> NAME/KEY: MISC_FEATURE
<222> LOCATION: (3)
<223> OTHER INFORMATION: Xaa is any amino acid
<220> FEATURE:
<221> NAME/KEY: MISC_FEATURE
<222> LOCATION: (4)
<223> OTHER INFORMATION: Xaa is any amino acid
<220> FEATURE:
<221> NAME/KEY: MISC_FEATURE
<222> LOCATION: (5)
<223> OTHER INFORMATION: Xaa is any amino acid
<220> FEATURE:
<221> NAME/KEY: MISC_FEATURE
<222> LOCATION: (6)
<223> OTHER INFORMATION: Xaa is any amino acid
<220> FEATURE:
<221> NAME/KEY: MISC_FEATURE
<222> LOCATION: (7)
<223> OTHER INFORMATION: Xaa is any amino acid
<220> FEATURE:
<221> NAME/KEY: MISC_FEATURE
<222> LOCATION: (8)
<223> OTHER INFORMATION: Xaa is any amino acid
<220> FEATURE:
<221> NAME/KEY: MISC_FEATURE
<222> LOCATION: (9)
<223> OTHER INFORMATION: Xaa is any amino acid

<400> SEQUENCE: 87

Cys Xaa Xaa Xaa Xaa Xaa Xaa Xaa Xaa
  1               5

<210> SEQ ID NO 88
<211> LENGTH: 25
<212> TYPE: DNA
<213> ORGANISM: Ancyclostoma caninum

<400> SEQUENCE: 88
tcagacatgt ataatctcat gttgg                                    25

<210> SEQ ID NO 89
<211> LENGTH: 22
<212> TYPE: DNA
<213> ORGANISM: Ancyclostoma caninum
```

```
<220> FEATURE:
<221> NAME/KEY: misc_feature
<223> OTHER INFORMATION: Oligonucleotide primer YG101

<400> SEQUENCE: 89
aaggcatacc cggagtgtgc tg                                        22

<210> SEQ ID NO 90
<211> LENGTH: 21
<212> TYPE: DNA
<213> ORGANISM: Ancyclostoma caninum
<220> FEATURE:
<221> NAME/KEY: Modified_base
<222> LOCATION: (3)
<223> OTHER INFORMATION: "r" stands for a or g
<220> FEATURE:
<221> NAME/KEY: Modified_base
<222> LOCATION: (6)
<223> OTHER INFORMATION: "n" stands for any base
<220> FEATURE:
<221> NAME/KEY: Modified_base
<222> LOCATION: (9)
<223> OTHER INFORMATION: "y" stands for c or t
<220> FEATURE:
<221> NAME/KEY: Modified_base
<222> LOCATION: (12)
<223> OTHER INFORMATION: "r" stands for a or g
<220> FEATURE:
<221> NAME/KEY: Modified_base
<222> LOCATION: (13)
<223> OTHER INFORMATION: "m" stands for a or c
<220> FEATURE:
<221> NAME/KEY: Modified_base
<222> LOCATION: (18)
<223> OTHER INFORMATION: "n" stands for any base
<220> FEATURE:
<221> NAME/KEY: Modified_base
<222> LOCATION: (21)
<223> OTHER INFORMATION: "y" stands for c or t

<400> SEQUENCE: 90
aarccntgyg armggaartg y                                         21

<210> SEQ ID NO 91
<211> LENGTH: 23
<212> TYPE: DNA
<213> ORGANISM: Ancyclostoma caninum
<220> FEATURE:
<221> NAME/KEY: Modified_base
<222> LOCATION: (2)
<223> OTHER INFORMATION: "w" stands for a or t
<220> FEATURE:
<221> NAME/KEY: Modified_base
<222> LOCATION: (3)
<223> OTHER INFORMATION: "r" stands for a or g
<220> FEATURE:
<221> NAME/KEY: Modified_base
<222> LOCATION: (4)
<223> OTHER INFORMATION: "w" stands for a or t
<220> FEATURE:
<221> NAME/KEY: Modified_base
<222> LOCATION: (6)
<223> OTHER INFORMATION: "n" stands for any base
<220> FEATURE:
<221> NAME/KEY: Modified_base
<222> LOCATION: (9)
<223> OTHER INFORMATION: "r" stands for a or g
<220> FEATURE:
<221> NAME/KEY: Modified_base
<222> LOCATION: (12)
<223> OTHER INFORMATION: "y" stands for c or t
<220> FEATURE:
<221> NAME/KEY: Modified_base
<222> LOCATION: (15)
<223> OTHER INFORMATION: "r" stands for a or g
```

```
<220> FEATURE:
<221> NAME/KEY: Modified_base
<222> LOCATION: (18)
<223> OTHER INFORMATION: "r" stands for a or g
<220> FEATURE:
<221> NAME/KEY: Modified_base
<222> LOCATION: (21)
<223> OTHER INFORMATION: "r" stands for a or g

<400> SEQUENCE: 91
twrwanccnt cyttrcanac rca                                               23

<210> SEQ ID NO 92
<211> LENGTH: 13
<212> TYPE: PRT
<213> ORGANISM: Ancyclostoma caninum

<400> SEQUENCE: 92

Lys Ala Tyr Pro Glu Cys Gly Glu Asn Glu Trp Leu Asp
 1               5                  10

<210> SEQ ID NO 93
<211> LENGTH: 11
<212> TYPE: PRT
<213> ORGANISM: Ancyclostoma caninum

<400> SEQUENCE: 93

Lys Ala Tyr Pro Glu Cys Gly Glu Asn Glu Trp
 1               5                  10

<210> SEQ ID NO 94
<211> LENGTH: 33
<212> TYPE: DNA
<213> ORGANISM: Ancyclostoma caninum
<220> FEATURE:
<221> NAME/KEY: Modified_base
<222> LOCATION: (3)
<223> OTHER INFORMATION: "r" stands for a or g
<220> FEATURE:
<221> NAME/KEY: Modified_base
<222> LOCATION: (6)
<223> OTHER INFORMATION: "n" stands for Inosine
<220> FEATURE:
<221> NAME/KEY: Modified_base
<222> LOCATION: (9)
<223> OTHER INFORMATION: "y" stands for c or t
<220> FEATURE:
<221> NAME/KEY: Modified_base
<222> LOCATION: (12)
<223> OTHER INFORMATION: "n" stands for Inosine
<220> FEATURE:
<221> NAME/KEY: Modified_base
<222> LOCATION: (15)
<223> OTHER INFORMATION: "r" stands for a or g
<220> FEATURE:
<221> NAME/KEY: Modified_base
<222> LOCATION: (18)
<223> OTHER INFORMATION: "y" stands for c or t
<220> FEATURE:
<221> NAME/KEY: Modified_base
<222> LOCATION: (21)
<223> OTHER INFORMATION: "r" stands for a or g
<220> FEATURE:
<221> NAME/KEY: Modified_base
<222> LOCATION: (24)
<223> OTHER INFORMATION: "r" stands for a or g
<220> FEATURE:
<221> NAME/KEY: Modified_base
<222> LOCATION: (27)
<223> OTHER INFORMATION: "y" stands for c or t
<220> FEATURE:
<221> NAME/KEY: Modified_base
<222> LOCATION: (30)
```

<223> OTHER INFORMATION: "r" stands for a or g

<400> SEQUENCE: 94
aargcntayc cngartgygg ngaraaygar tgg                33

<210> SEQ ID NO 95
<211> LENGTH: 28
<212> TYPE: DNA
<213> ORGANISM: Ancyclostoma caninum
<220> FEATURE:
<221> NAME/KEY: misc_feature
<223> OTHER INFORMATION: Oligonucleotide primer

<400> SEQUENCE: 95
aattcgcggc cgcttttttt tttttttt                28

<210> SEQ ID NO 96
<211> LENGTH: 24
<212> TYPE: DNA
<213> ORGANISM: Ancyclostoma caninum

<400> SEQUENCE: 96
ggtggcgacg actcctggag cccg                24

<210> SEQ ID NO 97
<211> LENGTH: 20
<212> TYPE: PRT
<213> ORGANISM: Ancyclostoma caninum

<400> SEQUENCE: 97

Cys Ala Tyr Pro Glu Cys Gly Glu Asn Glu Trp Leu Asp Asp Cys Gly Thr
1               5                   10                  15

Gln Lys Pro
        20

<210> SEQ ID NO 98
<211> LENGTH: 10
<212> TYPE: DNA
<213> ORGANISM: Ancyclostoma caninum

<400> SEQUENCE: 98
cggaattccg                10

<210> SEQ ID NO 99
<211> LENGTH: 18
<212> TYPE: DNA
<213> ORGANISM: Ancyclostoma caninum

<400> SEQUENCE: 99
tggcctagcg tcaggagt                18

<210> SEQ ID NO 100
<211> LENGTH: 18
<212> TYPE: DNA
<213> ORGANISM: Ancyclostoma caninum

<400> SEQUENCE: 100
cctgacgcta ggccatgg                18

<210> SEQ ID NO 101
<211> LENGTH: 24
<212> TYPE: DNA
<213> ORGANISM: Ancyclostoma caninum

```
<400> SEQUENCE: 101
agcggataac aatttcacac agga                                        24

<210> SEQ ID NO 102
<211> LENGTH: 66
<212> TYPE: DNA
<213> ORGANISM: Ancyclostoma caninum

<400> SEQUENCE: 102
atgttctctc caattttgtc cttggaaatt attttagctt tggctacttt gcaatctgtc  60
ttcgct                                                            66

<210> SEQ ID NO 103
<211> LENGTH: 57
<212> TYPE: DNA
<213> ORGANISM: Ancyclostoma caninum

<400> SEQUENCE: 103
cagccaggta tctccactac cgttggttcc gctgccgagg gttctttgga caagagg     57

<210> SEQ ID NO 104
<211> LENGTH: 51
<212> TYPE: DNA
<213> ORGANISM: Ancyclostoma caninum

<400> SEQUENCE: 104
cctatccgcg gaattcagat ctgaatgcgg ccgctcgaga ctagtggatc c           51

<210> SEQ ID NO 105
<211> LENGTH: 41
<212> TYPE: DNA
<213> ORGANISM: Ancyclostoma caninum
<220> FEATURE:
<221> NAME/KEY: misc_feature
<223> OTHER INFORMATION: Oligonucleotide primer YG103

<400> SEQUENCE: 105
gctcgctcta gaagcttcag acatgtataa tctcatgttg g                     41

<210> SEQ ID NO 106
<211> LENGTH: 5
<212> TYPE: PRT
<213> ORGANISM: Ancyclostoma caninum

<400> SEQUENCE: 106

Lys Ala Tyr Pro Glu
1               5

<210> SEQ ID NO 107
<211> LENGTH: 36
<212> TYPE: DNA
<213> ORGANISM: Ancyclostoma caninum
<220> FEATURE:
<221> NAME/KEY: misc_feature
<223> OTHER INFORMATION: Oligonucleotide primer YG102

<400> SEQUENCE: 107
gaccagtcta gacaatgaag atgctttacg ctatcg                           36

<210> SEQ ID NO 108
<211> LENGTH: 23
<212> TYPE: DNA
<213> ORGANISM: Ancyclostoma caninum
```

```
<400> SEQUENCE: 108
gtgggagacc tgatactctc aag                                               23

<210> SEQ ID NO 109
<211> LENGTH: 9
<212> TYPE: PRT
<213> ORGANISM: Ancyclostoma caninum

<400> SEQUENCE: 109

Arg Thr Val Arg Lys Ala Tyr Pro Glu
1               5

<210> SEQ ID NO 110
<211> LENGTH: 5
<212> TYPE: PRT
<213> ORGANISM: Ancyclostoma caninum

<400> SEQUENCE: 110

Arg Thr Val Arg Lys
1               5

<210> SEQ ID NO 111
<211> LENGTH: 33
<212> TYPE: DNA
<213> ORGANISM: Artificial Sequence
<220> FEATURE:
<221> NAME/KEY: misc_feature
<223> OTHER INFORMATION: Description of Artificial Sequence: pDONG
      vector amplified PCR primer fragment

<400> SEQUENCE: 111
atccgaagct ttgctaacat actgcgtaat aag                                    33

<210> SEQ ID NO 112
<211> LENGTH: 60
<212> TYPE: DNA
<213> ORGANISM: Artificial Sequence
<220> FEATURE:
<221> NAME/KEY: misc_feature
<223> OTHER INFORMATION: Description of Artificial Sequence: pDONG
      vector amplified PCR primer fragment

<400> SEQUENCE: 112
tatgggatgg ccgacttggc ctccgcctga gcctccacct ttatcccaat ccaaataaga       60

<210> SEQ ID NO 113
<211> LENGTH: 60
<212> TYPE: DNA
<213> ORGANISM: Artificial Sequence
<220> FEATURE:
<221> NAME/KEY: misc_feature
<223> OTHER INFORMATION: Description of Artificial Sequence: pDONG
      vector amplified PCR primer fragment

<400> SEQUENCE: 113
atgggatggc cgacttggcc tccgcctga gcctccacct ttatcccaat ccaaataaga        60

<210> SEQ ID NO 114
<211> LENGTH: 60
<212> TYPE: DNA
<213> ORGANISM: Artificial Sequence
<220> FEATURE:
<221> NAME/KEY: misc_feature
<223> OTHER INFORMATION: Description of Artificial Sequence: pDONG
      vector amplified PCR primer fragment

<400> SEQUENCE: 114
```

-continued

```
tatgggatgg ccgacttggc cgatccgcct gagcctccac ctttatccca atccaaataa      60
```

<210> SEQ ID NO 115
<211> LENGTH: 45
<212> TYPE: DNA
<213> ORGANISM: Artificial Sequence
<220> FEATURE:
<221> NAME/KEY: misc_feature
<223> OTHER INFORMATION: Description of Artificial Sequence: pDONG
    vector amplified PCR primer fragment

<400> SEQUENCE: 115

```
aggaggggat ccgcggccgc gtgatatggg atggccgact tggcc                     45
```

<210> SEQ ID NO 116
<211> LENGTH: 24
<212> TYPE: DNA
<213> ORGANISM: Artificial Sequence
<220> FEATURE:
<221> NAME/KEY: misc_feature
<223> OTHER INFORMATION: Description of Artificial Sequence: pUC119
    primer

<400> SEQUENCE: 116

```
cgccagggtt ttcccagtca cgac                                            24
```

<210> SEQ ID NO 117
<211> LENGTH: 28
<212> TYPE: DNA
<213> ORGANISM: Ancyclostoma caninum

<400> SEQUENCE: 117

```
gtttcgagtt ccgggatata taaagtcc                                        28
```

<210> SEQ ID NO 118
<211> LENGTH: 7
<212> TYPE: PRT
<213> ORGANISM: Necator americanus
<220> FEATURE:
<221> NAME/KEY: MISC_FEATURE
<222> LOCATION: (5)
<223> OTHER INFORMATION: Xaa is Arg, Pro or Lys

<400> SEQUENCE: 118

```
Lys Pro Cys Glu Xaa Lys Cys
1               5
```

<210> SEQ ID NO 119
<211> LENGTH: 8
<212> TYPE: PRT
<213> ORGANISM: Necator americanus
<220> FEATURE:
<221> NAME/KEY: MISC_FEATURE
<222> LOCATION: (2)
<223> OTHER INFORMATION: Xaa is Val,Ile or Gln
<220> FEATURE:
<221> NAME/KEY: MISC_FEATURE
<222> LOCATION: (4)
<223> OTHER INFORMATION: Xaa is Lys,Asp,Glu or Gln
<220> FEATURE:
<221> NAME/KEY: MISC_FEATURE
<222> LOCATION: (5)
<223> OTHER INFORMATION: Xaa is Asp or Glu
<220> FEATURE:
<221> NAME/KEY: MISC_FEATURE
<222> LOCATION: (7)
<223> OTHER INFORMATION: Xaa is Phe or Tyr

<400> SEQUENCE: 119

Cys Xaa Cys Xaa Xaa Gly Xaa Tyr
1               5

<210> SEQ ID NO 120
<211> LENGTH: 44
<212> TYPE: DNA
<213> ORGANISM: Ancyclostoma caninum
<220> FEATURE:
<221> NAME/KEY: misc_feature
<223> OTHER INFORMATION: Oligonucleotide primer

<400> SEQUENCE: 120
gaccagtcta gaccaccatg gcggtgcttt attcagtagc aata					44

<210> SEQ ID NO 121
<211> LENGTH: 40
<212> TYPE: DNA
<213> ORGANISM: Ancyclostoma caninum
<220> FEATURE:
<221> NAME/KEY: misc_feature
<223> OTHER INFORMATION: Oligonucleotide primer

<400> SEQUENCE: 121
gctcgctcta gattatcgtg aggtttctgg tgcaaaagtg						40

<210> SEQ ID NO 122
<211> LENGTH: 24
<212> TYPE: DNA
<213> ORGANISM: Ancyclostoma caninum
<220> FEATURE:
<221> NAME/KEY: misc_feature
<223> OTHER INFORMATION: Oligonucleotide primer

<400> SEQUENCE: 122
aaagcaacga tgcagtgtgg tgag								24

<210> SEQ ID NO 123
<211> LENGTH: 47
<212> TYPE: DNA
<213> ORGANISM: Ancyclostoma caninum
<220> FEATURE:
<221> NAME/KEY: misc_feature
<223> OTHER INFORMATION: Oligonucleotide primer

<400> SEQUENCE: 123
gctcgctcta gaagcttcag tttcgagttc cgggatatat aaagtcc				47

<210> SEQ ID NO 124
<211> LENGTH: 30
<212> TYPE: DNA
<213> ORGANISM: Ancyclostoma caninum
<220> FEATURE:
<221> NAME/KEY: misc_feature
<223> OTHER INFORMATION: Oligonucleotide primer

<400> SEQUENCE: 124
gagactttta aatcactgtc ggatcagaag							30

<210> SEQ ID NO 125
<211> LENGTH: 33
<212> TYPE: DNA
<213> ORGANISM: Ancyclostoma caninum
<220> FEATURE:
<221> NAME/KEY: misc_feature
<223> OTHER INFORMATION: Oligonucleotide primer

<400> SEQUENCE: 125

```
ttcaggacta gttcatggtg cgaaagtaat aaa                                33
```

<210> SEQ ID NO 126
<211> LENGTH: 28
<212> TYPE: DNA
<213> ORGANISM: Ancyclostoma caninum
<220> FEATURE:
<221> NAME/KEY: misc_feature
<223> OTHER INFORMATION: Oligonucleotide primer

<400> SEQUENCE: 126

```
gcgtttaaag caacgatgca gtgtggtg                                     28
```

<210> SEQ ID NO 127
<211> LENGTH: 46
<212> TYPE: DNA
<213> ORGANISM: Ancyclostoma caninum
<220> FEATURE:
<221> NAME/KEY: misc_feature
<223> OTHER INFORMATION: Oligonucleotide primer

<400> SEQUENCE: 127

```
cgctctagaa gcttcatggg tttcgagttc cgggatatat aaagtc                 46
```

<210> SEQ ID NO 128
<211> LENGTH: 91
<212> TYPE: PRT
<213> ORGANISM: Ancyclostoma caninum

<400> SEQUENCE: 128

Leu Val Ser Tyr Cys Ser Gly Lys Ala Thr Met Gln Cys Gly Glu Asn
 1               5                  10                  15

Glu Lys Tyr Asp Ser Cys Gly Ser Lys Glu Cys Asp Lys Lys Cys Lys
                20                  25                  30

Tyr Asp Gly Val Glu Glu Glu Asp Asp Glu Glu Pro Asn Val Pro Cys
            35                  40                  45

Leu Val Arg Val Cys His Gln Asp Cys Val Cys Glu Glu Gly Phe Tyr
        50                  55                  60

Arg Asn Lys Asp Asp Lys Cys Val Ser Ala Glu Asp Cys Glu Leu Asp
65                  70                  75                  80

Asn Met Asp Phe Ile Tyr Pro Gly Thr Arg Asn
                85                  90

<210> SEQ ID NO 129
<211> LENGTH: 8
<212> TYPE: PRT
<213> ORGANISM: Ancyclostoma caninum
<220> FEATURE:
<221> NAME/KEY: MISC_FEATURE
<222> LOCATION: (2)..(8)
<223> OTHER INFORMATION: Xaa is any amino acid

<400> SEQUENCE: 129

Cys Xaa Xaa Xaa Xaa Xaa Xaa Xaa
 1               5

<210> SEQ ID NO 130
<211> LENGTH: 7
<212> TYPE: PRT
<213> ORGANISM: Ancyclostoma caninum
<220> FEATURE:
<221> NAME/KEY: MISC_FEATURE
<222> LOCATION: (2)..(6)
<223> OTHER INFORMATION: Xaa is any amino acid

```
<400> SEQUENCE: 130

Cys Xaa Xaa Xaa Xaa Xaa Cys
1               5

<210> SEQ ID NO 131
<211> LENGTH: 6
<212> TYPE: PRT
<213> ORGANISM: Ancyclostoma caninum
<220> FEATURE:
<221> NAME/KEY: MISC_FEATURE
<222> LOCATION: (2)..(5)
<223> OTHER INFORMATION: Xaa is any amino acid

<400> SEQUENCE: 131

Cys Xaa Xaa Xaa Xaa Cys
1               5

<210> SEQ ID NO 132
<211> LENGTH: 5
<212> TYPE: PRT
<213> ORGANISM: Ancyclostoma caninum
<220> FEATURE:
<221> NAME/KEY: MISC_FEATURE
<222> LOCATION: (2)..(4)
<223> OTHER INFORMATION: Xaa is any amino acid

<400> SEQUENCE: 132

Cys Xaa Xaa Xaa Cys
1               5

<210> SEQ ID NO 133
<211> LENGTH: 4
<212> TYPE: PRT
<213> ORGANISM: Ancyclostoma caninum
<220> FEATURE:
<221> NAME/KEY: MISC_FEATURE
<222> LOCATION: (2)..(3)
<223> OTHER INFORMATION: Xaa is any amino acid

<400> SEQUENCE: 133

Cys Xaa Xaa Cys
1

<210> SEQ ID NO 134
<211> LENGTH: 21
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(21)
<223> OTHER INFORMATION: Xaa is any amino acid

<400> SEQUENCE: 134

Xaa Xaa Xaa Cys Xaa Xaa Xaa Xaa Xaa Xaa Xaa Xaa Xaa Xaa Xaa Xaa
1               5                   10                  15

Xaa Xaa Xaa Xaa Xaa
            20

<210> SEQ ID NO 135
<211> LENGTH: 20
<212> TYPE: PRT
<213> ORGANISM: Ancyclostoma caninum
<220> FEATURE:
```

```
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(20)
<223> OTHER INFORMATION: Xaa is any amino acid

<400> SEQUENCE: 135

Xaa Xaa Xaa Cys Xaa Xaa Xaa Xaa Xaa Xaa Xaa Xaa Xaa Xaa Xaa Xaa
1               5                   10                  15

Xaa Xaa Xaa Xaa
            20

<210> SEQ ID NO 136
<211> LENGTH: 19
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(19)
<223> OTHER INFORMATION: Xaa is any amino acid

<400> SEQUENCE: 136

Xaa Xaa Xaa Cys Xaa Xaa Xaa Xaa Xaa Xaa Xaa Xaa Xaa Xaa Xaa Xaa
1               5                   10                  15

Xaa Xaa Xaa

<210> SEQ ID NO 137
<211> LENGTH: 18
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(18)
<223> OTHER INFORMATION: Xaa is any amino acid

<400> SEQUENCE: 137

Xaa Xaa Xaa Cys Xaa Xaa Xaa Xaa Xaa Xaa Xaa Xaa Xaa Xaa Xaa Xaa
1               5                   10                  15

Xaa Xaa

<210> SEQ ID NO 138
<211> LENGTH: 17
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(17)
<223> OTHER INFORMATION: Xaa is any amino acid

<400> SEQUENCE: 138

Xaa Xaa Xaa Cys Xaa Xaa Xaa Xaa Xaa Xaa Xaa Xaa Xaa Xaa Xaa Xaa
1               5                   10                  15

Xaa
```

```
<210> SEQ ID NO 139
<211> LENGTH: 16
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(16)
<223> OTHER INFORMATION: Xaa is any amino acid

<400> SEQUENCE: 139

Xaa Xaa Xaa Cys Xaa Xaa Xaa Xaa Xaa Xaa Xaa Xaa Xaa Xaa Xaa Xaa
 1               5                  10                  15

<210> SEQ ID NO 140
<211> LENGTH: 15
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(15)
<223> OTHER INFORMATION: Xaa is any amino acid

<400> SEQUENCE: 140

Xaa Xaa Xaa Cys Xaa Xaa Xaa Xaa Xaa Xaa Xaa Xaa Xaa Xaa Xaa
 1               5                  10                  15

<210> SEQ ID NO 141
<211> LENGTH: 14
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(14)
<223> OTHER INFORMATION: Xaa is any amino acid

<400> SEQUENCE: 141

Xaa Xaa Xaa Cys Xaa Xaa Xaa Xaa Xaa Xaa Xaa Xaa Xaa Xaa
 1               5                  10

<210> SEQ ID NO 142
<211> LENGTH: 13
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(13)
<223> OTHER INFORMATION: Xaa is any amino aicd

<400> SEQUENCE: 142

Xaa Xaa Xaa Cys Xaa Xaa Xaa Xaa Xaa Xaa Xaa Xaa Xaa
 1               5                  10

<210> SEQ ID NO 143
<211> LENGTH: 12
```

```
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(12)
<223> OTHER INFORMATION: Xaa ia any amino aicd

<400> SEQUENCE: 143

Xaa Xaa Xaa Cys Xaa Xaa Xaa Xaa Xaa Xaa Xaa Xaa
 1               5                  10

<210> SEQ ID NO 144
<211> LENGTH: 11
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(11)
<223> OTHER INFORMATION: Xaa is any amino acid

<400> SEQUENCE: 144

Xaa Xaa Xaa Cys Xaa Xaa Xaa Xaa Xaa Xaa Xaa
 1               5                  10

<210> SEQ ID NO 145
<211> LENGTH: 10
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(10)
<223> OTHER INFORMATION: Xaa is any amino acid

<400> SEQUENCE: 145

Xaa Xaa Xaa Cys Xaa Xaa Xaa Xaa Xaa Xaa
 1               5                  10

<210> SEQ ID NO 146
<211> LENGTH: 5
<212> TYPE: PRT
<213> ORGANISM: Ancyclostoma caninum
<220> FEATURE:
<221> NAME/KEY: MISC_FEATURE
<222> LOCATION: (2)..(5)
<223> OTHER INFORMATION: Xaa is any amino acid

<400> SEQUENCE: 146

Cys Xaa Xaa Xaa Xaa
 1               5

<210> SEQ ID NO 147
<211> LENGTH: 4
<212> TYPE: PRT
<213> ORGANISM: Ancyclostoma caninum
<220> FEATURE:
<221> NAME/KEY: MISC_FEATURE
<222> LOCATION: (2)..(4)
<223> OTHER INFORMATION: Xaa is any amino acid
```

-continued

```
<400> SEQUENCE: 147

Cys Xaa Xaa Xaa
1

<210> SEQ ID NO 148
<211> LENGTH: 6
<212> TYPE: PRT
<213> ORGANISM: Ancyclostoma caninum
<220> FEATURE:
<221> NAME/KEY: MISC_FEATURE
<222> LOCATION: (2)..(6)
<223> OTHER INFORMATION: Xaa is any amino acid

<400> SEQUENCE: 148

Cys Xaa Xaa Xaa Xaa Xaa
1               5

<210> SEQ ID NO 149
<211> LENGTH: 5
<212> TYPE: PRT
<213> ORGANISM: Ancyclostoma caninum
<220> FEATURE:
<221> NAME/KEY: MISC_FEATURE
<222> LOCATION: (2)..(5)
<223> OTHER INFORMATION: Xaa is any amino acid

<400> SEQUENCE: 149

Cys Xaa Xaa Xaa Xaa
1               5

<210> SEQ ID NO 150
<211> LENGTH: 4
<212> TYPE: PRT
<213> ORGANISM: Ancyclostoma caninum
<220> FEATURE:
<221> NAME/KEY: MISC_FEATURE
<222> LOCATION: (2)..(4)
<223> OTHER INFORMATION: Xaa is any amino acid

<400> SEQUENCE: 150

Cys Xaa Xaa Xaa
1

<210> SEQ ID NO 151
<211> LENGTH: 15
<212> TYPE: PRT
<213> ORGANISM: Ancyclostoma caninum
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (4)..(15)
<223> OTHER INFORMATION: Xaa is any amino acid

<400> SEQUENCE: 151

Cys Xaa Cys Xaa Xaa Xaa Xaa Xaa Xaa Xaa Xaa Xaa Xaa Xaa Xaa
1               5                   10                  15

<210> SEQ ID NO 152
<211> LENGTH: 14
<212> TYPE: PRT
<213> ORGANISM: Ancyclostoma caninum
<220> FEATURE:
<221> NAME/KEY: MISC_FEATURE
<222> LOCATION: (2)..(2)
<223> OTHER INFORMATION: Xaa is any amino acid
<220> FEATURE:
```

```
<221> NAME/KEY: MISC_FEATURE
<222> LOCATION: (4)..(14)
<223> OTHER INFORMATION: Xaa is any amino acid

<400> SEQUENCE: 152

Cys Xaa Cys Xaa Xaa Xaa Xaa Xaa Xaa Xaa Xaa Xaa Xaa
1               5                   10

<210> SEQ ID NO 153
<211> LENGTH: 13
<212> TYPE: PRT
<213> ORGANISM: Ancyclostoma caninum
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (4)..(13)
<223> OTHER INFORMATION: Xaa is any amino acid

<400> SEQUENCE: 153

Cys Xaa Cys Xaa Xaa Xaa Xaa Xaa Xaa Xaa Xaa Xaa Xaa
1               5                   10

<210> SEQ ID NO 154
<211> LENGTH: 8
<212> TYPE: PRT
<213> ORGANISM: Ancyclostoma caninum
<220> FEATURE:
<221> NAME/KEY: MISC_FEATURE
<222> LOCATION: (2)..(7)
<223> OTHER INFORMATION: Xaa is any amino acid

<400> SEQUENCE: 154

Cys Xaa Xaa Xaa Xaa Xaa Xaa Cys
1               5

<210> SEQ ID NO 155
<211> LENGTH: 7
<212> TYPE: PRT
<213> ORGANISM: Ancyclostoma caninum
<220> FEATURE:
<221> NAME/KEY: MISC_FEATURE
<222> LOCATION: (2)..(6)
<223> OTHER INFORMATION: Xaa is any amino acid

<400> SEQUENCE: 155

Cys Xaa Xaa Xaa Xaa Xaa Cys
1               5

<210> SEQ ID NO 156
<211> LENGTH: 8
<212> TYPE: PRT
<213> ORGANISM: Ancyclostoma caninum
<220> FEATURE:
<221> NAME/KEY: MISC_FEATURE
<222> LOCATION: (2)..(8)
<223> OTHER INFORMATION: Xaa is any amino acid

<400> SEQUENCE: 156

Cys Xaa Xaa Xaa Xaa Xaa Xaa Xaa
1               5

<210> SEQ ID NO 157
<211> LENGTH: 7
<212> TYPE: PRT
<213> ORGANISM: Ancyclostoma caninum
<220> FEATURE:
```

-continued

<221> NAME/KEY: MISC_FEATURE
<222> LOCATION: (2)..(6)
<223> OTHER INFORMATION: Xaa is any amino acid

<400> SEQUENCE: 157

Cys Xaa Xaa Xaa Xaa Xaa Cys
1               5

<210> SEQ ID NO 158
<211> LENGTH: 6
<212> TYPE: PRT
<213> ORGANISM: Ancyclostoma caninum
<220> FEATURE:
<221> NAME/KEY: MISC_FEATURE
<222> LOCATION: (2)..(5)
<223> OTHER INFORMATION: Xaa is any amino acid

<400> SEQUENCE: 158

Cys Xaa Xaa Xaa Xaa Cys
1               5

<210> SEQ ID NO 159
<211> LENGTH: 5
<212> TYPE: PRT
<213> ORGANISM: Ancyclostoma caninum
<220> FEATURE:
<221> NAME/KEY: MISC_FEATURE
<222> LOCATION: (2)..(4)
<223> OTHER INFORMATION: Xaa is any amino acid

<400> SEQUENCE: 159

Cys Xaa Xaa Xaa Cys
1               5

<210> SEQ ID NO 160
<211> LENGTH: 23
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(23)
<223> OTHER INFORMATION: Xaa is any amino acid

<400> SEQUENCE: 160

Xaa Xaa Xaa Cys Xaa Xaa Xaa Xaa Xaa Xaa Xaa Xaa Xaa Xaa Xaa Xaa
1               5                   10                  15

Xaa Xaa Xaa Xaa Xaa Xaa Xaa
            20

<210> SEQ ID NO 161
<211> LENGTH: 22
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(22)
<223> OTHER INFORMATION: Xaa is any amino acid

<400> SEQUENCE: 161

Xaa Xaa Xaa Cys Xaa Xaa Xaa Xaa Xaa Xaa Xaa Xaa Xaa Xaa Xaa Xaa
1               5                   10                  15

```
Xaa Xaa Xaa Xaa Xaa Xaa
        20

<210> SEQ ID NO 162
<211> LENGTH: 21
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(21)
<223> OTHER INFORMATION: Xaa is any amino acid

<400> SEQUENCE: 162

Xaa Xaa Xaa Cys Xaa Xaa Xaa Xaa Xaa Xaa Xaa Xaa Xaa Xaa Xaa
1               5                   10                  15

Xaa Xaa Xaa Xaa Xaa Xaa
        20

<210> SEQ ID NO 163
<211> LENGTH: 20
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(20)
<223> OTHER INFORMATION: Xaa is any amino acid

<400> SEQUENCE: 163

Xaa Xaa Xaa Cys Xaa Xaa Xaa Xaa Xaa Xaa Xaa Xaa Xaa Xaa Xaa
1               5                   10                  15

Xaa Xaa Xaa Xaa
        20

<210> SEQ ID NO 164
<211> LENGTH: 19
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(19)
<223> OTHER INFORMATION: Xaa is any amino acid

<400> SEQUENCE: 164

Xaa Xaa Xaa Cys Xaa Xaa Xaa Xaa Xaa Xaa Xaa Xaa Xaa Xaa Xaa
1               5                   10                  15

Xaa Xaa Xaa

<210> SEQ ID NO 165
<211> LENGTH: 18
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
```

```
<221> NAME/KEY: MISC_FEATURE
<222> LOCATION: (5)..(18)
<223> OTHER INFORMATION: Xaa is any amino acid

<400> SEQUENCE: 165

Xaa Xaa Xaa Cys Xaa Xaa Xaa Xaa Xaa Xaa Xaa Xaa Xaa Xaa Xaa
1               5                   10                  15

Xaa Xaa

<210> SEQ ID NO 166
<211> LENGTH: 17
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(17)
<223> OTHER INFORMATION: Xaa is any amino acid

<400> SEQUENCE: 166

Xaa Xaa Xaa Cys Xaa Xaa Xaa Xaa Xaa Xaa Xaa Xaa Xaa Xaa Xaa
1               5                   10                  15

Xaa

<210> SEQ ID NO 167
<211> LENGTH: 16
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(16)
<223> OTHER INFORMATION: Xaa is any amino acid

<400> SEQUENCE: 167

Xaa Xaa Xaa Cys Xaa Xaa Xaa Xaa Xaa Xaa Xaa Xaa Xaa Xaa Xaa
1               5                   10                  15

<210> SEQ ID NO 168
<211> LENGTH: 15
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(15)
<223> OTHER INFORMATION: Xaa is any amino acid

<400> SEQUENCE: 168

Xaa Xaa Xaa Cys Xaa Xaa Xaa Xaa Xaa Xaa Xaa Xaa Xaa Xaa
1               5                   10                  15

<210> SEQ ID NO 169
<211> LENGTH: 14
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
```

```
<220> FEATURE:
<221> NAME/KEY: MISC_FEATURE
<222> LOCATION: (5)..(14)
<223> OTHER INFORMATION: Xaa is any amino aicd

<400> SEQUENCE: 169

Xaa Xaa Xaa Cys Xaa Xaa Xaa Xaa Xaa Xaa Xaa Xaa Xaa Xaa
1               5                   10

<210> SEQ ID NO 170
<211> LENGTH: 13
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(13)
<223> OTHER INFORMATION: Xaa is any amino acid

<400> SEQUENCE: 170

Xaa Xaa Xaa Cys Xaa Xaa Xaa Xaa Xaa Xaa Xaa Xaa Xaa
1               5                   10

<210> SEQ ID NO 171
<211> LENGTH: 12
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(12)
<223> OTHER INFORMATION: Xaa is any amino acid

<400> SEQUENCE: 171

Xaa Xaa Xaa Cys Xaa Xaa Xaa Xaa Xaa Xaa Xaa Xaa
1               5                   10

<210> SEQ ID NO 172
<211> LENGTH: 11
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(11)
<223> OTHER INFORMATION: Xaa is any amino acid

<400> SEQUENCE: 172

Xaa Xaa Xaa Cys Xaa Xaa Xaa Xaa Xaa Xaa Xaa
1               5                   10

<210> SEQ ID NO 173
<211> LENGTH: 10
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(10)
```

<223> OTHER INFORMATION: Xaa is any amino acid

<400> SEQUENCE: 173

Xaa Xaa Xaa Cys Xaa Xaa Xaa Xaa Xaa Xaa
1               5                   10

<210> SEQ ID NO 174
<211> LENGTH: 5
<212> TYPE: PRT
<213> ORGANISM: Ancyclostoma caninum
<220> FEATURE:
<221> NAME/KEY: MISC_FEATURE
<222> LOCATION: (2)..(5)
<223> OTHER INFORMATION: Xaa is any amino acid

<400> SEQUENCE: 174

Cys Xaa Xaa Xaa Xaa
1               5

<210> SEQ ID NO 175
<211> LENGTH: 4
<212> TYPE: PRT
<213> ORGANISM: Ancyclostoma caninum
<220> FEATURE:
<221> NAME/KEY: MISC_FEATURE
<222> LOCATION: (2)..(4)
<223> OTHER INFORMATION: Xaa is any amino acid

<400> SEQUENCE: 175

Cys Xaa Xaa Xaa
1

<210> SEQ ID NO 176
<211> LENGTH: 6
<212> TYPE: PRT
<213> ORGANISM: Ancyclostoma caninum
<220> FEATURE:
<221> NAME/KEY: MISC_FEATURE
<222> LOCATION: (2)..(6)
<223> OTHER INFORMATION: Xaa is any amino acid

<400> SEQUENCE: 176

Cys Xaa Xaa Xaa Xaa Xaa
1               5

<210> SEQ ID NO 177
<211> LENGTH: 5
<212> TYPE: PRT
<213> ORGANISM: Ancyclostoma caninum
<220> FEATURE:
<221> NAME/KEY: MISC_FEATURE
<222> LOCATION: (2)..(5)
<223> OTHER INFORMATION: Xaa is any amino acid

<400> SEQUENCE: 177

Cys Xaa Xaa Xaa Xaa
1               5

<210> SEQ ID NO 178
<211> LENGTH: 4
<212> TYPE: PRT
<213> ORGANISM: Ancyclostoma caninum
<220> FEATURE:
<221> NAME/KEY: MISC_FEATURE
<222> LOCATION: (2)..(4)
<223> OTHER INFORMATION: Xaa is any amino acid

<400> SEQUENCE: 178

-continued

```
Cys Xaa Xaa Xaa
1

<210> SEQ ID NO 179
<211> LENGTH: 15
<212> TYPE: PRT
<213> ORGANISM: Ancyclostoma caninum
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (4)..(15)
<223> OTHER INFORMATION: Xaa is any amino acid

<400> SEQUENCE: 179

Cys Xaa Cys Xaa Xaa Xaa Xaa Xaa Xaa Xaa Xaa Xaa Xaa Xaa Xaa
1               5                   10                  15

<210> SEQ ID NO 180
<211> LENGTH: 14
<212> TYPE: PRT
<213> ORGANISM: Ancyclostoma caninum
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (4)..(14)
<223> OTHER INFORMATION: Xaa is any amino acid

<400> SEQUENCE: 180

Cys Xaa Cys Xaa Xaa Xaa Xaa Xaa Xaa Xaa Xaa Xaa Xaa Xaa
1               5                   10

<210> SEQ ID NO 181
<211> LENGTH: 8
<212> TYPE: PRT
<213> ORGANISM: Ancyclostoma caninum
<220> FEATURE:
<221> NAME/KEY: MISC_FEATURE
<222> LOCATION: (2)..(8)
<223> OTHER INFORMATION: Xaa is any amino acid

<400> SEQUENCE: 181

Cys Xaa Xaa Xaa Xaa Xaa Xaa Xaa
1               5

<210> SEQ ID NO 182
<211> LENGTH: 7
<212> TYPE: PRT
<213> ORGANISM: Ancyclostoma caninum
<220> FEATURE:
<221> NAME/KEY: MISC_FEATURE
<222> LOCATION: (2)..(7)
<223> OTHER INFORMATION: Xaa is any amino acid

<400> SEQUENCE: 182

Cys Xaa Xaa Xaa Xaa Xaa Xaa
1               5

<210> SEQ ID NO 183
<211> LENGTH: 6
<212> TYPE: PRT
<213> ORGANISM: Ancyclostoma caninum
<220> FEATURE:
<221> NAME/KEY: MISC_FEATURE
<222> LOCATION: (2)..(6)
```

<223> OTHER INFORMATION: Xaa is any amino acid

<400> SEQUENCE: 183

Cys Xaa Xaa Xaa Xaa Xaa
1               5

<210> SEQ ID NO 184
<211> LENGTH: 26
<212> TYPE: PRT
<213> ORGANISM: Ancyclostoma caninum
<220> FEATURE:
<221> NAME/KEY: MISC_FEATURE
<222> LOCATION: (2)..(26)
<223> OTHER INFORMATION: Xaa is any amino acid

<400> SEQUENCE: 184

Cys Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa
            20                  25

<210> SEQ ID NO 185
<211> LENGTH: 25
<212> TYPE: PRT
<213> ORGANISM: Ancyclostoma caninum
<220> FEATURE:
<221> NAME/KEY: MISC_FEATURE
<222> LOCATION: (2)..(25)
<223> OTHER INFORMATION: Xaa is any amino acid

<400> SEQUENCE: 185

Cys Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa
            20                  25

<210> SEQ ID NO 186
<211> LENGTH: 24
<212> TYPE: PRT
<213> ORGANISM: Ancyclostoma caninum
<220> FEATURE:
<221> NAME/KEY: MISC_FEATURE
<222> LOCATION: (2)..(24)
<223> OTHER INFORMATION: Xaa is any amino acid

<400> SEQUENCE: 186

Cys Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa
            20

<210> SEQ ID NO 187
<211> LENGTH: 23
<212> TYPE: PRT
<213> ORGANISM: Ancyclostoma caninum
<220> FEATURE:
<221> NAME/KEY: MISC_FEATURE
<222> LOCATION: (2)..(23)
<223> OTHER INFORMATION: Xaa is any amino acid

<400> SEQUENCE: 187

Cys Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa
            20

<210> SEQ ID NO 188
<211> LENGTH: 22
<212> TYPE: PRT
<213> ORGANISM: Ancyclostoma caninum
<220> FEATURE:
<221> NAME/KEY: MISC_FEATURE
<222> LOCATION: (2)..(22)
<223> OTHER INFORMATION: Xaa is any amino acid

<400> SEQUENCE: 188

Cys Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa
            20

<210> SEQ ID NO 189
<211> LENGTH: 21
<212> TYPE: PRT
<213> ORGANISM: Ancyclostoma caninum
<220> FEATURE:
<221> NAME/KEY: MISC_FEATURE
<222> LOCATION: (2)..(21)
<223> OTHER INFORMATION: Xaa is any amino acid

<400> SEQUENCE: 189

Cys Xaa Xaa Xaa Xaa Xaa Xaa Xaa Xaa Xaa Xaa Xaa Xaa Xaa Xaa
1               5                   10                  15

Xaa Xaa Xaa Xaa Xaa
            20

<210> SEQ ID NO 190
<211> LENGTH: 20
<212> TYPE: PRT
<213> ORGANISM: Ancyclostoma caninum
<220> FEATURE:
<221> NAME/KEY: MISC_FEATURE
<222> LOCATION: (2)..(20)
<223> OTHER INFORMATION: Xaa is any amino acid

<400> SEQUENCE: 190

Cys Xaa Xaa Xaa Xaa Xaa Xaa Xaa Xaa Xaa Xaa Xaa Xaa Xaa Xaa
1               5                   10                  15

Xaa Xaa Xaa Xaa
            20

<210> SEQ ID NO 191
<211> LENGTH: 19
<212> TYPE: PRT
<213> ORGANISM: Ancyclostoma caninum
<220> FEATURE:
<221> NAME/KEY: MISC_FEATURE
<222> LOCATION: (2)..(19)
<223> OTHER INFORMATION: Xaa is any amino acid

<400> SEQUENCE: 191

Cys Xaa Xaa Xaa Xaa Xaa Xaa Xaa Xaa Xaa Xaa Xaa Xaa Xaa Xaa
1               5                   10                  15

Xaa Xaa Xaa

<210> SEQ ID NO 192
<211> LENGTH: 18
<212> TYPE: PRT
<213> ORGANISM: Ancyclostoma caninum
<220> FEATURE:
<221> NAME/KEY: MISC_FEATURE
<222> LOCATION: (2)..(18)

-continued

<223> OTHER INFORMATION: Xaa is any amino acid

<400> SEQUENCE: 192

Cys Xaa Xaa Xaa Xaa Xaa Xaa Xaa Xaa Xaa Xaa Xaa Xaa Xaa Xaa
1               5                   10                  15

Xaa Xaa

<210> SEQ ID NO 193
<211> LENGTH: 17
<212> TYPE: PRT
<213> ORGANISM: Ancyclostoma caninum
<220> FEATURE:
<221> NAME/KEY: MISC_FEATURE
<222> LOCATION: (2)..(17)
<223> OTHER INFORMATION: Xaa is any amino acid

<400> SEQUENCE: 193

Cys Xaa Xaa Xaa Xaa Xaa Xaa Xaa Xaa Xaa Xaa Xaa Xaa Xaa Xaa
1               5                   10                  15

Xaa

<210> SEQ ID NO 194
<211> LENGTH: 16
<212> TYPE: PRT
<213> ORGANISM: Ancyclostoma caninum
<220> FEATURE:
<221> NAME/KEY: MISC_FEATURE
<222> LOCATION: (2)..(16)
<223> OTHER INFORMATION: Xaa is any amino acid

<400> SEQUENCE: 194

Cys Xaa Xaa Xaa Xaa Xaa Xaa Xaa Xaa Xaa Xaa Xaa Xaa Xaa Xaa
1               5                   10                  15

<210> SEQ ID NO 195
<211> LENGTH: 15
<212> TYPE: PRT
<213> ORGANISM: Ancyclostoma caninum
<220> FEATURE:
<221> NAME/KEY: MISC_FEATURE
<222> LOCATION: (2)..(15)
<223> OTHER INFORMATION: Xaa is any amino acid

<400> SEQUENCE: 195

Cys Xaa Xaa Xaa Xaa Xaa Xaa Xaa Xaa Xaa Xaa Xaa Xaa Xaa Xaa
1               5                   10                  15

<210> SEQ ID NO 196
<211> LENGTH: 14
<212> TYPE: PRT
<213> ORGANISM: Ancyclostoma caninum
<220> FEATURE:
<221> NAME/KEY: MISC_FEATURE
<222> LOCATION: (2)..(14)
<223> OTHER INFORMATION: Xaa is any amino acid

<400> SEQUENCE: 196

Cys Xaa Xaa Xaa Xaa Xaa Xaa Xaa Xaa Xaa Xaa Xaa Xaa
1               5                   10

<210> SEQ ID NO 197
<211> LENGTH: 13
<212> TYPE: PRT
<213> ORGANISM: Ancyclostoma caninum
<220> FEATURE:
<221> NAME/KEY: MISC_FEATURE
<222> LOCATION: (2)..(13)

<223> OTHER INFORMATION: Xaa is any amino acid

<400> SEQUENCE: 197

Cys Xaa Xaa Xaa Xaa Xaa Xaa Xaa Xaa Xaa Xaa Xaa
1               5                   10

<210> SEQ ID NO 198
<211> LENGTH: 12
<212> TYPE: PRT
<213> ORGANISM: Ancyclostoma caninum
<220> FEATURE:
<221> NAME/KEY: MISC_FEATURE
<222> LOCATION: (2)..(12)
<223> OTHER INFORMATION: Xaa is any amino acid

<400> SEQUENCE: 198

Cys Xaa Xaa Xaa Xaa Xaa Xaa Xaa Xaa Xaa Xaa
1               5                   10

<210> SEQ ID NO 199
<211> LENGTH: 11
<212> TYPE: PRT
<213> ORGANISM: Ancyclostoma caninum
<220> FEATURE:
<221> NAME/KEY: MISC_FEATURE
<222> LOCATION: (2)..(11)
<223> OTHER INFORMATION: Xaa is any amino acid

<400> SEQUENCE: 199

Cys Xaa Xaa Xaa Xaa Xaa Xaa Xaa Xaa Xaa Xaa
1               5                   10

<210> SEQ ID NO 200
<211> LENGTH: 10
<212> TYPE: PRT
<213> ORGANISM: Ancyclostoma caninum
<220> FEATURE:
<221> NAME/KEY: MISC_FEATURE
<222> LOCATION: (2)..(10)
<223> OTHER INFORMATION: Xaa is any amino acid

<400> SEQUENCE: 200

Cys Xaa Xaa Xaa Xaa Xaa Xaa Xaa Xaa Xaa
1               5                   10

<210> SEQ ID NO 201
<211> LENGTH: 9
<212> TYPE: PRT
<213> ORGANISM: Ancyclostoma caninum
<220> FEATURE:
<221> NAME/KEY: MISC_FEATURE
<222> LOCATION: (2)..(9)
<223> OTHER INFORMATION: Xaa is any amino acid

<400> SEQUENCE: 201

Cys Xaa Xaa Xaa Xaa Xaa Xaa Xaa Xaa
1               5

<210> SEQ ID NO 202
<211> LENGTH: 8
<212> TYPE: PRT
<213> ORGANISM: Ancyclostoma caninum
<220> FEATURE:
<221> NAME/KEY: MISC_FEATURE
<222> LOCATION: (2)..(8)
<223> OTHER INFORMATION: Xaa is any amino acid

<400> SEQUENCE: 202

```
Cys Xaa Xaa Xaa Xaa Xaa Xaa
1               5

<210> SEQ ID NO 203
<211> LENGTH: 7
<212> TYPE: PRT
<213> ORGANISM: Ancyclostoma caninum
<220> FEATURE:
<221> NAME/KEY: MISC_FEATURE
<222> LOCATION: (2)..(7)
<223> OTHER INFORMATION: Xaa is any amino acid

<400> SEQUENCE: 203

Cys Xaa Xaa Xaa Xaa Xaa Xaa
1               5

<210> SEQ ID NO 204
<211> LENGTH: 6
<212> TYPE: PRT
<213> ORGANISM: Ancyclostoma caninum
<220> FEATURE:
<221> NAME/KEY: MISC_FEATURE
<222> LOCATION: (2)..(6)
<223> OTHER INFORMATION: Xaa is any amino acid

<400> SEQUENCE: 204

Cys Xaa Xaa Xaa Xaa Xaa
1               5

<210> SEQ ID NO 205
<211> LENGTH: 8
<212> TYPE: PRT
<213> ORGANISM: Ancyclostoma caninum
<220> FEATURE:
<221> NAME/KEY: MISC_FEATURE
<222> LOCATION: (2)..(8)
<223> OTHER INFORMATION: Xaa is any amino acid

<400> SEQUENCE: 205

Cys Xaa Xaa Xaa Xaa Xaa Xaa Xaa
1               5

<210> SEQ ID NO 206
<211> LENGTH: 7
<212> TYPE: PRT
<213> ORGANISM: Ancyclostoma caninum
<220> FEATURE:
<221> NAME/KEY: MISC_FEATURE
<222> LOCATION: (2)..(6)
<223> OTHER INFORMATION: Xaa is any amino acid

<400> SEQUENCE: 206

Cys Xaa Xaa Xaa Xaa Xaa Cys
1               5

<210> SEQ ID NO 207
<211> LENGTH: 6
<212> TYPE: PRT
<213> ORGANISM: Ancyclostoma caninum
<220> FEATURE:
<221> NAME/KEY: MISC_FEATURE
<222> LOCATION: (2)..(5)
<223> OTHER INFORMATION: Xaa is any amino acid

<400> SEQUENCE: 207

Cys Xaa Xaa Xaa Xaa Cys
1               5
```

```
<210> SEQ ID NO 208
<211> LENGTH: 5
<212> TYPE: PRT
<213> ORGANISM: Ancyclostoma caninum
<220> FEATURE:
<221> NAME/KEY: MISC_FEATURE
<222> LOCATION: (2)..(4)
<223> OTHER INFORMATION: Xaa is any amino acid

<400> SEQUENCE: 208

Cys Xaa Xaa Xaa Cys
1               5

<210> SEQ ID NO 209
<211> LENGTH: 23
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(23)
<223> OTHER INFORMATION: Xaa is any amino acid

<400> SEQUENCE: 209

Xaa Xaa Xaa Cys Xaa Xaa Xaa Xaa Xaa Xaa Xaa Xaa Xaa Xaa Xaa Xaa
1               5                   10                  15

Xaa Xaa Xaa Xaa Xaa Xaa Xaa
            20

<210> SEQ ID NO 210
<211> LENGTH: 22
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(22)
<223> OTHER INFORMATION: Xaa is any amino acid

<400> SEQUENCE: 210

Xaa Xaa Xaa Cys Xaa Xaa Xaa Xaa Xaa Xaa Xaa Xaa Xaa Xaa Xaa Xaa
1               5                   10                  15

Xaa Xaa Xaa Xaa Xaa Xaa
            20

<210> SEQ ID NO 211
<211> LENGTH: 21
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(21)
<223> OTHER INFORMATION: Xaa is any amino acid

<400> SEQUENCE: 211

Xaa Xaa Xaa Cys Xaa Xaa Xaa Xaa Xaa Xaa Xaa Xaa Xaa Xaa Xaa Xaa
1               5                   10                  15

Xaa Xaa Xaa Xaa Xaa
            20
```

<210> SEQ ID NO 212
<211> LENGTH: 20
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(20)
<223> OTHER INFORMATION: Xaa is any amino acid

<400> SEQUENCE: 212

Xaa Xaa Xaa Cys Xaa Xaa Xaa Xaa Xaa Xaa Xaa Xaa Xaa Xaa Xaa Xaa
1               5                   10                  15

Xaa Xaa Xaa Xaa
            20

<210> SEQ ID NO 213
<211> LENGTH: 19
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(19)
<223> OTHER INFORMATION: Xaa is any amino acid

<400> SEQUENCE: 213

Xaa Xaa Xaa Cys Xaa Xaa Xaa Xaa Xaa Xaa Xaa Xaa Xaa Xaa Xaa Xaa
1               5                   10                  15

Xaa Xaa Xaa

<210> SEQ ID NO 214
<211> LENGTH: 18
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(18)
<223> OTHER INFORMATION: Xaa is any amino acid

<400> SEQUENCE: 214

Xaa Xaa Xaa Cys Xaa Xaa Xaa Xaa Xaa Xaa Xaa Xaa Xaa Xaa Xaa Xaa
1               5                   10                  15

Xaa Xaa

<210> SEQ ID NO 215
<211> LENGTH: 17
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(17)
<223> OTHER INFORMATION: Xaa is any amino acid

```
<400> SEQUENCE: 215

Xaa Xaa Xaa Cys Xaa Xaa Xaa Xaa Xaa Xaa Xaa Xaa Xaa Xaa Xaa
1               5                   10                  15

Xaa

<210> SEQ ID NO 216
<211> LENGTH: 16
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(16)
<223> OTHER INFORMATION: Xaa is any amino acid

<400> SEQUENCE: 216

Xaa Xaa Xaa Cys Xaa Xaa Xaa Xaa Xaa Xaa Xaa Xaa Xaa Xaa Xaa
1               5                   10                  15

<210> SEQ ID NO 217
<211> LENGTH: 15
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(15)
<223> OTHER INFORMATION: Xaa is any amino acid

<400> SEQUENCE: 217

Xaa Xaa Xaa Cys Xaa Xaa Xaa Xaa Xaa Xaa Xaa Xaa Xaa Xaa Xaa
1               5                   10                  15

<210> SEQ ID NO 218
<211> LENGTH: 14
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(14)
<223> OTHER INFORMATION: Xaa is any amino acid

<400> SEQUENCE: 218

Xaa Xaa Xaa Cys Xaa Xaa Xaa Xaa Xaa Xaa Xaa Xaa Xaa Xaa
1               5                   10

<210> SEQ ID NO 219
<211> LENGTH: 13
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(13)
<223> OTHER INFORMATION: Xaa is any amino acid

<400> SEQUENCE: 219
```

```
Xaa Xaa Xaa Cys Xaa Xaa Xaa Xaa Xaa Xaa Xaa Xaa
1               5                   10
```

<210> SEQ ID NO 220
<211> LENGTH: 12
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(12)
<223> OTHER INFORMATION: Xaa is any amino acid

<400> SEQUENCE: 220

```
Xaa Xaa Xaa Cys Xaa Xaa Xaa Xaa Xaa Xaa Xaa
1               5                   10
```

<210> SEQ ID NO 221
<211> LENGTH: 11
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(11)
<223> OTHER INFORMATION: Xaa is any amino acid

<400> SEQUENCE: 221

```
Xaa Xaa Xaa Cys Xaa Xaa Xaa Xaa Xaa Xaa Xaa
1               5                   10
```

<210> SEQ ID NO 222
<211> LENGTH: 10
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(10)
<223> OTHER INFORMATION: Xaa is any amino acid

<400> SEQUENCE: 222

```
Xaa Xaa Xaa Cys Xaa Xaa Xaa Xaa Xaa Xaa
1               5                   10
```

<210> SEQ ID NO 223
<211> LENGTH: 5
<212> TYPE: PRT
<213> ORGANISM: Ancyclostoma caninum
<220> FEATURE:
<221> NAME/KEY: MISC_FEATURE
<222> LOCATION: (2)..(5)
<223> OTHER INFORMATION: Xaa is any amino acid

<400> SEQUENCE: 223

```
Cys Xaa Xaa Xaa Xaa
1               5
```

<210> SEQ ID NO 224
<211> LENGTH: 4

-continued

<212> TYPE: PRT
<213> ORGANISM: Ancyclostoma caninum
<220> FEATURE:
<221> NAME/KEY: MISC_FEATURE
<222> LOCATION: (2)..(4)
<223> OTHER INFORMATION: Xaa is any amino acid

<400> SEQUENCE: 224

Cys Xaa Xaa Xaa
1

<210> SEQ ID NO 225
<211> LENGTH: 6
<212> TYPE: PRT
<213> ORGANISM: Ancyclostoma caninum
<220> FEATURE:
<221> NAME/KEY: MISC_FEATURE
<222> LOCATION: (2)..(6)
<223> OTHER INFORMATION: Xaa is any amino acid

<400> SEQUENCE: 225

Cys Xaa Xaa Xaa Xaa Xaa
1               5

<210> SEQ ID NO 226
<211> LENGTH: 5
<212> TYPE: PRT
<213> ORGANISM: Ancyclostoma caninum
<220> FEATURE:
<221> NAME/KEY: MISC_FEATURE
<222> LOCATION: (2)..(5)
<223> OTHER INFORMATION: Xaa is any amino acid

<400> SEQUENCE: 226

Cys Xaa Xaa Xaa Xaa
1               5

<210> SEQ ID NO 227
<211> LENGTH: 4
<212> TYPE: PRT
<213> ORGANISM: Ancyclostoma caninum
<220> FEATURE:
<221> NAME/KEY: MISC_FEATURE
<222> LOCATION: (2)..(4)
<223> OTHER INFORMATION: Xaa is any amino acid

<400> SEQUENCE: 227

Cys Xaa Xaa Xaa
1

<210> SEQ ID NO 228
<211> LENGTH: 15
<212> TYPE: PRT
<213> ORGANISM: Ancyclostoma caninum
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (4)..(15)
<223> OTHER INFORMATION: Xaa is any amino acid

<400> SEQUENCE: 228

Cys Xaa Cys Xaa Xaa Xaa Xaa Xaa Xaa Xaa Xaa Xaa Xaa Xaa Xaa
1               5                   10                  15

<210> SEQ ID NO 229
<211> LENGTH: 14

```
<212> TYPE: PRT
<213> ORGANISM: Ancyclostoma caninum
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (4)..(14)
<223> OTHER INFORMATION: Xaa is any amino acid

<400> SEQUENCE: 229

Cys Xaa Cys Xaa Xaa Xaa Xaa Xaa Xaa Xaa Xaa Xaa Xaa
 1               5                   10

<210> SEQ ID NO 230
<211> LENGTH: 8
<212> TYPE: PRT
<213> ORGANISM: Ancyclostoma caninum
<220> FEATURE:
<221> NAME/KEY: MISC_FEATURE
<222> LOCATION: (2)..(8)
<223> OTHER INFORMATION: Xaa is any amino acid

<400> SEQUENCE: 230

Cys Xaa Xaa Xaa Xaa Xaa Xaa Xaa
 1               5

<210> SEQ ID NO 231
<211> LENGTH: 7
<212> TYPE: PRT
<213> ORGANISM: Ancyclostoma caninum
<220> FEATURE:
<221> NAME/KEY: MISC_FEATURE
<222> LOCATION: (2)..(7)
<223> OTHER INFORMATION: Xaa is any amino acid

<400> SEQUENCE: 231

Cys Xaa Xaa Xaa Xaa Xaa Xaa
 1               5

<210> SEQ ID NO 232
<211> LENGTH: 6
<212> TYPE: PRT
<213> ORGANISM: Ancyclostoma caninum
<220> FEATURE:
<221> NAME/KEY: MISC_FEATURE
<222> LOCATION: (2)..(6)
<223> OTHER INFORMATION: Xaa is any amino acid

<400> SEQUENCE: 232

Cys Xaa Xaa Xaa Xaa Xaa
 1               5

<210> SEQ ID NO 233
<211> LENGTH: 26
<212> TYPE: PRT
<213> ORGANISM: Ancyclostoma caninum
<220> FEATURE:
<221> NAME/KEY: MISC_FEATURE
<222> LOCATION: (2)..(26)
<223> OTHER INFORMATION: Xaa is any amino acid

<400> SEQUENCE: 233

Cys Xaa Xaa Xaa Xaa Xaa Xaa Xaa Xaa Xaa Xaa Xaa Xaa Xaa Xaa Xaa
 1               5                   10                  15

Xaa Xaa Xaa Xaa Xaa Xaa Xaa Xaa Xaa Xaa
            20                  25
```

```
<210> SEQ ID NO 234
<211> LENGTH: 25
<212> TYPE: PRT
<213> ORGANISM: Ancyclostoma caninum
<220> FEATURE:
<221> NAME/KEY: MISC_FEATURE
<222> LOCATION: (2)..(25)
<223> OTHER INFORMATION: Xaa is any amino acid

<400> SEQUENCE: 234

Cys Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa
            20                  25

<210> SEQ ID NO 235
<211> LENGTH: 24
<212> TYPE: PRT
<213> ORGANISM: Ancyclostoma caninum
<220> FEATURE:
<221> NAME/KEY: MISC_FEATURE
<222> LOCATION: (2)..(24)
<223> OTHER INFORMATION: Xaa is any amino acid

<400> SEQUENCE: 235

Cys Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa
            20

<210> SEQ ID NO 236
<211> LENGTH: 23
<212> TYPE: PRT
<213> ORGANISM: Ancyclostoma caninum
<220> FEATURE:
<221> NAME/KEY: MISC_FEATURE
<222> LOCATION: (2)..(23)
<223> OTHER INFORMATION: Xaa is any amino acid

<400> SEQUENCE: 236

Cys Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa
            20

<210> SEQ ID NO 237
<211> LENGTH: 22
<212> TYPE: PRT
<213> ORGANISM: Ancyclostoma caninum
<220> FEATURE:
<221> NAME/KEY: MISC_FEATURE
<222> LOCATION: (2)..(22)
<223> OTHER INFORMATION: Xaa is any amino acid

<400> SEQUENCE: 237

Cys Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa
            20

<210> SEQ ID NO 238
<211> LENGTH: 21
<212> TYPE: PRT
<213> ORGANISM: Ancyclostoma caninum
<220> FEATURE:
<221> NAME/KEY: MISC_FEATURE
```

```
<222> LOCATION: (2)..(21)
<223> OTHER INFORMATION: Xaa is any amino acid

<400> SEQUENCE: 238

Cys Xaa Xaa Xaa Xaa Xaa Xaa Xaa Xaa Xaa Xaa Xaa Xaa Xaa Xaa
1               5                   10                  15

Xaa Xaa Xaa Xaa Xaa
            20

<210> SEQ ID NO 239
<211> LENGTH: 20
<212> TYPE: PRT
<213> ORGANISM: Ancyclostoma caninum
<220> FEATURE:
<221> NAME/KEY: MISC_FEATURE
<222> LOCATION: (2)..(20)
<223> OTHER INFORMATION: Xaa is any amino acid

<400> SEQUENCE: 239

Cys Xaa Xaa Xaa Xaa Xaa Xaa Xaa Xaa Xaa Xaa Xaa Xaa Xaa Xaa
1               5                   10                  15

Xaa Xaa Xaa Xaa
            20

<210> SEQ ID NO 240
<211> LENGTH: 19
<212> TYPE: PRT
<213> ORGANISM: Ancyclostoma caninum
<220> FEATURE:
<221> NAME/KEY: MISC_FEATURE
<222> LOCATION: (2)..(19)
<223> OTHER INFORMATION: Xaa is any amino acid

<400> SEQUENCE: 240

Cys Xaa Xaa Xaa Xaa Xaa Xaa Xaa Xaa Xaa Xaa Xaa Xaa Xaa Xaa
1               5                   10                  15

Xaa Xaa Xaa

<210> SEQ ID NO 241
<211> LENGTH: 18
<212> TYPE: PRT
<213> ORGANISM: Ancyclostoma caninum
<220> FEATURE:
<221> NAME/KEY: MISC_FEATURE
<222> LOCATION: (2)..(18)
<223> OTHER INFORMATION: Xaa is any amino acid

<400> SEQUENCE: 241

Cys Xaa Xaa Xaa Xaa Xaa Xaa Xaa Xaa Xaa Xaa Xaa Xaa Xaa Xaa
1               5                   10                  15

Xaa Xaa

<210> SEQ ID NO 242
<211> LENGTH: 17
<212> TYPE: PRT
<213> ORGANISM: Ancyclostoma caninum
<220> FEATURE:
<221> NAME/KEY: MISC_FEATURE
<222> LOCATION: (2)..(17)
<223> OTHER INFORMATION: Xaa is any amino acid

<400> SEQUENCE: 242

Cys Xaa Xaa Xaa Xaa Xaa Xaa Xaa Xaa Xaa Xaa Xaa Xaa Xaa Xaa
1               5                   10                  15

Xaa
```

<210> SEQ ID NO 243
<211> LENGTH: 16
<212> TYPE: PRT
<213> ORGANISM: Ancyclostoma caninum
<220> FEATURE:
<221> NAME/KEY: MISC_FEATURE
<222> LOCATION: (2)..(16)
<223> OTHER INFORMATION: Xaa is any amino acid

<400> SEQUENCE: 243

Cys Xaa Xaa Xaa Xaa Xaa Xaa Xaa Xaa Xaa Xaa Xaa Xaa Xaa Xaa Xaa
 1               5                  10                  15

<210> SEQ ID NO 244
<211> LENGTH: 15
<212> TYPE: PRT
<213> ORGANISM: Ancyclostoma caninum
<220> FEATURE:
<221> NAME/KEY: MISC_FEATURE
<222> LOCATION: (2)..(15)
<223> OTHER INFORMATION: Xaa is any amino acid

<400> SEQUENCE: 244

Cys Xaa Xaa Xaa Xaa Xaa Xaa Xaa Xaa Xaa Xaa Xaa Xaa Xaa Xaa
 1               5                  10                  15

<210> SEQ ID NO 245
<211> LENGTH: 14
<212> TYPE: PRT
<213> ORGANISM: Ancyclostoma caninum
<220> FEATURE:
<221> NAME/KEY: MISC_FEATURE
<222> LOCATION: (2)..(14)
<223> OTHER INFORMATION: Xaa is any amino acid

<400> SEQUENCE: 245

Cys Xaa Xaa Xaa Xaa Xaa Xaa Xaa Xaa Xaa Xaa Xaa Xaa Xaa
 1               5                  10

<210> SEQ ID NO 246
<211> LENGTH: 13
<212> TYPE: PRT
<213> ORGANISM: Ancyclostoma caninum
<220> FEATURE:
<221> NAME/KEY: MISC_FEATURE
<222> LOCATION: (2)..(13)
<223> OTHER INFORMATION: Xaa is any amino acid

<400> SEQUENCE: 246

Cys Xaa Xaa Xaa Xaa Xaa Xaa Xaa Xaa Xaa Xaa Xaa Xaa
 1               5                  10

<210> SEQ ID NO 247
<211> LENGTH: 12
<212> TYPE: PRT
<213> ORGANISM: Ancyclostoma caninum
<220> FEATURE:
<221> NAME/KEY: MISC_FEATURE
<222> LOCATION: (2)..(12)
<223> OTHER INFORMATION: Xaa is any amino acid

<400> SEQUENCE: 247

Cys Xaa Xaa Xaa Xaa Xaa Xaa Xaa Xaa Xaa Xaa Xaa
 1               5                  10

<210> SEQ ID NO 248
<211> LENGTH: 11

```
<212> TYPE: PRT
<213> ORGANISM: Ancyclostoma caninum
<220> FEATURE:
<221> NAME/KEY: MISC_FEATURE
<222> LOCATION: (2)..(11)
<223> OTHER INFORMATION: Xaa is any amino acid

<400> SEQUENCE: 248

Cys Xaa Xaa Xaa Xaa Xaa Xaa Xaa Xaa Xaa
1               5                   10

<210> SEQ ID NO 249
<211> LENGTH: 10
<212> TYPE: PRT
<213> ORGANISM: Ancyclostoma caninum
<220> FEATURE:
<221> NAME/KEY: MISC_FEATURE
<222> LOCATION: (2)..(10)
<223> OTHER INFORMATION: Xaa is any amino acid

<400> SEQUENCE: 249

Cys Xaa Xaa Xaa Xaa Xaa Xaa Xaa Xaa Xaa
1               5                   10

<210> SEQ ID NO 250
<211> LENGTH: 9
<212> TYPE: PRT
<213> ORGANISM: Ancyclostoma caninum
<220> FEATURE:
<221> NAME/KEY: MISC_FEATURE
<222> LOCATION: (2)..(9)
<223> OTHER INFORMATION: Xaa is any amino acid

<400> SEQUENCE: 250

Cys Xaa Xaa Xaa Xaa Xaa Xaa Xaa Xaa
1               5

<210> SEQ ID NO 251
<211> LENGTH: 8
<212> TYPE: PRT
<213> ORGANISM: Ancyclostoma caninum
<220> FEATURE:
<221> NAME/KEY: MISC_FEATURE
<222> LOCATION: (2)..(8)
<223> OTHER INFORMATION: Xaa is any amino acid

<400> SEQUENCE: 251

Cys Xaa Xaa Xaa Xaa Xaa Xaa Xaa
1               5

<210> SEQ ID NO 252
<211> LENGTH: 7
<212> TYPE: PRT
<213> ORGANISM: Ancyclostoma caninum
<220> FEATURE:
<221> NAME/KEY: MISC_FEATURE
<222> LOCATION: (2)..(7)
<223> OTHER INFORMATION: Xaa is any amino acid

<400> SEQUENCE: 252

Cys Xaa Xaa Xaa Xaa Xaa Xaa
1               5

<210> SEQ ID NO 253
<211> LENGTH: 6
<212> TYPE: PRT
<213> ORGANISM: Ancyclostoma caninum
<220> FEATURE:
<221> NAME/KEY: MISC_FEATURE
```

<222> LOCATION: (2)..(6)
<223> OTHER INFORMATION: Xaa is any amino acid

<400> SEQUENCE: 253

Cys Xaa Xaa Xaa Xaa Xaa
1               5

<210> SEQ ID NO 254
<211> LENGTH: 8
<212> TYPE: PRT
<213> ORGANISM: Ancyclostoma caninum
<220> FEATURE:
<221> NAME/KEY: MISC_FEATURE
<222> LOCATION: (2)..(8)
<223> OTHER INFORMATION: Xaa is any amino acid

<400> SEQUENCE: 254

Cys Xaa Xaa Xaa Xaa Xaa Xaa Xaa
1               5

<210> SEQ ID NO 255
<211> LENGTH: 7
<212> TYPE: PRT
<213> ORGANISM: Ancyclostoma caninum
<220> FEATURE:
<221> NAME/KEY: MISC_FEATURE
<222> LOCATION: (2)..(6)
<223> OTHER INFORMATION: Xaa is any amino acid

<400> SEQUENCE: 255

Cys Xaa Xaa Xaa Xaa Xaa Cys
1               5

<210> SEQ ID NO 256
<211> LENGTH: 6
<212> TYPE: PRT
<213> ORGANISM: Ancyclostoma caninum
<220> FEATURE:
<221> NAME/KEY: MISC_FEATURE
<222> LOCATION: (2)..(5)
<223> OTHER INFORMATION: Xaa is any amino acid

<400> SEQUENCE: 256

Cys Xaa Xaa Xaa Xaa Cys
1               5

<210> SEQ ID NO 257
<211> LENGTH: 5
<212> TYPE: PRT
<213> ORGANISM: Ancyclostoma caninum
<220> FEATURE:
<221> NAME/KEY: MISC_FEATURE
<222> LOCATION: (2)..(4)
<223> OTHER INFORMATION: Xaa is any amino acid

<400> SEQUENCE: 257

Cys Xaa Xaa Xaa Cys
1               5

<210> SEQ ID NO 258
<211> LENGTH: 23
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE -continued

```
<222> LOCATION: (5)..(23)
<223> OTHER INFORMATION: Xaa is any amino acid

<400> SEQUENCE: 258

Xaa Xaa Xaa Cys Xaa Xaa Xaa Xaa Xaa Xaa Xaa Xaa Xaa Xaa Xaa
 1               5                   10                  15

Xaa Xaa Xaa Xaa Xaa Xaa Xaa
            20

<210> SEQ ID NO 259
<211> LENGTH: 22
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(22)
<223> OTHER INFORMATION: Xaa is any amino acid

<400> SEQUENCE: 259

Xaa Xaa Xaa Cys Xaa Xaa Xaa Xaa Xaa Xaa Xaa Xaa Xaa Xaa Xaa
 1               5                   10                  15

Xaa Xaa Xaa Xaa Xaa Xaa
            20

<210> SEQ ID NO 260
<211> LENGTH: 21
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(21)
<223> OTHER INFORMATION: Xaa is any amino acid

<400> SEQUENCE: 260

Xaa Xaa Xaa Cys Xaa Xaa Xaa Xaa Xaa Xaa Xaa Xaa Xaa Xaa Xaa
 1               5                   10                  15

Xaa Xaa Xaa Xaa Xaa
            20

<210> SEQ ID NO 261
<211> LENGTH: 20
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(20)
<223> OTHER INFORMATION: Xaa is any amino acid

<400> SEQUENCE: 261

Xaa Xaa Xaa Cys Xaa Xaa Xaa Xaa Xaa Xaa Xaa Xaa Xaa Xaa Xaa
 1               5                   10                  15

Xaa Xaa Xaa Xaa
            20

<210> SEQ ID NO 262
```

```
<211> LENGTH: 19
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(19)
<223> OTHER INFORMATION: Xaa is any amino acid

<400> SEQUENCE: 262

Xaa Xaa Xaa Cys Xaa Xaa Xaa Xaa Xaa Xaa Xaa Xaa Xaa Xaa Xaa Xaa
1               5                   10                  15

Xaa Xaa Xaa

<210> SEQ ID NO 263
<211> LENGTH: 18
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(18)
<223> OTHER INFORMATION: Xaa is any amino acid

<400> SEQUENCE: 263

Xaa Xaa Xaa Cys Xaa Xaa Xaa Xaa Xaa Xaa Xaa Xaa Xaa Xaa Xaa Xaa
1               5                   10                  15

Xaa Xaa

<210> SEQ ID NO 264
<211> LENGTH: 17
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(17)
<223> OTHER INFORMATION: Xaa is any amino acid

<400> SEQUENCE: 264

Xaa Xaa Xaa Cys Xaa Xaa Xaa Xaa Xaa Xaa Xaa Xaa Xaa Xaa Xaa Xaa
1               5                   10                  15

Xaa

<210> SEQ ID NO 265
<211> LENGTH: 16
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(16)
<223> OTHER INFORMATION: Xaa is any amino acid

<400> SEQUENCE: 265

Xaa Xaa Xaa Cys Xaa Xaa Xaa Xaa Xaa Xaa Xaa Xaa Xaa Xaa Xaa Xaa
1               5                   10                  15
```

```
<210> SEQ ID NO 266
<211> LENGTH: 15
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(15)
<223> OTHER INFORMATION: Xaa is any amino acid

<400> SEQUENCE: 266

Xaa Xaa Xaa Cys Xaa Xaa Xaa Xaa Xaa Xaa Xaa Xaa Xaa Xaa Xaa
1               5                   10                  15

<210> SEQ ID NO 267
<211> LENGTH: 14
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(14)
<223> OTHER INFORMATION: Xaa is any amino acid

<400> SEQUENCE: 267

Xaa Xaa Xaa Cys Xaa Xaa Xaa Xaa Xaa Xaa Xaa Xaa Xaa Xaa
1               5                   10

<210> SEQ ID NO 268
<211> LENGTH: 13
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(13)
<223> OTHER INFORMATION: Xaa is any amino acid

<400> SEQUENCE: 268

Xaa Xaa Xaa Cys Xaa Xaa Xaa Xaa Xaa Xaa Xaa Xaa Xaa
1               5                   10

<210> SEQ ID NO 269
<211> LENGTH: 12
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(12)
<223> OTHER INFORMATION: Xaa is any amino acid

<400> SEQUENCE: 269

Xaa Xaa Xaa Cys Xaa Xaa Xaa Xaa Xaa Xaa Xaa Xaa
1               5                   10

<210> SEQ ID NO 270
```

```
<211> LENGTH: 11
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(11)
<223> OTHER INFORMATION: Xaa is any amino acid

<400> SEQUENCE: 270

Xaa Xaa Xaa Cys Xaa Xaa Xaa Xaa Xaa Xaa Xaa
 1               5                  10

<210> SEQ ID NO 271
<211> LENGTH: 10
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(10)
<223> OTHER INFORMATION: Xaa is any amino acid

<400> SEQUENCE: 271

Xaa Xaa Xaa Cys Xaa Xaa Xaa Xaa Xaa Xaa
 1               5                  10

<210> SEQ ID NO 272
<211> LENGTH: 5
<212> TYPE: PRT
<213> ORGANISM: Ancyclostoma caninum
<220> FEATURE:
<221> NAME/KEY: MISC_FEATURE
<222> LOCATION: (2)..(5)
<223> OTHER INFORMATION: Xaa is any amino acid

<400> SEQUENCE: 272

Cys Xaa Xaa Xaa Xaa
 1               5

<210> SEQ ID NO 273
<211> LENGTH: 4
<212> TYPE: PRT
<213> ORGANISM: Ancyclostoma caninum
<220> FEATURE:
<221> NAME/KEY: MISC_FEATURE
<222> LOCATION: (2)..(4)
<223> OTHER INFORMATION: Xaa is any amino acid

<400> SEQUENCE: 273

Cys Xaa Xaa Xaa
 1

<210> SEQ ID NO 274
<211> LENGTH: 6
<212> TYPE: PRT
<213> ORGANISM: Ancyclostoma caninum
<220> FEATURE:
<221> NAME/KEY: MISC_FEATURE
<222> LOCATION: (2)..(6)
<223> OTHER INFORMATION: Xaa is any amino acid

<400> SEQUENCE: 274

Cys Xaa Xaa Xaa Xaa Xaa
```

-continued

```
1               5

<210> SEQ ID NO 275
<211> LENGTH: 5
<212> TYPE: PRT
<213> ORGANISM: Ancyclostoma caninum
<220> FEATURE:
<221> NAME/KEY: MISC_FEATURE
<222> LOCATION: (2)..(5)
<223> OTHER INFORMATION: Xaa is any amino acid

<400> SEQUENCE: 275

Cys Xaa Xaa Xaa Xaa
1               5

<210> SEQ ID NO 276
<211> LENGTH: 4
<212> TYPE: PRT
<213> ORGANISM: Ancyclostoma caninum
<220> FEATURE:
<221> NAME/KEY: MISC_FEATURE
<222> LOCATION: (2)..(4)
<223> OTHER INFORMATION: Xaa is any amino acid

<400> SEQUENCE: 276

Cys Xaa Xaa Xaa
1

<210> SEQ ID NO 277
<211> LENGTH: 15
<212> TYPE: PRT
<213> ORGANISM: Ancyclostoma caninum
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (4)..(15)
<223> OTHER INFORMATION: Xaa is any amino acid

<400> SEQUENCE: 277

Cys Xaa Cys Xaa Xaa Xaa Xaa Xaa Xaa Xaa Xaa Xaa Xaa Xaa Xaa
1               5                   10                  15

<210> SEQ ID NO 278
<211> LENGTH: 14
<212> TYPE: PRT
<213> ORGANISM: Ancyclostoma caninum
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (4)..(14)
<223> OTHER INFORMATION: Xaa is any amino acid

<400> SEQUENCE: 278

Cys Xaa Cys Xaa Xaa Xaa Xaa Xaa Xaa Xaa Xaa Xaa Xaa Xaa
1               5                   10

<210> SEQ ID NO 279
<211> LENGTH: 13
<212> TYPE: PRT
<213> ORGANISM: Ancyclostoma caninum
<220> FEATURE:
<221> NAME/KEY: MISC_FEATURE
<222> LOCATION: (2)..(2)
<223> OTHER INFORMATION: Xaa is any amino acid
```

-continued

```
<220> FEATURE:
<221> NAME/KEY: MISC_FEATURE
<222> LOCATION: (4)..(13)
<223> OTHER INFORMATION: Xaa is any amino acid

<400> SEQUENCE: 279

Cys Xaa Cys Xaa Xaa Xaa Xaa Xaa Xaa Xaa Xaa Xaa
1               5                   10

<210> SEQ ID NO 280
<211> LENGTH: 8
<212> TYPE: PRT
<213> ORGANISM: Ancyclostoma caninum
<220> FEATURE:
<221> NAME/KEY: MISC_FEATURE
<222> LOCATION: (2)..(8)
<223> OTHER INFORMATION: Xaa is any amino acid

<400> SEQUENCE: 280

Cys Xaa Xaa Xaa Xaa Xaa Xaa Xaa
1               5

<210> SEQ ID NO 281
<211> LENGTH: 7
<212> TYPE: PRT
<213> ORGANISM: Ancyclostoma caninum
<220> FEATURE:
<221> NAME/KEY: MISC_FEATURE
<222> LOCATION: (2)..(7)
<223> OTHER INFORMATION: Xaa is any amino acid

<400> SEQUENCE: 281

Cys Xaa Xaa Xaa Xaa Xaa Xaa
1               5

<210> SEQ ID NO 282
<211> LENGTH: 6
<212> TYPE: PRT
<213> ORGANISM: Ancyclostoma caninum
<220> FEATURE:
<221> NAME/KEY: MISC_FEATURE
<222> LOCATION: (2)..(6)
<223> OTHER INFORMATION: Xaa is any amino acid

<400> SEQUENCE: 282

Cys Xaa Xaa Xaa Xaa Xaa
1               5

<210> SEQ ID NO 283
<211> LENGTH: 26
<212> TYPE: PRT
<213> ORGANISM: Ancyclostoma caninum
<220> FEATURE:
<221> NAME/KEY: MISC_FEATURE
<222> LOCATION: (2)..(26)
<223> OTHER INFORMATION: Xaa is any amino acid

<400> SEQUENCE: 283

Cys Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa
            20                  25

<210> SEQ ID NO 284
<211> LENGTH: 25
<212> TYPE: PRT
<213> ORGANISM: Ancyclostoma caninum
<220> FEATURE:
```

-continued

```
<221> NAME/KEY: MISC_FEATURE
<222> LOCATION: (2)..(25)
<223> OTHER INFORMATION: Xaa is any amino acid

<400> SEQUENCE: 284

Cys Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa
            20                  25

<210> SEQ ID NO 285
<211> LENGTH: 24
<212> TYPE: PRT
<213> ORGANISM: Ancyclostoma caninum
<220> FEATURE:
<221> NAME/KEY: MISC_FEATURE
<222> LOCATION: (2)..(24)
<223> OTHER INFORMATION: Xaa is any amino acid

<400> SEQUENCE: 285

Cys Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa
            20

<210> SEQ ID NO 286
<211> LENGTH: 23
<212> TYPE: PRT
<213> ORGANISM: Ancyclostoma caninum
<220> FEATURE:
<221> NAME/KEY: MISC_FEATURE
<222> LOCATION: (2)..(23)
<223> OTHER INFORMATION: Xaa is any amino acid

<400> SEQUENCE: 286

Cys Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa
            20

<210> SEQ ID NO 287
<211> LENGTH: 22
<212> TYPE: PRT
<213> ORGANISM: Ancyclostoma caninum
<220> FEATURE:
<221> NAME/KEY: MISC_FEATURE
<222> LOCATION: (2)..(22)
<223> OTHER INFORMATION: Xaa is any amino acid

<400> SEQUENCE: 287

Cys Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa
            20

<210> SEQ ID NO 288
<211> LENGTH: 21
<212> TYPE: PRT
<213> ORGANISM: Ancyclostoma caninum
<220> FEATURE:
<221> NAME/KEY: MISC_FEATURE
<222> LOCATION: (2)..(21)
<223> OTHER INFORMATION: Xaa is any amino acid

<400> SEQUENCE: 288

Cys Xaa Xaa Xaa Xaa Xaa Xaa Xaa Xaa Xaa Xaa Xaa Xaa Xaa Xaa
```

```
1               5                   10                  15
Xaa Xaa Xaa Xaa Xaa
            20

<210> SEQ ID NO 289
<211> LENGTH: 20
<212> TYPE: PRT
<213> ORGANISM: Ancyclostoma caninum
<220> FEATURE:
<221> NAME/KEY: MISC_FEATURE
<222> LOCATION: (2)..(20)
<223> OTHER INFORMATION: Xaa is any amino acid

<400> SEQUENCE: 289

Cys Xaa Xaa Xaa Xaa Xaa Xaa Xaa Xaa Xaa Xaa Xaa Xaa Xaa Xaa
1               5                   10                  15

Xaa Xaa Xaa Xaa
            20

<210> SEQ ID NO 290
<211> LENGTH: 19
<212> TYPE: PRT
<213> ORGANISM: Ancyclostoma caninum
<220> FEATURE:
<221> NAME/KEY: MISC_FEATURE
<222> LOCATION: (2)..(19)
<223> OTHER INFORMATION: Xaa is any amino acid

<400> SEQUENCE: 290

Cys Xaa Xaa Xaa Xaa Xaa Xaa Xaa Xaa Xaa Xaa Xaa Xaa Xaa Xaa
1               5                   10                  15

Xaa Xaa Xaa

<210> SEQ ID NO 291
<211> LENGTH: 18
<212> TYPE: PRT
<213> ORGANISM: Ancyclostoma caninum
<220> FEATURE:
<221> NAME/KEY: MISC_FEATURE
<222> LOCATION: (2)..(18)
<223> OTHER INFORMATION: Xaa is any amino acid

<400> SEQUENCE: 291

Cys Xaa Xaa Xaa Xaa Xaa Xaa Xaa Xaa Xaa Xaa Xaa Xaa Xaa Xaa
1               5                   10                  15

Xaa Xaa

<210> SEQ ID NO 292
<211> LENGTH: 17
<212> TYPE: PRT
<213> ORGANISM: Ancyclostoma caninum
<220> FEATURE:
<221> NAME/KEY: MISC_FEATURE
<222> LOCATION: (2)..(17)
<223> OTHER INFORMATION: Xaa is any amino acid

<400> SEQUENCE: 292

Cys Xaa Xaa Xaa Xaa Xaa Xaa Xaa Xaa Xaa Xaa Xaa Xaa Xaa Xaa
1               5                   10                  15

Xaa

<210> SEQ ID NO 293
<211> LENGTH: 16
<212> TYPE: PRT
<213> ORGANISM: Ancyclostoma caninum
```

```
<220> FEATURE:
<221> NAME/KEY: MISC_FEATURE
<222> LOCATION: (2)..(16)
<223> OTHER INFORMATION: Xaa is any amino acid

<400> SEQUENCE: 293

Cys Xaa Xaa Xaa Xaa Xaa Xaa Xaa Xaa Xaa Xaa Xaa Xaa Xaa Xaa
1               5                   10                  15

<210> SEQ ID NO 294
<211> LENGTH: 15
<212> TYPE: PRT
<213> ORGANISM: Ancyclostoma caninum
<220> FEATURE:
<221> NAME/KEY: MISC_FEATURE
<222> LOCATION: (2)..(15)
<223> OTHER INFORMATION: Xaa is any amino acid

<400> SEQUENCE: 294

Cys Xaa Xaa Xaa Xaa Xaa Xaa Xaa Xaa Xaa Xaa Xaa Xaa Xaa Xaa
1               5                   10                  15

<210> SEQ ID NO 295
<211> LENGTH: 14
<212> TYPE: PRT
<213> ORGANISM: Ancyclostoma caninum
<220> FEATURE:
<221> NAME/KEY: MISC_FEATURE
<222> LOCATION: (2)..(14)
<223> OTHER INFORMATION: Xaa is any amino acid

<400> SEQUENCE: 295

Cys Xaa Xaa Xaa Xaa Xaa Xaa Xaa Xaa Xaa Xaa Xaa Xaa Xaa
1               5                   10

<210> SEQ ID NO 296
<211> LENGTH: 13
<212> TYPE: PRT
<213> ORGANISM: Ancyclostoma caninum
<220> FEATURE:
<221> NAME/KEY: MISC_FEATURE
<222> LOCATION: (2)..(13)
<223> OTHER INFORMATION: Xaa is any amino acid

<400> SEQUENCE: 296

Cys Xaa Xaa Xaa Xaa Xaa Xaa Xaa Xaa Xaa Xaa Xaa Xaa
1               5                   10

<210> SEQ ID NO 297
<211> LENGTH: 12
<212> TYPE: PRT
<213> ORGANISM: Ancyclostoma caninum
<220> FEATURE:
<221> NAME/KEY: MISC_FEATURE
<222> LOCATION: (2)..(12)
<223> OTHER INFORMATION: Xaa is any amino acid

<400> SEQUENCE: 297

Cys Xaa Xaa Xaa Xaa Xaa Xaa Xaa Xaa Xaa Xaa Xaa
1               5                   10

<210> SEQ ID NO 298
<211> LENGTH: 11
<212> TYPE: PRT
<213> ORGANISM: Ancyclostoma caninum
<220> FEATURE:
<221> NAME/KEY: MISC_FEATURE
<222> LOCATION: (2)..(11)
<223> OTHER INFORMATION: Xaa is any amino acid
```

```
<400> SEQUENCE: 298

Cys Xaa Xaa Xaa Xaa Xaa Xaa Xaa Xaa Xaa
1               5                   10

<210> SEQ ID NO 299
<211> LENGTH: 10
<212> TYPE: PRT
<213> ORGANISM: Ancyclostoma caninum
<220> FEATURE:
<221> NAME/KEY: MISC_FEATURE
<222> LOCATION: (2)..(10)
<223> OTHER INFORMATION: Xaa is any amino acid

<400> SEQUENCE: 299

Cys Xaa Xaa Xaa Xaa Xaa Xaa Xaa Xaa Xaa
1               5                   10

<210> SEQ ID NO 300
<211> LENGTH: 9
<212> TYPE: PRT
<213> ORGANISM: Ancyclostoma caninum
<220> FEATURE:
<221> NAME/KEY: MISC_FEATURE
<222> LOCATION: (2)..(9)
<223> OTHER INFORMATION: Xaa is any amino acid

<400> SEQUENCE: 300

Cys Xaa Xaa Xaa Xaa Xaa Xaa Xaa Xaa
1               5

<210> SEQ ID NO 301
<211> LENGTH: 8
<212> TYPE: PRT
<213> ORGANISM: Ancyclostoma caninum
<220> FEATURE:
<221> NAME/KEY: MISC_FEATURE
<222> LOCATION: (2)..(8)
<223> OTHER INFORMATION: Xaa is any amino acid

<400> SEQUENCE: 301

Cys Xaa Xaa Xaa Xaa Xaa Xaa Xaa
1               5

<210> SEQ ID NO 302
<211> LENGTH: 7
<212> TYPE: PRT
<213> ORGANISM: Ancyclostoma caninum
<220> FEATURE:
<221> NAME/KEY: MISC_FEATURE
<222> LOCATION: (2)..(7)
<223> OTHER INFORMATION: Xaa is any amino acid

<400> SEQUENCE: 302

Cys Xaa Xaa Xaa Xaa Xaa Xaa
1               5

<210> SEQ ID NO 303
<211> LENGTH: 6
<212> TYPE: PRT
<213> ORGANISM: Ancyclostoma caninum
<220> FEATURE:
<221> NAME/KEY: MISC_FEATURE
<222> LOCATION: (2)..(6)
<223> OTHER INFORMATION: Xaa is any amino acid

<400> SEQUENCE: 303

Cys Xaa Xaa Xaa Xaa Xaa
```

-continued

```
1               5

<210> SEQ ID NO 304
<211> LENGTH: 5
<212> TYPE: PRT
<213> ORGANISM: Ancyclostoma caninum
<220> FEATURE:
<221> NAME/KEY: MISC_FEATURE
<222> LOCATION: (2)..(5)
<223> OTHER INFORMATION: Xaa is any amino acid

<400> SEQUENCE: 304

Cys Xaa Xaa Xaa Xaa
1               5

<210> SEQ ID NO 305
<211> LENGTH: 4
<212> TYPE: PRT
<213> ORGANISM: Ancyclostoma caninum
<220> FEATURE:
<221> NAME/KEY: MISC_FEATURE
<222> LOCATION: (2)..(4)
<223> OTHER INFORMATION: Xaa is any amino acid

<400> SEQUENCE: 305

Cys Xaa Xaa Xaa
1

<210> SEQ ID NO 306
<211> LENGTH: 3
<212> TYPE: PRT
<213> ORGANISM: Ancyclostoma caninum
<220> FEATURE:
<221> NAME/KEY: MISC_FEATURE
<222> LOCATION: (2)..(3)
<223> OTHER INFORMATION: Xaa is any amino acid

<400> SEQUENCE: 306

Cys Xaa Xaa
1

<210> SEQ ID NO 307
<211> LENGTH: 2
<212> TYPE: PRT
<213> ORGANISM: Ancyclostoma caninum
<220> FEATURE:
<221> NAME/KEY: MISC_FEATURE
<222> LOCATION: (2)..(2)
<223> OTHER INFORMATION: Xaa is any amino acid

<400> SEQUENCE: 307

Cys Xaa
1

<210> SEQ ID NO 308
<211> LENGTH: 8
<212> TYPE: PRT
<213> ORGANISM: Ancyclostoma caninum
<220> FEATURE:
<221> NAME/KEY: MISC_FEATURE
<222> LOCATION: (2)..(8)
<223> OTHER INFORMATION: Xaa is any amino acid

<400> SEQUENCE: 308

Cys Xaa Xaa Xaa Xaa Xaa Xaa
1               5

<210> SEQ ID NO 309
```

```
<211> LENGTH: 7
<212> TYPE: PRT
<213> ORGANISM: Ancyclostoma caninum
<220> FEATURE:
<221> NAME/KEY: MISC_FEATURE
<222> LOCATION: (2)..(6)
<223> OTHER INFORMATION: Xaa is any amino acid

<400> SEQUENCE: 309

Cys Xaa Xaa Xaa Xaa Xaa Cys
1               5

<210> SEQ ID NO 310
<211> LENGTH: 6
<212> TYPE: PRT
<213> ORGANISM: Ancyclostoma caninum
<220> FEATURE:
<221> NAME/KEY: MISC_FEATURE
<222> LOCATION: (2)..(5)
<223> OTHER INFORMATION: Xaa is any amino acid

<400> SEQUENCE: 310

Cys Xaa Xaa Xaa Xaa Cys
1               5

<210> SEQ ID NO 311
<211> LENGTH: 5
<212> TYPE: PRT
<213> ORGANISM: Ancyclostoma caninum
<220> FEATURE:
<221> NAME/KEY: MISC_FEATURE
<222> LOCATION: (2)..(4)
<223> OTHER INFORMATION: Xaa is any amino acid

<400> SEQUENCE: 311

Cys Xaa Xaa Xaa Cys
1               5

<210> SEQ ID NO 312
<211> LENGTH: 23
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(23)
<223> OTHER INFORMATION: Xaa is any amino acid

<400> SEQUENCE: 312

Xaa Xaa Xaa Cys Xaa Xaa Xaa Xaa Xaa Xaa Xaa Xaa Xaa Xaa Xaa Xaa
1               5                   10                  15

Xaa Xaa Xaa Xaa Xaa Xaa Xaa
            20

<210> SEQ ID NO 313
<211> LENGTH: 22
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(22)
<223> OTHER INFORMATION: Xaa is any amino acid
```

-continued

<400> SEQUENCE: 313

Xaa Xaa Xaa Cys Xaa Xaa Xaa Xaa Xaa Xaa Xaa Xaa Xaa Xaa Xaa
1               5                   10                  15

Xaa Xaa Xaa Xaa Xaa Xaa
            20

<210> SEQ ID NO 314
<211> LENGTH: 21
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(21)
<223> OTHER INFORMATION: Xaa is any amino acid

<400> SEQUENCE: 314

Xaa Xaa Xaa Cys Xaa Xaa Xaa Xaa Xaa Xaa Xaa Xaa Xaa Xaa Xaa
1               5                   10                  15

Xaa Xaa Xaa Xaa Xaa
            20

<210> SEQ ID NO 315
<211> LENGTH: 20
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(20)
<223> OTHER INFORMATION: Xaa is any amino acid

<400> SEQUENCE: 315

Xaa Xaa Xaa Cys Xaa Xaa Xaa Xaa Xaa Xaa Xaa Xaa Xaa Xaa Xaa
1               5                   10                  15

Xaa Xaa Xaa Xaa
            20

<210> SEQ ID NO 316
<211> LENGTH: 19
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(19)
<223> OTHER INFORMATION: Xaa is any amino acid

<400> SEQUENCE: 316

Xaa Xaa Xaa Cys Xaa Xaa Xaa Xaa Xaa Xaa Xaa Xaa Xaa Xaa Xaa
1               5                   10                  15

Xaa Xaa Xaa

<210> SEQ ID NO 317
<211> LENGTH: 18
<212> TYPE: PRT
<213> ORGANISM: Ancyclostoma caninum
<220> FEATURE:

```
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(18)
<223> OTHER INFORMATION: Xaa is any amino acid

<400> SEQUENCE: 317

Xaa Xaa Xaa Cys Xaa Xaa Xaa Xaa Xaa Xaa Xaa Xaa Xaa Xaa Xaa
1               5                   10                  15

Xaa Xaa

<210> SEQ ID NO 318
<211> LENGTH: 17
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(17)
<223> OTHER INFORMATION: Xaa is any amino acid

<400> SEQUENCE: 318

Xaa Xaa Xaa Cys Xaa Xaa Xaa Xaa Xaa Xaa Xaa Xaa Xaa Xaa Xaa
1               5                   10                  15

Xaa

<210> SEQ ID NO 319
<211> LENGTH: 16
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(16)
<223> OTHER INFORMATION: Xaa is any amino acid

<400> SEQUENCE: 319

Xaa Xaa Xaa Cys Xaa Xaa Xaa Xaa Xaa Xaa Xaa Xaa Xaa Xaa Xaa
1               5                   10                  15

<210> SEQ ID NO 320
<211> LENGTH: 15
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(15)
<223> OTHER INFORMATION: Xaa is any amino acid

<400> SEQUENCE: 320

Xaa Xaa Xaa Cys Xaa Xaa Xaa Xaa Xaa Xaa Xaa Xaa Xaa Xaa Xaa
1               5                   10                  15

<210> SEQ ID NO 321
<211> LENGTH: 14
<212> TYPE: PRT
<213> ORGANISM: Ancyclostoma caninum
```

```
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(14)
<223> OTHER INFORMATION: Xaa is any amino acid

<400> SEQUENCE: 321

Xaa Xaa Xaa Cys Xaa Xaa Xaa Xaa Xaa Xaa Xaa Xaa Xaa Xaa
 1               5                  10

<210> SEQ ID NO 322
<211> LENGTH: 13
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(13)
<223> OTHER INFORMATION: Xaa is any amino acid

<400> SEQUENCE: 322

Xaa Xaa Xaa Cys Xaa Xaa Xaa Xaa Xaa Xaa Xaa Xaa Xaa
 1               5                  10

<210> SEQ ID NO 323
<211> LENGTH: 12
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(12)
<223> OTHER INFORMATION: Xaa is any amino acid

<400> SEQUENCE: 323

Xaa Xaa Xaa Cys Xaa Xaa Xaa Xaa Xaa Xaa Xaa Xaa
 1               5                  10

<210> SEQ ID NO 324
<211> LENGTH: 11
<212> TYPE: PRT
<213> ORGANISM: Ancyclostoma caninum
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(11)
<223> OTHER INFORMATION: Xaa is any amino acid

<400> SEQUENCE: 324

Xaa Xaa Xaa Cys Xaa Xaa Xaa Xaa Xaa Xaa Xaa
 1               5                  10

<210> SEQ ID NO 325
<211> LENGTH: 10
<212> TYPE: PRT
<213> ORGANISM: Ancyclostoma caninum
<220> FEATURE:
<221> NAME/KEY: MISC_FEATURE
<222> LOCATION: (1)..(3)
```

```
<223> OTHER INFORMATION: Xaa is any amino acid
<220> FEATURE:
<221> NAME/KEY: MISC_FEATURE
<222> LOCATION: (5)..(10)
<223> OTHER INFORMATION: Xaa is any amino acid

<400> SEQUENCE: 325

Xaa Xaa Xaa Cys Xaa Xaa Xaa Xaa Xaa Xaa
 1               5                  10

<210> SEQ ID NO 326
<211> LENGTH: 5
<212> TYPE: PRT
<213> ORGANISM: Ancyclostoma caninum
<220> FEATURE:
<221> NAME/KEY: MISC_FEATURE
<222> LOCATION: (2)..(5)
<223> OTHER INFORMATION: Xaa is any amino acid

<400> SEQUENCE: 326

Cys Xaa Xaa Xaa Xaa
 1               5

<210> SEQ ID NO 327
<211> LENGTH: 4
<212> TYPE: PRT
<213> ORGANISM: Ancyclostoma caninum
<220> FEATURE:
<221> NAME/KEY: MISC_FEATURE
<222> LOCATION: (2)..(4)
<223> OTHER INFORMATION: Xaa is any amino acid

<400> SEQUENCE: 327

Cys Xaa Xaa Xaa
 1

<210> SEQ ID NO 328
<211> LENGTH: 6
<212> TYPE: PRT
<213> ORGANISM: Ancyclostoma caninum
<220> FEATURE:
<221> NAME/KEY: MISC_FEATURE
<222> LOCATION: (2)..(6)
<223> OTHER INFORMATION: Xaa is any amino acid

<400> SEQUENCE: 328

Cys Xaa Xaa Xaa Xaa Xaa
 1               5

<210> SEQ ID NO 329
<211> LENGTH: 5
<212> TYPE: PRT
<213> ORGANISM: Ancyclostoma caninum
<220> FEATURE:
<221> NAME/KEY: MISC_FEATURE
<222> LOCATION: (2)..(5)
<223> OTHER INFORMATION: Xaa is any amino acid

<400> SEQUENCE: 329

Cys Xaa Xaa Xaa Xaa
 1               5

<210> SEQ ID NO 330
<211> LENGTH: 4
<212> TYPE: PRT
<213> ORGANISM: Ancyclostoma caninum
<220> FEATURE:
<221> NAME/KEY: MISC_FEATURE
<222> LOCATION: (2)..(4)
```

<223> OTHER INFORMATION: Xaa is any amino acid

<400> SEQUENCE: 330

Cys Xaa Xaa Xaa
1

<210> SEQ ID NO 331
<211> LENGTH: 15
<212> TYPE: PRT
<213> ORGANISM: Ancyclostoma caninum
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (4)..(15)
<223> OTHER INFORMATION: Xaa is any amino acid

<400> SEQUENCE: 331

Cys Xaa Cys Xaa Xaa Xaa Xaa Xaa Xaa Xaa Xaa Xaa Xaa Xaa Xaa
1               5                   10                  15

<210> SEQ ID NO 332
<211> LENGTH: 14
<212> TYPE: PRT
<213> ORGANISM: Ancyclostoma caninum
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (4)..(14)
<223> OTHER INFORMATION: Xaa is any amino acid

<400> SEQUENCE: 332

Cys Xaa Cys Xaa Xaa Xaa Xaa Xaa Xaa Xaa Xaa Xaa Xaa Xaa
1               5                   10

<210> SEQ ID NO 333
<211> LENGTH: 8
<212> TYPE: PRT
<213> ORGANISM: Ancyclostoma caninum
<220> FEATURE:
<221> NAME/KEY: MISC_FEATURE
<222> LOCATION: (2)..(8)
<223> OTHER INFORMATION: Xaa is any amino acid

<400> SEQUENCE: 333

Cys Xaa Xaa Xaa Xaa Xaa Xaa Xaa
1               5

<210> SEQ ID NO 334
<211> LENGTH: 7
<212> TYPE: PRT
<213> ORGANISM: Ancyclostoma caninum
<220> FEATURE:
<221> NAME/KEY: MISC_FEATURE
<222> LOCATION: (2)..(7)
<223> OTHER INFORMATION: Xaa is any amino acid

<400> SEQUENCE: 334

Cys Xaa Xaa Xaa Xaa Xaa Xaa
1               5

<210> SEQ ID NO 335
<211> LENGTH: 6
<212> TYPE: PRT

```
<213> ORGANISM: Ancyclostoma caninum
<220> FEATURE:
<221> NAME/KEY: MISC_FEATURE
<222> LOCATION: (2)..(6)
<223> OTHER INFORMATION: Xaa is any amino acid

<400> SEQUENCE: 335

Cys Xaa Xaa Xaa Xaa Xaa
1               5

<210> SEQ ID NO 336
<211> LENGTH: 26
<212> TYPE: PRT
<213> ORGANISM: Ancyclostoma caninum
<220> FEATURE:
<221> NAME/KEY: MISC_FEATURE
<222> LOCATION: (2)..(26)
<223> OTHER INFORMATION: Xaa is any amino acid

<400> SEQUENCE: 336

Cys Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa
            20                  25

<210> SEQ ID NO 337
<211> LENGTH: 25
<212> TYPE: PRT
<213> ORGANISM: Ancyclostoma caninum
<220> FEATURE:
<221> NAME/KEY: MISC_FEATURE
<222> LOCATION: (2)..(25)
<223> OTHER INFORMATION: Xaa is any amino acid

<400> SEQUENCE: 337

Cys Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa
            20                  25

<210> SEQ ID NO 338
<211> LENGTH: 24
<212> TYPE: PRT
<213> ORGANISM: Ancyclostoma caninum
<220> FEATURE:
<221> NAME/KEY: MISC_FEATURE
<222> LOCATION: (2)..(24)
<223> OTHER INFORMATION: Xaa is any amino acid

<400> SEQUENCE: 338

Cys Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa
            20

<210> SEQ ID NO 339
<211> LENGTH: 23
<212> TYPE: PRT
<213> ORGANISM: Ancyclostoma caninum
<220> FEATURE:
<221> NAME/KEY: MISC_FEATURE
<222> LOCATION: (2)..(23)
<223> OTHER INFORMATION: Xaa is any amino acid

<400> SEQUENCE: 339

Cys Xaa Xaa Xaa Xaa Xaa Xaa Xaa Xaa Xaa Xaa Xaa Xaa Xaa Xaa
1               5                   10                  15
```

Xaa Xaa Xaa Xaa Xaa Xaa Xaa
            20

<210> SEQ ID NO 340
<211> LENGTH: 22
<212> TYPE: PRT
<213> ORGANISM: Ancyclostoma caninum
<220> FEATURE:
<221> NAME/KEY: MISC_FEATURE
<222> LOCATION: (2)..(22)
<223> OTHER INFORMATION: Xaa is any amino acid

<400> SEQUENCE: 340

Cys Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa
            20

<210> SEQ ID NO 341
<211> LENGTH: 21
<212> TYPE: PRT
<213> ORGANISM: Ancyclostoma caninum
<220> FEATURE:
<221> NAME/KEY: MISC_FEATURE
<222> LOCATION: (2)..(21)
<223> OTHER INFORMATION: Xaa is any amino acid

<400> SEQUENCE: 341

Cys Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa
            20

<210> SEQ ID NO 342
<211> LENGTH: 20
<212> TYPE: PRT
<213> ORGANISM: Ancyclostoma caninum
<220> FEATURE:
<221> NAME/KEY: MISC_FEATURE
<222> LOCATION: (2)..(20)
<223> OTHER INFORMATION: Xaa is any amino acid

<400> SEQUENCE: 342

Cys Xaa Xaa Xaa Xaa Xaa Xaa Xaa Xaa Xaa Xaa Xaa Xaa Xaa Xaa Xaa
1               5                   10                  15

Xaa Xaa Xaa Xaa
            20

<210> SEQ ID NO 343
<211> LENGTH: 19
<212> TYPE: PRT
<213> ORGANISM: Ancyclostoma caninum
<220> FEATURE:
<221> NAME/KEY: MISC_FEATURE
<222> LOCATION: (2)..(19)
<223> OTHER INFORMATION: Xaa is any amino acid

<400> SEQUENCE: 343

Cys Xaa Xaa Xaa Xaa Xaa Xaa Xaa Xaa Xaa Xaa Xaa Xaa Xaa Xaa Xaa
1               5                   10                  15

Xaa Xaa Xaa

<210> SEQ ID NO 344
<211> LENGTH: 18
<212> TYPE: PRT

```
<213> ORGANISM: Ancyclostoma caninum
<220> FEATURE:
<221> NAME/KEY: MISC_FEATURE
<222> LOCATION: (2)..(18)
<223> OTHER INFORMATION: Xaa is any amino acid

<400> SEQUENCE: 344

Cys Xaa Xaa Xaa Xaa Xaa Xaa Xaa Xaa Xaa Xaa Xaa Xaa Xaa Xaa
1               5                   10                  15

Xaa Xaa

<210> SEQ ID NO 345
<211> LENGTH: 17
<212> TYPE: PRT
<213> ORGANISM: Ancyclostoma caninum
<220> FEATURE:
<221> NAME/KEY: MISC_FEATURE
<222> LOCATION: (2)..(17)
<223> OTHER INFORMATION: Xaa is any amino acid

<400> SEQUENCE: 345

Cys Xaa Xaa Xaa Xaa Xaa Xaa Xaa Xaa Xaa Xaa Xaa Xaa Xaa Xaa
1               5                   10                  15

Xaa

<210> SEQ ID NO 346
<211> LENGTH: 16
<212> TYPE: PRT
<213> ORGANISM: Ancyclostoma caninum
<220> FEATURE:
<221> NAME/KEY: MISC_FEATURE
<222> LOCATION: (2)..(16)
<223> OTHER INFORMATION: Xaa is any amino acid

<400> SEQUENCE: 346

Cys Xaa Xaa Xaa Xaa Xaa Xaa Xaa Xaa Xaa Xaa Xaa Xaa Xaa Xaa
1               5                   10                  15

<210> SEQ ID NO 347
<211> LENGTH: 15
<212> TYPE: PRT
<213> ORGANISM: Ancyclostoma caninum
<220> FEATURE:
<221> NAME/KEY: MISC_FEATURE
<222> LOCATION: (2)..(15)
<223> OTHER INFORMATION: Xaa is any amino acid

<400> SEQUENCE: 347

Cys Xaa Xaa Xaa Xaa Xaa Xaa Xaa Xaa Xaa Xaa Xaa Xaa Xaa
1               5                   10                  15

<210> SEQ ID NO 348
<211> LENGTH: 14
<212> TYPE: PRT
<213> ORGANISM: Ancyclostoma caninum
<220> FEATURE:
<221> NAME/KEY: MISC_FEATURE
<222> LOCATION: (2)..(14)
<223> OTHER INFORMATION: Xaa is any amino acid

<400> SEQUENCE: 348

Cys Xaa Xaa Xaa Xaa Xaa Xaa Xaa Xaa Xaa Xaa Xaa Xaa
1               5                   10

<210> SEQ ID NO 349
<211> LENGTH: 13
<212> TYPE: PRT
```

-continued

```
<213> ORGANISM: Ancyclostoma caninum
<220> FEATURE:
<221> NAME/KEY: MISC_FEATURE
<222> LOCATION: (2)..(13)
<223> OTHER INFORMATION: Xaa is any amino acid

<400> SEQUENCE: 349

Cys Xaa Xaa Xaa Xaa Xaa Xaa Xaa Xaa Xaa Xaa Xaa
1               5                   10

<210> SEQ ID NO 350
<211> LENGTH: 12
<212> TYPE: PRT
<213> ORGANISM: Ancyclostoma caninum
<220> FEATURE:
<221> NAME/KEY: MISC_FEATURE
<222> LOCATION: (2)..(12)
<223> OTHER INFORMATION: Xaa is any amino acid

<400> SEQUENCE: 350

Cys Xaa Xaa Xaa Xaa Xaa Xaa Xaa Xaa Xaa Xaa
1               5                   10

<210> SEQ ID NO 351
<211> LENGTH: 11
<212> TYPE: PRT
<213> ORGANISM: Ancyclostoma caninum
<220> FEATURE:
<221> NAME/KEY: MISC_FEATURE
<222> LOCATION: (2)..(11)
<223> OTHER INFORMATION: Xaa is any amino acid

<400> SEQUENCE: 351

Cys Xaa Xaa Xaa Xaa Xaa Xaa Xaa Xaa Xaa Xaa
1               5                   10

<210> SEQ ID NO 352
<211> LENGTH: 10
<212> TYPE: PRT
<213> ORGANISM: Ancyclostoma caninum
<220> FEATURE:
<221> NAME/KEY: MISC_FEATURE
<222> LOCATION: (2)..(10)
<223> OTHER INFORMATION: Xaa is any amino acid

<400> SEQUENCE: 352

Cys Xaa Xaa Xaa Xaa Xaa Xaa Xaa Xaa Xaa
1               5                   10

<210> SEQ ID NO 353
<211> LENGTH: 9
<212> TYPE: PRT
<213> ORGANISM: Ancyclostoma caninum
<220> FEATURE:
<221> NAME/KEY: MISC_FEATURE
<222> LOCATION: (2)..(9)
<223> OTHER INFORMATION: Xaa is any amino acid

<400> SEQUENCE: 353

Cys Xaa Xaa Xaa Xaa Xaa Xaa Xaa Xaa
1               5

<210> SEQ ID NO 354
<211> LENGTH: 8
<212> TYPE: PRT
<213> ORGANISM: Ancyclostoma caninum
<220> FEATURE:
<221> NAME/KEY: MISC_FEATURE
<222> LOCATION: (2)..(8)
```

```
<223> OTHER INFORMATION: Xaa is any amino acid

<400> SEQUENCE: 354

Cys Xaa Xaa Xaa Xaa Xaa Xaa Xaa
1               5

<210> SEQ ID NO 355
<211> LENGTH: 7
<212> TYPE: PRT
<213> ORGANISM: Ancyclostoma caninum
<220> FEATURE:
<221> NAME/KEY: MISC_FEATURE
<222> LOCATION: (2)..(7)
<223> OTHER INFORMATION: Xaa is any amino acid

<400> SEQUENCE: 355

Cys Xaa Xaa Xaa Xaa Xaa Xaa
1               5

<210> SEQ ID NO 356
<211> LENGTH: 6
<212> TYPE: PRT
<213> ORGANISM: Ancyclostoma caninum
<220> FEATURE:
<221> NAME/KEY: MISC_FEATURE
<222> LOCATION: (2)..(6)
<223> OTHER INFORMATION: Xaa is any amino acid

<400> SEQUENCE: 356

Cys Xaa Xaa Xaa Xaa Xaa
1               5

<210> SEQ ID NO 357
<211> LENGTH: 4
<212> TYPE: PRT
<213> ORGANISM: Ancyclostoma caninum
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (4)..(4)
<223> OTHER INFORMATION: Xaa is any amino acid

<400> SEQUENCE: 357

Leu Xaa Arg Xaa
1
```